United States Patent
McGowan et al.

(10) Patent No.: US 11,793,815 B2
(45) Date of Patent: Oct. 24, 2023

(54) OXINDOLES AND METHODS OF USE THEREOF

(71) Applicant: ALIGOS THERAPEUTICS, INC., South San Francisco, CA (US)

(72) Inventors: David Craig McGowan, Brussels (BE); Pierre Jean-Marie Bernard Raboisson, Wavre (BE); Koen Vandyck, Beringen (BE); Jerome Deval, El Granada, CA (US); Leonid Beigelman, San Mateo, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 50 days.

(21) Appl. No.: 17/520,168

(22) Filed: Nov. 5, 2021

(65) Prior Publication Data

US 2022/0143031 A1    May 12, 2022

Related U.S. Application Data

(60) Provisional application No. 63/110,814, filed on Nov. 6, 2020, provisional application No. 63/195,969, filed on Jun. 2, 2021.

(51) Int. Cl.

| | |
|---|---|
| *C07D 471/04* | (2006.01) |
| *A61K 31/4245* | (2006.01) |
| *A61K 31/53* | (2006.01) |
| *A61P 1/16* | (2006.01) |
| *A61P 3/04* | (2006.01) |
| *A61K 31/404* | (2006.01) |
| *A61K 31/437* | (2006.01) |
| *A61K 31/451* | (2006.01) |
| *A61K 31/46* | (2006.01) |
| *A61K 31/506* | (2006.01) |
| *A61K 31/575* | (2006.01) |
| *C07D 209/46* | (2006.01) |
| *C07D 209/96* | (2006.01) |
| *C07D 403/12* | (2006.01) |
| *C07D 413/12* | (2006.01) |

(52) U.S. Cl.
CPC ............ *A61K 31/53* (2013.01); *A61K 31/404* (2013.01); *A61K 31/4245* (2013.01); *A61K 31/437* (2013.01); *A61K 31/451* (2013.01); *A61K 31/46* (2013.01); *A61K 31/506* (2013.01); *A61K 31/575* (2013.01); *A61P 1/16* (2018.01); *A61P 3/04* (2018.01); *C07D 209/46* (2013.01); *C07D 209/96* (2013.01); *C07D 403/12* (2013.01); *C07D 413/12* (2013.01); *C07D 471/04* (2013.01)

(58) Field of Classification Search
CPC ........................... C07D 471/04; A61K 31/4245
USPC ........................................................ 514/287
See application file for complete search history.

(56) References Cited

U.S. PATENT DOCUMENTS 7,199,265 B2 * 4/2007 Yi-Lin ................... A61P 25/24
560/12

FOREIGN PATENT DOCUMENTS

| WO | WO-01/98256 A1 | 12/2001 |
| WO | 2009080835 | * 7/2009 |
| WO | 2020169069 | * 8/2020 |
| WO | 2020227549 | * 11/2020 |
| WO | WO-2020/227549 A1 | 11/2020 |
| WO | WO-2021/043185 A1 | 3/2021 |

OTHER PUBLICATIONS

International Search Report and Written Opinion dated Feb. 7, 2022 in PCT/US2021/058326.
Aleiwi et al., "A reliable Pd-mediated hydrogenolytic deprotection of BOM group of uridine ureido nitrogen," Tetrahedron Letters, 2012, 53:3758-3762.
Bernardelli et al., "Spiroquinazolinones as novel, potent, and selective PDE7 inhibitors. Part 2: Optimization of 5,8-disubstituted derivatives," Bioorganic & Medicinal Chemistry Letters, 2004, 14(18):4627-4631.
Bookout et al., "Anatomical Profiling of Nuclear Receptor Expression Reveals a Hierarchical Transcriptional Network," Cell, Aug. 25, 2006, 126(4):789-799.
Chalasani et al., "The Diagnosis and Management of Non-alcoholic Fatty Liver Disease: Practice Guideline by the American Gastroenterological Association, American Association for the Study of Liver Diseases, and American College of Gastroenterology," Gastroenterology, 2012, 142(7):1592-1609.

(Continued)

*Primary Examiner* — Niloofar Rahmani
(74) *Attorney, Agent, or Firm* — Foley & Lardner LLP

(57) ABSTRACT

Disclosed herein are compounds of Formula I':

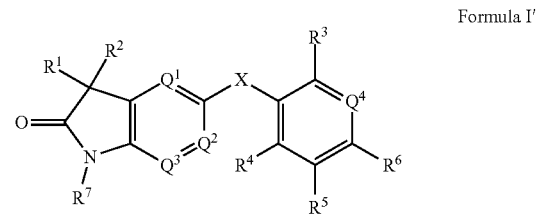

or a stereoisomer or a tautomer thereof, or a pharmaceutically acceptable salt thereof, pharmaceutical compositions comprising such compounds, and methods of treating disease by administering or contacting a subject with one or more of the above compounds.

23 Claims, No Drawings

(56) References Cited

OTHER PUBLICATIONS

Chen et al., "DABCO-Catalyzed Michael/Alkylation Cascade Reactions Involving alpha-Substituted Ammonium Ylides for the Construction of Spirocyclopropyl Oxindoles: Access to the Powerful Chemical Leads against HIV-1," Journal of Organic Chemistry, 2020, 85:5203-5219.
Drummond et al., "Evaluation and Synthesis of Aminohydroxyisoxazoles and Pyrazoles as Potential Glycine Agonists," J. Med. Chem., 1989, 32(9):2116-2128.
Dulai et al., "Increased Risk of Mortality by Fibrosis Stage in Nonalcoholic Fatty Liver Disease: Systematic Review and Meta-Analysis," Hepatology, May 2017, 65(5):1557-1565.
Endo et al., "One-Pot Synthesis of Symmetrical and Unsymmetrical Diarylmethanes via Diborylmethane," J. Org. Chem., 2012, 77:7223-7231.
Erion et al., "Targeting thyroid hormone receptor-B agonists to the liver reduces cholesterol and triglycerides and improves the therapeutic index," PNAS, Sep. 25, 2007, 104(39):15490-15495.
Flamant et al., "International Union of Pharmacology. LIX. The Pharmacology and Classification of the Nuclear Receptor Superfamily: Thyroid Hormone Receptors," Pharmacological Reviews, 2006, 58(4):705-711.
Hajra et al., "Domino Corey-Chaykovsky Reaction for One-Pot Access to Spirocyclopropyl Oxindoles," Org. Lett., 2018, 20:4540-4544.
Haning et al., "Novel heterocyclic thryomimetics," Bioorganic & Medicinal Chemistry Letters, Apr. 1, 2005, 15(7):1835-1840.
Hartley et al., "A Thyroid Hormone-Based Strategy for Correcting the Biochemical Abnormality in X-Linked Adrenoleukodystrophy," Endocrinology, May 2017, 158(5):1328-1338.
Harvey et al., "Mechanism of Thyroid Hormone Action," Thyroid, Jun. 2002, 12(6):441-446.
Hirano et al., "Thyromimetics: a review of recent reports and patents (2004-2009)," Expert Opin. Ther. Pat., Feb. 2010, 20(2):213-228.
Iikuni et al., "Development of the 99mTc-Hydroxamamide Complex as a Probe Targeting Carbonic Anhydrase IX," Molecular Pharmaceutics, 2019, 16(4):1489-1497.
Katane et al., "Identification of Novel D-Amino Acid Oxidase Inhibitors by in Silico Screening and Their Functional Characterization in Vitro," J. Med. Chem., 2013, 56(5):1894-1907.
Kowalik et al., "Thyroid Hormones, Thyromimetics and Their Metabolites in the Treatment of Liver Disease," Frontiers in Endocrinology, Jul. 10, 2018, 9:382, 11 pages.
Lazo et al., "Nonalcoholic Fatty Liver disease (NAFLD): Is It Really a Serious Condition?", Hepatology, Oct. 2012, 56(4):1580-1584.
Li et al., "Highly Chemoselective, Transition-Metal-Free Transamidation of Unactivated Amides and Direct Amidation of Alkyl Esters by N-C/O-C Cleavage," J. Am. Chem. Soc. 2019, 141:11161-11172.
Liljebris et al., "Investigation of Potential Bioisosteric Replacements for the Carboxyl Groups of Peptidomimetic Inhibitors of Protein Tyrosine Phosphatase 1B: Identification of a Tetrazole-Containing Inhibitor with Cellular Activity," J. Med. Chem. 2002, 45(9):1785-1798.
Milanesi et al., "Beam Me In: Thyroid Hormone Analog Targets Alternative Transporter in Mouse Model of X-Linked Adrenoleukodystrophy," Endocrinology, May 2017, 158:1116-1119.
Serfaty et al., "Definition and natural history of metabolic steatosis: clinical aspects of NAFLD, NASH and cirrhosis," Diabetes and Metabolism, 2008, 34:634-637.
Sorensen et al., "A Novel Route to 5-Substituted 3-Isoxazolols. Cyclization of N, O-DiBoc Beta-keto Hydroxamic Aids Synthesized via Acyl Meldrum's Acids," J. Org. Chem., 2000, 65(4):1003-1007.
Ushkov et al., "Rational Catalysis Design on the Basis of Mechanistic Understanding: Highly Efficient PD-Catalyzed Cyanation of Aryl Bromides with NaCN in Recyclable Solvents," J. Am. Chem. Soc., 2011, 133:10999-11005.
Wolff et al., "Some Observations on the Brunner Reaction," Tetrahedron, 1996, 42:4267-4272.
Wu et al., "Organocatalytic Highly Enantioselective Monofluoroalkylation of 3-Bromooxindoles: Construction of Fluorinated 3,3'-Disubstituted Oxindoles and their Derivatives," Organic Letters, 2014, 16(7):1960-1963.
Ye et al., "Therapeutic Potential of Spirooxindoles as Antiviral Agents," ACS Infect Dis., 2016, 2:382-392.
Younossi et al., "Current and Future Therapeutic Regimens for Nonalcoholic Fatty Liver Disease and Nonalcoholic Steatohepatitis," Hepatology, Jul. 2018, 68(1):361-371.
Younossi et al., "Global Epidemiology of Nonalcoholic Fatty Liver Disease—Meta-Analytic Assessment of Prevalence, Incidence and Outcomes," Hepatology, Jul. 2016, 64(1):73-84.
Zaytsev et al., "Nucleophilic Ring Opening of Donor-Acceptor Cyclopropanes with the Cyanate Ion: Access to Spiro[pyrrolidone-3,3'-oxindoles," Journal of Organic Chemistry, 2018, 83:8695-8709.
Zhang et al., "5-Ureidobenzofuranone indoles as potent and efficacious inhibitors of PI3 kinase-alpha and mTOR for the treatment of breast cancer," Bioorganic and Med. Chem. Letters, 2010, 20(12):3526-3529.

* cited by examiner

OXINDOLES AND METHODS OF USE THEREOF

CROSS-REFERENCE TO RELATED APPLICATIONS

This application claims the benefit of priority to U.S. Provisional Patent Application Ser. No. 63/110,814, filed on Nov. 6, 2020, and U.S. Provisional Patent Application Ser. No. 63/195,969, filed on Jun. 2, 2021, the entire disclosures of which are hereby incorporated by reference herein.

FIELD OF THE DISCLOSURE

The present disclosure is in the field of pharmaceutical compounds and preparations and method of their use in the treatment of disease. In particular, the present disclosure is in the field of THR-β modulators and their use.

BACKGROUND OF THE DISCLOSURE

In parallel with the global increase in obesity, nonalcoholic fatty liver disease (NAFLD) is becoming the leading cause of chronic liver disease and liver transplantation worldwide [1,2]. NAFLD is believed to affect 30% of the adult population and 70-80% of individuals who are obese and diabetic. NAFLD is defined as excess liver fat accumulation greater than 5% induced by causes other than alcohol intake. NAFLD progresses to liver inflammation (nonalcoholic steatohepatitis, NASH) and fibrosis in a variable proportion of individuals, ultimately leading to liver failure and hepatocellular carcinoma (HCC) in susceptible individuals [3].

In the United States alone, NASH is the third most common indication for liver transplantation and is on a trajectory to become the most common [4]. The most important medical need in patients with NAFLD and NASH is an effective treatment to halt the progression and possibly reverse fibrosis, which is the main predictor of liver disease evolution [5,6].

Thyroid hormone (TH) is essential for normal development, growth and metabolism of all vertebrates. Its effects are mediated principally through triiodothyronine (T3), which acts as a ligand for the TH receptors (TRs, or THRs) β1, β2 and α1 [7]. In the absence of ligand, TR first binds as a heterodimer or homodimer on TH response elements (TRE) located in the promoter regions of target genes, where it interacts with corepressors. Upon ligand binding, the TR homodimers are dissociated in favor of heterodimer formation with the retinoid-X receptor (RXR), resulting in release of the corepressors and recruitment of coactivators. This new complex attracts a large number of proteins which engage the RNA polymerase II in the transcription of the targeted genes.

Two different genetic loci, denoted THRA and THRB, are responsible for encoding multiple interrelated TR isoforms that have distinct tissue distributions and biological functions. The two major isoforms with the broadest level of tissue expression are TRα1 and TRβ1 [8]. While TRα1 is expressed first during fetal development and is widely expressed in adult tissues, TRβ1 appears later in development and displays highest expression in the adult liver, kidney, and lung [9]. TRα1 is a key regulator of cardiac output, whereas TRβ1 helps in the control of metabolism in the liver. Importantly, the natural thyroid hormone T3 activates both TRα1 and TRβ1 without any significant selectivity.

Design of thyromimetic small molecule agents led to the identification of TR (or THR) agonists with varying levels of TRβ selectivity despite high structural similarity between the ligand-binding domains for TRβ and TRα. TRβ selectivity achieved by some of these compounds resulted in an improved therapeutic index for lipid lowering relative to cardiac effects such as heart rate, cardiac hypertrophy, and contractility [10-12].

Another strategy to avoid activation of TRα in cardiac tissue is to design prodrugs of phosphonate-containing TR agonists that are specifically converted to the active agonist in the liver but remain stable as an inactive prodrug in blood and extrahepatic tissues, including the heart [13]. TRα and TRβ agonists are also used in indications other than liver-related disorders, as has been known in the art. For example, TRβ selective agonists may be useful in the treatment of X-linked adrenoleukodystrophy [14, 15].

SUMMARY

Provided herein, in one aspect, are compounds of Formula I:

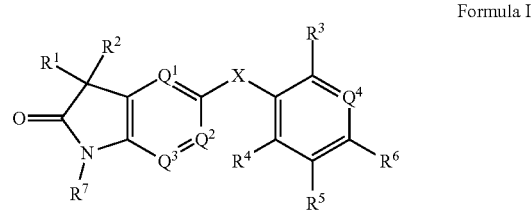

Formula I or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen; or $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

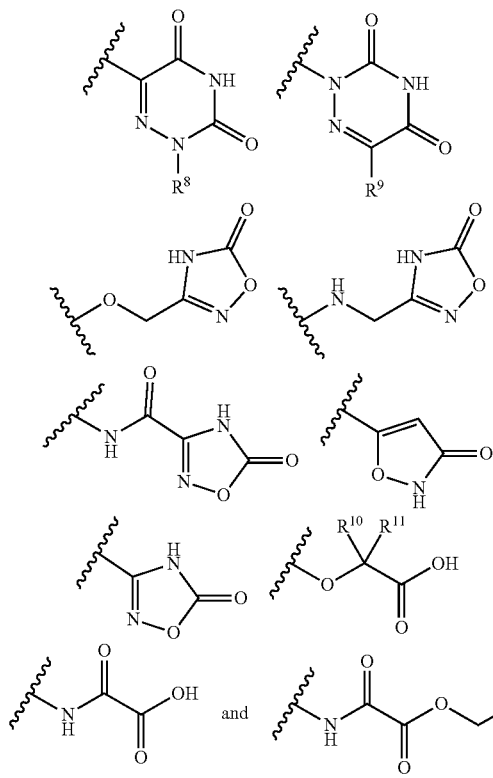

$R^7$ is H or $C_1$-$C_3$ alkyl;

$R^8$ is H or $C_1$-$C_3$ alkyl;

$R^9$ is selected from H, —CN, —CH$_3$, and —NH$_2$;

$R^{10}$ and $R^{11}$ are each independently F or $C_1$-$C_3$ alkyl; or $R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;

$R^{12}$ is H, halogen, —CN, optionally substituted $C_1$-$C_3$ alkoxy, or optionally substituted $C_1$-$C_6$ alkyl; or $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

$R^{13}$ is independently selected from H, halogen, —CN, —OCH$_3$, and $C_1$-$C_3$ alkyl; and X is O or CH$_2$;

wherein 0 to 10 hydrogen atoms that are attached to one or more carbon atoms are replaced with deuterium atom(s);

provided that:

if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, optionally substituted cyclopropyl, and halogen;

if $Q^1$, $Q^2$, and $Q^3$ are all CH, and $R^{10}$ and $R^{11}$ are not both H, then $R^6$ is selected from:

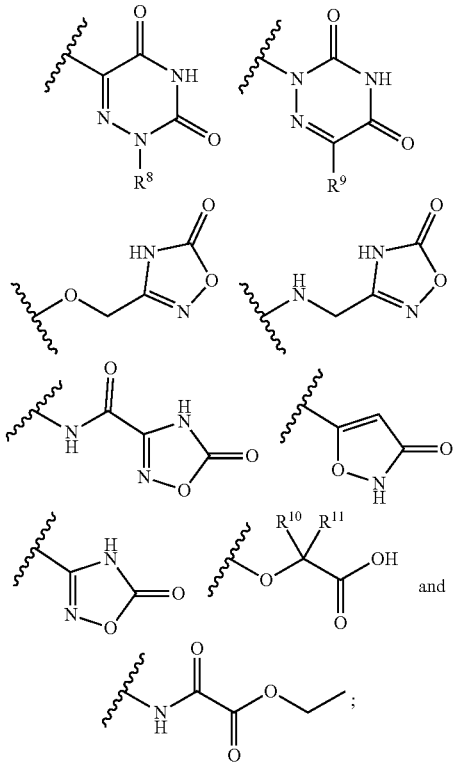

the compound is not selected from:
2-(3,5-dichloro-4-((5,5-dimethyl-6-oxo-6,7-dihydro-5H-pyrrolo[2,3-c]pyridazin-3-yl)oxy)phenyl)-3,5-dioxo-2,3,4,5-tetrahydro-1,2,4-triazine-6-carbonitrile;
6-amino-2-(3,5-dichloro-4-((3,3-dimethyl-2-oxoindolin-5-yl)oxy)phenyl)-1,2,4-triazine-3,5(2H,4H)-dione;
6-amino-2-(3,5-dichloro-4-((2'-oxospiro[cyclopentane-1,3'-indolin]-5'-yl)oxy)phenyl)-1,2,4-triazine-3,5(2H,4H)-dione;
6-amino-2-(3,5-dichloro-4-((3-isopropyl-3-methyl-2-oxoindolin-5-yl)oxy)phenyl)-1,2,4-triazine-3,5(2H,4H)-dione;
6-amino-2-(3,5-dichloro-4-((2'-oxospiro[cyclohexane-1,3'-indolin]-5'-yl)oxy)phenyl)-1,2,4-triazine-3,5(2H,4H)-dione;
6-amino-2-(3,5-dichloro-4-((2'-oxospiro[cyclopropane-1,3'-indolin]-5'-yl)oxy)phenyl)-1,2,4-triazine-3,5(2H,4H)-dione;
2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile;
6-amino-2-(3,5-dimethyl-4-((2'-oxospiro[cyclopentane-1,3'-indolin]-5'-yl)methyl)phenyl)-1,2,4-triazine-3,5(2H,4H)-dione;
6-amino-2-(3,5-dimethyl-4-((2'-oxospiro[cyclopropane-1,3'-indolin]-5'-yl)methyl)phenyl)-1,2,4-triazine-3,5(2H,4H)-dione;
2-(3,5-dimethyl-4-((2'-oxospiro[cyclopropane-1,3'-indolin]-5'-yl)methyl)phenyl)-1,2,4-triazine-3,5(2H,4H)-dione; and
2-(3,5-dimethyl-4-((2'-oxospiro[cyclobutane-1,3'-indolin]-5'-yl)methyl)phenyl)-3,5-dioxo-2,3,4,5-tetrahydro-1,2,4-triazine-6-carbonitrile.

Provided herein, in another aspect, are compounds of Formula I':

Formula I' or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen; or $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

$R^7$ is H or $C_1$-$C_3$ alkyl;

$R^8$ is H or $C_1$-$C_3$ alkyl;

$R^9$ is selected from H, —CN, —CH$_3$, and —NH$_2$;

$R^{10}$ and $R^{11}$ are each independently H, F, or $C_1$-$C_3$ alkyl; or $R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;

$R^{12}$ is H, halogen, —CN, optionally substituted $C_1$-$C_3$ alkoxy, or optionally substituted $C_1$-$C_6$ alkyl; or $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

$R^{13}$ is independently selected from H, halogen, —CN, —OCH$_3$, and $C_1$-$C_3$ alkyl; and X is O or CH$_2$;

wherein 0 to 10 hydrogen atoms that are attached to one or more carbon atoms are replaced with deuterium atom(s);

provided that:

if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, optionally substituted cyclopropyl, and halogen;

when $R^{10}$ and $R^{11}$ are present, $R^{10}$, $R^{11}$ and $R^5$ cannot all be H; and the compound is not selected from:

2-(3,5-dichloro-4-((5,5-dimethyl-6-oxo-6,7-dihydro-5H-pyrrolo[2,3-c]pyridazin-3-yl)oxy)phenyl)-3,5-dioxo-2,3,4,5-tetrahydro-1,2,4-triazine-6-carbonitrile;

6-amino-2-(3,5-dichloro-4-((3,3-dimethyl-2-oxoindolin-5-yl)oxy)phenyl)-1,2,4-triazine-3,5(2H,4H)-dione;

6-amino-2-(3,5-dichloro-4-((2'-oxospiro[cyclopentane-1,3'-indolin]-5'-yl)oxy)phenyl)-1,2,4-triazine-3,5(2H,4H)-dione;

6-amino-2-(3,5-dichloro-4-((3-isopropyl-3-methyl-2-oxoindolin-5-yl)oxy)phenyl)-1,2,4-triazine-3,5(2H,4H)-dione;

6-amino-2-(3,5-dichloro-4-((2'-oxospiro[cyclohexane-1,3'-indolin]-5'-yl)oxy)phenyl)-1,2,4-triazine-3,5(2H,4H)-dione;

6-amino-2-(3,5-dichloro-4-((2'-oxospiro[cyclopropane-1,3'-indolin]-5'-yl)oxy)phenyl)-1,2,4-triazine-3,5(2H,4H)-dione;

2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

6-amino-2-(3,5-dimethyl-4-((2'-oxospiro[cyclopentane-1,3'-indolin]-5'-yl)methyl)phenyl)-1,2,4-triazine-3,5(2H,4H)-dione;

6-amino-2-(3,5-dimethyl-4-((2'-oxospiro[cyclopropane-1, 3'-indolin]-5'-yl)methyl)phenyl)-1,2,4-triazine-3,5(2H, 4H)-dione;

2-(3,5-dimethyl-4-((2'-oxospiro[cyclopropane-1,3'-indolin]-5'-yl)methyl)phenyl)-1,2,4-triazine-3,5(2H,4H)-dione; and 2-(3,5-dimethyl-4-((2'-oxospiro[cyclobutane-1,3'-indolin]-5'-yl)methyl)phenyl)-3,5-dioxo-2,3,4,5-tetrahydro-1,2,4-triazine-6-carbonitrile;

2-(3,5-dichloro-4-((2'-oxospiro[cyclopropane-1,3'-indolin]-5'-yl)oxy)phenyl)-3,5-dioxo-2,3,4,5-tetrahydro-1,2,4-triazine-6-carbonitrile;

2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carbonitrile; and 2-(3,5-dichloro-4-((2'-oxospiro[cyclopentane-1,3'-indolin]-5'-yl)oxy)phenyl)-3,5-dioxo-2,3,4,5-tetrahydro-1,2,4-triazine-6-carbonitrile.

Provided herein, in another aspect, are compounds of Formula IA:

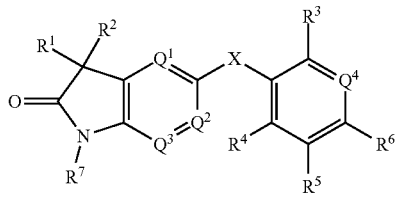

Formula IA or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl and halogen; or $R^1$ and $R^2$ together with the carbon atom to which they are attached form a polycyclic ring optionally substituted with 1 to 3 substituents independently selected from $C_1$-$C_3$ alkyl and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

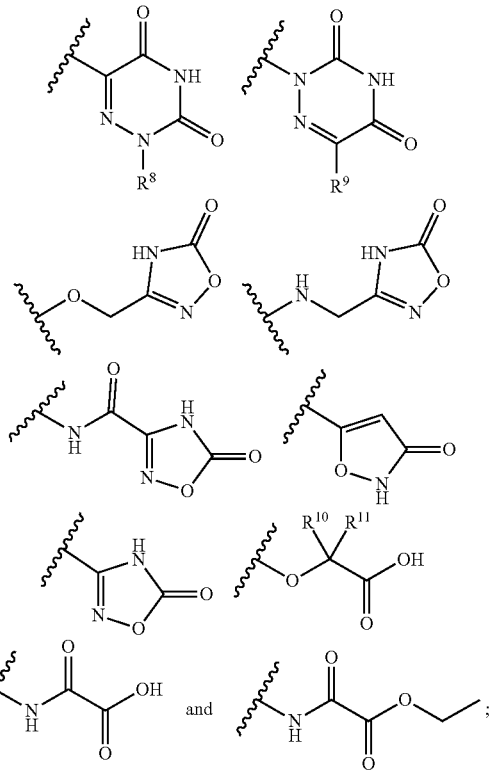

$R^7$ is H or $C_1$-$C_3$ alkyl;
$R^8$ is H or $C_1$-$C_3$ alkyl;
$R^9$ is selected from H, —CN, —$CH_3$, and —$NH_2$;
$R^{10}$ and $R^{11}$ are each independently H, F, or $C_1$-$C_3$ alkyl; or $R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;

$R^{12}$ is H, halogen, —CN, optionally substituted $C_1$-$C_3$ alkoxy, or optionally substituted $C_1$-$C_6$ alkyl; or $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

$R^{13}$ is independently selected from H, halogen, —CN, —$OCH_3$, and $C_1$-$C_3$ alkyl; and X is O or $CH_2$;

wherein 0 to 10 hydrogen atoms that are attached to one or more carbon atoms are replaced with deuterium atom(s);

provided that:

if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are substituted with 1 to 3 substituents independently selected from $C_1$-$C_3$ alkyl and halogen;

when $R^{10}$ and $R^{11}$ are present, $R^{10}$, $R^{11}$ and $R^5$ cannot all be H; and the compound is not selected from:

2-(3,5-dichloro-4-((5,5-dimethyl-6-oxo-6,7-dihydro-5H-pyrrolo[2,3-c]pyridazin-3-yl)oxy)phenyl)-3,5-dioxo-2,3, 4,5-tetrahydro-1,2,4-triazine-6-carbonitrile;

6-amino-2-(3,5-dichloro-4-((3,3-dimethyl-2-oxoindolin-5-yl)oxy)phenyl)-1,2,4-triazine-3,5(2H,4H)-dione;
6-amino-2-(3,5-dichloro-4-((2'-oxospiro[cyclopentane-1,3'-indolin]-5'-yl)oxy)phenyl)-1,2,4-triazine-3,5(2H,4H)-dione;
6-amino-2-(3,5-dichloro-4-((3-isopropyl-3-methyl-2-oxoindolin-5-yl)oxy)phenyl)-1,2,4-triazine-3,5(2H,4H)-dione;
6-amino-2-(3,5-dichloro-4-((2'-oxospiro[cyclohexane-1,3'-indolin]-5'-yl)oxy)phenyl)-1,2,4-triazine-3,5(2H,4H)-dione;
6-amino-2-(3,5-dichloro-4-((2'-oxospiro[cyclopropane-1,3'-indolin]-5'-yl)oxy)phenyl)-1,2,4-triazine-3,5(2H,4H)-dione;
6-amino-2-(3,5-dimethyl-4-((2'-oxospiro[cyclopentane-1,3'-indolin]-5'-yl)methyl)phenyl)-1,2,4-triazine-3,5(2H,4H)-dione;
6-amino-2-(3,5-dimethyl-4-((2'-oxospiro[cyclopropane-1,3'-indolin]-5'-yl)methyl)phenyl)-1,2,4-triazine-3,5(2H,4H)-dione; and
2-(3,5-dimethyl-4-((2'-oxospiro[cyclopropane-1,3'-indolin]-5'-yl)methyl)phenyl)-1,2,4-triazine-3,5(2H,4H)-dione.

In some embodiments, at least one of $Q^1$, $Q^2$, and $Q^3$ are N. In some embodiments, $Q^1$ is N. In some embodiments, $Q^2$ is N. In some embodiments, $Q^3$ is N. In some embodiments, $Q^1$ is $CR^{12}$. In some embodiments, $Q^1$ is $CR^{12}$, and $Q^2$ and $Q^3$ are both $CR^{13}$. In some embodiments, $Q^2$ is CH. In some embodiments, $Q^1$, $Q^2$, and $Q^3$ are all CH. In some embodiments, $Q^4$ is N. In some embodiments, $Q^4$ is $CR^{13}$. In some embodiments, $Q^4$ is CH. In some embodiments, $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from halogen and $C_1$-$C_3$ alkyl. In some embodiments, $R^3$ and $R^4$ are both halogen. In some embodiments, $R^3$ and $R^4$ are both —Cl. In some embodiments, $R^3$ and $R^4$ are both methyl. In some embodiments, $R^5$ is H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen. In some embodiments, $R^5$ is hydrogen or $C_1$-$C_3$ alkyl. In some embodiments, $R^5$ is hydrogen. In some embodiments, $R^6$ is

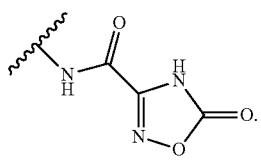 [SMILES: *NC(=O)c1noc(=O)[nH]1]

In some embodiments, $R^6$ is

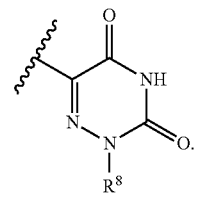

In some embodiments, $R^8$ is H. In some embodiments, $R^8$ is $C_1$-$C_3$ alkyl. In some embodiments, $R^8$ is $CH_3$. In some embodiments, $R^6$ is

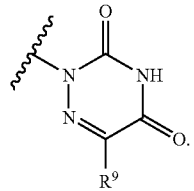

In some embodiments, $R^9$ is —CN or —$NH_2$. In some embodiments, $R^9$ is —$NH_2$. In some embodiments, $R^9$ is H. In some embodiments, $R^9$ is $CH_3$. In some embodiments, $R^6$ is

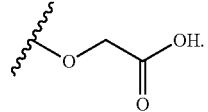 [SMILES: *OCC(=O)O]

In some embodiments, $R^7$ is H. In some embodiments, $R^{12}$ is H, halogen, or $C_1$-$C_6$ alkyl. In some embodiments, $R^{12}$ is H, F, or $C_1$-$C_6$ alkyl. In some embodiments, $R^{12}$ is H. In some embodiments, $R^{12}$ is F. In some embodiments, $R^{12}$ is Cl. In some embodiments, $R^{12}$ is $CH_3$. In some embodiments, $R^{12}$ is H, halogen, —CN, $C_1$-$C_3$ alkoxy, or $C_1$-$C_6$ alkyl; wherein the $C_1$-$C_3$ alkoxy, or $C_1$-$C_6$ alkyl are optionally substituted with 1-5 halogens. In some embodiments, $R^{12}$ is $C_1$-$C_3$ alkyl, optionally substituted with 1-3 halogens. In some embodiments, $R^{12}$ is $CF_3$. In some embodiments, $R^1$ and $R^2$ together with the carbon atom to which they are attached form a $C_3$-$C_4$ cyclic ring optionally substituted with 1 to 3 substituents independently selected from $C_1$-$C_3$ alkyl, optionally substituted cyclopropyl, and halogen. In some embodiments, $R^1$ and $R^2$ together with the carbon atom to which they are attached form a $C_3$-$C_4$ cyclic ring optionally substituted with 1 to 3 substituents independently selected from $C_1$-$C_3$ alkyl and halogen. In some embodiments, $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen; wherein a single carbon of the $C_3$-$C_6$ cyclic ring contains no more than one halogen atoms. In some embodiments, $R^1$ and $R^2$ together with the carbon atom to which they are attached form a $C_3$-$C_6$ cyclic ring optionally substituted with 1 to 3 substituents independently selected from $C_1$-$C_3$ alkyl and halogen; wherein a single carbon of the $C_3$-$C_6$ cyclic ring contains no more than one halogen atoms. In some embodiments, $R^1$ and $R^2$ together with the carbon atom to which they are attached form an unsubstituted $C_3$-$C_6$ cyclic ring. In some embodiments, $Q^1$ is $CR^{12}$, and $R^{12}$ and one of $R^1$ and $R^2$, together with the carbon atoms to which they are attached, form a $C_5$-$C_7$ partially unsaturated carbocyclic ring or a partially unsaturated polycyclic ring. In some embodiments, $Q^1$ is CH, $Q^2$ and $Q^3$ are N, and $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, cyclopropyl, and halogen. In some embodiments, $R^{13}$ is independently selected from H, F, —CN, —OCH₃, and C₁-C₃ alkyl. In some embodiments, R¹³ is H. In some embodiments, R¹³ is CH₃. In some embodiments, X is O. In some embodiments, X is CH₂. In some embodiments, the compound has the chemical structure of:

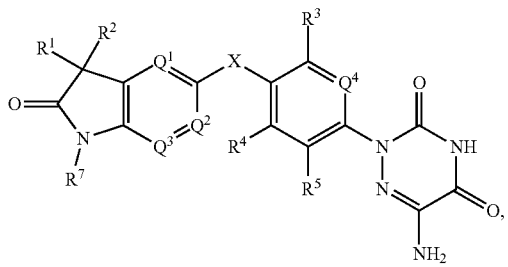

or a stereoisomer or a tautomer thereof, or a pharmaceutically acceptable salt thereof. In some embodiments, the compound has the chemical structure of:

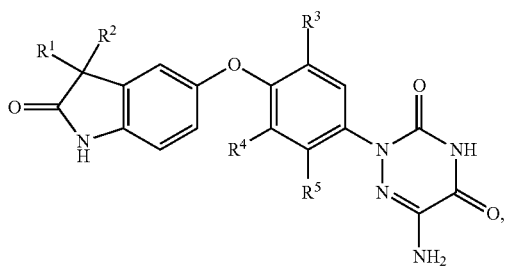

or a stereoisomer or a tautomer thereof, or a pharmaceutically acceptable salt thereof. In some embodiments, the compound has the chemical structure of:

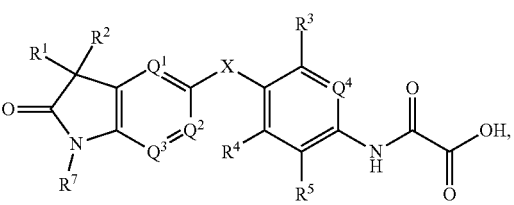

or a stereoisomer or a tautomer thereof, or a pharmaceutically acceptable salt thereof. In some embodiments, the compound has the chemical structure of:

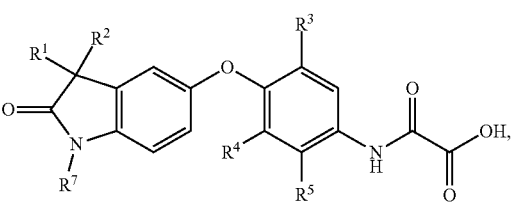

or a stereoisomer or a tautomer thereof, or a pharmaceutically acceptable salt thereof. In some embodiments, the compound has the chemical structure of:

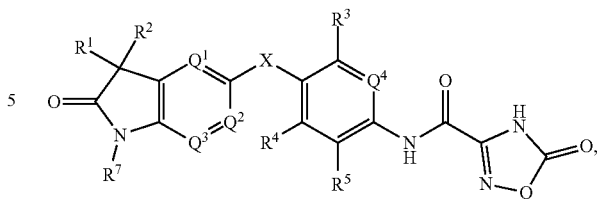

or a stereoisomer or a tautomer thereof, or a pharmaceutically acceptable salt thereof. In some embodiments, the compound has the chemical structure of:

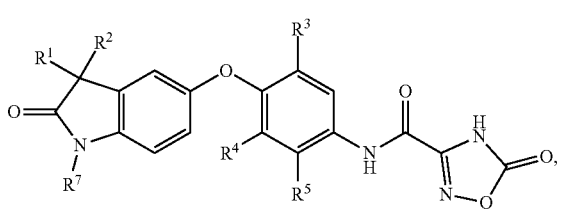

or a stereoisomer or a tautomer thereof, or a pharmaceutically acceptable salt thereof. In some embodiments, the compound has the chemical structure of:

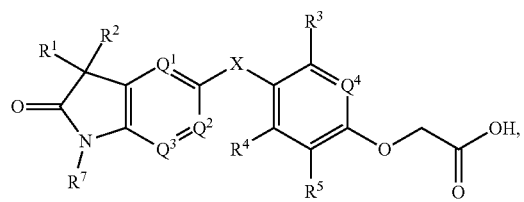

or a stereoisomer or a tautomer thereof, or a pharmaceutically acceptable salt thereof. In some embodiments, the compound has the chemical structure of:

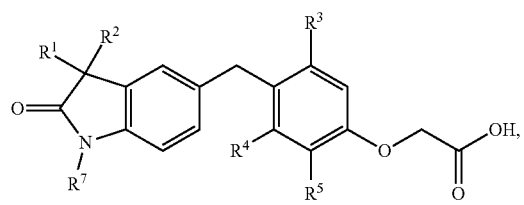

or a stereoisomer or a tautomer thereof, or a pharmaceutically acceptable salt thereof.

Provided herein, in another aspect, is a compound selected from the group consisting of:

4-([3,3-dimethyl-2-oxo-1H-pyrrolo[3,2-b]pyridin-5-yl]methyl)-2,3,5-trimethylphenoxyacetic acid;

6-amino-2-(3,5-dichloro-4-((2'-oxospiro[cyclobutane-1,3'-indolin]-5'-yl)oxy)phenyl)-1,2,4-triazine-3,5(2H,4H)-dione;

6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;

2-((4-methyl-5-((2'-oxospiro[cyclobutane-1,3'-indolin]-5'-yl)oxy)bicyclo[4.2.0]octan-2-yl)oxy)acetic acid;

6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;

6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;

6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;

6-amino-2-(3,5-dichloro-4-((1'-methyl-2'-oxospiro[cyclopropane-1,3'-indolin]-5'-yl)oxy)phenyl)-1,2,4-triazine-3,5(2H,4H)-dione;

2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;

2-(4-((3,3-difluoro-2'-oxospiro[cyclobutane-1,3'-indolin]-5'-yl)methyl)-3,5-dimethylphenyl)-3,5-dioxo-2,3,4,5-tetrahydro-1,2,4-triazine-6-carbonitrile;

6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;

6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione;

6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;

6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;

2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;

2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;

2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

6-amino-2-(3,5-dichloro-4-((2'-oxospiro[cyclobutane-1,3'-indolin]-5'-yl)methyl)phenyl)-1,2,4-triazine-3,5(2H,4H)-dione;

6-amino-2-(3,5-dimethyl-4-{2'-oxo-1'H-spiro[cyclobutane-1,3'-indol]-5'-ylmethyl}phenyl)-4H-1,2,4-triazine-3,5-dione;

2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;

2-(2,3,5-trimethyl-4-((2'-oxospiro[cyclopropane-1,3'-indolin]-5'-yl)methyl)phenoxy)acetic acid;

2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;

3-(3,5-dichloro-4-((2'-oxospiro[cyclobutane-1,3'-indolin]-5'-yl)oxy)phenyl)-1,2,4-oxadiazol-5(4H)-one;

N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;

2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;

6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;

2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;

6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;

2-((3,5-dichloro-4-((2a-methyl-2-oxo-1,2,2a,3,4,5-hexahydrobenzo[cd]indol-6-yl)oxy)phenyl)amino)-2-oxoacetic acid;

ethyl 2-((3,5-dichloro-4-((2a-methyl-2-oxo-1,2,2a,3,4,5-hexahydrobenzo[cd]indol-6-yl)oxy)phenyl)amino)-2-oxoacetate;

N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;

6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;

3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;

3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;

6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;

6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;

2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile; and 6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;

or a stereoisomer or a tautomer thereof, or a pharmaceutically acceptable salt thereof.

Provided herein, in another aspect, is a compound selected from the group consisting of:

4-([3,3-dimethyl-2-oxo-1H-pyrrolo[3,2-b]pyridin-5-yl]methyl)-2,3,5-trimethylphenoxyacetic acid;

6-amino-2-(3,5-dichloro-4-((2'-oxospiro[cyclobutane-1,3'-indolin]-5'-yl)oxy)phenyl)-1,2,4-triazine-3,5(2H,4H)-dione;

6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;

2-((4-methyl-5-((2'-oxospiro[cyclobutane-1,3'-indolin]-5'-yl)oxy)bicyclo[4.2.0]octan-2-yl)oxy)acetic acid;

6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;

6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;

6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;

2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;

6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;
6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;
6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione;
6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;
6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;
2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;
2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;
2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;
6-amino-2-(3,5-dichloro-4-((2'-oxospiro[cyclobutane-1,3'-indolin]-5'-yl)methyl)phenyl)-1,2,4-triazine-3,5(2H,4H)-dione;
6-amino-2-(3,5-dimethyl-4-{2'-oxo-1'H-spiro[cyclobutane-1,3'-indol]-5'-ylmethyl}phenyl)-4H-1,2,4-triazine-3,5-dione;
2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;
2-(2,3,5-trimethyl-4-((2'-oxospiro[cyclopropane-1,3'-indolin]-5'-yl)methyl)phenoxy)acetic acid;
2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;
3-(3,5-dichloro-4-((2'-oxospiro[cyclobutane-1,3'-indolin]-5'-yl)oxy)phenyl)-1,2,4-oxadiazol-5(4H)-one;
N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;
2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;
6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;
2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;
6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;
2-((3,5-dichloro-4-((2a-methyl-2-oxo-1,2,2a,3,4,5-hexahydrobenzo[cd]indol-6-yl)oxy)phenyl)amino)-2-oxoacetic acid;
ethyl 2-((3,5-dichloro-4-((2a-methyl-2-oxo-1,2,2a,3,4,5-hexahydrobenzo[cd]indol-6-yl)oxy)phenyl)amino)-2-oxoacetate;
N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;
6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;
3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;
3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;
6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;
6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;
2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile;
6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;
6-amino-2-[4-({3,3-dimethyl-2-oxo-1H-pyrrolo[3,2-b]pyridin-5-yl}methyl)-3,5-dimethylphenyl]-4H-1,2,4-triazine-3,5-dione;
6-(3,5-dichloro-4-((2'-oxospiro[cyclobutane-1,3'-indolin]-5'-yl)oxy)phenyl)-1,2,4-triazine-3,5(2H,4H)-dione;
6-(3,5-dichloro-4-((2'-oxospiro[cyclobutane-1,3'-indolin]-5'-yl)oxy)phenyl)-2-methyl-1,2,4-triazine-3,5(2H,4H)-dione;
N-(3,5-dichloro-4-((2'-oxospiro[cyclopropane-1,3'-indolin]-5'-yl)oxy)phenyl)-5-oxo-4,5-dihydro-1,2,4-oxadiazole-3-carboxamide;
N-(3,5-dichloro-4-((4'-methyl-2'-oxospiro[cyclopropane-1,3'-indolin]-5'-yl)oxy)phenyl)-5-oxo-4,5-dihydro-1,2,4-oxadiazole-3-carboxamide;
6-amino-2-(3,5-dimethyl-4-((2'-oxospiro[cyclobutane-1,3'-indolin]-5'-yl)oxy)phenyl)-1,2,4-triazine-3,5(2H,4H)-dione;
N-(3,5-dimethyl-4-((2'-oxospiro[cyclobutane-1,3'-indolin]-5'-yl)oxy)phenyl)-5-oxo-4,5-dihydro-1,2,4-oxadiazole-3-carboxamide;
6-amino-2-(3,5-dichloro-4-((7'-methyl-2'-oxospiro[cyclobutane-1,3'-indolin]-5'-yl)oxy)phenyl)-1,2,4-triazine-3,5(2H,4H)-dione;
6-amino-2-(3,5-dimethyl-4-((2'-oxospiro[cyclopentane-1,3'-indolin]-5'-yl)oxy)phenyl)-1,2,4-triazine-3,5(2H,4H)-dione;
N-(3,5-dichloro-4-((4'-chloro-2'-oxospiro[cyclopropane-1,3'-indolin]-5'-yl)oxy)phenyl)-5-oxo-4,5-dihydro-1,2,4-oxadiazole-3-carboxamide;
6-amino-2-(3,5-dichloro-4-((4'-chloro-2'-oxospiro[cyclopropane-1,3'-indolin]-5'-yl)oxy)phenyl)-1,2,4-triazine-3,5(2H,4H)-dione;
2-(3,5-dichloro-4-((4'-chloro-2'-oxospiro[cyclopropane-1,3'-indolin]-5'-yl)oxy)phenyl)-1,2,4-triazine-3,5(2H,4H)-dione;
6-amino-2-(3,5-dichloro-4-((2-methyl-2'-oxospiro[cyclopropane-1,3'-indolin]-5'-yl)oxy)phenyl)-1,2,4-triazine-3,5(2H,4H)-dione;
2-((3,5-dichloro-4-((2-methyl-2'-oxospiro[cyclopropane-1,3'-indolin]-5'-yl)oxy)phenyl)amino)-2-oxoacetic acid;
2-((3,5-dichloro-4-((3,3-difluoro-2-oxoindolin-5-yl)oxy)phenyl)amino)-2-oxoacetic acid;

6-(3,5-dichloro-4-((4'-methyl-2'-oxospiro[cyclopropane-1, 3'-indolin]-5'-yl)oxy)phenyl)-2-methyl-1,2,4-triazine-3,5 (2H,4H)-dione;

6-amino-2-(3,5-dichloro-4-((4'-methyl-2'-oxospiro[cyclopropane-1,3'-indolin]-5'-yl)oxy)phenyl)-1,2,4-triazine-3, 5(2H,4H)-dione;

N-(3,5-dimethyl-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-fluoro-2'-oxospiro[cyclopropane-1, 3'-indolin]-5'-yl)oxy)phenyl)-5-oxo-4,5-dihydro-1,2,4-oxadiazole-3-carboxamide;

6-amino-2-(3,5-dichloro-4-((4'-fluoro-2'-oxospiro[cyclopropane-1,3'-indolin]-5'-yl)oxy)phenyl)-1,2,4-triazine-3, 5(2H,4H)-dione;

6-(3,5-dichloro-4-((4'-fluoro-2'-oxospiro[cyclopropane-1, 3'-indolin]-5'-yl)oxy)phenyl)-2-methyl-1,2,4-triazine-3,5 (2H,4H)-dione;

6-(3,5-dichloro-4-((4'-chloro-2'-oxospiro[cyclopropane-1, 3'-indolin]-5'-yl)oxy)phenyl)-2-methyl-1,2,4-triazine-3,5 (2H,4H)-dione;

N-(3-chloro-4-((2'-oxospiro[cyclopropane-1,3'-indolin]-5'-yl)oxy)-5-(trifluoromethyl)phenyl)-5-oxo-4,5-dihydro-1, 2,4-oxadiazole-3-carboxamide;

2-(3,5-dichloro-4-((2'-oxospiro[cyclobutane-1,3'-indolin]-5'-yl)oxy)phenyl)-1,2,4-triazine-3,5(2H,4H)-dione; and 2-((3,5-dichloro-4-((2'-oxospiro[cyclobutane-1,3'-indolin]-5'-yl)oxy)phenyl)amino)-2-oxoacetic acid;

or a stereoisomer or a tautomer thereof, or a pharmaceutically acceptable salt thereof.

Provided herein, in another aspect, is a pharmaceutical composition comprising a compound disclosed herein and at least one pharmaceutically acceptable excipient.

Provided herein, in another aspect, is a method of treating a disorder or disease in a subject in need thereof, the method comprising administering to the subject a therapeutically effective amount of a compound disclosed herein or a therapeutically effective amount of a pharmaceutical composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a use of a compound disclosed herein for the manufacture of a medicament for the treatment of a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a compound disclosed herein for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a composition disclosed herein for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a method of treating a thyroid hormone receptor related disorder in a patient, the method comprising the steps of identifying a patient in need of treatment for the thyroid hormone receptor related disorder, and administering to the patient, or contacting the patient with, a compound disclosed herein or a therapeutically effective amount of a pharmaceutical composition disclosed herein. In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a method of selectively modulating the activity of a thyroid hormone receptor beta (THR-β) comprising contacting a compound disclosed herein with the thyroid hormone receptor. In some embodiments, the contacting is in vitro or ex vivo. In some embodiments, the contacting is in vivo.

Provided herein, in another aspect, is a compound disclosed herein for use in selectively modulating the activity of a thyroid hormone receptor beta (THR-β).

Provided herein, in another aspect, is a composition disclosed herein for use in selectively modulating the activity of a thyroid hormone receptor beta (THR-β).

DETAILED DESCRIPTION

Definitions

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In the definition of chemical substituents, each of $R_x$ and $R_y$ is independently hydrogen, alkyl, carbocyclic ring, heterocyclic ring, aryl, or heteroaryl, all of which, except hydrogen, are optionally substituted.

Unless otherwise indicated, the abbreviations "TR" and "THR" refer to thyroid hormone receptors.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methane-sulfonates, ethanesulfonates, p-toluenesulfonates and salicylates.

As used herein, "pharmaceutically acceptable ester" refers to an ester of a compound that does not cause significant irritation to a patient to which it is administered. The ester is metabolized in the body to result in the parent compound, e.g., the claimed compound. Accordingly, the ester does not abrogate the biological activity and properties of the compound. Pharmaceutical esters can be obtained by reaction of a compound disclosed herein with an alcohol. Methyl, ethyl, and isopropyl esters are some of the common esters to be prepared. Other esters suitable are well-known to those skilled in the art (see, for example Wuts, P. G. M., Greene's Protective Groups in Organic Synthesis, 5$^{th}$ Ed., John Wiley & Sons, New York, N.Y., 2014, which is incorporated herein by reference in its entirety).

Where the compounds disclosed herein have at least one chiral center, they may exist as a racemate or as individual enantiomers. It should be noted that all such isomers and mixtures thereof are included in the scope of the present disclosure. Thus, the illustration of a chiral center without a designation of R or S signifies that the scope of the disclosure includes the R isomer, the S isomer, the racemic mixture of the isomers, or mixtures where one isomer is present in greater abundance than the other.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides followed by chromatographic separation and removal of the chiral auxiliary.

Unless otherwise indicated, when a substituent is deemed to be "optionally substituted" it is meant that the substituent is a group that may be substituted with one or more (e.g., 1 to 2, or 1 to 3, or 1 to 4, or 1 to 5, or 1 to 6) group(s) individually and independently selected, without limitation, from alkyl, alkenyl, alkynyl, cycloalkyl, aryl, heteroaryl, heterocycloalkyl, hydroxy, alkoxy, aryloxy, mercapto, alkylthio, arylthio, cyano, halo, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, O-carboxy, is O-cyanato, thiocyanato, isothiocyanato, nitro, silyl, trihalomethanesulfonyl, and amino (e.g., $-NR_xR_y$), including mono- and di-substituted amino groups, and the protected derivatives thereof. The protecting groups that may form the protective derivatives of the above substituents are known to those of skill in the art and may be found in references such as Wuts, above.

As used herein, a "carbocyclic ring" is an aromatic or non-aromatic ring structure in which all the atoms in the ring are carbon atoms. As such, the ring structure may be fully saturated, fully unsaturated, or partially saturated. If any of the atoms in the ring is anything other than a carbon atom, then the ring is a "heterocyclic ring." Examples of atoms that are within a ring include sulfur, oxygen, and nitrogen. A carbocyclic ring or a heterocyclic ring may be polycyclic, e.g., a fused ring system, a spirocyclic ring system, or a bridged ring system. These polycyclic rings include, for example, adamantyl, norbornyl (i.e., bicyclo[2.2.1]heptanyl), norbornenyl, decalinyl, 7,7-dimethyl-bicyclo[2.2.1] heptanyl, and the like. Additional non-limiting examples include bicyclic rings such as but not limited to:

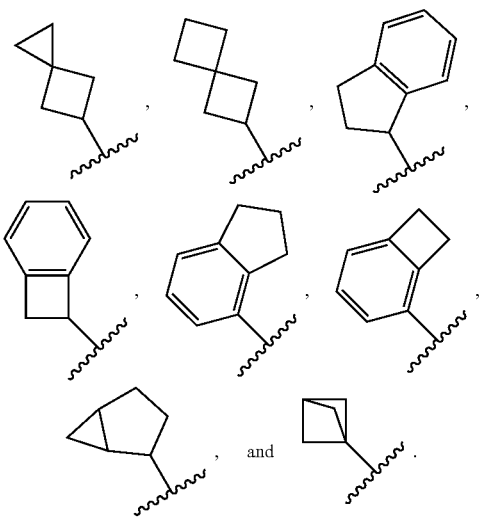

As used herein, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Further, the other ring(s) may or may not contain one or more heteroatoms (e.g., O, N, or S). Examples of aryl groups include, without limitation, the radicals of benzene, naphthalene and azulene. Additional non-limiting examples include:

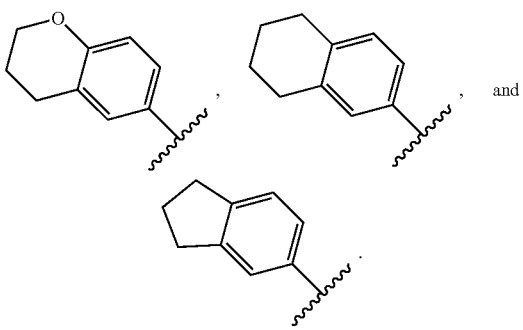

As used herein, "heteroaryl" refers to a ring that has a fully delocalized pi-electron system and contains one or more heteroatoms selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "alkyl" refers to a straight or branched chain fully saturated (no double or triple bonds) hydrocarbon group. An alkyl group of the presently disclosed compounds may comprise from 1 to 20 carbon atoms. An alkyl group herein may also be of medium size having 1 to 10 carbon atoms. An alkyl group herein may also be a lower alkyl having 1 to 5 carbon atoms or 1 to 6 carbon atoms. Examples of alkyl groups include, without limitation, methyl, ethyl, n-propyl, isopropyl, n-butyl, i-butyl, sec-butyl, t-butyl, amyl, t-amyl, hexyl, heptyl, octyl, nonyl, decyl, undecyl and dodecyl.

An alkyl group of the presently disclosed compounds may be substituted or unsubstituted. When substituted, the substituent group(s) can be one or more group(s) independently selected from cycloalkyl, aryl, heteroaryl, heterocycloalkyl, hydroxy, protected hydroxy, alkoxy, aryloxy, mercapto, alkylthio, arylthio, cyano, halogen, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, amino (e.g., —$NR_xR_y$), and protected amino.

As used herein, "alkenyl" refers to an alkyl group that contains in the straight or branched hydrocarbon chain one or more double bonds. An alkenyl group of the presently disclosed compounds may comprise from 2 to 20 carbon atoms. An alkenyl group herein may also be of medium size having 2 to 10 carbon atoms. An alkenyl group herein may also be a lower alkenyl having 2 to 5 carbon atoms or 2 to 6 carbon atoms. An alkenyl group of the presently disclosed compounds may be unsubstituted or substituted. When substituted, the substituent(s) may be selected from the same groups disclosed above regarding alkyl group substitution, or with regard to optional substitution.

As used herein, "alkynyl" refers to an alkyl group that contains in the straight or branched hydrocarbon chain one or more triple bonds. An alkynyl group of the presently disclosed compounds may comprise from 2 to 20 carbon atoms. An alkynyl group herein may also be of medium size having 2 to 10 carbon atoms. An alkynyl group herein may also be a lower alkynyl having 2 to 5 carbon atoms or 2 to 6 carbon atoms. An alkynyl group of the presently disclosed compounds may be unsubstituted or substituted. When substituted, the substituent(s) may be selected from the same groups disclosed above regarding alkyl group substitution, or with regard to optional substitution.

As used herein, "alkoxy" refers to an "—O-(alkyl)" group, wherein "alkyl" is as defined above.

As used herein, "acyl" refers to an "$R_xC(=O)$—" group.

As used herein, "cycloalkyl" refers to a completely saturated (no double bonds) hydrocarbon ring. In some embodiments, cycloalkyl refers to a hydrocarbon ring containing no double bonds or one or more double bonds provided that they do not form a fully delocalized pi-electron system in the ring. Cycloalkyl groups of the presently disclosed compounds may range from $C_3$ to $C_8$. A cycloalkyl group may be unsubstituted or substituted. If substituted, the substituent(s) may be selected from those indicated above regarding substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heterocycloalkyl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of the presently disclosed compounds may unsubstituted or substituted. When substituted, the substituent(s) may be selected from the same groups disclosed above regarding alkyl group substitution. The "cycloalkenyl" group can be made up of two or more fused rings (rings that share two adjacent carbon atoms). When the cycloalkenyl is a fused ring system, then the ring that is connected to the rest of the molecule is a cycloalkenyl as defined above. The other ring(s) in the fused ring system may be a cycloalkyl, a cycloalkenyl, an aryl, a heteroaryl, or a heterocycloalkyl.

The term "alkylene" refers to an alkyl group, as defined herein, which is a biradical and is connected to two other moieties. Thus, methylene (—$CH_2$—), ethylene (—$CH_2CH_2$—), propylene (—$CH_2CH_2CH_2$—), isopropylene (IUPAC: (methyl)ethylene) (—$CH_2$—$CH(CH_3)$—), and isobutylene (IUPAC: 2-(methyl)propylene) (—$CH_2$—$CH(CH_3)$—$CH_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "heterocycloalkyl," "heteroalicyclic," or "heteroali-cyclyl" refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heterocycloalkyl groups of the presently disclosed compounds may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethane-sulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heterocycloalkyl.

As used herein, "aralkyl" refers to an alkylene substituted with an aryl group.

As used herein, "(carbocyclic)alkyl" refers to an alkylene substituted with a carbocyclic group.

As used herein, (heterocyclic)alkyl" refers to an alkylene substituted with a heterocyclic group.

As used herein, "(heteroaryl)alkyl" refers to an alkylene substituted with a heteroaryl group.

An "O-carboxy" group refers to a "$R_xC(=O)O—$" group.

A "C-carboxy" group refers to a "$—C(=O)OR_x$" group.

An "acetyl" group refers to a $CH_3C(=O)—$ group.

A "C-amido" group refers to a "$—C(=O)NR_xR_y$" group.

An "N-amido" group refers to a "$R_yC(=O)NR_x—$" group.

The term "perhaloalkyl" refers to an alkyl group in which all the hydrogen atoms are replaced by halogen atoms.

Any unsubstituted or monosubstituted amine group on a compound herein can be converted to an amide, any hydroxy group can be converted to an ester and any carboxyl group can be converted to either an amide or ester using techniques well-known to those skilled in the art (see, for example Wuts, above).

It is understood that, in any compound of the presently disclosed compounds having one or more chiral centers, if an absolute stereochemistry is not expressly indicated, then each center may independently be R or S or a mixture thereof. In addition, it is understood that, in any compound of the presently disclosed compounds having one or more double bond(s) generating geometrical isomers that can be defined as E or Z each double bond may independently be E or Z, or a mixture thereof.

It is understood that the disclosure of a compound herein inherently includes the disclosure of a tautomer thereof, if applicable. For instance, the disclosure of:

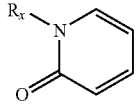

(wherein $R_x$ is H)

also includes the disclosure of:

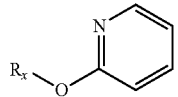

and vice versa, even if only one of the two structures is disclosed.

Throughout the present disclosure, when a compound is illustrated or named, it is understood that the isotopically enriched analogs of the compound are also contemplated. For example, a compound may have a deuterium incorporated instead of a hydrogen, or a carbon-13 instead of carbon with natural isotopic distribution. The isotopic enrichment may be in one location on the compound, i.e., only one hydrogen is replaced by a deuterium, or in more than one location. The present disclosure also encompasses compounds where all the similar atoms are replaced by their less common isotope, for example, a perdeutero compound where all the hydrogen atoms are replaced by a deuterium. The isotopically enriched compounds are useful when obtaining NMR spectra or when making use of an isotope effect in managing the kinetics of the reaction the compound undergoing.

The term "pharmaceutical composition" refers to a mixture of one or more compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "pharmaceutically acceptable" defines a carrier or diluent that does not abrogate the biological activity and properties of the compound.

Compounds

In one aspect, provided herein are compounds of Formula I:

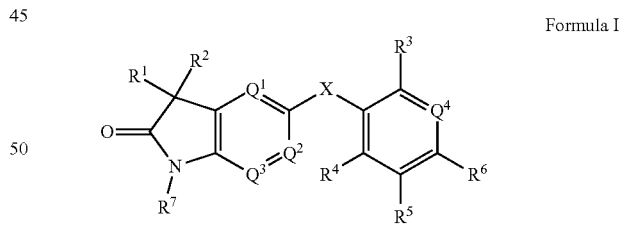

Formula I or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen; or $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

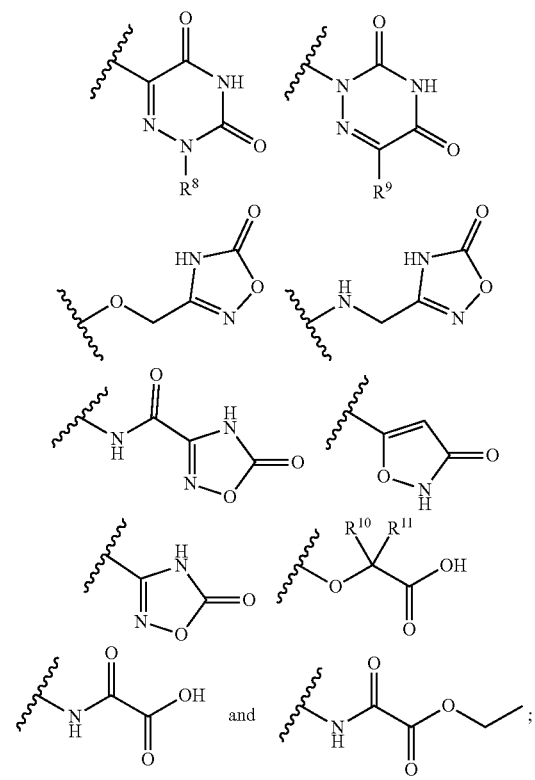

$R^7$ is H or $C_1$-$C_3$ alkyl;
$R^8$ is H or $C_1$-$C_3$ alkyl;
$R^9$ is selected from H, —CN, —CH$_3$, and —NH$_2$;
$R^{10}$ and $R^{11}$ are each independently F or $C_1$-$C_3$ alkyl; or
$R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;

$R^{12}$ is H, halogen, —CN, optionally substituted $C_1$-$C_3$ alkoxy, or optionally substituted $C_1$-$C_6$ alkyl; or $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

$R^{13}$ is independently selected from H, halogen, —CN, —OCH$_3$, and $C_1$-$C_3$ alkyl; and X is O or CH$_2$;

wherein 0 to 10 hydrogen atoms that are attached to one or more carbon atoms are replaced with deuterium atom(s);

provided that:

if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, optionally substituted cyclopropyl, and halogen;

if $Q^1$, $Q^2$, and $Q^3$ are all CH, and $R^{10}$ and $R^{11}$ are not both H, then $R^6$ is selected from:

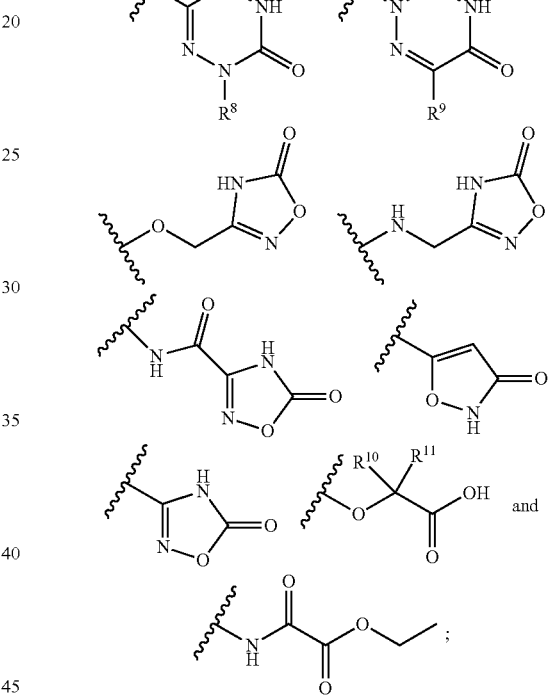

and
the compound is not selected from:
2-(3,5-dichloro-4-((5,5-dimethyl-6-oxo-6,7-dihydro-5H-pyrrolo[2,3-c]pyridazin-3-yl)oxy)phenyl)-3,5-dioxo-2,3,4,5-tetrahydro-1,2,4-triazine-6-carbonitrile;
6-amino-2-(3,5-dichloro-4-((3,3-dimethyl-2-oxoindolin-5-yl)oxy)phenyl)-1,2,4-triazine-3,5(2H,4H)-dione;
6-amino-2-(3,5-dichloro-4-((2'-oxospiro[cyclopentane-1,3'-indolin]-5'-yl)oxy)phenyl)-1,2,4-triazine-3,5(2H,4H)-dione;
6-amino-2-(3,5-dichloro-4-((3-isopropyl-3-methyl-2-oxoindolin-5-yl)oxy)phenyl)-1,2,4-triazine-3,5(2H,4H)-dione;
6-amino-2-(3,5-dichloro-4-((2'-oxospiro[cyclohexane-1,3'-indolin]-5'-yl)oxy)phenyl)-1,2,4-triazine-3,5(2H,4H)-dione;
6-amino-2-(3,5-dichloro-4-((2'-oxospiro[cyclopropane-1,3'-indolin]-5'-yl)oxy)phenyl)-1,2,4-triazine-3,5(2H,4H)-dione;
2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

6-amino-2-(3,5-dimethyl-4-((2'-oxospiro[cyclopentane-1, 3'-indolin]-5'-yl)methyl)phenyl)-1,2,4-triazine-3,5(2H, 4H)-dione;

6-amino-2-(3,5-dimethyl-4-((2'-oxospiro[cyclopropane-1, 3'-indolin]-5'-yl)methyl)phenyl)-1,2,4-triazine-3,5(2H, 4H)-dione;

2-(3,5-dimethyl-4-((2'-oxospiro[cyclopropane-1,3'-indolin]-5'-yl)methyl)phenyl)-1,2,4-triazine-3,5(2H,4H)-dione; and 2-(3,5-dimethyl-4-((2'-oxospiro[cyclobutane-1,3'-indolin]-5'-yl)methyl)phenyl)-3,5-dioxo-2,3,4,5-tetrahydro-1,2,4-triazine-6-carbonitrile.

In another aspect, provided herein are compounds of Formula I':

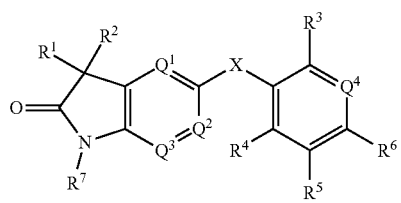

Formula I' or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen; or $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

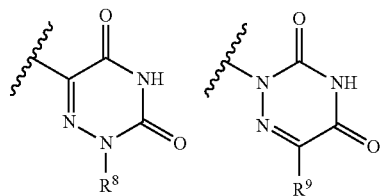

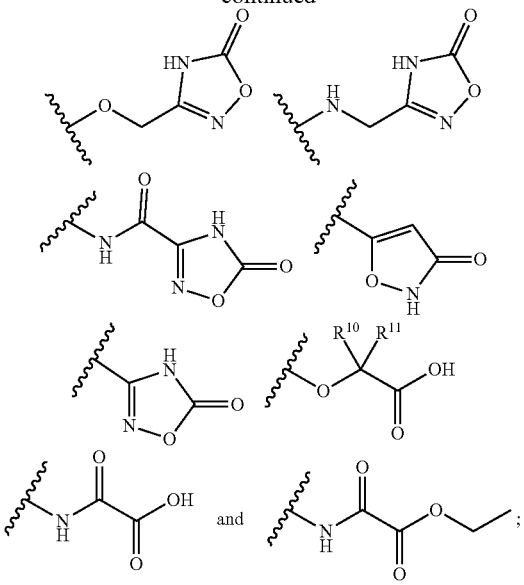

$R^7$ is H or $C_1$-$C_3$ alkyl;

$R^8$ is H or $C_1$-$C_3$ alkyl;

$R^9$ is selected from H, —CN, —$CH_3$, and —$NH_2$;

$R^{10}$ and $R^{11}$ are each independently H, F, or $C_1$-$C_3$ alkyl; or $R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;

$R^{12}$ is H, halogen, —CN, optionally substituted $C_1$-$C_3$ alkoxy, or optionally substituted $C_1$-$C_6$ alkyl; or $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

$R^{13}$ is independently selected from H, halogen, —CN, —$OCH_3$, and $C_1$-$C_3$ alkyl; and X is O or $CH_2$;

wherein 0 to 10 hydrogen atoms that are attached to one or more carbon atoms are replaced with deuterium atom(s);

provided that:

if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, optionally substituted cyclopropyl, and halogen;

when $R^{10}$ and $R^{11}$ are present, $R^{10}$, $R^{11}$ and $R^5$ cannot all be H; and the compound is not selected from:

2-(3,5-dichloro-4-((5,5-dimethyl-6-oxo-6,7-dihydro-5H-pyrrolo[2,3-c]pyridazin-3-yl)oxy)phenyl)-3,5-dioxo-2,3, 4,5-tetrahydro-1,2,4-triazine-6-carbonitrile;

6-amino-2-(3,5-dichloro-4-((3,3-dimethyl-2-oxoindolin-5-yl)oxy)phenyl)-1,2,4-triazine-3,5(2H,4H)-dione;

6-amino-2-(3,5-dichloro-4-((2'-oxospiro[cyclopentane-1,3'-indolin]-5'-yl)oxy)phenyl)-1,2,4-triazine-3,5(2H,4H)-dione;

6-amino-2-(3,5-dichloro-4-((3-isopropyl-3-methyl-2-oxoindolin-5-yl)oxy)phenyl)-1,2,4-triazine-3,5(2H,4H)-dione;

6-amino-2-(3,5-dichloro-4-((2'-oxospiro[cyclohexane-1,3'-indolin]-5'-yl)oxy)phenyl)-1,2,4-triazine-3,5(2H,4H)-dione;

6-amino-2-(3,5-dichloro-4-((2'-oxospiro[cyclopropane-1,3'-indolin]-5'-yl)oxy)phenyl)-1,2,4-triazine-3,5(2H,4H)-dione;

2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

6-amino-2-(3,5-dimethyl-4-((2'-oxospiro[cyclopentane-1,3'-indolin]-5'-yl)methyl)phenyl)-1,2,4-triazine-3,5(2H,4H)-dione;

6-amino-2-(3,5-dimethyl-4-((2'-oxospiro[cyclopropane-1,3'-indolin]-5'-yl)methyl)phenyl)-1,2,4-triazine-3,5(2H,4H)-dione;

2-(3,5-dimethyl-4-((2'-oxospiro[cyclopropane-1,3'-indolin]-5'-yl)methyl)phenyl)-1,2,4-triazine-3,5(2H,4H)-dione; and 2-(3,5-dimethyl-4-((2'-oxospiro[cyclobutane-1,3'-indolin]-5'-yl)methyl)phenyl)-3,5-dioxo-2,3,4,5-tetrahydro-1,2,4-triazine-6-carbonitrile;

2-(3,5-dichloro-4-((2'-oxospiro[cyclopropane-1,3'-indolin]-5'-yl)oxy)phenyl)-3,5-dioxo-2,3,4,5-tetrahydro-1,2,4-triazine-6-carbonitrile;

2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carbonitrile; and 2-(3,5-dichloro-4-((2'-oxospiro[cyclopentane-1,3'-indolin]-5'-yl)oxy)phenyl)-3,5-dioxo-2,3,4,5-tetrahydro-1,2,4-triazine-6-carbonitrile.

In another aspect, provided herein are compounds of Formula IA:

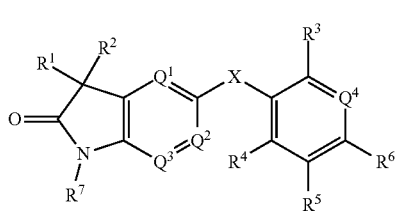

Formula IA or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl and halogen; or $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

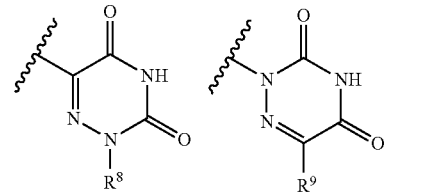

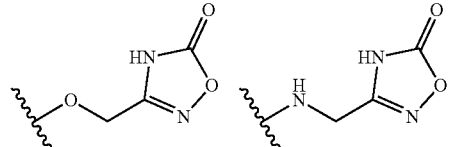

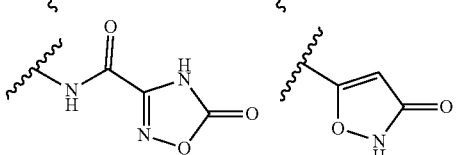

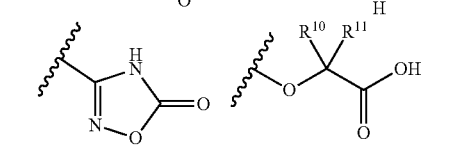

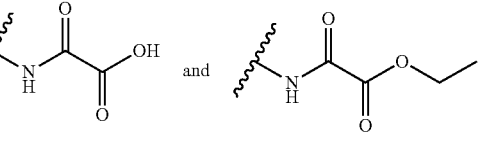

$R^7$ is H or $C_1$-$C_3$ alkyl;

$R^8$ is H or $C_1$-$C_3$ alkyl;

$R^9$ is selected from H, —CN, —$CH_3$, and —$NH_2$;

$R^{10}$ and $R^{11}$ are each independently H, F, or $C_1$-$C_3$ alkyl; or $R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;

$R^{12}$ is H, halogen, —CN, optionally substituted $C_1$-$C_3$ alkoxy, or optionally substituted $C_1$-$C_6$ alkyl; or $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

$R^{13}$ is independently selected from H, halogen, —CN, —$OCH_3$, and $C_1$-$C_3$ alkyl; and X is O or $CH_2$;

wherein 0 to 10 hydrogen atoms that are attached to one or more carbon atoms are replaced with deuterium atom(s);

provided that:

if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are substituted with 1 to 3 substituents independently selected from $C_1$-$C_3$ alkyl and halogen;

when $R^{10}$ and $R^{11}$ are present, $R^{10}$, $R^{11}$ and $R^5$ cannot all be H; and the compound is not selected from:
2-(3,5-dichloro-4-((5,5-dimethyl-6-oxo-6,7-dihydro-5H-pyrrolo[2,3-c]pyridazin-3-yl)oxy)phenyl)-3,5-dioxo-2,3,4,5-tetrahydro-1,2,4-triazine-6-carbonitrile;
6-amino-2-(3,5-dichloro-4-((3,3-dimethyl-2-oxoindolin-5-yl)oxy)phenyl)-1,2,4-triazine-3,5(2H,4H)-dione;
6-amino-2-(3,5-dichloro-4-((2'-oxospiro[cyclopentane-1,3'-indolin]-5'-yl)oxy)phenyl)-1,2,4-triazine-3,5(2H,4H)-dione;
6-amino-2-(3,5-dichloro-4-((3-isopropyl-3-methyl-2-oxoindolin-5-yl)oxy)phenyl)-1,2,4-triazine-3,5(2H,4H)-dione;
6-amino-2-(3,5-dichloro-4-((2'-oxospiro[cyclohexane-1,3'-indolin]-5'-yl)oxy)phenyl)-1,2,4-triazine-3,5(2H,4H)-dione;
6-amino-2-(3,5-dichloro-4-((2'-oxospiro[cyclopropane-1,3'-indolin]-5'-yl)oxy)phenyl)-1,2,4-triazine-3,5(2H,4H)-dione;
6-amino-2-(3,5-dimethyl-4-((2'-oxospiro[cyclopentane-1,3'-indolin]-5'-yl)methyl)phenyl)-1,2,4-triazine-3,5(2H,4H)-dione;
6-amino-2-(3,5-dimethyl-4-((2'-oxospiro[cyclopropane-1,3'-indolin]-5'-yl)methyl)phenyl)-1,2,4-triazine-3,5(2H,4H)-dione; and
2-(3,5-dimethyl-4-((2'-oxospiro[cyclopropane-1,3'-indolin]-5'-yl)methyl)phenyl)-1,2,4-triazine-3,5(2H,4H)-dione.

In some embodiments, $Q^1$ is N. In some embodiments, $Q^2$ is N. In some embodiments, $Q^3$ is N. In some embodiments, only one of $Q^1$, $Q^2$, and $Q^3$ are N. In some embodiments, $Q^3$ is N. In some embodiments, at least one of $Q^1$, $Q^2$, and $Q^3$ is N.

In some embodiments, $Q^1$ is $CR^{12}$. In some embodiments, $Q^1$ is $CR^{12}$, and $Q^2$ and $Q^3$ are both $CR^{13}$. In some embodiments, $Q^1$ is CH. In some embodiments, $Q^1$, $Q^2$, and $Q^3$ are all CH.

In some embodiments, $Q^4$ is N. In some embodiments, $Q^4$ is $CR^{13}$. In some embodiments, $Q^4$ is CH.

In some embodiments, $Q^1$ is $CR^{12}$, and $Q^2$, $Q^3$, and $Q^4$ are both $CR^{13}$. In some embodiments, $Q^1$, $Q^2$, $Q^3$, and $Q^4$ are all CH.

In some embodiments, $R^{12}$ is H, halogen, —CN, $C_1$-$C_3$ alkoxy, or $C_1$-$C_6$ alkyl. In some embodiments, $R^{12}$ is H, F, or $C_1$-$C_6$ alkyl. In some embodiments, $R^{12}$ is H or $C_1$-$C_6$ alkyl. In some embodiments, $R^{12}$ is H. In some embodiments, $R^{12}$ is $C_1$-$C_6$ alkyl. In some embodiments, $R^{12}$ is F.

In some embodiments, $R^{13}$ is independently selected from H, F, —CN, —OCH$_3$, and $C_1$-$C_3$ alkyl. In some embodiments, $R^{13}$ is independently selected from H and $C_1$-$C_3$ alkyl. In some embodiments, $R^{13}$ is H. In some embodiments, $R^{13}$ is $C_1$-$C_3$ alkyl. In some embodiments, $R^{13}$ is CH$_3$.

In some embodiments, $R^1$ and $R^2$ are each independently selected from H, halogen, optionally substituted $C_3$-$C_6$ cycloalkyl, and optionally substituted $C_1$-$C_3$ alkyl. In some embodiments, $R^1$ and $R^2$ are each independently selected from H; halogen; $C_3$-$C_6$ cycloalkyl optionally substituted with 1 to 3 substituents independently selected from halogen and $C_1$-$C_3$ alkyl; and $C_1$-$C_3$ alkyl optionally substituted with 1 to 3 substituents independently selected from halogen and cyclopropyl optionally substituted with 1 to 5 substituents independently selected from halogen and $C_1$-$C_3$ alkyl.

In some embodiments, $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen. In some embodiments, $R^1$ and $R^2$ together with the carbon atom to which they are attached form a $C_3$-$C_6$ cyclic ring optionally substituted with 1 to 3 substituents independently selected from $C_1$-$C_3$ alkyl, halogen, and cyclopropyl optionally substituted with 1 to 5 substituents independently selected from halogen and $C_1$-$C_3$ alkyl.

In some embodiments, $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen. In some embodiments, $R^1$ and $R^2$ together with the carbon atom to which they are attached form a polycyclic ring optionally substituted with 1 to 3 substituents independently selected from $C_1$-$C_3$ alkyl, halogen, and cyclopropyl optionally substituted with 1 to 5 substituents independently selected from halogen and $C_1$-$C_3$ alkyl. In some embodiments, the polycyclic ring is a spirocyclic ring system. In some embodiments, the polycyclic ring is a fused ring system. In some embodiments, the polycyclic ring is a bridged ring system.

In some embodiments, $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring. In some embodiments, the polycyclic ring is a spirocyclic ring system. In some embodiments, the polycyclic ring is a fused ring system. In some embodiments, the polycyclic ring is a bridged ring system.

In some embodiments, $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from Cl; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from halogen and $C_1$-$C_3$ alkyl. In some embodiments, $R^3$ and $R^4$ are both halogen. In some embodiments, $R^3$ and $R^4$ are both Cl. In some embodiments, $R^3$ and $R^4$ are both methyl.

In some embodiments, $R^5$ is H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen. In some embodiments, $R^5$ is hydrogen or $C_1$-$C_3$ alkyl. In some embodiments, $R^5$ is hydrogen.

In some embodiments, $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl. In some embodiments, $R^4$ and $R^5$ together with the carbon atoms to which they are attached form a 4-, 5-, or 6-membered partially unsaturated carbocyclic ring optionally substituted with 1 to 5 substituents independently selected from halogen and $C_1$-$C_3$ alkyl. In some embodiments, $R^4$ and $R^5$ together with the carbon atoms to which they are attached form a 4-, 5-, or 6-membered partially unsaturated heterocyclic ring optionally substituted with 1 to 5 substituents independently selected from halogen and $C_1$-$C_3$ alkyl. In some embodiments, $R^4$ and $R^5$ together with the carbon atoms to which they are attached form a $C_6$-$C_{10}$ aryl ring optionally substituted with 1 to 5 substituents independently selected from halogen and $C_1$-$C_3$ alkyl. In some embodiments, $R^4$ and $R^5$ together with the carbon atoms to which they are attached form a 5- or 6-membered heteroaryl ring optionally substituted with 1 to 5 substituents independently selected from halogen and $C_1$-$C_3$ alkyl.

In some embodiments, $R^6$ is

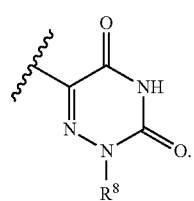

In some embodiments, $R^6$ is

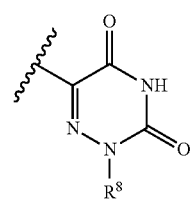

and $R^8$ is H. In some embodiments, $R^6$ is

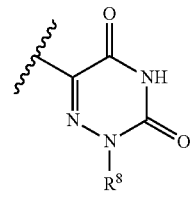

and $R^8$ is $C_1$-$C_3$ alkyl. In some embodiments, $R^6$ is

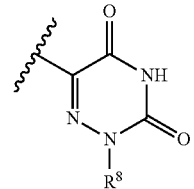

and $R^8$ is $CH_3$.

In some embodiments, $R^8$ is H. In some embodiments, $R^8$ is $C_1$-$C_3$ alkyl. In some embodiments, $R^8$ is $CH_3$.

In some embodiments, $R^6$ is

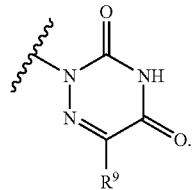

In some embodiments, $R^6$ is

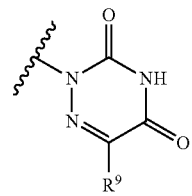

and $R^9$ is —CN or —$NH_2$. In some embodiments, $R^6$ is

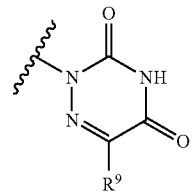

and $R^9$ is —$NH_2$. In some embodiments, $R^6$ is

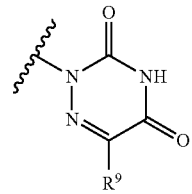

and $R^9$ is H. In some embodiments, $R^6$ is

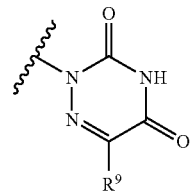

and $R^9$ is $CH_3$.

In some embodiments, $R^9$ is —CN or —$NH_2$. In some embodiments, $R^9$ is —$NH_2$. In some embodiments, $R^9$ is H. In some embodiments, $R^9$ is $CH_3$.

In some embodiments, $R^6$ is

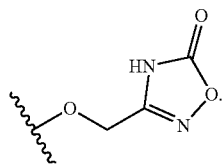 [SMILES: *OCc1noc(=O)[nH]1]

In some embodiments, $R^6$ is

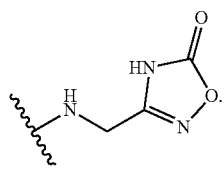 [SMILES: *NCc1noc(=O)[nH]1]

In some embodiments, $R^6$ is

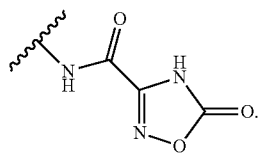 [SMILES: *NC(=O)c1noc(=O)[nH]1]

In some embodiments, $R^6$ is

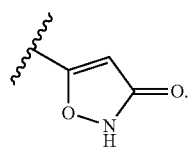 [SMILES: *c1cc(=O)[nH]o1]

In some embodiments, $R^6$ is

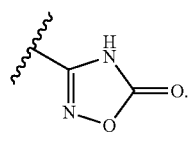 [SMILES: *c1noc(=O)[nH]1]

In some embodiments, $R^6$ is

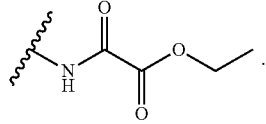 [SMILES: *NC(=O)C(=O)OCC]

In some embodiments, $R^6$ is

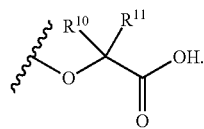

In some embodiments, $R^6$ is

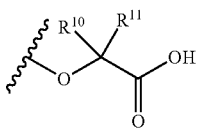

and $R^{10}$ and $R^{11}$ are each independently F or $C_1$-$C_3$ alkyl. In some embodiments, $R^6$ is

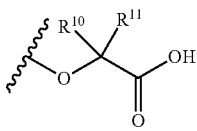

and $R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl. In some embodiments, $R^6$ is

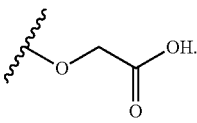 [SMILES: *OCC(=O)O]

In some embodiments, $R^7$ is H.

In some embodiments, $Q^1$ is $CR^{12}$, and $R^{12}$ and one of $R^1$ and $R^2$, together with the carbon atoms to which they are attached, form a $C_5$-$C_7$ partially unsaturated carbocyclic ring or a partially unsaturated polycyclic ring.

In some embodiments, $R^{12}$ is H, halogen, or $C_1$-$C_6$ alkyl. In embodiments, $R^{12}$ is H. In embodiments, $R^{12}$ is halogen. In embodiments, $R^{12}$ is F. In embodiments, $R^{12}$ is Cl. In embodiments, $R^{12}$ is or $C_1$-$C_6$ alkyl. In embodiments, $R^{12}$ is $CH_3$. In some embodiments, $R^{12}$ is H, halogen, —CN, $C_1$-$C_3$ alkoxy, or $C_1$-$C_6$ alkyl; wherein the $C_1$-$C_3$ alkoxy, or $C_1$-$C_6$ alkyl are optionally substituted with 1-5 halogens. In some embodiments, $R^{12}$ is $C_1$-$C_3$ alkyl, optionally substituted with 1-3 halogens. In some embodiments, $R^{12}$ is $CF_3$.

In some embodiments, $R^1$ and $R^2$ together with the carbon atom to which they are attached form a $C_3$-$C_4$ cyclic ring optionally substituted with 1 to 3 substituents independently selected from $C_1$-$C_3$ alkyl; optionally substituted cyclopropyl, and halogen. In some embodiments, $R^1$ and $R^2$ together with the carbon atom to which they are attached form a $C_3$-$C_4$ cyclic ring optionally substituted with 1 to 3 substituents independently selected from $C_1$-$C_3$ alkyl and halogen. In some embodiments, $R^1$ and $R^2$ together with the carbon atom to which they are attached form a $C_3$-$C_6$ cyclic ring optionally substituted with 1 to 3 substituents independently selected from $C_1$-$C_3$ alkyl; optionally substituted cyclopropyl, and halogen; wherein a single carbon of the $C_3$-$C_6$ cyclic ring contains no more than one halogen atoms. In some embodiments, $R^1$ and $R^2$ together with the carbon atom to which they are attached form a $C_3$-$C_6$ cyclic ring optionally substituted with 1 to 3 substituents independently selected from $C_1$-$C_3$ alkyl and halogen; wherein a single carbon of the $C_3$-$C_6$ cyclic ring contains no more than one halogen atoms. In some embodiments, $R^1$ and $R^2$ together with the carbon atom to which they are attached form an unsubstituted $C_3$-$C_6$ cyclic ring.

In some embodiments, $Q^1$ is $CR^{12}$, and $R^{12}$ and one of $R^1$ and $R^2$, together with the carbon atoms to which they are attached, form a $C_5$-$C_7$ partially unsaturated carbocyclic ring or a partially unsaturated polycyclic ring.

In some embodiments, $Q^1$ is CH, $Q^2$ and $Q^3$ are N, and $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, cyclopropyl, and halogen.

In some embodiments, X is O. In some embodiments, X is $CH_2$.

In some embodiments, the compound of Formula I, I' or IA have the chemical structure of:

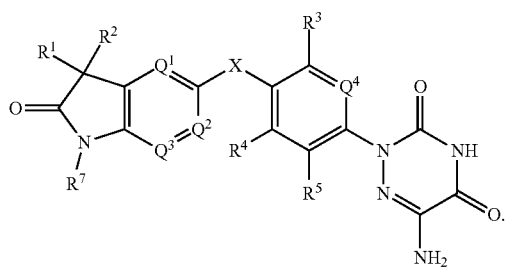

In some embodiments, the compound of Formula I, I' or IA have the chemical structure of:

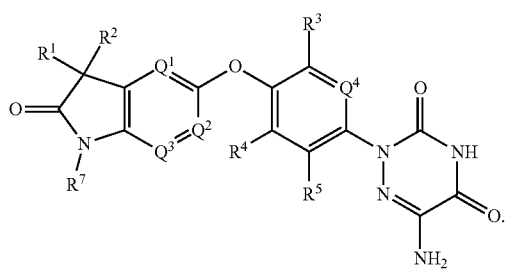

In some embodiments, the compound of Formula I, I' or IA have the chemical structure of:

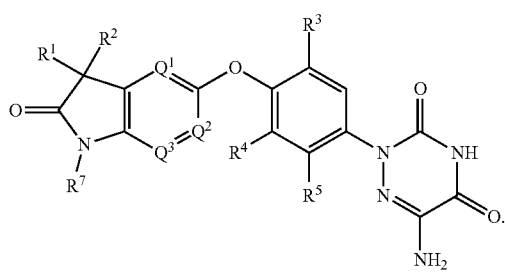

In some embodiments, the compound of Formula I, I' or IA have the chemical structure of:

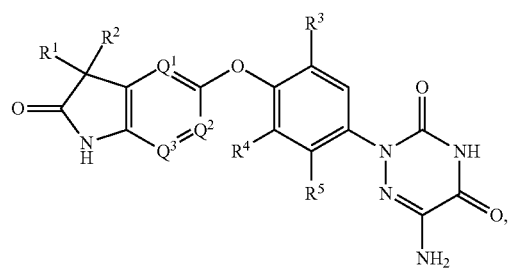

wherein at least one of $Q^1$, $Q^2$, and $Q^3$ is N.

In some embodiments, the compound of Formula I, I' or IA have the chemical structure of:

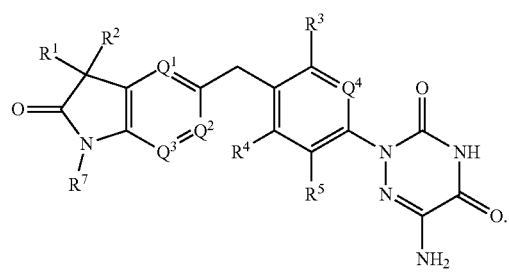

In some embodiments, the compound of Formula I, I' or IA have the chemical structure of:

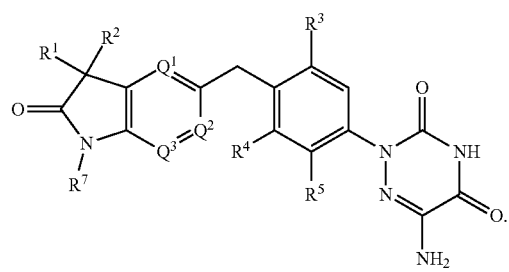

In some embodiments, the compound of Formula I, I' or IA have the chemical structure of:

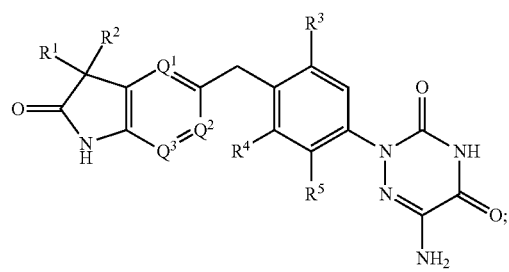

wherein $R^1$ and $R^2$ together with the carbon atom to which they are attached form a $C_3$-$C_6$ cyclic ring substituted with 1 to 3 substituents independently selected from $C_1$-$C_3$ alkyl, halogen, and cyclopropyl optionally substituted with 1 to 5 substituents independently selected from halogen and $C_1$-$C_3$ alkyl; or $R^1$ and $R^2$ together with the carbon atom to which they are attached form a polycyclic ring optionally substituted with 1 to 3 substituents independently selected from $C_1$-$C_3$ alkyl, halogen, and cyclopropyl optionally substituted with 1 to 5 substituents independently selected from halogen and $C_1$-$C_3$ alkyl.

In some embodiments, the compound of Formula I, I' or IA have the chemical structure of:

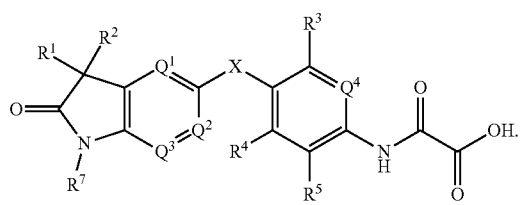

In some embodiments, the compound of Formula I, I' or IA have the chemical structure of:

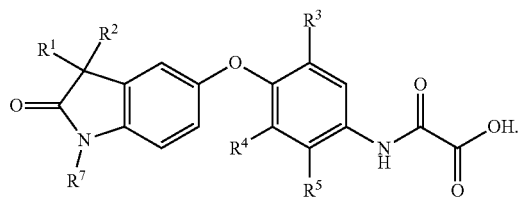

In some embodiments, the compound of Formula I, I' or IA have the chemical structure of:

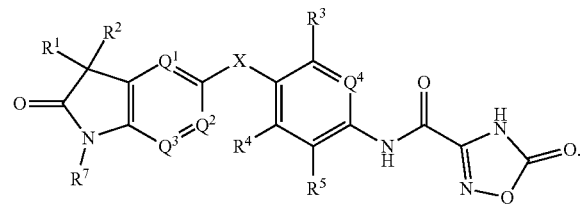

In some embodiments, the compound of Formula I, I' or IA have the chemical structure of:

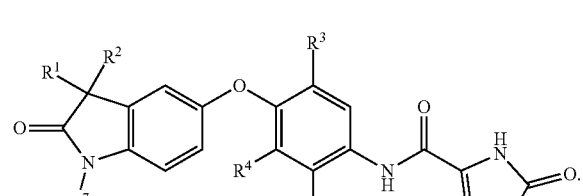

In some embodiments, the compound of Formula I, I' or IA have the chemical structure of:

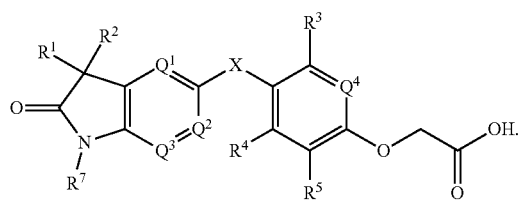

In some embodiments, the compound of Formula I, I' or IA have the chemical structure of:

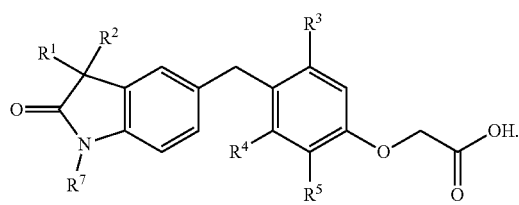

In another aspect, disclosed herein is a compound selected from the group consisting of:

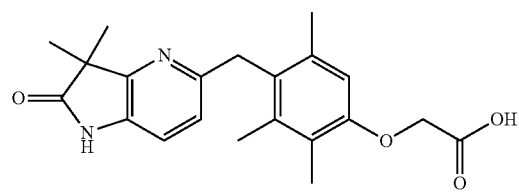 [SMILES: Cc1cc(OCC(=O)O)c(C)c(C)c1Cc1ccc2c(n1)C(C)(C)C(=O)N2]

4-([3,3-dimethyl-2-oxo-1H-pyrrolo[3,2-b]pyridin-5-yl]methyl)-2,3,5-trimethylphenoxyacetic acid;

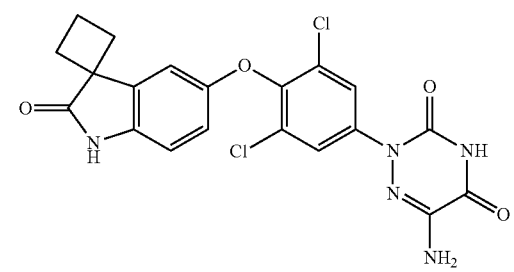

6-amino-2-(3,5-dichloro-4-((2'-oxospiro[cyclobutane-1,3'-indolin]-5'-yl)oxy)phenyl)-1,2,4-triazine-3,5(2H,4H)-dione;

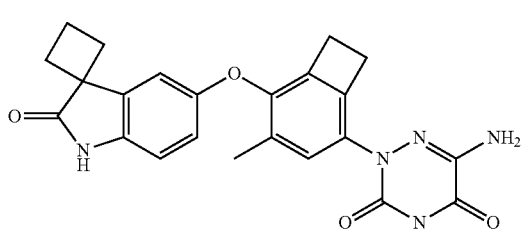

6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;

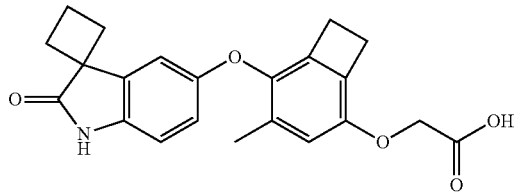 [SMILES: Cc1cc(OCC(=O)O)c2c(c1Oc1ccc3c(c1)C1(CCC1)C(=O)N3)CC2]

2-((4-methyl-5-((2'-oxospiro[cyclobutane-1,3'-indolin]-5'-yl)oxy)bicyclo[4.2.0]octan-2-yl)oxy)acetic acid;

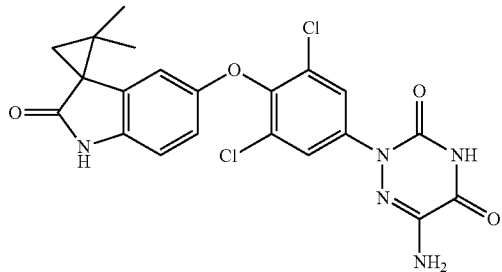 [SMILES: CC1(C)CC12C(=O)Nc1ccc(Oc3c(Cl)cc(-n4nc(N)c(=O)[nH]c4=O)cc3Cl)cc12]

6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;

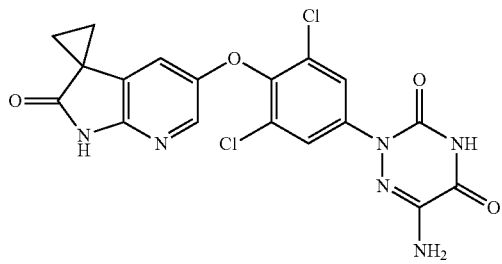 [SMILES: Nc1nn(-c2cc(Cl)c(Oc3cnc4c(c3)C3(CC3)C(=O)N4)c(Cl)c2)c(=O)[nH]c1=O]

6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;

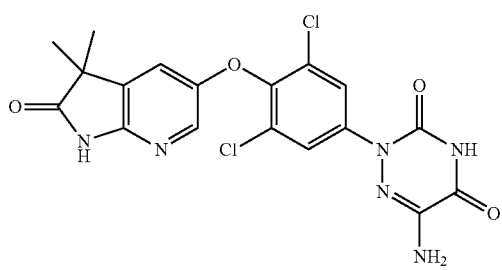 [SMILES: CC1(C)C(=O)Nc2ncc(Oc3c(Cl)cc(-n4nc(N)c(=O)[nH]c4=O)cc3Cl)cc21]

6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;

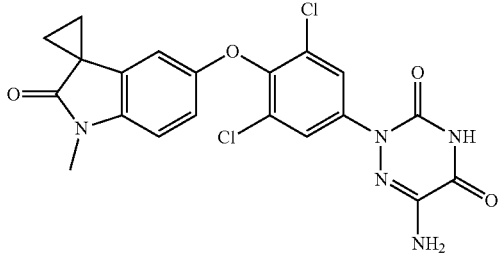 [SMILES: CN1C(=O)C2(CC2)c2cc(Oc3c(Cl)cc(-n4nc(N)c(=O)[nH]c4=O)cc3Cl)ccc21]

6-amino-2-(3,5-dichloro-4-((1'-methyl-2'-oxospiro[cyclopropane-1,3'-indolin]-5'-yl)oxy)phenyl)-1,2,4-triazine-3,5(2H,4H)-dione;

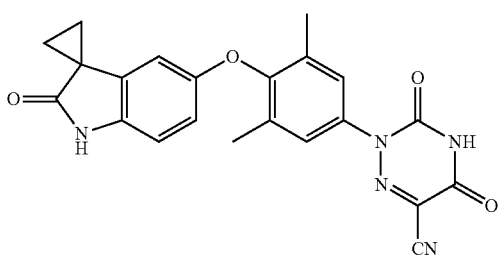 [SMILES: Cc1cc(-n2nc(C#N)c(=O)[nH]c2=O)cc(C)c1Oc1ccc2c(c1)C1(CC1)C(=O)N2]

2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;

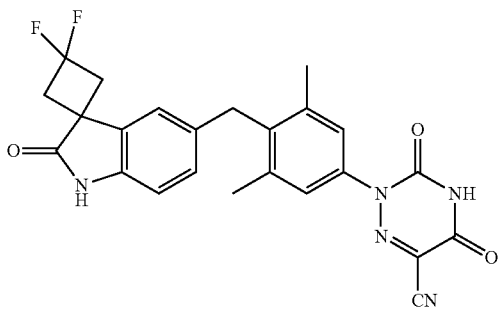 [SMILES: Cc1cc(-n2nc(C#N)c(=O)[nH]c2=O)cc(C)c1Cc1ccc2c(c1)C1(CC(F)(F)C1)C(=O)N2]

2-(4-((3,3-difluoro-2'-oxospiro[cyclobutane-1,3'-indolin]-5'-yl)methyl)-3,5-dimethylphenyl)-3,5-dioxo-2,3,4,5-tetrahydro-1,2,4-triazine-6-carbonitrile;

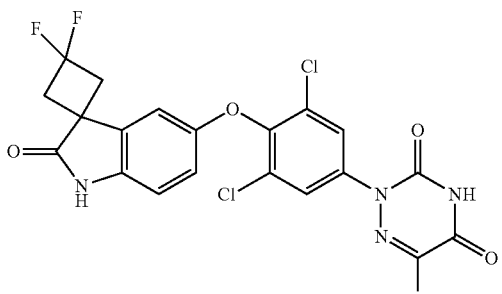

6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;

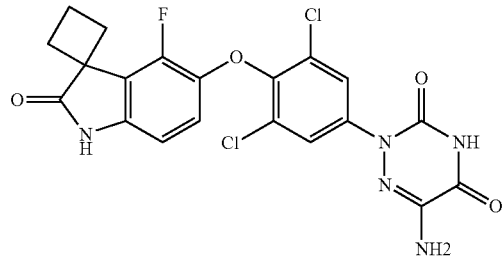 [SMILES: Cc1c(Oc2c(Cl)cc(-n3nc(N)c(=O)[nH]c3=O)cc2Cl)ccc2c1C1(CCC1)C(=O)N2]

6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;

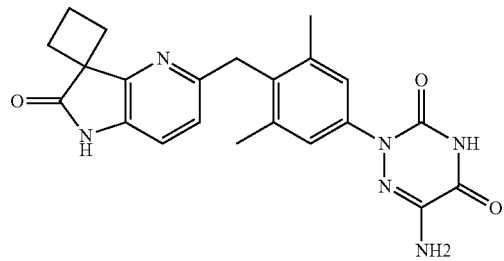

6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione

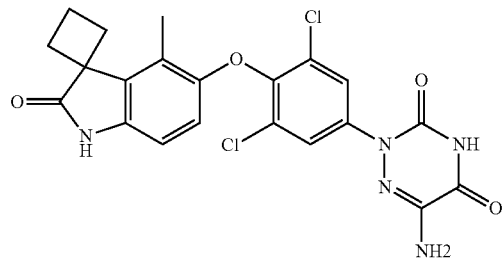

6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;

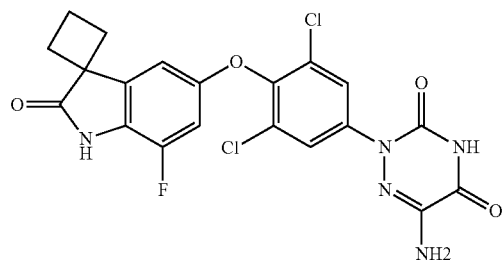 [SMILES: Nc1nn(-c2cc(Cl)c(Oc3cc(F)c4c(c3)C3(CCC3)C(=O)N4)c(Cl)c2)c(=O)[nH]c1=O]

6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;

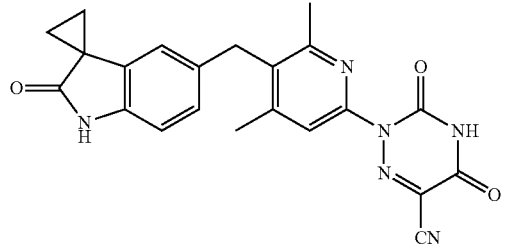

2-(4,6-dimethyl-5-(((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;

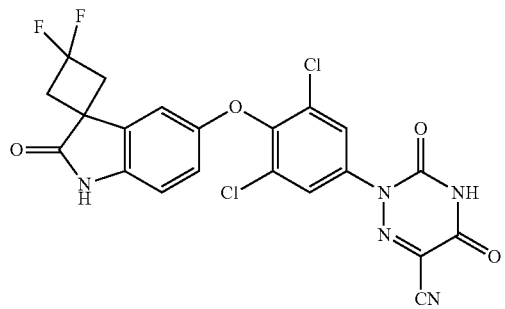 [SMILES: N#Cc1nn(-c2cc(Cl)c(Oc3ccc4c(c3)C3(CC(F)(F)C3)C(=O)N4)c(Cl)c2)c(=O)[nH]c1=O]

2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

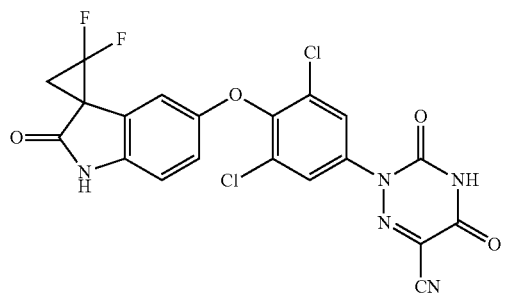 [SMILES: N#Cc1nn(-c2cc(Cl)c(Oc3ccc4c(c3)C3(CC3(F)F)C(=O)N4)c(Cl)c2)c(=O)[nH]c1=O]

2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;

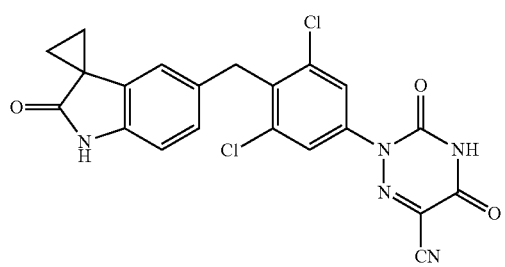 [SMILES: N#Cc1nn(-c2cc(Cl)c(Cc3ccc4c(c3)C3(CC3)C(=O)N4)c(Cl)c2)c(=O)[nH]c1=O]

2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

2-(2,3,5-trimethyl-4-((2'-oxospiro[cyclopropane-1,3'-indolin]-5'-yl)methyl)phenoxy)acetic acid;

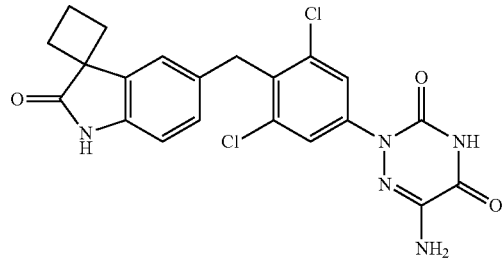
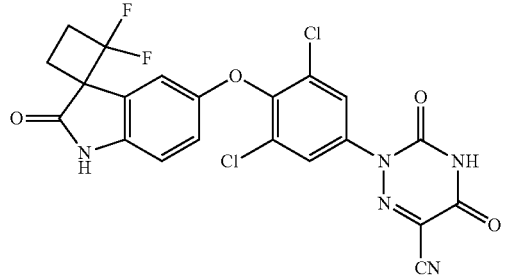

6-amino-2-(3,5-dichloro-4-((2'-oxospiro[cyclobutane-1,3'-indolin]-5'-yl)methyl)phenyl)-1,2,4-triazine-3,5(2H,4H)-dione;

2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

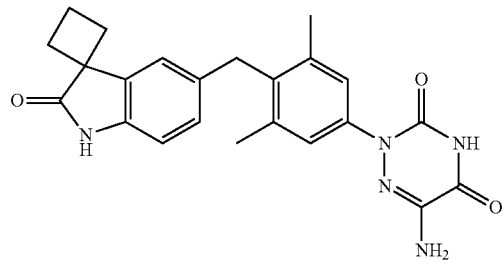
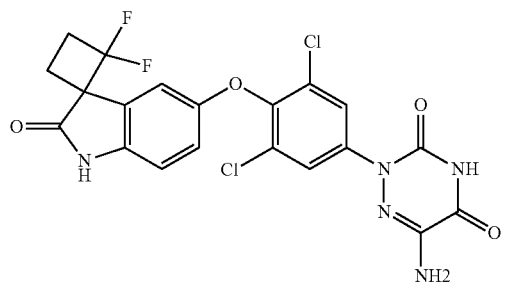

6-amino-2-(3,5-dimethyl-4-{2'-oxo-1'H-spiro[cyclobutane-1,3'-indol]-5'-ylmethyl}phenyl)-4H-1,2,4-triazine-3,5-dione;

6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;

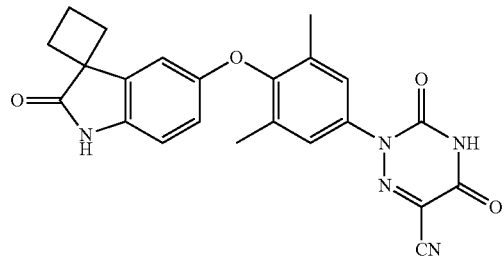 [SMILES: Cc1cc(-n2nc(C#N)c(=O)[nH]c2=O)cc(C)c1Oc1ccc2c(c1)C1(CCC1)C(=O)N2]
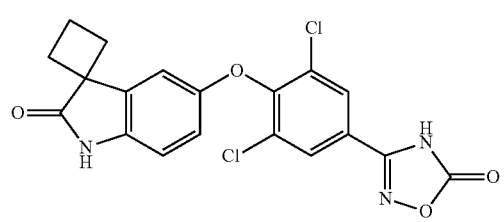

2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;

3-(3,5-dichloro-4-((2'-oxospiro[cyclobutane-1,3'-indolin]-5'-yl)oxy)phenyl)-1,2,4-oxadiazol-5(4H)-one;

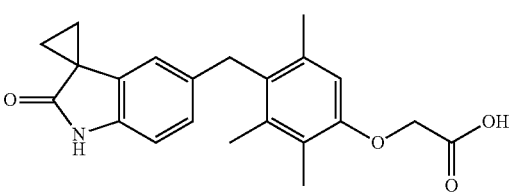 [SMILES: Cc1cc(OCC(=O)O)c(C)c(C)c1Cc1ccc2c(c1)C1(CC1)C(=O)N2]
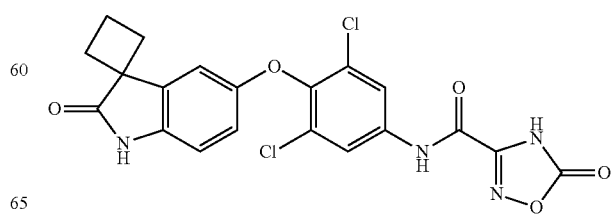

N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;

6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;

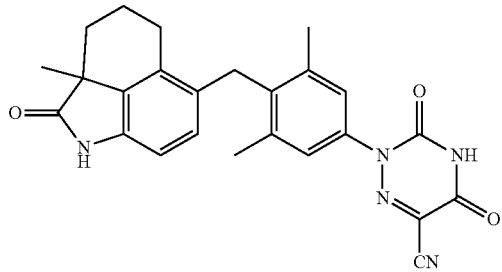 [SMILES: Cc1cc(-n2nc(C#N)c(=O)[nH]c2=O)cc(C)c1Cc1ccc2c3c1CCCC3(C)C(=O)N2]

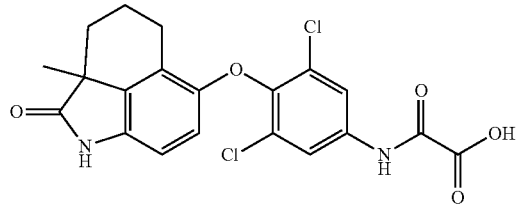

2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;

2-((3,5-dichloro-4-((2a-methyl-2-oxo-1,2,2a,3,4,5-hexahydrobenzo[cd]indol-6-yl)oxy)phenyl)amino)-2-oxoacetic acid;

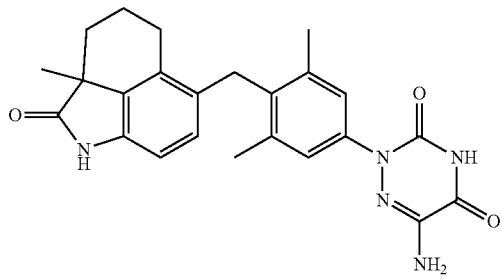 [SMILES: Cc1cc(-n2nc(N)c(=O)[nH]c2=O)cc(C)c1Cc1ccc2c3c1CCCC3(C)C(=O)N2]

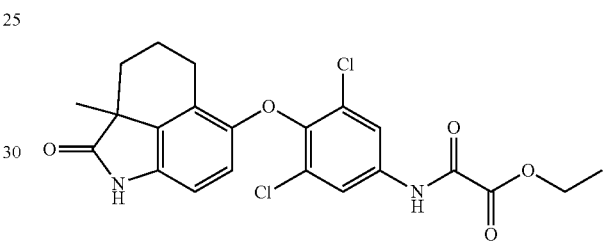

6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;

ethyl 2-((3,5-dichloro-4-((2a-methyl-2-oxo-1,2,2a,3,4,5-hexahydrobenzo[cd]indol-6-yl)oxy)phenyl)amino)-2-oxoacetate;

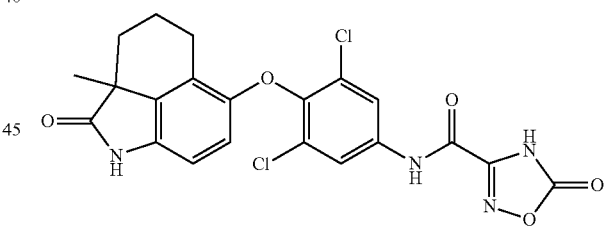

2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;

N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;

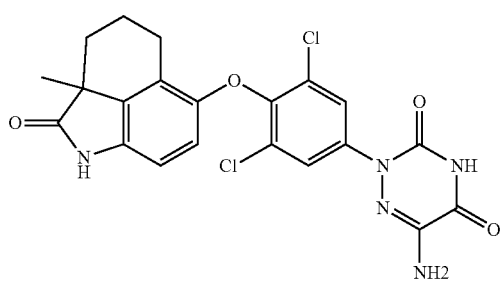 [SMILES: CC12CCCc3c(Oc4c(Cl)cc(-n5nc(N)c(=O)[nH]c5=O)cc4Cl)ccc(c31)NC2=O]

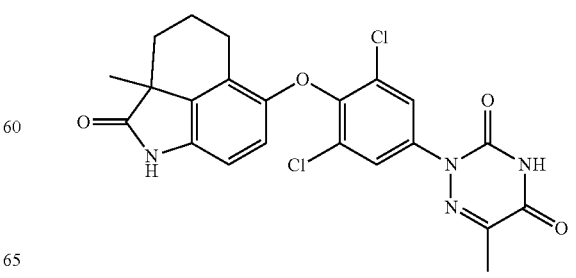

6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;

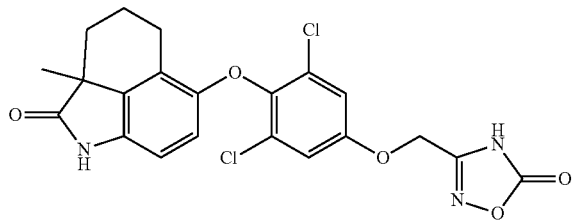 [SMILES: CC12CCCc3c(Oc4c(Cl)cc(OCc5noc(=O)[nH]5)cc4Cl)ccc(c31)NC2=O]

3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;

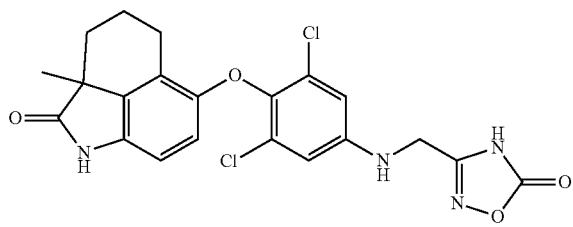 [SMILES: CC12CCCc3c(Oc4c(Cl)cc(NCc5noc(=O)[nH]5)cc4Cl)ccc(c31)NC2=O]

3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;

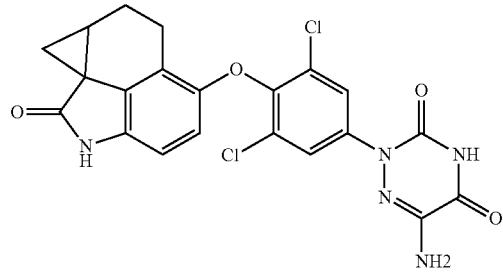 [SMILES: Nc1nn(-c2cc(Cl)c(Oc3ccc4c5c3CCC3CC53C(=O)N4)c(Cl)c2)c(=O)[nH]c1=O]

6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;

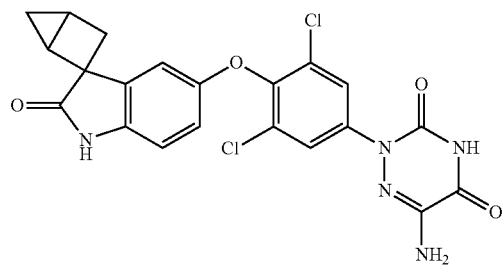 [SMILES: Nc1nn(-c2cc(Cl)c(Oc3ccc4c(c3)C3(CC5CC53)C(=O)N4)c(Cl)c2)c(=O)[nH]c1=O]

6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;

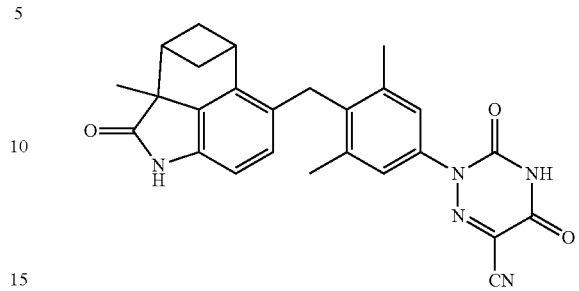

2-(3,5-dimethyl-4-((2a-methyl-2-oxo-1,2,2a,3,4,5'-hexahydro-3,5-methanobenzo[cd]indol-6-yl)methyl)phenyl)-3,5-dioxo-2,3,4,5-tetrahydro-1,2,4-triazine-6-carbonitrile; and

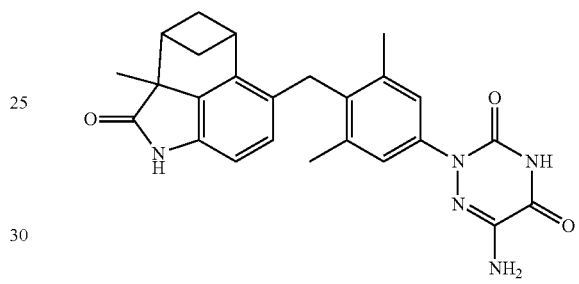

6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;
or a stereoisomer or a tautomer thereof, or a pharmaceutically acceptable salt thereof.

In another aspect, disclosed herein is a compound selected from the group consisting of:
4-([3,3-dimethyl-2-oxo-1H-pyrrolo[3,2-b]pyridin-5-yl]methyl)-2,3,5-trimethylphenoxyacetic acid;
6-amino-2-(3,5-dichloro-4-((2'-oxospiro[cyclobutane-1,3'-indolin]-5'-yl)oxy)phenyl)-1,2,4-triazine-3,5(2H,4H)-dione;
6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;
2-((4-methyl-5-((2'-oxospiro[cyclobutane-1,3'-indolin]-5'-yl)oxy)bicyclo[4.2.0]octan-2-yl)oxy)acetic acid;
6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;
6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;
6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;
2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;
2-(4-((3,3-difluoro-2'-oxospiro[cyclobutane-1,3'-indolin]-5'-yl)methyl)-3,5-dimethylphenyl)-3,5-dioxo-2,3,4,5-tetrahydro-1,2,4-triazine-6-carbonitrile;
6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;

6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione;

6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;

6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;

2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;

2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;

2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

6-amino-2-(3,5-dichloro-4-((2'-oxospiro[cyclobutane-1,3'-indolin]-5'-yl)methyl)phenyl)-1,2,4-triazine-3,5(2H,4H)-dione;

6-amino-2-(3,5-dimethyl-4-{2'-oxo-1'H-spiro[cyclobutane-1,3'-indol]-5'-ylmethyl}phenyl)-4H-1,2,4-triazine-3,5-dione;

2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;

2-(2,3,5-trimethyl-4-((2'-oxospiro[cyclopropane-1,3'-indolin]-5'-yl)methyl)phenoxy)acetic acid;

2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;

3-(3,5-dichloro-4-((2'-oxospiro[cyclobutane-1,3'-indolin]-5'-yl)oxy)phenyl)-1,2,4-oxadiazol-5(4H)-one;

N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;

2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;

6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;

2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;

6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;

2-((3,5-dichloro-4-((2a-methyl-2-oxo-1,2,2a,3,4,5-hexahydrobenzo[cd]indol-6-yl)oxy)phenyl)amino)-2-oxoacetic acid;

ethyl 2-((3,5-dichloro-4-((2a-methyl-2-oxo-1,2,2a,3,4,5-hexahydrobenzo[cd]indol-6-yl)oxy)phenyl)amino)-2-oxoacetate;

N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;

6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;

3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;

3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;

6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;

6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;

2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile;

6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;

6-amino-2-[4-({3,3-dimethyl-2-oxo-1H-pyrrolo[3,2-b]pyridin-5-yl}methyl)-3,5-dimethylphenyl]-4H-1,2,4-triazine-3,5-dione;

6-(3,5-dichloro-4-((2'-oxospiro[cyclobutane-1,3'-indolin]-5'-yl)oxy)phenyl)-1,2,4-triazine-3,5(2H,4H)-dione;

6-(3,5-dichloro-4-((2'-oxospiro[cyclobutane-1,3'-indolin]-5'-yl)oxy)phenyl)-2-methyl-1,2,4-triazine-3,5(2H,4H)-dione;

N-(3,5-dichloro-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-methyl-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dimethyl-4-((2'-oxospiro[cyclobutane-1,3'-indolin]-5'-yl)oxy)phenyl)-1,2,4-triazine-3,5(2H,4H)-dione;

N-(3,5-dimethyl-4-((2'-oxospiro[cyclobutane-1,3'-indolin]-5'-yl)oxy)phenyl)-5-oxo-4,5-dihydro-1,2,4-oxadiazole-3-carboxamide;

6-amino-2-(3,5-dichloro-4-((7'-methyl-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxospiro[cyclopentane-1,3'-indolin]-5'-yl)oxy)phenyl)-1,2,4-triazine-3,5(2H,4H)-dione;

N-(3,5-dichloro-4-((4'-chloro-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dichloro-4-((4'-chloro-2'-oxospiro[cyclopropane-1,3'-indolin]-5'-yl)oxy)phenyl)-1,2,4-triazine-3,5(2H,4H)-dione;

2-(3,5-dichloro-4-((4'-chloro-2'-oxospiro[cyclopropane-1,3'-indolin]-5'-yl)oxy)phenyl)-1,2,4-triazine-3,5(2H,4H)-dione;

6-amino-2-(3,5-dichloro-4-((2-methyl-2'-oxospiro[cyclopropane-1,3'-indolin]-5'-yl)oxy)phenyl)-1,2,4-triazine-3,5(2H,4H)-dione;

2-((3,5-dichloro-4-((2-methyl-2'-oxospiro[cyclopropane-1,3'-indolin]-5'-yl)oxy)phenyl)amino)-2-oxoacetic acid;

2-((3,5-dichloro-4-((3,3-difluoro-2-oxoindolin-5-yl)oxy)phenyl)amino)-2-oxoacetic acid;

6-(3,5-dichloro-4-((4'-methyl-2'-oxospiro[cyclopropane-1,3'-indolin]-5'-yl)oxy)phenyl)-2-methyl-1,2,4-triazine-3,5(2H,4H)-dione;

6-amino-2-(3,5-dichloro-4-((4'-methyl-2'-oxospiro[cyclopropane-1,3'-indolin]-5'-yl)oxy)phenyl)-1,2,4-triazine-3,5(2H,4H)-dione;
N-(3,5-dimethyl-4-((2'-oxospiro[cyclopropane-1,3'-indolin]-5'-yl)oxy)phenyl)-5-oxo-4,5-dihydro-1,2,4-oxadiazole-3-carboxamide;
N-(3,5-dichloro-4-((4'-fluoro-2'-oxospiro[cyclopropane-1,3'-indolin]-5'-yl)oxy)phenyl)-5-oxo-4,5-dihydro-1,2,4-oxadiazole-3-carboxamide;
6-amino-2-(3,5-dichloro-4-((4'-fluoro-2'-oxospiro[cyclopropane-1,3'-indolin]-5'-yl)oxy)phenyl)-1,2,4-triazine-3,5(2H,4H)-dione;
6-(3,5-dichloro-4-((4'-fluoro-2'-oxospiro[cyclopropane-1,3'-indolin]-5'-yl)oxy)phenyl)-2-methyl-1,2,4-triazine-3,5(2H,4H)-dione;
6-(3,5-dichloro-4-((4'-chloro-2'-oxospiro[cyclopropane-1,3'-indolin]-5'-yl)oxy)phenyl)-2-methyl-1,2,4-triazine-3,5(2H,4H)-dione;
N-(3-chloro-4-((2'-oxospiro[cyclopropane-1,3'-indolin]-5'-yl)oxy)-5-(trifluoromethyl)phenyl)-5-oxo-4,5-dihydro-1,2,4-oxadiazole-3-carboxamide; and
2-((3,5-dichloro-4-((2'-oxospiro[cyclopropane-1,3'-indolin]-5'-yl)oxy)phenyl)amino)-2-oxoacetic acid;
or a stereoisomer or a tautomer thereof, or a pharmaceutically acceptable salt thereof.

In another aspect, disclosed herein is a compound selected from the group consisting of:
4-([3,3-dimethyl-2-oxo-1H-pyrrolo[3,2-b]pyridin-5-yl]methyl)-2,3,5-trimethylphenoxyacetic acid;
6-amino-2-(3,5-dichloro-4-((2'-oxospiro[cyclobutane-1,3'-indolin]-5'-yl)oxy)phenyl)-1,2,4-triazine-3,5(2H,4H)-dione;
6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;
2-((4-methyl-5-((2'-oxospiro[cyclobutane-1,3'-indolin]-5'-yl)oxy)bicyclo[4.2.0]octan-2-yl)oxy)acetic acid;
6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;
6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;
6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;
2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;
6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;
6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;
6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione;
6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;
6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;
2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;
2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;
2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;
6-amino-2-(3,5-dichloro-4-((2'-oxospiro[cyclobutane-1,3'-indolin]-5'-yl)methyl)phenyl)-1,2,4-triazine-3,5(2H,4H)-dione;
6-amino-2-(3,5-dimethyl-4-{2'-oxo-1'H-spiro[cyclobutane-1,3'-indol]-5'-ylmethyl}phenyl)-4H-1,2,4-triazine-3,5-dione;
2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;
2-(2,3,5-trimethyl-4-((2'-oxospiro[cyclopropane-1,3'-indolin]-5'-yl)methyl)phenoxy)acetic acid;
2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;
3-(3,5-dichloro-4-((2'-oxospiro[cyclobutane-1,3'-indolin]-5'-yl)oxy)phenyl)-1,2,4-oxadiazol-5(4H)-one;
N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;
2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;
6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;
2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;
6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;
2-((3,5-dichloro-4-((2a-methyl-2-oxo-1,2,2a,3,4,5-hexahydrobenzo[cd]indol-6-yl)oxy)phenyl)amino)-2-oxoacetic acid;
ethyl 2-((3,5-dichloro-4-((2a-methyl-2-oxo-1,2,2a,3,4,5-hexahydrobenzo[cd]indol-6-yl)oxy)phenyl)amino)-2-oxoacetate;
N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;
6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;
3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;
3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;
6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;
6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;

2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile;

6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;

6-amino-2-[4-({3,3-dimethyl-2-oxo-1H-pyrrolo[3,2-b]pyridin-5-yl}methyl)-3,5-dimethylphenyl]-4H-1,2,4-triazine-3,5-dione;

6-(3,5-dichloro-4-((2'-oxospiro[cyclobutane-1,3'-indolin]-5'-yl)oxy)phenyl)-1,2,4-triazine-3,5(2H,4H)-dione;

6-(3,5-dichloro-4-((2'-oxospiro[cyclobutane-1,3'-indolin]-5'-yl)oxy)phenyl)-2-methyl-1,2,4-triazine-3,5(2H,4H)-dione;

N-(3,5-dichloro-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-methyl-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dimethyl-4-((2'-oxospiro[cyclobutane-1,3'-indolin]-5'-yl)oxy)phenyl)-1,2,4-triazine-3,5(2H,4H)-dione;

N-(3,5-dimethyl-4-((2'-oxospiro[cyclobutane-1,3'-indolin]-5'-yl)oxy)phenyl)-5-oxo-4,5-dihydro-1,2,4-oxadiazole-3-carboxamide;

6-amino-2-(3,5-dichloro-4-((7'-methyl-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxospiro[cyclopentane-1,3'-indolin]-5'-yl)oxy)phenyl)-1,2,4-triazine-3,5(2H,4H)-dione;

N-(3,5-dichloro-4-((4'-chloro-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dichloro-4-((4'-chloro-2'-oxospiro[cyclopropane-1,3'-indolin]-5'-yl)oxy)phenyl)-1,2,4-triazine-3,5(2H,4H)-dione;

2-(3,5-dichloro-4-((4'-chloro-2'-oxospiro[cyclopropane-1,3'-indolin]-5'-yl)oxy)phenyl)-1,2,4-triazine-3,5(2H,4H)-dione;

6-amino-2-(3,5-dichloro-4-((2-methyl-2'-oxospiro[cyclopropane-1,3'-indolin]-5'-yl)oxy)phenyl)-1,2,4-triazine-3,5(2H,4H)-dione;

2-((3,5-dichloro-4-((2-methyl-2'-oxospiro[cyclopropane-1,3'-indolin]-5'-yl)oxy)phenyl)amino)-2-oxoacetic acid;

2-((3,5-dichloro-4-((3,3-difluoro-2-oxoindolin-5-yl)oxy)phenyl)amino)-2-oxoacetic acid;

6-(3,5-dichloro-4-((4'-methyl-2'-oxospiro[cyclopropane-1,3'-indolin]-5'-yl)oxy)phenyl)-2-methyl-1,2,4-triazine-3,5(2H,4H)-dione;

6-amino-2-(3,5-dichloro-4-((4'-methyl-2'-oxospiro[cyclopropane-1,3'-indolin]-5'-yl)oxy)phenyl)-1,2,4-triazine-3,5(2H,4H)-dione;

N-(3,5-dimethyl-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-fluoro-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dichloro-4-((4'-fluoro-2'-oxospiro[cyclopropane-1,3'-indolin]-5'-yl)oxy)phenyl)-1,2,4-triazine-3,5(2H,4H)-dione;

6-(3,5-dichloro-4-((4'-fluoro-2'-oxospiro[cyclopropane-1,3'-indolin]-5'-yl)oxy)phenyl)-2-methyl-1,2,4-triazine-3,5(2H,4H)-dione;

6-(3,5-dichloro-4-((4'-chloro-2'-oxospiro[cyclopropane-1,3'-indolin]-5'-yl)oxy)phenyl)-2-methyl-1,2,4-triazine-3,5(2H,4H)-dione;

N-(3-chloro-4-((2'-oxospiro[cyclopropane-1,3'-indolin]-5'-yl)oxy)-5-(trifluoromethyl)phenyl)-5-oxo-4,5-dihydro-1,2,4-oxadiazole-3-carboxamide;

2-((3,5-dichloro-4-((2'-oxospiro[cyclobutane-1,3'-indolin]-5'-yl)oxy)phenyl)amino)-2-oxoacetic acid; and 2-(3,5-dichloro-4-((2'-oxospiro[cyclobutane-1,3'-indolin]-5'-yl)oxy)phenyl)-1,2,4-triazine-3,5(2H, 4H)-dione;

or a stereoisomer or a tautomer thereof, or a pharmaceutically acceptable salt thereof.

Synthesis of the Compounds

The presently disclosed compounds were synthesized using the general synthetic procedures set forth in Schemes below. The carrying out of each individual illustrated step is within the skill of an ordinary artisan, who also knows how to modify the synthetic procedures of the below schemes to synthesize the full scope of the compounds disclosed herein. The synthetic procedure for individual compounds is provided in the Examples section, below.

Several compounds of formula A are commercially available and many methods are described in the literature to prepare compounds of formula A, which include but are not limited to the methods found in the following references or referenced therein: (a) Hajra, S. et al. Org. Lett. 2018, 20, 4540-4544. (b) Zaytsev, S. et al. Journal of Organic Chemistry 2018, 83, 8695-8709. (c) Wu, C. et al. Organic Letters (2014), 16(7), 1960-1963. (d) Ye, N. et al. ACS Infect Dis. 2016, 2, p 382-392 (e) Chen, L. et al. Journal of Organic Chemistry 2020, 85, p 5203. Compounds of formula A can be reacted to form final products following the general schemes below.

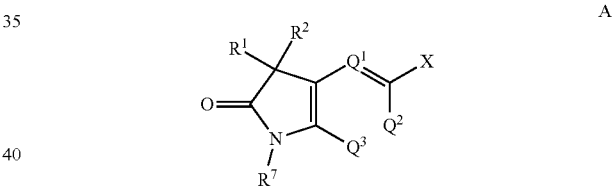

A

Scheme 1 depicts the synthesis of a compound of formula B2 from a compound of formula B1 in a Suzuki Miyaura coupling reaction with 4,4,5,5-tetramethyl-2-[(4,4,5,5-tetramethyl-1,3,2-dioxaborolan-2-yl)methyl]-1,3,2-dioxaborolane employing conditions found in the literature (e.g., J. Org. Chem. 2012, 77, 7223-7231). Z can be O or N, functionalized with an appropriate protecting group or groups (Pg).

Scheme 1.

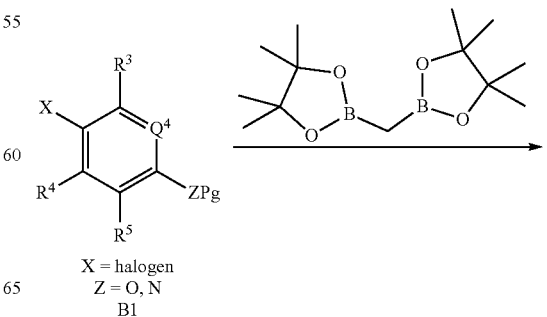

X = halogen
Z = O, N
B1

-continued

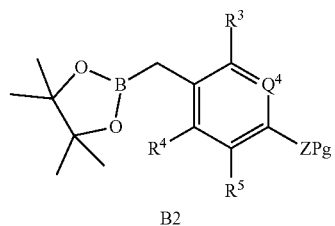

B2

Scheme 2 describes the synthesis of a compound of Formula A4. A transmetalation reaction of a compound of Formula A1 ('X' in the compounds of formula A1 represents a halogen, such as Br or I) is followed by an addition to the aldehyde of general formula A2 affording the alcohol compound of Formula A3, which is then reduced to a compound of Formula A4. Removal of the protecting group (Pg) of the compound of Formula A4 results in the formation of a compound of Formula A5. It is understood that in this scheme that the amide nitrogen may require an additional, or perhaps orthogonal, protecting group (optionally $R^7$) to be optionally removed in a later step.

Scheme 3 describes the general synthesis of compounds of Formula B3. Compounds of formula B1, where X=boronic acid, may be coupled with the phenolic compounds of formula B1a under a Cu(I) mediated coupling reaction in a polar aprotic solvent with base (e.g., $K_2CO_3$) at elevated temperature to afford intermediates of type B2. Alternatively, when X=Br, or iodine (formula B1) the coupling may take place with a Pd catalyst in an appropriate solvent with base. Subsequent global or stepwise deprotection of the protecting groups ($Pg_1$ and Pg) leads to the formation of compounds of B3.

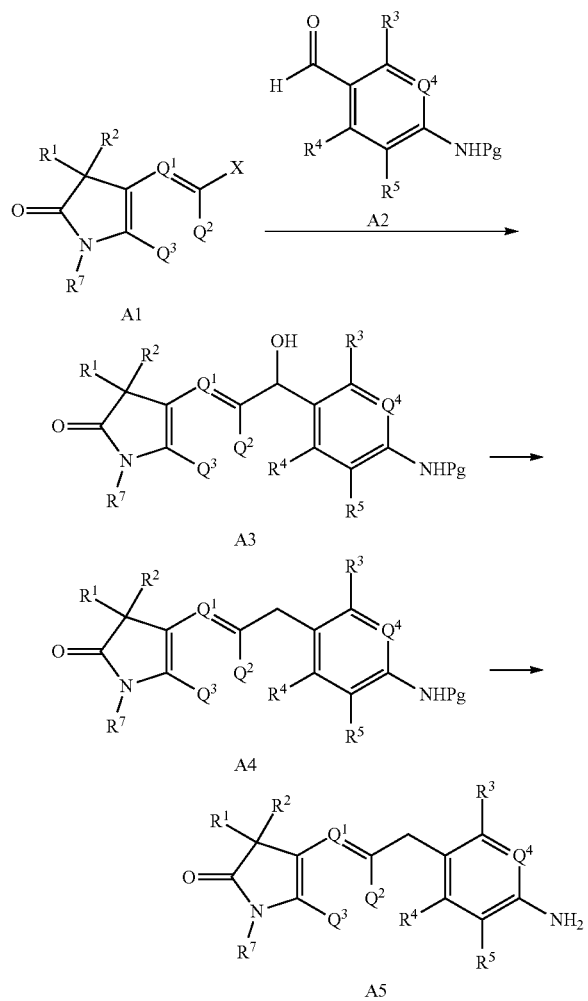

Scheme 2.

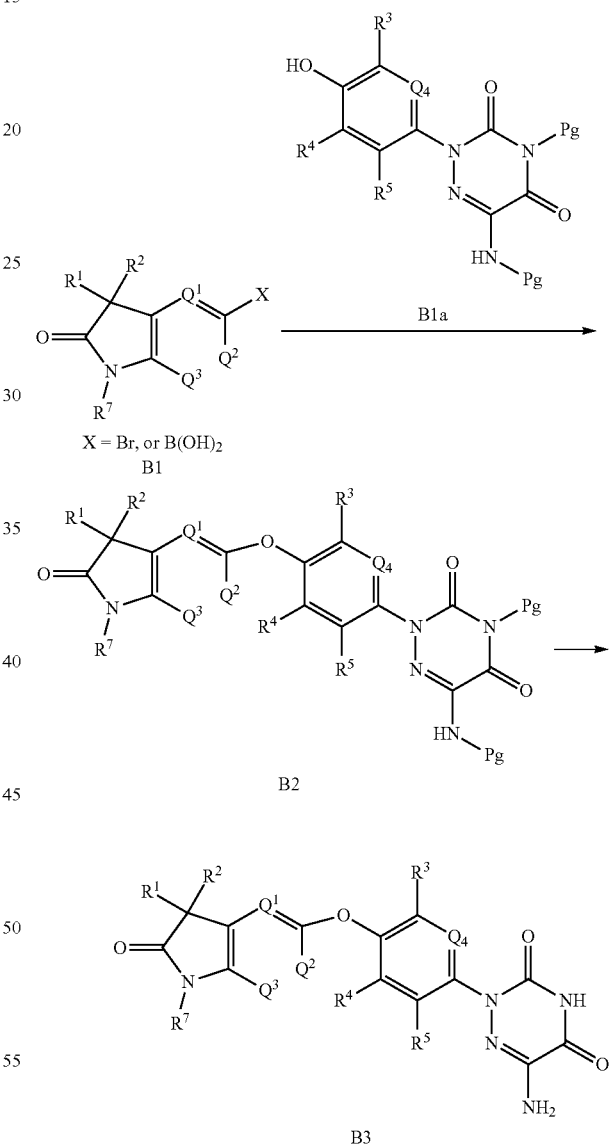

Scheme 3.

Described in scheme 4 is the reaction of compounds of formula C1 with nitroaromatic compounds of formula C1a under basic conditions in a suitable solvent, perhaps at elevated temperature to afford compounds of formula C2. The nitro group can then be reduced using methods described in the literature (e.g., Fe, $NH_4Cl$) to afford compounds of formula C3.

Scheme 4.

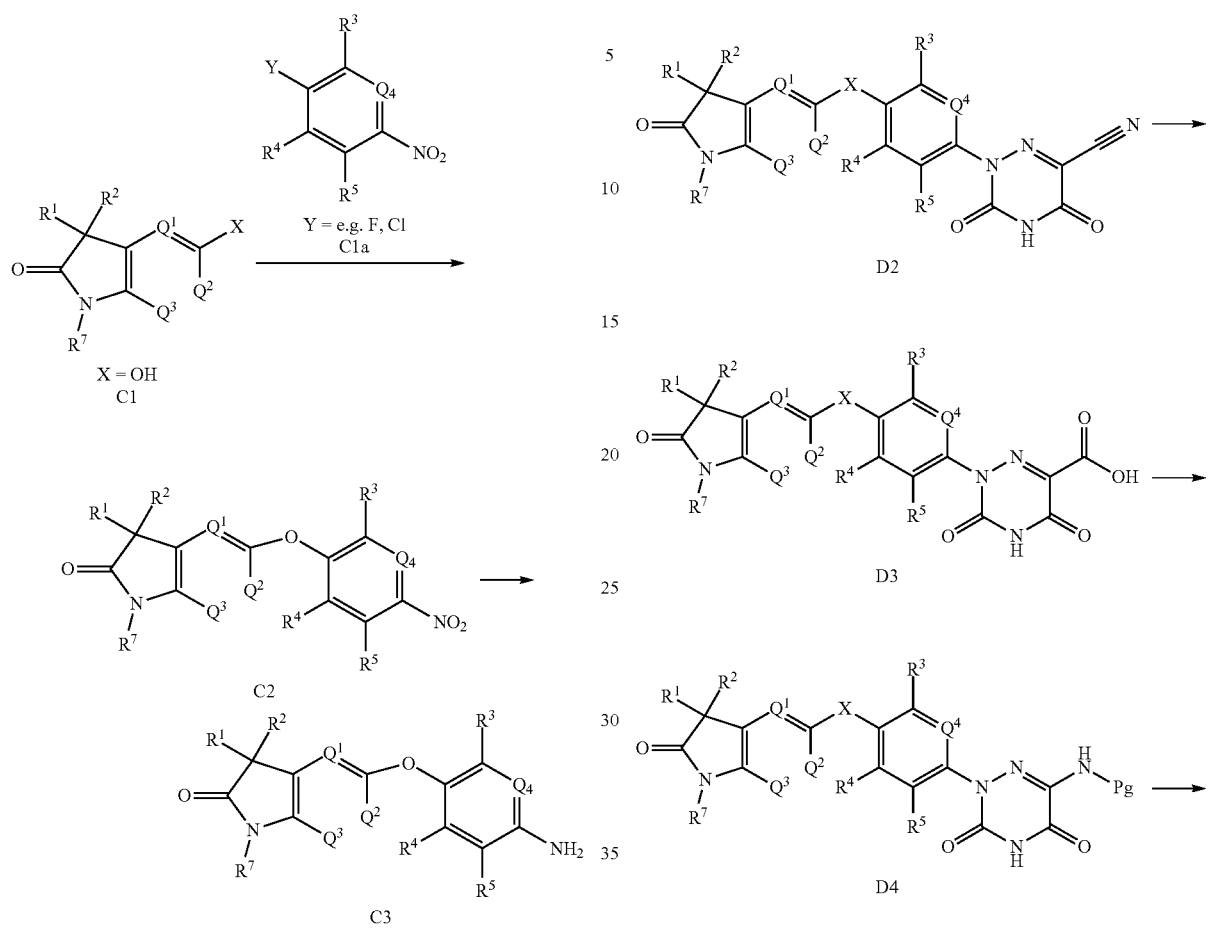

As described in Scheme 5, an aromatic amine compound of Formula D1 is transformed to an aza-uracil compound of Formula D2, first by generation of the corresponding diazonium salt, followed by reaction with an N-(2-cyanoacetyl)-carbamate, then subsequent cyclization, to afford a compound of Formula D2. Subsequent hydrolysis of the nitrile of Formula D2 to a carboxylic acid compound of Formula D3 using conditions described in the chemistry literature. The compound of Formula D3 may then form an acyl azide intermediate, followed by a Curtius rearrangement resulting in the formation of a compound of Formula D4. Subsequent deprotection (i.e., removal of the protecting group(s) Pg) can afford compounds of formula D5.

Scheme 5.

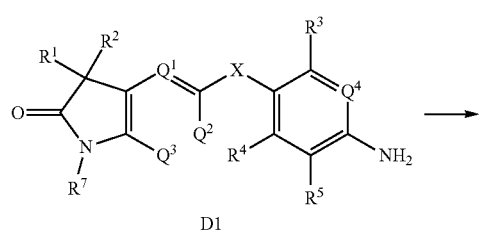

Scheme 6 depicts an aromatic amine compound of Formula D1 that can be converted to a boronic acid compound of Formula E2, first by generation of the diazonium salt, followed by reaction with tetrahydroxydiborane. Alternatively, the aromatic amine can be converted to a halogen via the Sandmeyer reaction. The aryl halide is then converted to the boronic acid, for example in a reaction with B(IprO)$_3$, then quenching with HCl (aq.) to afford compounds of formula E2. The corresponding boronic acid (formula E2) can be coupled with a suitably protected (protecting group 'Pg') bromo-azauracil compound of Formula E1a. The resulting aryl bromide compound of Formula E3 can be transformed, either by a substitution reaction, or by transition metal catalyzed transformations to afford compounds of formula E4. Removal of the protecting group (Pg) results in a compound of Formula E5.

Scheme 6.

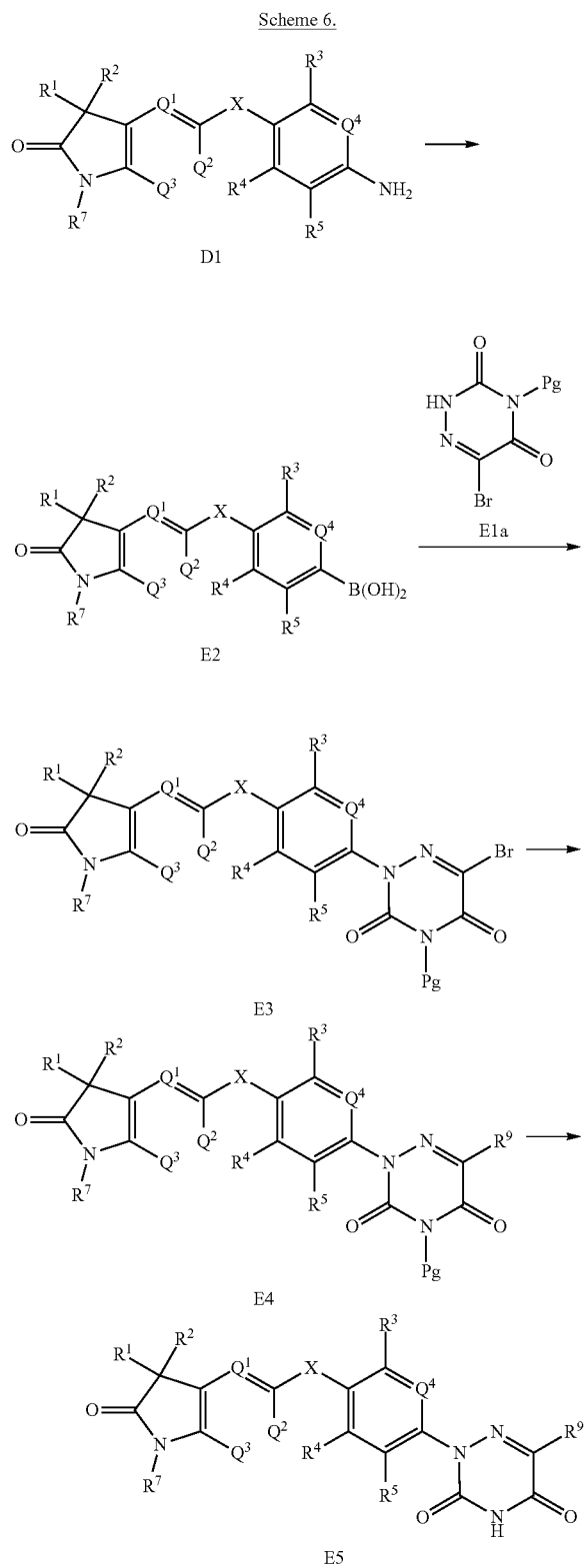

Scheme 7.

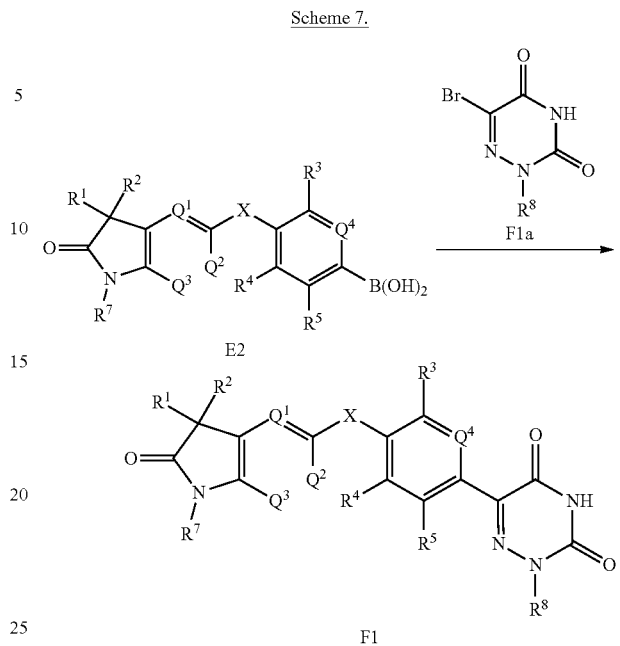

A compound of Formula G1 may be obtained by coupling a boronic acid compound of Formula E2 with an aza-uracil compound of Formula G1a, as described in Scheme 8. The benzyloxymethyl acetal protecting group can then be deprotected using a variety of methods described in the literature (e.g., Tetrahedron Letters 2012, 53, pp 3758-3762).

Scheme 8.

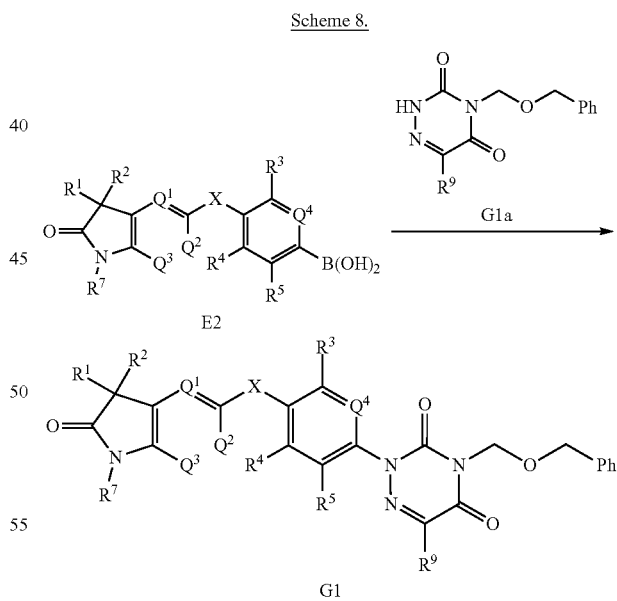

Scheme 7 describes boronic acid compounds of Formula E2 are coupled to compounds of formula F1a bearing a bromide under typical Suzuki-Miyaura cross-coupling reaction conditions to afford compounds of formula F1. The coupling may occur if $R^8$ is H.

A compound of Formula K1 (Scheme 9) can be formed by reacting the aromatic amine with ethyl 2-chloro-2-oxoacetate in the presence of an organic base, in an appropriate organic solvent. Standard hydrolysis conditions are performed to afford compounds of formula K2. Compounds of the formula D1 may also be reacted with 5-oxo-4,5-dihydro-1,2,4-oxadiazole-3-carbonyl chloride in a non-polar organic solvent in the presence of a base to afford compounds of the formula K3. Alternatively, compounds of the formula D1 may also be reacted with 5-oxo-4,5-dihydro-1,2,4-oxadiazole-3-carboxylic acid in a polar aprotic solvent in the presence of a base and coupling agent to afford compounds of the formula K3. Compounds of the formula K4 may be produced by reaction of compounds of formula D1 with 5-oxo-4,5-dihydro-1,2,4-oxadiazole-3-carbaldehyde under standard reductive amination conditions. Alternatively, compounds of the formula K4 may be produced by reaction of compounds of formula D1 with 3-(bromomethyl)-1,2,4-oxadiazol-5(4H)-one (or, for example, 3-(chloromethyl)-1,2,4-oxadiazol-5(4H)-one) under basic conditions with optional heating.

alkylated to form ether L2 via Williamson-type ether synthesis. For example, using a chloroacetate with a suitable protecting group (Pg=methyl, ethyl, t-butyl, etc.). Alternatively, an hydroxyacetate compound can be reacted with the phenol L1 under typical Mitsunobu conditions to afford compounds of L2. Standard hydrolysis conditions can be used to cleave the ester group, affording the acid compounds of formula L3. Compounds of the formula L4 may be afforded through methods described in the literature (e.g., Bioorganic & Medicinal Chemistry Letters, 14(18), 4627-4631; 2004) where the oxygen is alkylated with bromoacetonitrile, the ether product is then cyclized to compounds of

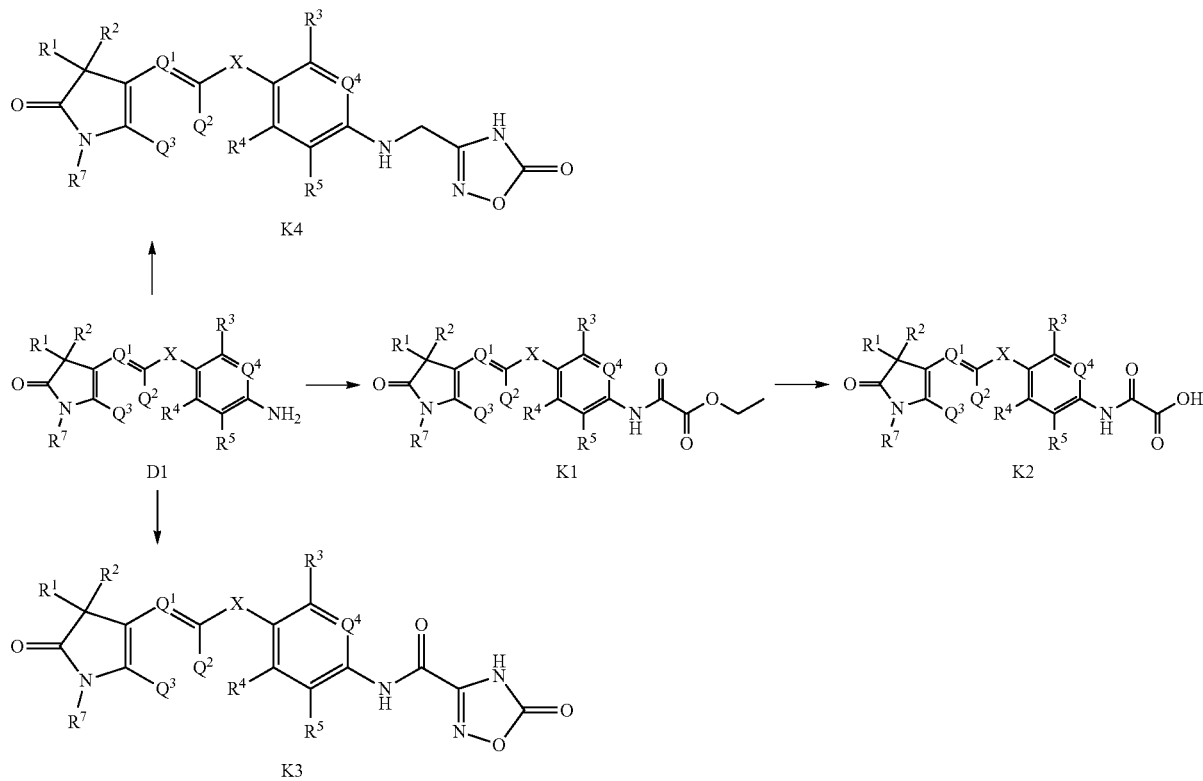

Scheme 9.

Scheme 10 describes the formation of compound of formula L3. Phenolic compounds of formula L1 can be the formula L4 by reaction with hydroxylamine and cyclization with CDI.

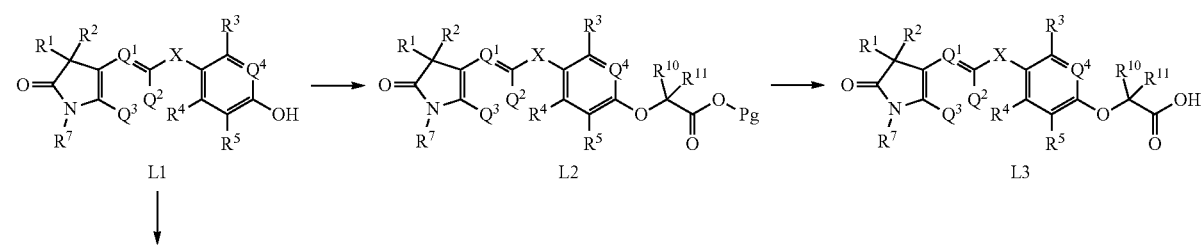

Scheme 10.

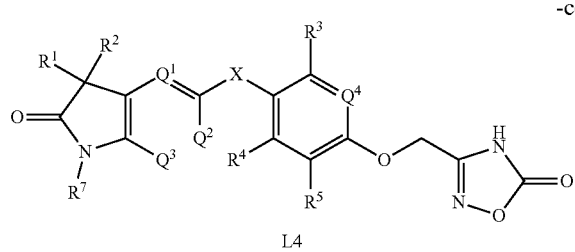

L4

Scheme 11 depicts the synthesis of compounds of formula M2. The aryl halide compounds M1 are reacted with methyl propiolate under typical Sonogoshira conditions to afford compounds of formula M2. Cyclization towards heterocycles of the formula M3 occurs under conditions described in the literature (e.g., J. Med. Chem. 2002, 45, 9, 1785-1798, J. Med. Chem. 2013, 56, 5, 1894-1907). Compounds of formula M3 can alternatively be generated via other described methods (e.g., J. Org. Chem. 2000, 65, 4, 1003-1007; J. Med. Chem. 1989, 32, 9, 2116-2128).

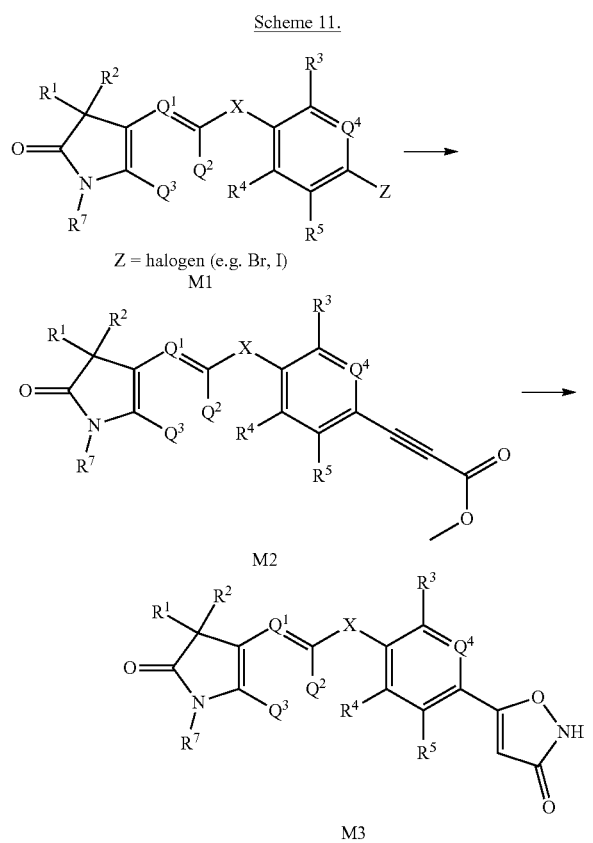

Scheme 12 describes the synthesis of compounds of formula M12. Aryl cyanide compounds M10 can be transformed to compounds of formula M11 via the addition of hydroxylamine. Further conversion to compounds of formula M12 proceeds via the addition of carbonyl diimidazole with base in an appropriate solvent, often at elevated temperature (see, e.g., Molecular Pharmaceutics, 16(4), 1489-1497; 2019). Compounds of the formula M10 may be synthesized from the aryl halides M1 via several described methods using either a copper catalyst (Rosenmund-von Braun reaction) or alternatively using a Pd catalyst (e.g., J. Am. Chem. Soc., 2011, 133, 10999-11005). The aryl cyanides of formula M10 may also be generated from the amine using the Sandmeyer reaction.

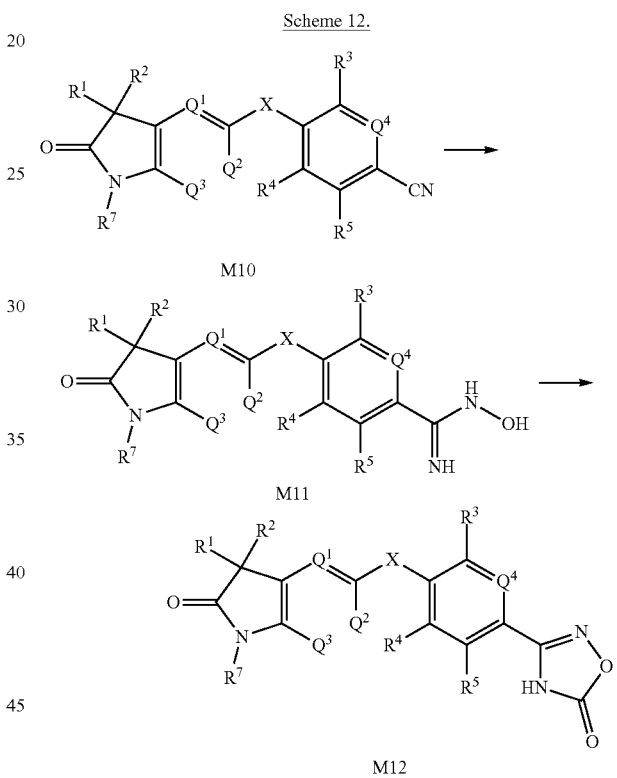

An alternative synthesis of compounds of the formula K3 would be to react anilines D1 with ethyl 5-oxo-4,5-dihydro-1,2,4-oxadiazole-3-carboxylate in an organic solvent (e.g. THF), in the presence of one or more equivalents of LiHMDS (reference: J. Am. Chem. Soc. 2019, 141, 11161-11172).

An alternative synthesis of compounds of formula A are described in Scheme 13. Hydrazines hydrochlorides of formula N1 where $Q^1$, $Q^2$, and $Q^3$ are C-alkyl or C-halogen are acylated with a carboxylic acid chloride, or alternatively coupled with the corresponding acid using a typical coupling agent (e.g. HATU) in a polar aprotic solvent (e.g. DMF). Cyclization to form spirooxindoles of formula N3 (where $R^7$ is H) proceeds under oxidative conditions (e.g. CaO) in a high boiling solvent (e.g. quinoline) at elevated temperature. Certain compounds of formula N3 can then be brominated under standard conditions to afford compounds of formula A where X=Br. Alternatively, where substitution allows, compounds N3 can be oxidized to form compounds of formula A where X=O (See Brenner, Tetrahedron, 42, p 4267-4272, 1996).

Scheme 13.

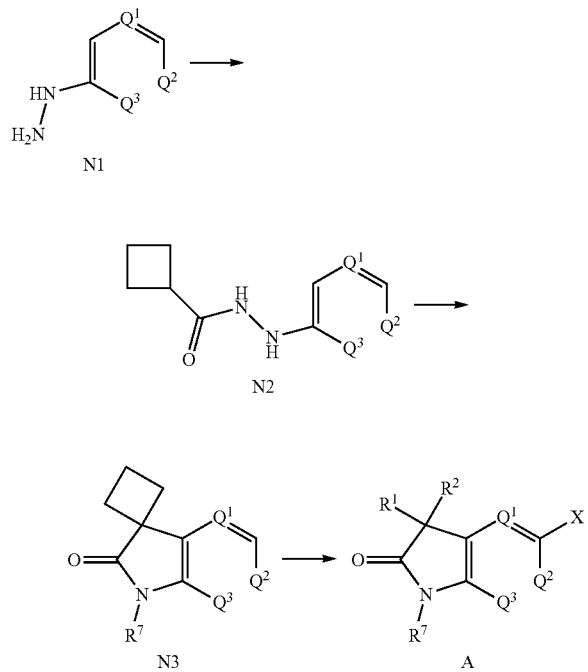

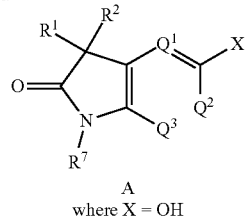

where X = OH

An additional method to provide compounds of formula A is described in Scheme 14. Nitroaromatics of the formula N10 can react with thioesters to form oxindoles N11 according to literature (Bioorganic and Med. Chem. Letters, 20(12), 3526-3529; 2010). In subsequent steps, N11 is alkylated to form compounds of the formula N12, where the methoxy group can be deprotected in a later step to afford compounds of formula A where X is OH.

Scheme 14.

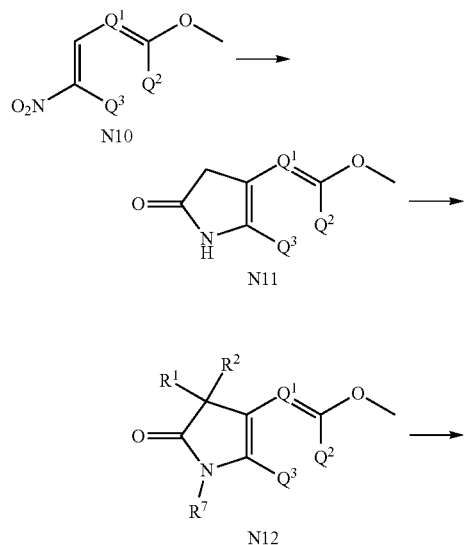

Pharmaceutical Compositions

In another aspect, disclosed herein are pharmaceutical compositions comprising, consisting essentially of, or consisting of a compound as described herein, and at least one pharmaceutically acceptable excipient.

In another aspect, disclosed herein are pharmaceutical compositions comprising, consisting essentially of, or consisting of a compound of Formula I, as described herein, and at least one pharmaceutically acceptable excipient.

The pharmaceutical composition disclosed herein may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition disclosed herein may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, transdermal, rectal, transmucosal, or intestinal administration; parenteral delivery, including intramuscular, subcutaneous, intravenous, intramedullary injections, as well as inhalation, intrathecal, direct intraventricular, intraperitoneal, intranasal, or intraocular injections.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. These pharmaceutical compositions, then, may be formulated in a conventional manner using one or more known physiologically acceptable carriers comprising excipients and/or auxiliaries, which facilitate processing of the active compounds into preparations that can be used pharmaceutically. Any of the well-known techniques, carriers, and excipients may be used as suitable and as understood in the art; e.g., in Remington's Pharmaceutical Sciences, above.

Pharmaceutical compositions suitable for use in the presently disclosed formulations include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. In some embodiments, a therapeutically effective amount means an amount of compound effective to alleviate or ameliorate symptoms of disease or prolong the survival of the subject being treated.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example, 1 to 200 mg or each active ingredient of the pharmaceutical compositions disclosed herein or a pharmaceutically acceptable salt thereof calculated as the free base or free acid, the composition being administered 1 to 4 times per day or per week. Alternatively, the compositions disclosed herein may be administered by continuous such as sustained, delayed, or extended release, preferably at a dose of each ingredient up to 500 mg per day. Thus, the total daily dosage by oral administration of each ingredient will typically be in the range 0.1 mg to 2000 mg.

Methods of Treatment

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound as described herein.

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound of Formula I, as described herein.

In some embodiments, a health care professional, such as a physician, physician's assistant, nurse practitioner, or the like, identifies an individual as being in need of treatment for the thyroid hormone receptor related disorder, and/or a candidate for treatment with a compound disclosed herein. The identification may be based on medical test results, non-responsiveness to other, first-line therapies, the specific nature of the particular liver disorder, or the like.

In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating a disorder or disease in a subject in need thereof, the method comprising, consisting essentially of, or consisting of administering to the subject a therapeutically effective amount of a compound or composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating NASH in a subject in need thereof, the method comprising, consisting essentially of, or consisting of administering to the subject a therapeutically effective amount of a compound or composition disclosed herein.

In another aspect, disclosed herein are methods of treating obesity in a subject in need thereof, the method comprising, consisting essentially of, or consisting of administering to the subject a therapeutically effective amount of a compound or composition disclosed herein.

In another aspect, disclosed herein are methods of treating hyperlipidemia in a subject in need thereof, the method comprising, consisting essentially of, or consisting of administering to the subject a therapeutically effective amount of a compound or composition disclosed herein.

In another aspect, disclosed herein are methods of treating hypercholesterolemia in a subject in need thereof, the method comprising, consisting essentially of, or consisting of administering to the subject a therapeutically effective amount of a compound or composition disclosed herein.

In another aspect, disclosed herein are methods of treating diabetes in a subject in need thereof, the method comprising, consisting essentially of, or consisting of administering to the subject a therapeutically effective amount of a compound or composition disclosed herein.

In another aspect, disclosed herein are methods of treating liver steatosis in a subject in need thereof, the method comprising, consisting essentially of, or consisting of administering to the subject a therapeutically effective amount of a compound or composition disclosed herein.

In another aspect, disclosed herein are methods of selectively modulating the activity of a thyroid hormone receptor beta (THR-0) comprising, consisting essentially of, or consisting of contacting a compound as described herein, with a thyroid hormone receptor. In some embodiments, the contacting is in vitro or ex vivo, whereas in other embodiments, the contacting is in vivo.

In some embodiments, the compound of Formulas I, I', or IA, as described herein, or the stereoisomer or the tautomer thereof, or the pharmaceutically acceptable salt thereof, or a therapeutically effective amount of the pharmaceutical composition; is administered in combination with a KHK inhibitor, an FXR agonist, a SSAO inhibitor, a FASN inhibitor, or a SCD1 modulator. In some embodiments, the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

In another aspect, disclosed herein are methods of selectively modulating the activity of a thyroid hormone receptor beta (THR-0) comprising, consisting essentially of, or consisting of contacting a compound of Formula I, as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-0) comprising, consisting essentially of, or consisting of contacting a composition described herein, with a thyroid hormone receptor. In some embodiments, the contacting is in vitro or ex vivo, whereas in other embodiments, the contacting is in vivo.

EXAMPLES

Table of abbreviations

| Abbreviation | Meaning |
| --- | --- |
| EtOAc, or EA | Ethyl Acetate |
| CyH | Cyclohexane |
| DCM | dichloromethane |
| PIFA | (Bis(trifluoroacetoxy)iodo)benzene |
| ACN or MeCN | Acetonitrile |
| Rt | Retention time |
| MeOH | methanol |

-continued

Table of abbreviations

| Abbreviation | Meaning |
| --- | --- |
| EtOH | ethanol |
| iPrOH | isopropanol |

Example 1. Preparation of Compound 1

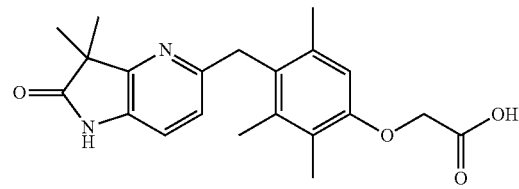 [SMILES: Cc1cc(OCC(=O)O)c(C)c(C)c1Cc1ccc2c(n1)C(C)(C)C(=O)N2]

n-Butyllithium (6 mL, 2.5M in hexane, 15.0 mmol) was added dropwise to a mixture of 5-bromo-1H,3H-pyrrolo[3,2-b]pyridin-2-one (0.80 g, 3.76 mmol) and tetramethylethylenediamine (1.75 g, 15.0 mmol) in tetrahydrofuran (36 mL) at −78° C. under nitrogen. The mixture was stirred at −78° C. for 1 h, then CH$_3$I (2.13 g, 15.02 mmol) was added dropwise over 5 min. The mixture was warmed to room temperature and stirred for 5 h. The reaction was quenched with NH$_4$Cl (sat., aq.) at room temperature. The resulting mixture was extracted with ethyl acetate (3×50 mL). The combined organic layers were washed with brine (50 mL), dried over anhydrous Na$_2$SO$_4$. The solids were removed by filtration, the filtrate was concentrated under reduced pressure. The residue was purified by silica gel column chromatography, eluted with petroleum ether/ethyl acetate (17/83) to afford 5-bromo-3,3-dimethyl-1H-pyrrolo[3,2-b]pyridin-2-one (350 mg, 39/a) as a yellow solid. LC-MS (ESI, m/z): 241 [M+H]$^+$.

A 40-mL vial was charged with 5-bromo-3,3-dimethyl-1H-pyrrolo[3,2-b]pyridin-2-one (0.35 g, 1.45 mmol), dihydropyran (2.44 g, 29.0 mmol), p-toluene sulfonic acid (0.10 g, 0.57 mmol), CH$_2$Cl$_2$ (7 mL). The reaction was stirred for 3 days at 40° C. The reaction was quenched with water (20 mL). The resulting mixture was extracted with dichloromethane (3×30 mL). The combined organic layers were washed with brine (50 mL), dried over anhydrous Na$_2$SO$_4$. The solids were removed by filtration, and the filtrate was concentrated under reduced pressure. The desired product was purified by silica gel column chromatography, eluted with petroleum ether/ethyl acetate (9/1) to afford 5-bromo-3,3-dimethyl-1-(oxan-2-yl)pyrrolo[3,2-b]pyridin-2-one (210 mg, 40%) as a yellow solid. LC-MS (ESI, m/z): 325 [M+H]$^+$.

A 40 mL vial was charged with 5-bromo-3,3-dimethyl-1-(oxan-2-yl)pyrrolo[3,2-b]pyridin-2-one (210 mg, 0.65 mmol), t-butyl 2-[2,3,5-trimethyl-4-[(4,4,5,5-tetramethyl-1,3,2-dioxaborolan-2-yl)methyl]phenoxy]acetate (277 mg, 0.711 mmol), dichlorobis(tri-o-tolylphosphine) palladium (II) (76.0 mg, 0.097 mmol), dioxane (7 mL), potassium phosphate (411 mg, 1.94 mmol) and water (0.7 mL) at room temperature. The resulting mixture was stirred for 16 h at 100° C. under nitrogen atmosphere. The reaction was quenched with water (20 mL) at room temperature. The resulting mixture was extracted with ethyl acetate (3×20 mL). The combined organic layers were washed with brine (30 mL), dried over anhydrous Na$_2$SO$_4$. The solids were removed by filtration, the filtrate was concentrated under reduced pressure. The residue was purified by silica gel column chromatography, eluted with petroleum ether/ethyl acetate (9/1) to afford tert-butyl 2-(4-[[3,3-dimethyl-1-(oxan-2-yl)-2-oxopyrrolo[3,2-b]pyridin-5-yl]methyl]-2,3,5-trimethylphenoxy)acetate (30 mg, 9%) as an off-white solid. LC-MS (ESI, m/z): 509 [M+H]$^+$.

An 8 mL vial was charged with t-butyl 2-(4-[[3,3-dimethyl-1-(oxan-2-yl)-2-oxopyrrolo[3,2-b]pyridin-5-yl] methyl]-2,3,5-trimethylphenoxy)acetate (30.0 mg, 0.059 mmol), HCl (conc., 1 mL), dioxane (2 mL). The reaction was stirred overnight at 50° C. and concentrated under reduced pressure. The crude product was purified by Prep-HPLC with the following conditions (Column: XBridge Prep OBD C18, 30×150 mm, 5 mm; Mobile Phase A: Water (50 mmol/L NH$_4$HCO$_3$), Mobile Phase B: ACN; Flow rate: 25 mL/min; Gradient: 10% B to 30% B in 7 min; collected at 254 nm) to afford 4-([3,3-dimethyl-2-oxo-1H-pyrrolo[3,2-b]pyridin-5-yl]methyl)-2,3,5-trimethylphenoxyacetic acid (8.7 mg, 40%) as a white solid. $^1$H NMR (400 MHz, DMSO-d$_6$) δ 10.39 (s, 1H), 7.02 (d, J=8.0 Hz, 1H), 6.45-6.50 (m, 2H), 6.26 (s, 2H), 4.00 (s, 2H), 2.05-2.33 (m, 9H), 1.24 (s, 6H). LC-MS, Method A, Rt: 0.595 (ESI, m/z): 369 [M+H]$^+$.

Example 2. Preparation of Compound 2

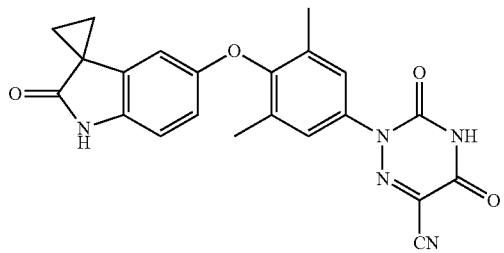 [SMILES: Cc1cc(-n2nc(C#N)c(=O)[nH]c2=O)cc(C)c1Oc1ccc2c(c1)C1(CC1)C(=O)N2]

A solution of 5'-bromo-1'H-spiro[cyclopropane-1,3'-indol]-2'-one (740 mg, 3.11 mmol), 3,4-dihydro-2H-pyran (2.61 g, 31.1 mmol) and TsOH (53.5 mg, 0.311 mmol) in DCM (15 mL) was stirred for overnight at 40° C. and quenched water (80 mL). The resulting mixture was extracted with DCM (3×40 mL). The combined organic layers were washed with brine (80 mL), dried over anhydrous Na$_2$SO$_4$. After filtration, the filtrate was concentrated under reduced pressure. The residue was purified by silica gel column chromatography, eluted with ethyl acetate/petroleum ether (6:94) to provide 5'-bromo-1'-(oxan-2-yl)spiro[cyclopropane-1,3'-indol]-2'-one (850 mg, 85%) as a yellow solid. LC-MS (ESI, m/z): 322 [M+H]$^+$.

A solution of 5'-bromo-1'-(oxan-2-yl)spiro[cyclopropane-1,3'-indol]-2'-one (700 mg, 2.17 mmol), 2-(5,5-dimethyl-1,3,2-dioxaborinan-2-yl)-5,5-dimethyl-1,3,2-dioxaborinane (981 mg, 4.35 mmol), dichlorobis(triphenylphosphine)Palladium (152 mg, 0.217 mmol) and potassium acetate (639 mg, 6.52 mmol) in DMSO (20 ml) under nitrogen was stirred for overnight at 60° C. and quenched with water (60 mL). The resulting mixture was extracted with ethyl acetate (3×40 mL). The combined organic layers were washed with brine (80 mL), dried over anhydrous Na$_2$SO$_4$. The solids were removed by filtration, and the filtrate was concentrated under reduced pressure. The residue was purified by silica gel column chromatography, eluted with petroleum ether/ ethyl acetate (9/1) to afford 5'-(5,5-dimethyl-1,3,2-dioxaborinan-2-yl)-1'-(oxan-2-yl)spiro[cyclopropane-1,3'-indol]-2'-one (600 mg, 78%) as a yellow oil. LC-MS (ESI, m/z): 356 [M+H]$^+$.

To a solution of 5'-(5,5-dimethyl-1,3,2-dioxaborinan-2-yl)-1'-(oxan-2-yl)spiro[cyclopropane-1,3'-indol]-2'-one (600 mg, 1.69 mmol) in THF (10 mL) was added acetic acid (2.53 g, 42.2 mmol) and hydrogen peroxide (1.43 g, 42.2 mmol). The resulting mixture was stirred for overnight at room temperature and quenched with NaHCO$_3$ (80 mL). The mixture was extracted with ethyl acetate (3×30 mL) and the organic layers were combined, washed with brine (80 mL), dried over anhydrous Na$_2$SO$_4$, the solids were removed by filtration and the filtrate was concentrated under reduced pressure. The residue was chromatographed on a silica gel column with ethyl acetate/petroleum ether (3/7) to provide 5'-hydroxy-1'-(oxan-2-yl)spiro[cyclopropane-1,3'-indol]-2'-one (230 mg, 52.5%) as a yellow solid. LC-MS (ESI, m/z): 260 [M+H]$^+$.

A solution of 5'-hydroxy-1'-(oxan-2-yl)spiro[cyclopropane-1,3'-indol]-2'-one (230 mg, 0.887 mmol), 2-fluoro-1,3-dimethyl-5-nitrobenzene (300 mg, 1.77 mmol) and potassium carbonate (245 mg, 1.77 mmol) in DMF (10 mL) was stirred for overnight at 120° C. The resulting mixture was quenched with water (50 mL). The resulting mixture was extracted with ethyl acetate (3×20 mL). The combined organic layers were washed with brine (60 mL), dried over anhydrous Na$_2$SO$_4$, the solids were removed by filtration and the filtrate was concentrated under reduced pressure. The residue was chromatographed on a silica gel column with ethyl acetate/petroleum ether (7/93) to provide 5'-(2,6-dimethyl-4-nitrophenoxy)-1'-(oxan-2-yl)spiro[cyclopropane-1,3'-indol]-2'-one (210 mg, 58%) as a yellow solid. LC-MS (ESI, m/z): 409 [M+H]$^+$.

A solution of 5'-(2,6-dimethyl-4-nitrophenoxy)-1'-(oxan-2-yl)spiro[cyclopropane-1,3'-indol]-2'-one (180 mg, 0.441 mmol) and trifluoroacetic acid (5 mL) in DCM (5 mL) was stirred for overnight at room temperature. The resulting mixture was quenched with NaHCO$_3$ (40 mL). The resulting solution was extracted with ethyl acetate (3×20 mL). The combined organic layers were washed with brine (60 mL), dried over anhydrous Na$_2$SO$_4$, the solids were removed by filtration and the filtrate was concentrated under reduced pressure to provide 5'-(2,6-dimethyl-4-nitrophenoxy)-1'H-spiro[cyclopropane-1,3'-indol]-2'-one (150 mg crude) as a brown oil. LC-MS (ESI, m/z): 325 [M+H]$^+$.

A solution of 5'-(2,6-dimethyl-4-nitrophenoxy)-1'H-spiro [cyclopropane-1,3'-indol]-2'-one (150 mg, 0.462 mmol), Fe (154 mg, 2.77 mmol) and ammonium chloride (197 mg, 3.70 mmol) in ethanol (6 mL) and water (3 mL) was stirred for 3 h at 60° C. The resulting mixture was quenched with water (30 ml). The resulting solution was extracted with ethyl acetate (3×15 mL). The combined organic layers were washed with brine (40 mL), dried over anhydrous Na$_2$SO$_4$, the solids were removed by filtration and the filtrate was concentrated under reduced pressure to provide 5'-(4-amino-2,6-dimethylphenoxy)-1'H-spiro[cyclopropane-1,3'-indol]-2'-one (110 mg crude) as a brown oil. LC-MS (ESI, m/z): 295 [M+H]$^+$.

To a solution of 5'-(4-amino-2,6-dimethylphenoxy)-1'H-spiro[cyclopropane-1,3'-indol]-2'-one (110 mg, 0.374 mmol) in water (8 mL), HCl (conc., 3 mL) and acetic acid (12 mL) was added sodium nitrite (51.6 mg, 0.748 mmol) in water (3 mL) dropwise at 0° C. After the addition, the reaction was stirred at 0° C. for 45 min. Then the reaction mixture was added to a solution of ethyl N-(2-cyanoacetyl) carbamate (233 mg, 1.50 mmol) in water (16 mL) and pyridine (6 mL) at 0° C. quickly. The resulting mixture was stirred at 0° C. for 1 h and filtered. The filter cake was washed with water (30 mL) and petroleum ether (30 mL) and dried under IR lamp to provide ethyl (2-cyano-2-(2-(3,5-dimethyl-4-((2'-oxospiro[cyclopropane-1,3'-indolin]-5'-yl)oxy)phenyl)hydrazineylidene)acetyl)carbamate (80 mg crude) as a yellow solid that was used in the next step without further purification. LC-MS (ESI, m/z): 462 [M+H]+.

A solution of ethyl (2-cyano-2-(2-(3,5-dimethyl-4-((2'-oxospiro[cyclopropane-1,3'-indolin]-5'-yl)oxy)phenyl)hydrazineylidene)acetyl)carbamate (80 mg, 0.173 mmol) and potassium acetate (85.1 mg, 0.865 mmol) in DMA (3 mL) was stirred for 2 h at 120° C. under nitrogen atmosphere. The resulting solution was purified by Pre-HPLC (YMC-Actus Triart C18, 30 mm×150 mm, 5 µm; Mobile Phase A: Water (10 mmol/L NH$_4$HCO$_3$+0.1% NH$_3$·H$_2$O), Mobile Phase B: ACN; Flow rate: 60 mL/min; Gradient: 18 B to 48 B in 7 min, 254 nm; RT1:6.05 min) to afford 2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile (37.4 mg, 21%) as an off-white solid. $^1$H NMR (400 MHz, CD$_3$OD) δ 7.25 (s, 2H), 6.85 (d, J=8.4 Hz, 1H), 6.55-6.57 (m, 1H), 6.51 (d, J=2.4 Hz, 1H), 2.14 (s, 6H), 1.60-1.63 (m, 2H), 1.52-1.59 (m, 2H). LC-MS (ESI, m/z): 416 [M+H]+. LC-MS, Method A, Rt: 0.686.

Example 3. Preparation of Compound 3

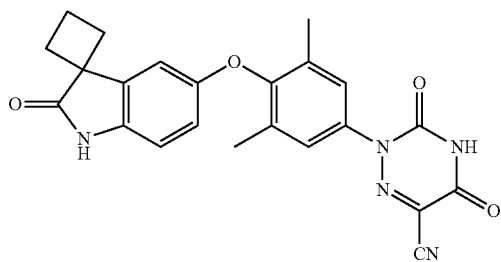 [SMILES: Cc1cc(-n2nc(C#N)c(=O)[nH]c2=O)cc(C)c1Oc1ccc2c(c1)C1(CCC1)C(=O)N2]

n-BuLi (10 mL, 16 mmol) was added to a solution of 5-bromoindolin-2-one (1 g, 4.72 mmol) in anhydrous THF (63 mL) under N2 at 0° C. The reaction mixture was stirred at 0° C. for 30 min. Then, TMEDA (2.42 mL, 16 mmol) and 1,3-diiodopropane (0.54 mL, 4.72 mmol) were added at 0° C. and the reaction mixture warmed to room temperature. The reaction mixture was stirred at rt for 28 h. The reaction mixture was quenched with sat. aq. NH$_4$Cl, diluted in EtOAc, washed with sat. aq. NH$_4$Cl (2×), washed with brine, dried over Na$_2$SO$_4$, the solids were removed by filtration and the filtrate was evaporated to dryness. The crude mixture was purified by flash chromatography on silica gel (0% to 5% CH$_3$OH in CH$_2$Cl$_2$) to give 5'-bromospiro[cyclobutane-1,3'-indolin]-2'-one (268 mg, 23%) as an orange solid. LC-MS (ESI, m/z): C$_{11}$H$_{10}$BrNO [M+H]+: 252. $^1$H-NMR (DMSO-d$_6$, 300 MHz): 2.14-2.25 (m, 2H), 2.27-2.42 (m, 4H), 6.74 (d, J=8.2 Hz, 1H), 7.33 (dd, J=8.3 Hz, 1.9 Hz, 1H), 7.75 (d, J=1.5 Hz, 1H), 10.36 (s, 1H) ppm.

A solution of 5'-bromo-1'H-spiro[cyclobutane-1,3'-indol]-2'-one (1 g, 3.97 mmol), DHP (3.34 g, 39.7 mmol) and TsOH (70 mg, 0.397 mmol) in DCM (10 mL) was stirred for overnight at 40° C. and quenched water (50 mL). The resulting mixture was extracted with DCM (3×30 mL). The combined organic layers were washed with brine (60 mL), dried over anhydrous Na$_2$SO$_4$. The solids were removed by filtration, and the filtrate was concentrated under reduced pressure. The residue was chromatographed on a silica gel column with ethyl acetate/petroleum ether (5/95) to provide 5'-bromo-1'-(oxan-2-yl)spiro[cyclobutane-1,3'-indol]-2'-one (800 mg, 60%) as a yellow solid. LC-MS (ESI, m/z): 336 [M+H]+.

A solution of 5'-bromo-1'-(oxan-2-yl)spiro[cyclobutane-1,3'-indol]-2'-one (800 mg, 2.38 mmol), 2-(5,5-dimethyl-1,3,2-dioxaborinan-2-yl)-5,5-dimethyl-1,3,2-dioxaborinane (1.07 g, 4.76 mmol), dichlorobis(triphenylphosphine)palladium (167 mg, 0.238 mmol) and potassium acetate (700 mg, 7.14 mmol) in DMSO (15 mL) was stirred for overnight at 60° C. under nitrogen and quenched with water (60 mL). The resulting mixture was extracted with ethyl acetate (3×30 mL). The combined organic layers were washed with brine (60 mL), dried over anhydrous Na$_2$SO$_4$. The solids were removed by filtration, and the filtrate was concentrated under reduced pressure. The residue was chromatographed on a silica gel column with petroleum ether/ethyl acetate (9/1) to provide 5'-(5,5-dimethyl-1,3,2-dioxaborinan-2-yl)-1'-(oxan-2-yl)spiro[cyclobutane-1,3'-indol]-2'-one (620 mg, 71%) as a yellow oil. LC-MS (ESI, m/z): 370 [M+H]+.

To a solution of 5'-(5,5-dimethyl-1,3,2-dioxaborinan-2-yl)-1'-(oxan-2-yl)spiro[cyclobutane-1,3'-indol]-2'-one (620 mg, 1.68 mmol) in THF (10 mL) was added acetic acid (2.52 g, 42.0 mmol) and hydrogen peroxide (1.43 g, 42.0 mmol). The resulting mixture was stirred for overnight at room temperature and quenched with NaHCO$_3$ (60 mL). The mixture was extracted with ethyl acetate (3×30 mL) and the organic layers were combined, washed with brine (60 mL), dried over anhydrous Na$_2$SO$_4$, the solids were removed by filtration and the filtrate was concentrated under reduced pressure. The residue was chromatographed on a silica gel column with ethyl acetate/petroleum ether (21/79) to provide 5'-hydroxy-1'-(oxan-2-yl)spiro[cyclobutane-1,3'-indol]-2'-one (270 mg, 59%) as a pink solid. LC-MS (ESI, m/z): 274 [M+H]+.

A solution of 5'-hydroxy-1'-(oxan-2-yl)spiro[cyclobutane-1,3'-indol]-2'-one (270 mg, 0.988 mmol), 2-fluoro-1,3-dimethyl-5-nitrobenzene (334 mg, 1.98 mmol) and potassium carbonate (273 mg, 1.98 mmol) in DMF (10 mL) was stirred for overnight at 120° C. The resulting mixture was quenched with water (50 mL). The resulting mixture was extracted with ethyl acetate (3×20 mL). The combined organic layers were washed with brine (60 mL), dried over anhydrous Na$_2$SO$_4$, the solids were removed by filtration and the filtrate was concentrated under reduced pressure. The residue was chromatographed on a silica gel column with ethyl acetate/petroleum ether (7/93) to provide 5'-(2,6-dimethyl-4-nitrophenoxy)-1'-(oxan-2-yl)spiro[cyclobutane-1,3'-indol]-2'-one (320 mg, 77%) as a white solid. LC-MS (ESI, m/z): 423[M+H]+.

A solution of 5'-(2,6-dimethyl-4-nitrophenoxy)-1'-(oxan-2-yl)spiro[cyclobutane-1,3'-indol]-2'-one (320 mg, 0.757 mmol) and trifluoroacetic acid (6 mL) in CH$_2$Cl$_2$ (6 mL) was stirred for 2 h at room temperature. The resulting mixture was quenched with sodium bicarbonate (40 mL). The resulting solution was extracted with ethyl acetate (3×20 mL). The combined organic layers were washed with brine (60 mL), dried over anhydrous Na$_2$SO$_4$, the solids were removed by filtration and the filtrate was concentrated under reduced pressure to provide 5'-(2,6-dimethyl-4-nitrophenoxy)-1'H-spiro[cyclobutane-1,3'-indol]-2'-one (310 mg crude) as a brown oil. LC-MS (ESI, m/z): 339 [M+H]+.

A solution of 5'-(2,6-dimethyl-4-nitrophenoxy)-1'H-spiro[cyclobutane-1,3'-indol]-2'-one (250 mg, 0.739 mmol), iron dust (247 mg, 4.43 mmol) and ammonium chloride (316 mg, 5.91 mmol) in ethanol (8 mL) and water (4 mL) was stirred for 3 h at 60° C. The resulting mixture was quenched with water (30 mL). The resulting solution was extracted with ethyl acetate (3×15 mL). The combined organic layers were washed with brine (40 mL), dried over anhydrous $Na_2SO_4$, the solids were removed by filtration and the filtrate was concentrated under reduced pressure to provide 5'-(4-amino-2,6-dimethylphenoxy)-1'H-spiro[cyclobutane-1,3'-indol]-2'-one (230 mg crude) as a brown oil. LC-MS (ESI, m/z): 309 [M+H]$^+$.

To a solution of 5'-(4-amino-2,6-dimethylphenoxy)-1'H-spiro[cyclobutane-1,3'-indol]-2'-one (230 mg, 0.746 mmol) in water (16 mL), HCl (conc., 6 mL) and acetic acid (24 mL) was added sodium nitrite (103 mg, 1.49 mmol) in water (5 mL) dropwise at 0° C. After the addition, the reaction was stirred at 0° C. for 45 min. Then the reaction mixture was added to a solution of ethyl N-(2-cyanoacetyl)carbamate (698 mg, 4.48 mmol) in water (16 mL) and pyridine (6 mL) at 0° C. quickly. The resulting mixture was stirred at 0° C. for 1 h and filtered. The filter cake was washed with water (50 mL) and petroleum ether (50 mL), dried under IR lamp to provide ethyl (2-cyano-2-(2-(3,5-dimethyl-4-((2'-oxospiro[cyclobutane-1,3'-indolin]-5'-yl)oxy)phenyl)hydrazineylidene)acetyl)carbamate (200 mg crude) as a yellow solid. LC-MS (ESI, m/z): 476 [M+H]$^+$.

A solution of ethyl N-[cyano[2-(3,5-dimethyl-4-{1'H-spiro[cyclobutane-1,3'-indol]-2'-oneoxy}phenyl)hydrazin-1-ylidene]carbonyl]carbamate (200 mg, 0.421 mmol) and potassium acetate (206 mg, 2.11 mmol) in DMA (8 mL) was stirred for 2 h at 120° C. under nitrogen atmosphere. The resulting solution was purified by Column: Kinetex EVO C18 Column, 30×150.5 µm; Mobile Phase A: Water (10 mmol/L $NH_4HCO_3$), Mobile Phase B: ACN; Flow rate: 60 mL/min; Gradient: 12% B to 42% B in 7 min; 254 nm; RT: 6.53 min) to provide 2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile (60.2 mg, 33%) as a yellow solid. $^1$H NMR (300 MHz, $CD_3OD$) δ 7.30 (s, 2H), 7.12 (d, J=2.1 Hz, 1H), 6.74 (d, J=8.4 Hz, 1H), 6.51-6.54 (m, 1H), 2.50-2.69 (m, 2H), 2.33-2.39 (m, 3H), 2.14-2.26 (m, 7H). LC-MS (ESI, m/z): 430 [M+H]$^+$. LC-MS, Method A, Rt: 0.708.

Example 4. Preparation of Compound 4

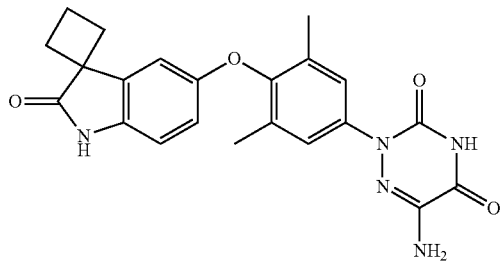 [SMILES: Cc1cc(-n2nc(N)c(=O)[nH]c2=O)cc(C)c1Oc1ccc2c(c1)C1(CCC1)C(=O)N2]

To a solution of 4-bromo-3,5-dimethylaniline (10 g, 50.0 mmol) in $CH_2Cl_2$ (150 mL) was added trifluoroacetic anhydride (14.70 g, 70.0 mmol) at 0° C. The reaction was stirred at 0° C. for 2 h and quenched with $NaHCO_3$ solution. The mixture was extracted with $CH_2Cl_2$ (2×150 mL) and the organic layers were combined, washed with $NaHCO_3$ solution, washed with brine (80 mL), dried over anhydrous sodium sulfate, the solids were removed by filtration and the filtrate was concentrated under reduced pressure to afford N-(4-bromo-3,5-dimethylphenyl)-2,2,2-trifluoroacetamide (14 g, 90%) as a gray solid. LC-MS (ESI, m/z): 296 [M+H]$^+$.

To a solution of N-(4-bromo-3,5-dimethylphenyl)-2,2,2-trifluoroacetamide (7.00 g, 23.6 mmol) in THF (200 mL) at −78° C. under a nitrogen atmosphere was added dropwise $CH_3Li/LiBr$ (33.1 mL, 33.1 mmol, 1M in diethyl ether). The mixture was stirred at −78° C. for 5 min then sec-BuLi (25.5 mL, 1.3M in hexane, 33.1 mmol) was added dropwise. After 5 min of stirring at −78° C., DMF (12.1 g, 165 mmol) was added dropwise. After the addition was complete, the mixture was allowed to warm to ambient temperature and stirred for 30 min. The mixture was quenched with water and was extracted with methylene chloride. The organic phase was washed with water and brine and was dried over anhydrous $Na_2SO_4$. The solvent was removed under reduced pressure to give the crude product. The crude product was chromatographed on a silica gel column with ethyl acetate/petroleum ether (⅓) to get 2,2,2-trifluoro-N-(4-formyl-3,5-dimethylphenyl)acetamide (1.5 g, 23%) as an orange solid. LC-MS (ESI, m/z): 246 [M+H]$^+$.

To a solution of 5-bromo-1,3-dihydroindol-2-one (3.00 g, 14.1 mmol) in THF (60 mL) was added n-butyllithium (3.08 g, 48.1 mmol) at 0° C. The reaction mixture was stirred at 0° C. for 30 min. Then TMEDA (5.59 g, 48.1 mmol) and 1,3-diiodopropane (4.19 g, 14.1 mmol) was added and the reaction was warmed to room temperature. The resulting solution was stirred at room temperature for overnight and quenched with $NH_4Cl$ solution. The mixture was extracted with ethyl acetate (3×100 mL) and the organic layers were combined, washed with brine, dried over anhydrous $Na_2SO_4$, the solids were removed by filtration and the filtrate was concentrated under reduced pressure. The residue was chromatographed on a silica gel column with ethyl acetate/petroleum ether (⅓) to get 5'-bromo-1'H-spiro[cyclobutane-1,3'-indol]-2'-one (600 mg, 16%) as an off-white solid. $^1$H NMR (300 MHz, DMSO-$d_6$) δ 10.36 (s, 1H), 7.74 (s, 1H), 7.33-7.36 (m, 1H), 6.73-6.76 (m, 1H), 2.12-2.46 (m, 6H). LC-MS (ESI, m/z): 252 [M+H]$^+$.

To a solution of 5'-bromo-1'H-spiro[cyclobutane-1,3'-indol]-2'-one (1.50 g, 5.95 mmol) in THF (30 mL) was added sodium hydride (357 mg, 60% in mineral oil, 8.92 mmol) at 0° C. Then the reaction was stirred at room temperature for 50 min and cooled to −78° C. n-BuLi (5.2 mL, 2.5M in hexane, 13.1 mmol) was added to the reaction at −78° C. and stirred at −78° C. for 1 h. Then a solution of 2,2,2-trifluoro-N-(4-formyl-3,5-dimethylphenyl)acetamide (1.46 g, 5.95 mmol) in THF (10 mL) was added to the reaction dropwise. Then the resulting mixture was warmed to room temperature and stirred at room temperature for 2 h and quenched with $NH_4Cl$ solution. The mixture was extracted with ethyl acetate (3×100 mL) and the organic layers were combined, washed with brine, dried over anhydrous $Na_2SO_4$, the solids were removed by filtration and the filtrate was concentrated under reduced pressure. The residue was chromatographed on a silica gel column with ethyl acetate/petroleum ether (1/1) to get 2,2,2-trifluoro-N-{4-[hydroxy(2'-oxo-1'H-spiro[cyclobutane-1,3'-indol]-5'-yl)methyl]-3,5-dimethylphenyl}acetamide (700 mg, 26%) as a yellow solid. LC-MS (ESI, m/z): 419 [M+H]$^+$.

To a solution of 2,2,2-trifluoro-N-{4-[hydroxy(2'-oxo-1'H-spiro[cyclobutane-1,3'-indol]-5'-yl)methyl]-3,5-dimethylphenyl}acetamide (700 mg, 1.67 mmol) in $CH_2Cl_2$ (50 mL) was added triethylsilane (1.17 g, 10.0 mmol) and TBSOTf (97.3 mg, 0.368 mmol) at 0° C. The reaction was stirred at room temperature for 2 h and quenched with $NaHCO_3$ solution. The resulting mixture was extracted with CH₂Cl₂ (3×50 mL) and the organic layers were combined, washed with brine, dried over anhydrous Na₂SO₄, the solids were removed by filtration and the filtrate was concentrated under reduced pressure to give N-(3,5-dimethyl-4-{2'-oxo-1'H-spiro[cyclobutane-1,3'-indol]-5'-ylmethyl}phenyl)-2,2,2-trifluoroacetamide (660 mg, 88%) as a yellow solid. LC-MS (ESI, m/z): 403 [M+H]⁺.

To a solution of N-(3,5-dimethyl-4-{2'-oxo-1'H-spiro[cyclobutane-1,3'-indol]-5'-ylmethyl}phenyl)-2,2,2-trifluoroacetamide (660 mg, 1.64 mmol) in CH₃OH (33 mL) was added NaOH (262 mg, 6.56 mmol) in H₂O (6.6 mL). The reaction was stirred at 60° C. overnight. The reaction was added water (50 mL) and extracted with CH₂Cl₂ (3×100 mL) and the organic layers were combined, washed with brine, dried over anhydrous sodium sulfate, the solids were removed by filtration and the filtrate was concentrated under reduced pressure to get 5'-[(4-amino-2,6-dimethylphenyl)methyl]-1'H-spiro[cyclobutane-1,3'-indol]-2'-one (500 mg, 90%) as a yellow solid. LC-MS (ESI, m/z): 307 [M+H]⁺.

To a solution of 5'-[(4-amino-2,6-dimethylphenyl)methyl]-1'H-spiro[cyclobutane-1,3'-indol]-2'-one (500 mg, 1.63 mmol) in acetic acid (42 mL), HCl (conc., 14 mL) and water (34 mL) was added sodium nitrite (236 mg, 3.43 mmol) in water (3 mL) at 0° C. The reaction was stirred at 0° C. for 45 min. Then the reaction mixture was added to a solution of ethyl N-(2-cyanoacetyl)carbamate (510 mg, 3.26 mmol) in pyridine (16 mL) and water (35 mL) which was stirred at 0° C. for 10 min. Then the resulting solution was stirred at 0° C. for 1 h and filtered. The precipitate was washed with H₂O (50 mL)/PE (50 mL) and dried under IR lamp to get ethyl (2-cyano-2-(2-(3,5-dimethyl-4-((2'-oxospiro[cyclobutane-1,3'-indolin]-5'-yl)methyl)phenyl)hydrazineylidene)acetyl)carbamate (580 mg, 71%) as a yellow solid. LC-MS (ESI, m/z): 474 [M+H]⁺.

To a solution of ethyl (2-cyano-2-(2-(3,5-dimethyl-4-((2'-oxospiro[cyclobutane-1,3'-indolin]-5'-yl)methyl)phenyl)hydrazineylidene)acetyl)carbamate (480 mg, 1.01 mmol) in DMA (10 mL) was added potassium acetate (497 mg, 5.07 mmol). The reaction was stirred at 120° C. for 2 h. The reaction was cooled to room temperature and added water (50 mL). The mixture was extracted with ethyl acetate (3×50 mL) and the organic layers were combined, washed with brine (50 mL), dried over anhydrous Na₂SO₄, the solids were removed by filtration and the filtrate was concentrated under reduced pressure to get 2-(3,5-dimethyl-4-{2'-oxo-1'H-spiro[cyclobutane-1,3'-indol]-5'-ylmethyl}phenyl)-3,5-dioxo-4H-1,2,4-triazine-6-carbonitrile (450 mg, crude) as a yellow oil. The crude (250 mg) was purified by Prep-HPLC (Column: Kinetex EVO prep C18, 30×150, 5 µm; Mobile Phase A: Water (50 mmol/L NH₄HCO₃), Mobile Phase B: CH₃CN; Flow rate: 60 mL/min; Gradient: 5% B to 38% B in 9 min; 254 nm; RT: 6.67 min) to get 2-(3,5-dimethyl-4-{2'-oxo-1'H-spiro[cyclobutane-1,3'-indol]-5'-ylmethyl}phenyl)-3,5-dioxo-4H-1,2,4-triazine-6-carbonitrile (108.4 mg, 47.74%) as a yellow solid. ¹H NMR (300 MHz, methanol-d₄) δ 7.30 (s, 1H), 7.22 (s, 2H), 6.70-6.77 (m, 2H), 4.13 (s, 2H), 2.49-2.57 (m, 2H), 2.17-2.36 (m, 10H). LC-MS (ESI, m/z): 428 [M+H]⁺.

To a solution of 2-(3,5-dimethyl-4-((2'-oxospiro[cyclobutane-1,3'-indolin]-5'-yl)methyl)phenyl)-3,5-dioxo-2,3,4,5-tetrahydro-1,2,4-triazine-6-carbonitrile (150 mg, 0.324 mmol) in acetic acid (5 mL) was added HCl (conc., 2.5 mL). The reaction was stirred at 100° C. for 1 h. The reaction was concentrated under reduced pressure and added NaHCO₃ solution (50 mL). The mixture was extracted with ethyl acetate (3×40 mL) and the organic layers were discarded. The PH value of the aqueous layers was adjusted to 3 with concentrated HCl. The resulting solution was extracted with ethyl acetate (2×50 mL). The organic layers were combined, washed with brine, dried over anhydrous Na₂SO₄, the solids were removed by filtration and the filtrate was concentrated under reduced pressure to afford 2-(3,5-dimethyl-4-((2'-oxospiro[cyclobutane-1,3'-indolin]-5'-yl)methyl)phenyl)-3,5-dioxo-2,3,4,5-tetrahydro-1,2,4-triazine-6-carboxylic acid (80 mg, 48%) as a yellow solid. LC-MS (ESI, m/z): 447 [M+H]⁺.

To a solution of 2-(3,5-dimethyl-4-{2'-oxo-1'H-spiro[cyclobutane-1,3'-indol]-5'-ylmethyl}phenyl)-3,5-dioxo-4H-1,2,4-triazine-6-carboxylic acid (100 mg, 0.224 mmol) in t-butanol (5 mL) was added triethylamine (1812 mg, 1.79 mmol) and diphenylphosphoryl azide (308 mg, 1.12 mmol). The reaction was stirred at 80° C. overnight and concentrated under reduced pressure. The crude was dissolved in ethyl acetate (100 mL) and the organic layers were combined, washed with NaHCO₃ solution (3×50 mL) and brine (50 mL), dried over anhydrous Na₂SO₄, the solids were removed by filtration and the filtrate was concentrated under reduced pressure to afford t-butyl N-[2-(3,5-dimethyl-4-{2'-oxo-1'H-spiro[cyclobutane-1,3'-indol]-5'-ylmethyl}phenyl)-3,5-dioxo-4H-1,2,4-triazin-6-yl]carbamate (110 mg, 85.40%) as a yellow oil. LC-MS (ESI, m/z): 518 [M+H]⁺.

To a solution of t-butyl N-[2-(3,5-dimethyl-4-{2'-oxo-1'H-spiro[cyclobutane-1,3'-indol]-5'-ylmethyl}phenyl)-3,5-dioxo-4H-1,2,4-triazin-6-yl]carbamate (100 mg, 0.193 mmol) in CH₂Cl₂ (6 mL) was added trifluoroacetic acid (2 mL). The reaction was stirred at room temperature for 2 h and concentrated under reduced pressure. The sample was purified by Prep-HPLC (Column: XBridge Prep OBD C18 Column, 30×150 mm 5 µm; Mobile Phase A: Water (10 mmol/L NH₄HCO₃), Mobile Phase B: CH₃CN; Flow rate: 60 mL/min; Gradient: 14% B to 40% B in 9 min; 254 nm; RT: 8.50 min) to afford 6-amino-2-(3,5-dimethyl-4-{2'-oxo-1'H-spiro[cyclobutane-1,3'-indol]-5'-ylmethyl}phenyl)-4H-1,2,4-triazine-3,5-dione (4) (18.3 mg, 22%) as an off-white solid. ¹H NMR (400 MHz, DMSO-d₆) δ 11.93 (br, 1H), 10.14 (s, 1H), 7.35 (s, 1H), 7.21 (s, 2H), 6.66 (d, J=8.0 Hz, 1H), 6.60 (d, J=8.0 Hz, 1H), 6.29 (s, 2H), 4.00 (s, 2H), 2.32-2.43 (m, 2H), 2.12-2.25 (m, 10H). LC-MS (ESI, m/z): 418 [M+H]⁺. LC-MS, Method B, Rt: 0.925.

Example 5. Preparation of Compound 5

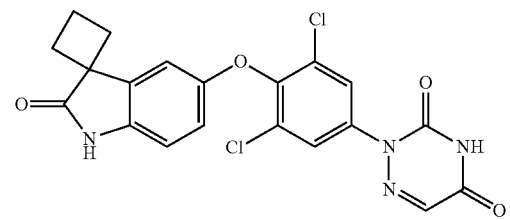 [SMILES: O=C1Nc2ccc(Oc3c(Cl)cc(-n4ncc(=O)[nH]c4=O)cc3Cl)cc2C12CCC2]

Cyclobutanecarbonyl chloride (23.7 mL, 207 mmol) was added dropwise to a solution of phenylhydrazinium chloride (30 g, 207 mmol) and pyridine (50 mL, 622 mmol) in anhydrous DMF (100 mL) at −20° C. under N₂. The reaction mixture was stirred at −20° C. for 2 h. The reaction mixture was poured in ice cold water (1.2 L) and the precipitate was filtered off, washed with water (3×) and dried at 60° C. under reduced pressure to give N-phenylcyclobutanecarbohydrazide (39 g, 99%) as a white solid which was used without further purification in the next step. ¹H-NMR (DMSO-d₆, 300 MHz): 1.73-1.83 (m, 1H), 1.87-1.98 (m, 1H), 2.02-2.22 (m, 4H), 3.11 (quint., J=8.3 Hz, 1H), 6.62-6.72 (m, 3H), 7.08-7.17 (m, 2H), 9.48 (s, 1H) ppm. LCMS: $C_{11}H_{14}N_2O$ $[M+H]^+$: 191

CaO (115 g, 2049 mmol) was added to a solution of N-phenylcyclobutanecarbohydrazide (39 g, 205 mmol) in quinoline (39 mL) under $N_2$. The reaction mixture was stirred at 260° C. for 17 h. The reaction mixture was cooled in an ice bath and quenched by slow addition of 37% HCl until reaching an acidic pH. The residue was diluted with EtOAc and the precipitate was removed by filtration. The organic phase was separated and washed with 37% HCl (2×) and brine (2×) and dried over $MgSO_4$. The solids were removed by filtration and the filtrate was evaporated to dryness. The crude mixture was purified by flash chromatography on silica gel (10% to 30% EtOAc in CyH) to give spiro[cyclobutane-1,3'-indolin]-2'-one 3 (4.6 g, 13%) as a yellow solid. $^1$H-NMR (DMSO-$d_6$, 300 MHz): 2.15-2.32 (m, 4H), 2.35-2.46 (m, 2H), 6.78 (d, J=7.4 Hz, 1H), 6.99 (t, J=7.4 Hz, 1H), 7.15 (t, J=7.6 Hz, 1H), 7.53 (d, J=7.4 Hz, 1H), 10.20 (s, 1H) ppm. LCMS: $C_{11}H_{11}NO$ $[M+H]^+$: 174

NBS (5.67 g, 31.9 mmol) was added to a solution of spiro[cyclobutane-1,3'-indolin]-2'-one (4.6 g, 26.6 mmol) in MeCN (48 mL) under $N_2$. The reaction mixture was stirred at room temperature for 1 h. The reaction mixture was poured into crushed ice and the precipitate was filtered and washed with water. The precipitate was dissolved in EtOAc and dried over $Na_2SO_4$. The solids were removed by filtration and the filtrate was evaporated to dryness providing 5'-bromospiro[cyclobutane-1,3'-indolin]-2'-one (6.3 g, 94%) as a beige product which was used without further purification in the next step. $^1$H-NMR (DMSO-$d_6$, 300 MHz): 2.11-2.24 (m, 2H), 2.26-2.42 (m, 4H), 6.74 (d, J=8.3 Hz, 1H), 7.33 (dd, J=7.9, 1.5 Hz, 1H), 7.75 (d, J=1.2 Hz, 1H), 10.34 (s, 1H) ppm. LCMS: $C_{11}H_{10}BrNO$ $[M+H]^+$: 252/254

3,4-dihydro-2 h-pyran (45 mL, 497 mmol) was added to a solution of 5'-bromospiro[cyclobutane-1,3'-indolin]-2'-one (6.27 g, 24.9 mmol) and p-TsOH·$H_2O$ (1.89 g, 9.95 mmol) in anhydrous DCM (150 mL) under $N_2$. The reaction mixture was stirred at 40° C. for 30 h. Extra 3,4-dihydro-2 h-pyran (45 mL, 497 mmol) and p-TsOH·$H_2O$ (1.89 g, 9.95 mmol) were added and the reaction mixture was stirred at 40° C. for 10 h. The reaction mixture was quenched with sat. aq. $NaHCO_3$ (200 mL). The phases were separated, and the aqueous phase was extracted with DCM (2×). The combined organic layers were washed with brine and dried over $Na_2SO_4$. The solids were removed by filtration and the filtrate was evaporated to dryness. The crude mixture was purified by flash chromatography on silica gel (0% to 20% EtOAc in CyH) to give 5'-bromo-1'-(tetrahydro-2H-pyran-2-yl)spiro[cyclobutane-1,3'-indolin]-2'-one (5.21 g, 62%) as a yellow oil. $^1$H-NMR (DMSO-$d_6$, 300 MHz): 1.44-1.68 (m, 5H), 1.84-1.96 (m, 1H), 2.12-2.26 (m, 2H), 2.29-2.46 (m, 4H), 3.58 (t, J=11.0 Hz, 1H), 4.00 (d, J=11.1 Hz, 1H), 5.36 (d, J=11.1 Hz, 1H), 7.17 (d, J=8.4 Hz, 1H), 7.40 (dd, J=8.4, 1.7 Hz, 1H), 7.84 (d, J=1.6 Hz, 1H) ppm. LC-MS: $C_{16}H_{18}BrNO_2$ $[M+H]^+$: 336/338.

A mixture of 5'-bromo-1'-(tetrahydro-2H-pyran-2-yl)spiro[cyclobutane-1,3'-indolin]-2'-one (5.2 g, 15.5 mmol), bis(neopentyl glycolato)diboron (10.5 g, 46.5 mmol), KOAc (4.56 g, 46.5 mmol) and $PdCl_2[P(o-Tol)_3]_2$ (0.12 g, 0.15 mmol) in anhydrous DMSO (103 mL) under N2 was stirred at 90° C. for 22 h. Extra KOAc (6.96 g, 71.0 mmol), bis(neopentyl glycolato)diboron (16.0 g, 71.0 mmol) and $PdCl_2[P(o-Tol)_3]_2$ (0.24 g, 0.30 mmol) were added and the reaction mixture was stirred at 90° C. for 20 h. The reaction mixture was diluted in EtOAc, washed with brine (2×) and dried over $Na_2SO_4$. The solids were removed by filtration and the filtrate was evaporated to dryness. The crude mixture was purified by flash chromatography on silica gel (0% to 20% EtOAc in CyH) to give 5'-(5,5-dimethyl-1,3,2-dioxaborinan-2-yl)-1'-(tetrahydro-2H-pyran-2-yl)spiro[cyclobutane-1,3'-indolin]-2'-one (5.72 g, quant.) as a white solid. $^1$H-NMR (DMSO-$d_6$, 300 MHz): 0.97 (s, 6H), 1.44-1.68 (m, 5H), 1.87-1.95 (m, 1H), 2.10-2.38 (m, 6H), 3.59 (t, J=11.0 Hz, 1H), 3.76 (s, 4H), 4.01 (d, J=11.1 Hz, 1H), 5.37 (d, J=11.0 Hz, 1H), 7.21 (d, J=7.9 Hz, 1H), 7.59 (d, J=7.7 Hz, 1H), 7.87 (s, 1H) ppm.

$H_2O_2$ 30% (40 mL, 387 mmol) and AcOH (22 mL, 387 mmol) were added to a solution of 5'-(5,5-dimethyl-1,3,2-dioxaborinan-2-yl)-1'-(tetrahydro-2H-pyran-2-yl)spiro[cyclobutane-1,3'-indolin]-2'-one (5.72 g, 15.5 mmol) in THF (97 mL) under $N_2$. The reaction mixture was stirred at room temperature for 1 h. The reaction mixture was neutralized with sat. aq. $NaHCO_3$ and extracted with EtOAc (3×). The combined organic layers were washed with brine and dried over $Na_2SO_4$. The solids were removed by filtration and the filtrate was evaporated to dryness. The crude mixture was purified by flash chromatography on silica gel (15% to 30% EtOAc in CyH) to give 5'-hydroxy-1'-(tetrahydro-2H-pyran-2-yl)spiro[cyclobutane-1,3'-indolin]-2'-one (1.65 g, 39%) as a white solid. $^1$H-NMR (DMSO-$d_6$, 300 MHz): 1.43-1.73 (m, 5H), 1.85-1.96 (m, 1H), 2.07-2.31 (m, 6H), 3.55 (t, J=10.6 Hz, 1H), 3.98 (d, J=11.2 Hz, 1H), 5.32 (d, J=10.7 Hz, 1H), 6.62 (d, J=8.5 Hz, 1H), 6.98-7.04 (m, 1H), 9.15 (br s, 1H) ppm. LC-MS: $C_{16}H_{19}NO_3$ $[M+H]^+$: 274

A mixture of 5'-hydroxy-1'-(tetrahydro-2H-pyran-2-yl)spiro[cyclobutane-1,3'-indolin]-2'-one (1.65 g, 6.04 mmol), 1,3-dichloro-2-fluoro-5-nitrobenzene (1.27 g, 6.04 mmol, CAS: 3107-19-5) and $K_2CO_3$ (1.25 g, 9.055 mmol) in DMF (44 mL) under N2 was stirred at 60° C. for 1 h. The reaction mixture was diluted in water and extracted with EtOAc (3×). The combined organic phases were washed with sat. aq. $NH_4Cl$ and dried over $Na_2SO_4$. The solids were removed by filtration and the filtrate was evaporated to dryness. The crude mixture was purified by flash chromatography on silica gel (4% to 10% MeOH in DCM) to give 5'-(2,6-dichloro-4-nitrophenoxy)-1'-(tetrahydro-2H-pyran-2-yl)spiro[cyclobutane-1,3'-indolin]-2'-one (1.96 g, 70%) as a yellow oil. $^1$H-NMR (DMSO-$d_6$, 300 MHz): 1.38-1.74 (m, 5H), 1.84-1.94 (m, 1H), 2.08-2.22 (m, 2H), 2.26-2.41 (m, 4H), 3.51-3.62 (m, 1H), 3.98 (d, J=11.2 Hz, 1H), 5.35 (d, J=11.0 Hz, 1H), 6.69 (dd, J=8.6, 2.4 Hz, 1H), 7.15 (d, J=8.6 Hz, 1H), 7.35 (d, J=2.4 Hz, 1H), 8.55 (s, 2H) ppm. LC-MS: $C_{22}H_{20}Cl_2N_2O_5$ $[M+H]^+$: 463/465

TFA (3 mL, 40.1 mmol) was added to a solution of 5'-(2,6-dichloro-4-nitrophenoxy)-1'-(tetrahydro-2H-pyran-2-yl)spiro[cyclobutane-1,3'-indolin]-2'-one (1.86 g, 4.01 mmol) in anhydrous DCM (39 mL) under $N_2$. The reaction mixture was stirred at room temperature for 18 h. Extra TFA (3 mL, 40.1 mmol) was added and the reaction mixture was stirred at 50° C. for 18 h. The reaction mixture was evaporated to dryness and co-evaporated with MeCN (3×) to give 5'-(2,6-dichloro-4-nitrophenoxy)spiro[cyclobutane-1,3'-indolin]-2'-one (1.52 g, quant.) as a dark green solid which was used without further purification in the next step. $^1$H-NMR (DMSO-$d_6$, 300 MHz): 2.06-2.22 (m, 2H), 2.27-2.39 (m, 4H), 6.59 (dd, J=8.3, 2.3 Hz, 1H), 6.71 (d, J=8.5 Hz, 1H), 7.30 (d, J=2.0 Hz, 1H), 8.54 (s, 2H), 10.19 (s, 1H) ppm. LC-MS: $C_{17}H_{12}Cl_2N_2O_4$ $[M-H]^-$: 377/379

Fe (1.12 g, 20.0 mmol) was added to a solution of 5'-(2,6-dichloro-4-nitrophenoxy)spiro[cyclobutane-1,3'-indolin]-2'-one (1.52 g, 4.01 mmol) and $NH_4Cl$ (2.14 g, 40.1 mmol) in EtOH (27 mL) and water (14 mL) under $N_2$. The reaction mixture was stirred at 70° C. for 1 h. The reaction mixture was filtered over celite and diluted in EtOAc. The resulting solution was washed with water and brine and dried over $Na_2SO_4$. The solids were removed by filtration and the filtrate was evaporated to dryness providing 5'-(4-amino-2,6-dichlorophenoxy)spiro[cyclobutane-1,3'-indolin]-2'-one (1.19 g, 85%) as a brown solid which was used without further purification in the next step. $^1$H-NMR (DMSO-$d_6$, 300 MHz): 2.05-2.32 (m, 4H), 2.33-2.45 (m, 2H), 5.62 (br s, 2H), 6.42 (d, J=8.1 Hz, 1H), 6.66 (d, J=8.4 Hz, 1H), 6.71 (s, 2H), 7.15 (s, 1H), 10.10 (s, 1H) ppm. LC-MS: $C_{17}H_{14}Cl_2N_2O_2$ [M+H]$^+$: 349/351.

A solution of $NaNO_2$ (402.5 mg, 5.83 mmol) in water (58 mL) was added to a solution of 5'-(4-amino-2,6-dichlorophenoxy)spiro[cyclobutane-1,3'-indolin]-2'-one (970 mg, 2.78 mmol) in HCl 37% (24 mL), AcOH (95 mL) and water (58 mL) at 0° C. under $N_2$. The reaction mixture was stirred at 0° C. for 1 h. In parallel, a solution of ethyl N-(2-cyanoacetyl)carbamate (650.6 mg, 4.17 mmol) in water (71 mL) and pyridine (24 mL) was stirred at 0° C. for 15 min. The first reaction mixture was quickly added to the second one and the resulting reaction mixture was stirred at 0° C. for 1 h. The reaction mixture was diluted in water (50 mL). The precipitate was filtered, washed with water, dissolved in EtOAc and dried over $Na_2SO_4$. The solids were removed by filtration and the filtrate was evaporated to dryness to give ethyl (2-cyano-2-(2-(3,5-dichloro-4-((2'-oxospiro[cyclobutane-1,3'-indolin]-5'-yl)oxy)phenyl)hydrazineylidene)acetyl)carbamate (972 mg, 68%) as a dark orange solid which was used without further purification in the next step. $^1$H-NMR (DMSO-$d_6$, 400 MHz): 1.27 (t, J=7.1 Hz, 3H), 2.07-2.31 (m, 4H), 2.35-2.43 (m, 2H), 4.20 (q, J=7.1 Hz, 2H), 6.49 (dd, J=8.4, 2.7 Hz, 1H), 6.69 (d, J=8.4 Hz, 1H), 7.21 (d, J=2.5 Hz, 1H), 8.04 (s, 2H), 10.15 (s, 1H), 10.92 (s, 1H), 12.15 (br s, 1H) ppm. LC-MS: $C_{23}H_{19}Cl_2N_5O_5$ [M+H]$^+$: 516/518.

A mixture of ethyl (2-cyano-2-(2-(3,5-dichloro-4-((2'-oxospiro[cyclobutane-1,3'-indolin]-5'-yl)oxy)phenyl)hydrazineylidene)acetyl)carbamate (942 mg, 1.82 mmol) and KOAc (358.1 mg, 3.65 mmol) in DMA (31 mL) under N2 was stirred at 120° C. for 2 h. The reaction mixture was cooled to room temperature, diluted in water (50 mL) and extracted with EtOAc (3×). The combined organic phases were washed with brine (3×) and dried over $MgSO_4$. The solids were removed by filtration and the filtrate was evaporated to dryness to give 2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carbonitrile (856 mg, quant.) as a brown oil which was used without further purification in the next step. $^1$H-NMR (DMSO-$d_6$, 400 MHz): 2.10-2.24 (m, 2H), 2.28-2.40 (m, 4H), 6.49 (dd, J=8.4, 2.7 Hz, 1H), 6.70 (d, J=8.3 Hz, 1H), 7.33 (d, J=2.7 Hz, 1H), 7.80 (s, 2H), 10.18 (s, 1H), 13.26 (br s, 1H) ppm. LC-MS: $C_{21}H_{13}Cl_2N_5O_4$ [M–H]$^-$: 468/470.

A solution of 2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carbonitrile (586 mg, 1.82 mmol) in HCl (conc., 1.4 mL) and AcOH (2.8 mL) under N2 was stirred at 120° C. for 4 h. The reaction mixture was cooled to room temperature and water (50 mL) was added. The precipitate was filtered, washed with water, dissolved in MeOH and evaporated to dryness to give 2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carboxylic acid (890 mg, 99%) as a brown solid which was used without further purification in the next step. $^1$H-NMR (DMSO-$d_6$, 300 MHz): 2.09-2.23 (m, 2H), 2.27-2.41 (m, 4H), 6.48 (dd, J=8.5, 2.2 Hz, 1H), 6.70 (d, J=8.4 Hz, 1H), 7.33 (d, J=1.6 Hz, 1H), 7.84 (s, 2H), 10.17 (s, 1H), 12.69 (br s, 1H) ppm. LC-MS: $C_{21}H_{14}Cl_2N_4O_6$ [M–H]$^-$: 487/489.

A solution of 2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carboxylic acid (317 mg, 0.65 mmol) in mercaptoacetic acid (1.1 mL) under N2 was stirred at 100° C. for 18 h. The reaction mixture was cooled to room temperature and diluted in water. The precipitate was filtered, washed with water, dissolved in methanol and evaporated to dryness. The crude mixture was purified by flash chromatography on silica gel (0% to 5% methanol in DCM) to give, after co-evaporation with ethanol (3×), 2-(3,5-dichloro-4-((2'-oxospiro[cyclobutane-1,3'-indolin]-5'-yl)oxy)phenyl)-1,2,4-triazine-3,5(2H,4H)-dione (5) (162 mg, 76%) as a yellow solid. $^1$H-NMR (DMSO-$d_6$, 400 MHz): 2.10-2.24 (m, 2H), 2.27-2.35 (m, 2H), 2.36-2.42 (m, 2H), 6.46 (dd, J=8.4, 2.7 Hz, 1H), 6.70 (d, J=8.5 Hz, 1H), 7.31 (d, J=2.7 Hz, 1H), 7.71 (s, 1H), 7.83 (s, 2H), 10.17 (s, 1H), 12.50 (br s, 1H) ppm. LC-MS: $C_{20}H_{14}Cl_2N_4O_4$ [M+H]$^+$: 445/447.

Example 6. Preparation of Compound 6

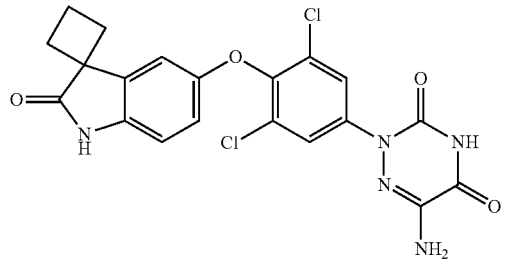 [SMILES: Nc1nn(-c2cc(Cl)c(Oc3ccc4c(c3)C3(CCC3)C(=O)N4)c(Cl)c2)c(=O)[nH]c1=O]

Triethylamine (0.41 mL, 2.94 mmol) and diphenyl phosphoryl azide (0.48 mL, 2.21 mmol) were added to a solution of 2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carboxylic acid (360 mg, 0.74 mmol) in t-butanol (10 mL) under $N_2$. The resulting mixture was stirred at 85° C. for 20 h. The reaction mixture was quenched with sat. aq. $NH_4Cl$ (40 mL) and extracted with EtOAc (2×). The combined organic phases were washed with sat. aq. $NH_4Cl$ and brine and dried over $Na_2SO_4$. The solids were removed by filtration and the filtrate was evaporated to dryness. The crude mixture was purified by flash chromatography on silica gel (0% to 10% MeOH in DCM) to give tert-butyl (2-(3,5-dichloro-4-((2'-oxospiro[cyclobutane-1,3'-indolin]-5'-yl)oxy)phenyl)-3,5-dioxo-2,3,4,5-tetrahydro-1,2,4-triazin-6-yl)carbamate (76 mg, 18%) as a beige solid. $^1$H-NMR (DMSO-$d_6$, 300 MHz): 1.45 (s, 9H), 2.07-2.24 (m, 2H), 2.25-2.43 (m, 4H), 6.47 (dd, J=8.2, 2.3 Hz, 1H), 6.70 (d, J=8.6 Hz, 1H), 7.31 (s, 1H), 7.91 (s, 2H), 9.00 (br s, 1H), 10.16 (s, 1H), 12.61 (br s, 1H) ppm. LC-MS: $C_{25}H_{23}Cl_2N_5O_6$ [M+H]$^+$: 560/562.

A solution of tert-butyl (2-(3,5-dichloro-4-((2'-oxospiro[cyclobutane-1,3'-indolin]-5'-yl)oxy)phenyl)-3,5-dioxo-2,3,4,5-tetrahydro-1,2,4-triazin-6-yl)carbamate (76 mg, 0.14 mmol) in 4N HCl in 1,4-dioxane (0.68 mL, 2.71 mmol) under N2 was stirred at room temperature for 20 h. The reaction mixture was evaporated to dryness and the crude mixture was purified by flash chromatography on silica gel (2% to 10% MeOH in DCM) to afford 6-amino-2-(3,5- dichloro-4-((2'-oxospiro[cyclobutane-1,3'-indolin]-5'-yl)oxy)phenyl)-1,2,4-triazine-3,5(2H,4H)-dione (6) (51 mg, 82%) as a yellow solid. $^1$H-NMR (DMSO-$d_6$, 400 MHz): 2.06-2.24 (m, 2H), 2.25-2.35 (m, 2H), 2.35-2.43 (m, 2H), 6.46 (dd, J=8.4, 2.7 Hz, 1H), 6.54 (br s, 2H), 6.70 (d, J=8.5 Hz, 1H), 7.28 (d, J=2.7 Hz, 1H), 7.90 (s, 2H), 10.16 (s, 1H), 12.28 (s, 1H) ppm. LC-MS: $C_{20}H_{15}Cl_2N_5O_4$ [M+H]$^+$: 460/462.

Example 7. Preparation of Compound 7

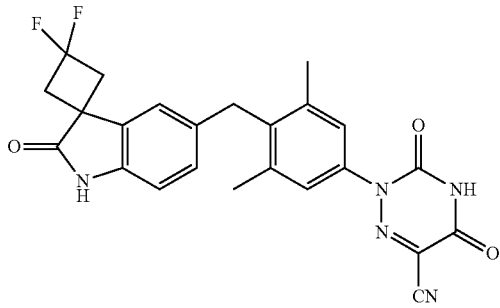 [SMILES: Cc1cc(-n2nc(C#N)c(=O)[nH]c2=O)cc(C)c1Cc1ccc2c(c1)C1(CC(F)(F)C1)C(=O)N2]

Into a 500 mL round-bottom flask were added 3,3-difluorocyclobutane-1-carboxylic acid (27.0 g, 198 mmol), phenylhydrazine HCl (25.8 g, 238 mmol), DMAP (31.5 g, 258 mmol), DCM (300 mL) and EDCI (49.4 g, 258 mmol) at room temperature. The resulting mixture was stirred for overnight at room temperature. The reaction was quenched with water at room temperature. The resulting mixture was extracted with DCM (3×200 mL). The combined organic layers were washed with brine (200 mL), dried over anhydrous sodium sulfate. After filtration, the filtrate was concentrated under reduced pressure. The residue was purified by silica gel column chromatography, eluted with EA/PE (½) to afford 3,3-difluoro-N'-phenylcyclobutane-1-carbohydrazide (36 g, 80%) as a yellow solid. LC-MS (ESI, m/z): 227 [M+H]$^+$.

Into a 1 L, 3-necked round-bottom flask were added 3,3-difluoro-N'-phenylcyclobutane-1-carbohydrazide (35 g, 155 mmol), quinoline (500 mL) and CaO (4.95 g, 88.5 mmol) at room temperature. The resulting mixture was stirred for 3 h at 230° C. The reaction was quenched with HCl (6M) at room temperature. The resulting mixture was diluted with water (1 L), and extracted with EtOAc (3×1 L). The combined organic layers were washed with brine (2×500 mL), and dried over anhydrous sodium sulfate. The solids were removed by filtration, and the filtrate was concentrated under reduced pressure. The residue was purified by silica gel column chromatography, eluted with EA/PE (¼) to afford 3,3-difluoro-1'H-spiro[cyclobutane-1,3'-indol]-2'-one (5 g, 15%) as a brown solid. $^1$H NMR (400 MHz, DMSO-$d_6$) δ 10.59 (s, 1H), 7.40 (d, J=6.0 Hz, 1H), 7.19-7.28 (m, 1H), 7.01-7.09 (m, 1H), 6.87 (d, J=6.0 Hz, 1H), 2.99-3.18 (m, 2H), 2.80-2.95 (m, 2H). LC-MS (ESI, m/z): 210 [M+H]$^+$.

To a solution of 3,3-difluoro-1'H-spiro[cyclobutane-1,3'-indol]-2'-one (4 g, 19.1 mmol) in MeCN (60 mL) was added NBS (4.08 g, 22.9 mmol) at room temperature. The resulting mixture was stirred for 2 h at room temperature. The mixture was poured into crushed ice, the formed solid was filtered and washed with water (300 mL). The resulting solid was dried under vacuum to afford 5'-bromo-3,3-difluoro-1'H-spiro[cyclobutane-1,3'-indol]-2'-one (4 g, 73%) as a brown solid. $^1$H NMR (400 MHz, DMSO-$d_6$) δ 10.72 (s, 1H), 7.51 (s, 1H), 7.41-7.45 (m, 1H), 6.83 (d, J=8.0 Hz, 1H), 2.95-3.14 (m, 4H). LC-MS (ESI, m/z): 286 [M−H]$^-$.

To a solution of 5'-bromo-3,3-difluoro-1'H-spiro[cyclobutane-1,3'-indol]-2'-one (1 g, 3.47 mmol) in THF (20 mL) was added NaH (0.208 g, 60% in mineral oil, 5.21 mmol) at 0° C. The resulting mixture was stirred for 50 min at room temperature under $N_2$. Then to the above mixture was added n-BuLi (3.1 mL, 2.5M in hexane, 7.64 mmol) dropwise. The mixture was stirred for 1 h at −78° C. Then 2,2,2-trifluoro-N-(4-formyl-3,5-dimethylphenyl)acetamide (0.85 g, 3.47 mmol) in THF (10 mL) was added dropwise over 5 min at −78° C. The resulting mixture was stirred for 1 h at room temperature and quenched with water (20 mL). The resulting mixture was extracted with EA (3×50 mL). The combined organic layers were washed with brine (2×50 mL), dried over anhydrous sodium sulfate, the solids were removed by filtration and the filtrate was concentrated under reduced pressure. The residue was purified by silica gel column chromatography, eluted with EA/PE (½) to afford N-(4-{3,3-difluoro-2'-oxo-1'H-spiro[cyclobutane-1,3'-indol]-5'-yl(hydroxy)methyl}-3,5-dimethylphenyl)-2,2,2-trifluoroacetamide (450 mg, 29%) as a yellow solid. $^1$H NMR (300 MHz, DMSO-$d_6$) δ 11.10 (s, 1H), 10.53 (s, 1H), 7.51 (s, 1H), 7.31 (s, 2H), 6.75-6.84 (m, 2H), 6.10 (d, J=3.0 Hz, 1H), 5.88 (d, J=6.0 Hz, 1H), 2.25 (s, 6H), 2.00 (s, 4H). LC-MS (ESI, m/z): 455 [M+H]$^+$.

To a solution of N-(4-{3,3-difluoro-2'-oxo-1'H-spiro[cyclobutane-1,3'-indol]-5'-yl(hydroxy)methyl}-3,5-dimethylphenyl)-2,2,2-trifluoroacetamide (450 mg, 0.99 mmol) in DCM (20 mL) was added triethylsilane (691 mg, 5.94 mmol) and TBSOTf (57.6 mg, 0.22 mmol) at 0° C. under nitrogen atmosphere. The resulting mixture was stirred for 2 h at room temperature and quenched with NaHCO$_3$ (aq.). The resulting mixture was extracted with DCM (3×30 mL). The combined organic layers were washed with brine (50 mL), dried over anhydrous sodium sulfate. After filtration, the filtrate was concentrated under reduced pressure to afford N-(4-{3,3-difluoro-2'-oxo-1'H-spiro[cyclobutane-1,3'-indol]-5'-ylmethyl}-3,5-dimethylphenyl)-2,2,2-trifluoroacetamide (400 mg crude) as a yellow solid. LC-MS (ESI, m/z): 439 [M+H]$^+$.

Into a 40 mL vial were added N-(4-{3,3-difluoro-2'-oxo-1'H-spiro[cyclobutane-1,3'-indol]-5'-ylmethyl}-3,5-dimethylphenyl)-2,2,2-trifluoroacetamide (210 mg, 0.48 mmol), methanol (18 mL) and sodium hydroxide (76.6 mg, 1.92 mmol) in water (2 mL) at room temperature. The resulting mixture was stirred for 2 h at 60° C. under nitrogen atmosphere and quenched with water at room temperature. The resulting mixture was extracted with DCM (3×30 mL). The combined organic layers were washed with brine (40 mL), dried over anhydrous sodium sulfate. After filtration, the filtrate was concentrated under reduced pressure. The residue was purified by prep-TLC with PE/EA (⅓) to afford 5'-[(4-amino-2,6-dimethylphenyl)methyl]-3,3-difluoro-1'H-spiro[cyclobutane-1,3'-indol]-2'-one (150 mg, 91%) as a yellow solid. LC-MS (ESI, m/z): 343 [M+H]$^+$.

To a solution of 5'-[(4-amino-2,6-dimethylphenyl)methyl]-3,3-difluoro-1'H-spiro[cyclobutane-1,3'-indol]-2'-one (150 mg, 0.438 mmol) in water (10 mL), concentrated HCl (10 mL) and acetic acid (15 mL) was added NaNO$_2$ (121 mg, 1.75 mmol) in water (4 mL) dropwise at 0° C. After the addition, the reaction was stirred at 0° C. for 45 min. Then the reaction mixture was added to a solution of ethyl N-(2-cyanoacetyl)carbamate (171 mg, 1.09 mmol) in water (10 mL) and pyridine (8 mL) at 0° C. quickly. The resulting mixture was stirred at 0° C. for 1 h and filtered. The filter cake was washed with water (100 mL) and PE (100 mL), dried under IR lamp to provide ethyl (2-cyano-2-(2-(4-((3,3-difluoro-2'-oxospiro[cyclobutane-1,3'-indol]-5'-yl)methyl)-3,5-dimethylphenyl)hydrazineylidene)acetyl)carbamate (150 mg crude) as a yellow solid. LC-MS (ESI, m/z): 510 [M+H]$^+$.

Into a 40 mL vial were added ethyl (2-cyano-2-(2-(4-((3,3-difluoro-2'-oxospiro[cyclobutane-1,3'-indol]-5'-yl)methyl)-3,5-dimethylphenyl)hydrazineylidene)acetyl)carbamate (150 mg, 0.29 mmol), DMA (8 mL) and potassium acetate (144 mg, 1.47 mmol) at room temperature. The resulting mixture was stirred for 2 h at 120° C. The reaction was quenched with water at room temperature. The resulting mixture was extracted with EtOAc (3×20 mL). The combined organic layers were washed with brine (20 mL), dried over anhydrous sodium sulfate. After filtration, the filtrate was concentrated under reduced pressure to afford 2-(4-((3,3-difluoro-2'-oxospiro[cyclobutane-1,3'-indol]-5'-yl)methyl)-3,5-dimethylphenyl)-3,5-dioxo-2,3,4,5-tetrahydro-1,2,4-triazine-6-carbonitrile (7) (130 mg crude) as a yellow solid. The crude product (50 mg) was purified by prep-HPLC with the following conditions (Xselect CSH OBD Column 30×150 mm 5 μm; Mobile Phase A: Water (50 MMOL/L NH$_4$HCO$_3$), Mobile Phase B: ACN; Flow rate: 60 mL/min; Gradient: 18% B to 48% B in 9 min, 48% B; Wave Length: 254 nm; RT1 (min): 7.4) to afford 2-(4-((3,3-difluoro-2'-oxospiro[cyclobutane-1,3'-indol]-5'-yl)methyl)-3,5-dimethylphenyl)-3,5-dioxo-2,3,4,5-tetrahydro-1,2,4-triazine-6-carbonitrile (7) (13.5 mg, 26%) as a yellow solid. $^1$H NMR (400 MHz, DMSO-d$_6$) δ 13.00 (br, 1H), 10.52 (s, 1H), 7.17-7.27 (m, 3H), 6.67-6.76 (m, 2H), 4.04 (s, 2H), 3.01-3.12 (m, 2H), 2.80-2.89 (m, 2H), 2.26 (s, 6H). LC-MS (ESI, m/z): 462 [M−H]$^-$.

Example 8. Synthesis of Compound 8

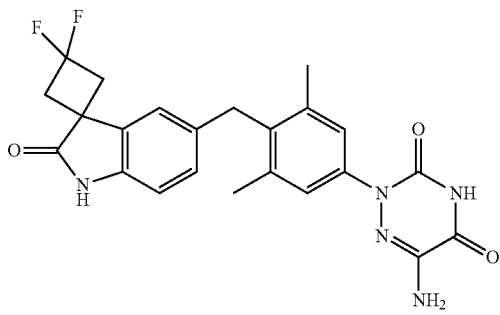 [SMILES: Cc1cc(-n2nc(N)c(=O)[nH]c2=O)cc(C)c1Cc1ccc2c(c1)C1(CC(F)(F)C1)C(=O)N2]

To a solution of 2-(4-((3,3-difluoro-2'-oxospiro[cyclobutane-1,3'-indol]-5'-yl)methyl)-3,5-dimethylphenyl)-3,5-dioxo-2,3,4,5-tetrahydro-1,2,4-triazine-6-carbonitrile (80 mg, 0.173 mmol) in acetic acid (2 mL) was added concentrated HCl (1 mL). The resulting mixture was stirred 3 h at 120° C. and concentrated reduced pressure. The residue was diluted with saturated sodium bicarbonate solution (20 mL), the resulting mixture was extracted with EA (2×15 mL) and the organic layers were discarded. The PH value of the aqueous layers was adjusted to 5-6 with concentrated hydrochloride acid. The resulting solution was extracted with EA (3×15 mL) and the organic layers were combined, washed with brine (40 mL), dried over anhydrous sodium sulfate, filtered and concentrated under reduced pressure to provide 2-(4-{3,3-difluoro-2'-oxo-1'H-spiro[cyclobutane-1,3'-indol]-5'-ylmethyl}-3,5-dimethylphenyl)-3,5-dioxo-4H-1,2,4-triazine-6-carboxylic acid (70 mg crude) as an orange solid. LC-MS (ESI, m/z): 483 [M+H]$^+$.

Into a 8 mL vial were added 2-(4-{3,3-difluoro-2'-oxo-1'H-spiro[cyclobutane-1,3'-indol]-5'-ylmethyl}-3,5-dimethylphenyl)-3,5-dioxo-4H-1,2,4-triazine-6-carboxylic acid (80 mg, 0.17 mmol), diphenylphosphoryl azide (137 mg, 0.498 mmol), triethylamine (100 mg, 0.99 mmol) and t-BuOH (3 mL) at room temperature. The resulting mixture was stirred for overnight at 85° C. and concentrated under reduced pressure. The resulting mixture was dissolved in EtOAc (30 mL) and washed with sodium bicarbonate solution (2×20 mL) and brine (20 mL). The organic layer was dried over anhydrous sodium sulfate, filtered and concentrated under reduced pressure. The crude was purified by a C18 column with ACN/H$_2$O (6/4) to afford t-butyl N-[2-(4-{3,3-difluoro-2'-oxo-1'H-spiro[cyclobutane-1,3'-indol]-5'-ylmethyl}-3,5-dimethylphenyl)-3,5-dioxo-4H-1,2,4-triazin-6-yl]carbamate (15 mg, 16%) as a yellow solid. LC-MS (ESI, m/z): 554 [M+H]+.

Into a 8 mL vial was added t-butyl N-[2-(4-{3,3-difluoro-2'-oxo-1'H-spiro[cyclobutane-1,3'-indol]-5'-ylmethyl}-3,5-dimethylphenyl)-3,5-dioxo-4H-1,2,4-triazin-6-yl]carbamate (10 mg, 0.02 mmol), DCM (2 mL) and TFA (1 mL) at room temperature. The resulting mixture was stirred for 2 h at room temperature and concentrated under reduced pressure. The crude product (10 mg) was purified by prep-HPLC with the following conditions (YMC-Actus Triart C18 ExRS, 30 mm×150 mm, 5 μm; Mobile Phase A: Water (10 MMOL/L NH$_4$HCO$_3$+0.1% NH$_3$·H$_2$O), Mobile Phase B: ACN; Flow rate: 60 mL/min; Gradient: 23 B to 43 B in 7 min, 43 B to B in min, 254 nm; RT1:5.62) to afford 6-amino-2-(4-{3,3-difluoro-2'-oxo-1'H-spiro[cyclobutane-1,3'-indol]-5'-ylmethyl}-3,5-dimethylphenyl)-4H-1,2,4-triazine-3,5-dione (8) (3.6 mg, 43%) as a white solid. $^1$H NMR (400 MHz, DMSO-d$_6$) δ 12.04 (br, 1H), 10.51 (s, 1H), 7.22-7.26 (m, 3H), 6.74 (d, J=8.0 Hz, 1H), 6.67 (d, J=8.0 Hz, 1H), 6.27 (br, 2H), 4.00 (s, 2H), 2.95-3.18 (m, 2H), 2.80-2.86 (m, 2H), 2.23 (s, 6H). LC-MS (ESI, m/z): 454 [M+H]$^+$.

Example 9. Preparation of Compound 9

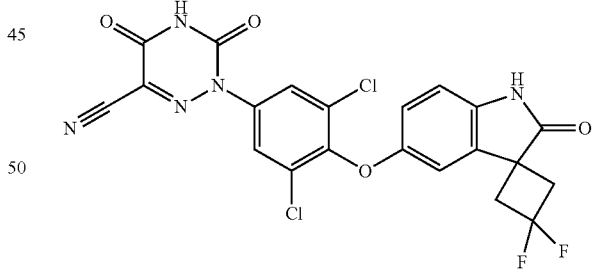

A solution of 5'-bromo-3,3-difluoro-1'H-spiro[cyclobutane-1,3'-indol]-2'-one (2.00 g, 6.94 mmol), 2-(5,5-dimethyl-1,3,2-dioxaborinan-2-yl)-5,5-dimethyl-1,3,2-dioxaborinane (3.14 g, 13.9 mmol), Pd(PPh3)$_2$Cl$_2$ (0.97 g, 1.39 mmol) and potassium acetate (2.04 g, 20.8 mmol) in DMSO (30 mL) was stirred for overnight at 80° C. under nitrogen atmosphere and quenched with water (200 mL). The resulting mixture was extracted with EA (3×100 mL). The combined organic layers were washed with brine (200 mL), dried over anhydrous sodium sulfate. After filtration, the filtrate was concentrated under reduced pressure. The residue was purified by silica gel column chromatography, eluted with PE/EA (2/1) to afford 5'-(5,5-dimethyl-1,3,2-dioxaborinan-2-yl)-3,3-difluoro-1'H-spiro[cyclobutane-1,3'-indol]-2'-one (2 g, 90/a) as a yellow solid. LC-MS (ESI, m/z): 322[M+H]$^+$.

A solution of 5'-(5,5-dimethyl-1,3,2-dioxaborinan-2-yl)-3,3-difluoro-1'H-spiro[cyclobutane-1,3'-indol]-2'-one (2 g, 6.23 mmol) and $H_2O_2$ (5.30 g, 156 mmol) in acetic acid (30 mL) was stirred for 3 h at room temperature and quenched with water (200 mL). The resulting mixture was extracted with EA (3×80 mL). The combined organic layers were washed with brine (200 mL), dried over anhydrous sodium sulfate. After filtration, the filtrate was concentrated under reduced pressure. The crude was purified by a C18 column with ACN/$H_2O$ (6/4) to afford 3, 3-difluoro-5'-hydroxy-1'H-spiro [cyclobutane-1, 3'-indol]-2'-one (0.8 g, 57%) as a yellow solid. $^1$H NMR (400 MHz, DMSO-$d_6$) δ 10.30 (s, 1H), 9.15 (s, 1H), 6.89 (d, J=4.0 Hz, 1H), 6.60-6.69 (m, 2H), 2.97-3.17 (m, 2H), 2.74-2.91 (m, 2H). LC-MS (ESI, m/z): 226 [M+H]$^+$.

To a solution of 3,3-difluoro-5'-hydroxy-1'H-spiro[cyclobutane-1,3'-indol]-2'-one (800 mg, 3.55 mmol) in MeCN (40 mL) was added t-BuOK (399 mg, 3.55 mmol) at 0° C. The resulting mixture was stirred for 30 min at 0° C. and concentrated under reduced pressure. To the above mixture was added 1,3-dichloro-2-fluoro-5-nitrobenzene (821 mg, 3.91 mmol) in DMF (40 mL) at room temperature. The resulting mixture was stirred for additional 3 h at 110° C. The reaction was quenched with water (200 mL). The resulting mixture was extracted with EA (3×100 mL). The combined organic layers were washed with brine (200 mL), dried over anhydrous sodium sulfate, the solids were removed by filtration, and the filtrate was concentrated under reduced pressure. The residue was purified by silica gel column chromatography, eluted with PE/EA (1:1) to afford 5'-(2, 6-dichloro-4-nitrophenoxy)-3,3-difluoro-1'H-spiro[cyclobutane-1,3'-indol]-2'-one (510 mg, 35%) as a yellow solid. $^1$H NMR (400 MHz, DMSO-$d_6$) δ 10.58 (s, 1H), 8.56 (s, 2H), 7.14 (d, J=4.0 Hz, 1H), 6.79 (d, J=8.0 Hz, 1H), 6.61-6.65 (m, 1H), 3.03-3.14 (m, 2H), 2.87-2.96 (m, 2H). LC-MS (ESI, m/z): 415 [M+H]$^+$.

A solution of 5'-(2,6-dichloro-4-nitrophenoxy)-3,3-difluoro-1'H-spiro[cyclobutane-1,3'-indol]-2'-one (510 mg, 1.23 mmol), $NH_4Cl$ (526 mg, 9.82 mmol), Fe (412 mg, 7.37 mmol) in water (11 mL) and ethanol (22 mL) was stirred for overnight at 60° C. The resulting mixture was quenched with water (30 mL). The resulting solution was extracted with EA (3×50 mL). The combined organic layers were washed with brine (100 mL), dried over anhydrous sodium sulfate, the solids were removed by filtration and the filtrate was concentrated under reduced pressure to afford 5'-(4-amino-2,6-dichlorophenoxy)-3,3-difluoro-1'H-spiro[cyclobutane-1,3'-indol]-2'-one (440 mg crude) as a yellow solid. LC-MS (ESI, m/z): 385 [M+H]$^+$.

To a solution of 5'-(4-amino-2,6-dichlorophenoxy)-3,3-difluoro-1'H-spiro[cyclobutane-1,3'-indol]-2'-one (440 mg, 1.14 mmol) in water (25 mL), concentrated HCl (12 mL) and acetic acid (30 mL) was added $NaNO_2$ (315 mg, 4.57 mmol) in water (5 mL) dropwise at 0° C. After the addition, the reaction was stirred at 0° C. for 45 min. Then the reaction mixture was added to a solution of ethyl N-(2-cyanoacetyl) carbamate (446 mg, 2.86 mmol) in water (30 mL) and pyridine (15 mL) at 0° C. quickly. The resulting mixture was stirred at 0° C. for 1 h and filtered. The filter cake was washed with water (30 mL) and PE (30 mL), dried under IR lamp to provide ethyl (2-cyano-2-(2-(3,5-dichloro-4-((3,3-difluoro-2'-oxospiro[cyclobutane-1,3'-indolin]-5'-yl)oxy)phenyl)hydrazineylidene)acetyl)carbamate (515 mg crude) as an orange solid. LC-MS (ESI, m/z): 552 [M+H]$^+$.

A solution of ethyl (2-cyano-2-(2-(3,5-dichloro-4-((3,3-difluoro-2'-oxospiro[cyclobutane-1,3'-indolin]-5'-yl)oxy) phenyl)hydrazineylidene)acetyl)carbamate (500 mg, 0.90 mmol) and sodium acetate (371 mg, 4.52 mmol) in acetic acid (10 mL) was stirred for 2 h at 120° C. The reaction mixture was poured into water (300 mL) and isolated by filtration. The precipitate was washed with water (100 mL) and dried with IR lamp to get to afford 2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile (400 mg, 87.28%) as a yellow solid. The crude product (15 mg) was purified by prep-HPLC (Xselect CSH OBD Column 30×150 mm×5 μm; Mobile Phase A: Water (50 MMOL/L $NH_4HCO_3$), Mobile Phase B: ACN; Flow rate: 60 mL/min; Gradient: 18% B to 48% B in 9 min, 48% B; Wave Length: 254 nm; RT1 (min): 7.40; to afford 2-(3,5-dichloro-4-((3,3-difluoro-2'-oxospiro[cyclobutane-1, 3'-indolin]-5'-yl)oxy)phenyl)-3,5-dioxo-2,3,4,5-tetrahydro-1,2,4-triazine-6-carbonitrile (9×6.6 mg, 48%) as a yellow solid. $^1$H NMR (400 MHz, $CD_3OD$) δ 7.77 (s, 2H), 7.18 (s, 1H), 6.82 (d, J=8.5 Hz, 1H), 6.60-6.63 (m, 1H), 3.15-3.21 (m, 2H), 2.84-2.86 (m, 2H). LC-MS (ESI, m/z): 506 [M+H]$^+$.

Example 11. Preparation of Compound 11

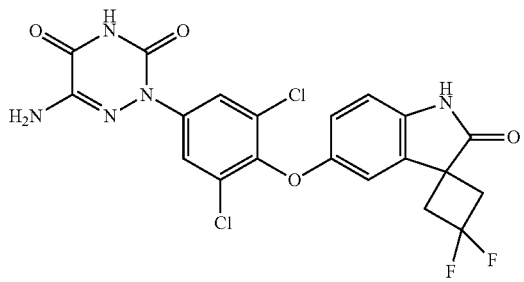 [SMILES: Nc1nn(-c2cc(Cl)c(Oc3ccc4c(c3)C3(CC(F)(F)C3)C(=O)N4)c(Cl)c2)c(=O)[nH]c1=O]

A solution of 2-(3,5-dichloro-4-((3,3-difluoro-2'-oxospiro [cyclobutane-1,3'-indolin]-5'-yl)oxy)phenyl)-3,5-dioxo-2,3, 4,5-tetrahydro-1,2,4-triazine-6-carbonitrile (400 mg, 0.79 mmol) in concentrated HCl (3 mL) and acetic acid (6 mL) was stirred for 2 h at 120° C. The resulting liquid was dried under vacuum. $NaHCO_3$ (sat., aq., 50 mL) was added. The mixture was extracted with EA (3×50 mL). The organic layers were discarded. The aqueous phase was neutralized to pH=3 with concentrated HCl. The resulting mixture was extracted with EA (3×50 mL). The combined organic layers were washed with brine (100 mL), dried over anhydrous sodium sulfate, the solids were removed by filtration and the filtrate was concentrated under reduced pressure to afford 2-(3,5-dichloro-4-((3,3-difluoro-2'-oxospiro[cyclobutane-1, 3'-indolin]-5'-yl)oxy)phenyl)-3,5-dioxo-2,3,4,5-tetrahydro-1,2,4-triazine-6-carboxylic acid (300 mg crude) as a yellow solid. LC-MS (ESI, m/z): 525 [M+H]$^+$.

A solution of 2-(3,5-dichloro-4-((3,3-difluoro-2'-oxospiro [cyclobutane-1,3'-indolin]-5'-yl)oxy)phenyl)-3,5-dioxo-2,3, 4,5-tetrahydro-1,2,4-triazine-6-carboxylic acid (300 mg, 0.57 mmol), diphenylphosphoryl azide (472 mg, 1.71 mmol), triethylamine (345 mg, 3.43 mmol) in tert-butanol (10 mL) was stirred for overnight at 85° C. and concentrated under reduced pressure. The residue was dissolved in EA (100 mL) and saturated sodium bicarbonate solution (100 mL). The resulting mixture was extracted with EA (3×100 mL). The combined organic layers were washed with brine (200 mL), dried over anhydrous sodium sulfate. After filtration, the filtrate was concentrated under reduced pressure to provide t-butyl (2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazin-6-yl)carbamate (300 mg crude) as a yellow solid. LC-MS (ESI, m/z): 596 [M+H]$^+$.

To a solution of tert-butyl (2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazin-6-yl)carbamate (300 mg, 0.50 mmol) in dichloromethane (6 mL) was added trifluoroacetic acid (2.5 mL). The reaction was stirred overnight at room temperature and concentrated under reduced pressure. The residue was dissolved in THF (5 mL). The crude product (300 mg) was purified by prep-HPLC with the following conditions (XBridge Shield RP18 OBD Column, 30×150 mm, 5 µm; Mobile Phase A: Water (10 mmol/L NH$_4$HCO$_3$+0.1% NH$_3$·H$_2$O), Mobile Phase B: ACN; Flow rate: 60 mL/min; Gradient: 14% B to 35% B in 7 min, 35% B; Wave Length: 254 nm; RT1 (min): 9.47) to afford 6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione (11) (56 mg, 22%) as a white solid. $^1$H NMR (400 MHz, DMSO-d$_6$) δ 12.33 (s, 1H), 10.56 (s, 1H), 7.91 (s, 2H), 7.06 (d, J=2.6 Hz, 1H), 6.81 (d, J=8.5 Hz, 1H), 6.51-6.59 (m, 3H), 3.02-3.15 (m, 2H), 2.82-2.95 (m, 2H). LC-MS (ESI, m/z): 496 [M+H]$^+$.

Example 12. Preparation of Compound 12

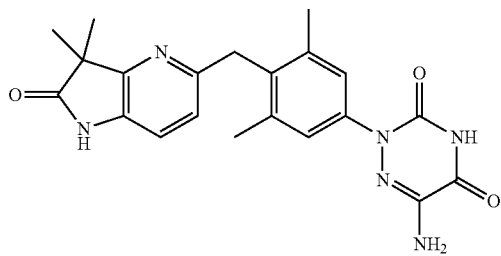 [SMILES: Cc1cc(-n2nc(N)c(=O)[nH]c2=O)cc(C)c1Cc1ccc2c(n1)C(C)(C)C(=O)N2]

n-BuLi (722 mg, 11.3 mmol) was added dropwise to a mixture of 5-bromo-1H,3H-pyrrolo[3,2-b]pyridin-2-one (600 mg, 2.82 mmol) and TMEDA (1.31 g, 11.3 mmol) in THF (10 mL) at −78° C. The mixture was stirred at −78° C. for 1 h, then CH$_3$I (1.60 g, 11.3 mmol) was added dropwise. The mixture was warmed to room temperature and stirred for 4 h. The reaction was quenched with saturated aqueous NH$_4$Cl (20 mL). The resulting mixture was extracted with EA (3×30 mL). The combined organic layers were washed with brine (60 mL), dried over anhydrous sodium sulfate. After filtration, the filtrate was concentrated under reduced pressure. The residue was purified by silica gel column chromatography, eluted with EA/PE (18/82) to provide 5-bromo-3,3-dimethyl-1H-pyrrolo[3,2-b]pyridin-2-one (380 mg, 56%) as a white solid. LC-MS (ESI, m/z): 241 [M+H]$^+$.

To a solution of 5-bromo-3,3-dimethyl-1H-pyrrolo[3,2-b]pyridin-2-one (380 mg, 1.58 mmol) in THF (15 mL) was added sodium hydride (94.5 mg, 60% in mineral oil, 2.36 mmol) at 0° C. under nitrogen atmosphere. The resulting reaction mixture was stirred at room temperature for 50 min. Then, the mixture was cooled to −78° C. and n-BuLi (222 mg, 3.47 mmol) was added dropwise and the reaction mixture was stirred at −78° C. for 1 h. Then a solution of 2,2,2-trifluoro-N-(4-formyl-3,5-dimethylphenyl)acetamide (386 mg, 1.58 mmol) in THF (10 mL) was added dropwise at −78° C. The reaction mixture was allowed to slowly warm up to room temperature and was stirred for 100 min. The reaction mixture was quenched with NH$_4$Cl (10 mL). The resulting mixture was extracted with EA (3×20 mL). The combined organic layers were washed with brine (40 mL), dried over anhydrous sodium sulfate and concentrated under reduced pressure. The residue was purified by silica gel column chromatography, eluted with PE/EA (63/37) to provide N-[4-({3,3-dimethyl-2-oxo-1H-pyrrolo[3,2-b]pyridin-5-yl}(hydroxy)methyl)-3,5-dimethylphenyl]-2,2,2-trifluoroacetamide (280 mg, 44%) as a brown solid. LC-MS (ESI, m/z): 408 [M+H]$^+$.

To a solution of N-[4-({3,3-dimethyl-2-oxo-1H-pyrrolo[3,2-b]pyridin-5-yl}(hydroxy)methyl)-3,5-dimethylphenyl]-2,2,2-trifluoroacetamide (100 mg, 0.245 mmol) in dichloromethane (10 mL) were added triethylsilane (171 mg, 1.47 mmol) and TBSOTf (129 mg, 0.490 mmol) at 0° C. under nitrogen atmosphere. The resulting mixture was stirred for overnight at 50° C. and quenched with sodium bicarbonate (20 mL). The mixture was extracted with dichloromethane (3×20 mL) and the organic layers were combined, washed with brine (40 mL), dried over anhydrous sodium sulfate and concentrated under reduced pressure to provide N-[4-({3,3-dimethyl-2-oxo-1H-pyrrolo[3,2-b]pyridin-5-yl}methyl)-3,5-dimethylphenyl]-2,2,2-trifluoroacetamide (70 mg crude) as a brown oil. LC-MS (ESI, m/z): 392 [M+H]$^+$.

A solution of N-[4-({3,3-dimethyl-2-oxo-1H-pyrrolo[3,2-b]pyridin-5-yl}methyl)-3,5-dimethylphenyl]-2,2,2-trifluoroacetamide (70 mg, 0.179 mmol) and sodium hydroxide (28.6 mg, 0.716 mmol) in MeOH (11 mL) and water (1.1 mL) was stirred for overnight at 60° C. under nitrogen atmosphere. The resulting mixture was quenched with water (20 mL). The resulting mixture was extracted with dichloromethane (3×20 mL). The combined organic layers were washed with brine (40 mL), dried over anhydrous sodium sulfate and concentrated under reduced pressure. The residue was purified by prep-TLC petroleum ether/EA (3/1) to provide 5-[(4-amino-2,6-dimethylphenyl)methyl]-3,3-dimethyl-1H-pyrrolo[3,2-b]pyridin-2-one (40 mg crude) as a brown oil. LC-MS (ESI, m/z): 296[M+H]$^+$.

To a solution of 5-[(4-amino-2,6-dimethylphenyl)methyl]-3,3-dimethyl-1H-pyrrolo[3,2-b]pyridin-2-one (40 mg, 0.135 mmol) in water (3 mL), HCl (conc., 1 mL) and acetic acid (4 mL) was added NaNO$_2$ (18.7 mg, 0.270 mmol) in water (1 mL) dropwise at 0° C. After the addition, the reaction was stirred at 0° C. for 45 min. Then the reaction mixture was added to a solution of ethyl N-(2-cyanoacetyl)carbamate (42.3 mg, 0.270 mmol) in water (6 mL) and pyridine (3 mL) at 0° C. quickly. The resulting mixture was stirred at 0° C. for 1 h. The resulting mixture was extracted with EA (3×20 mL). The combined organic layers were washed with brine (40 ml), dried over anhydrous sodium sulfate and concentrated under reduced pressure to provide ethyl (2-cyano-2-(2-(4-((3,3-dimethyl-2-oxo-2,3-dihydro-1H-pyrrolo[3,2-b]pyridin-5-yl)methyl)-3,5-dimethylphenyl)hydrazineylidene)acetyl)carbamate (40 mg crude) as a brown oil. LC-MS (ESI, m/z): 463 [M+H]$^+$.

A solution of ethyl (2-cyano-2-(2-(4-((3,3-dimethyl-2-oxo-2,3-dihydro-1H-pyrrolo[3,2-b]pyridin-5-yl)methyl)-3,5-dimethylphenyl)hydrazineylidene)acetyl)carbamate (40 mg, 0.086 mmol) and potassium acetate (42.4 mg, 0.430 mmol) in DMA (3 mL) was stirred for 2 h at 120° C. The resulting mixture was quenched with water (20 mL). The resulting solution was extracted with EA (3×20 mL). The combined organic layers were washed with brine (40 mL), dried over anhydrous sodium sulfate, filtered and concentrated under reduced pressure to provide 2-[4-({3,3-dimethyl-2-oxo-1H-pyrrolo[3,2-b]pyridin-5-yl}methyl)-3,5-dimethylphenyl]-3,5-dioxo-4H-1,2,4-triazine-6-carbonitrile (40 mg crude) as a brown oil. LC-MS (ESI, m/z): 417 [M+H]$^+$.

To a solution of 2-[4-({3,3-dimethyl-2-oxo-1H-pyrrolo[3,2-b]pyridin-5-yl}methyl)-3,5-dimethylphenyl]-3,5-dioxo-4H-1,2,4-triazine-6-carbonitrile (30 mg, 0.072 mmol) in acetic acid (2 mL) was added conc. HCl (1 mL). The resulting mixture was stirred 4 h at 100° C. and concentrated reduced pressure. The residue was diluted with saturated sodium bicarbonate solution (20 mL), the resulting mixture was extracted with EA (2×15 mL) and the organic layers were discarded. The pH value of the aqueous layers was adjusted to 5-6 with conc. HCl. The resulting solution was extracted with EA (3×15 mL) and the organic layers were combined, washed with brine (40 mL), dried over anhydrous sodium sulfate, filtered and concentrated under reduced pressure to provide 2-[4-({3,3-dimethyl-2-oxo-1H-pyrrolo[3,2-b]pyridin-5-yl}methyl)-3,5-dimethylphenyl]-3,5-dioxo-4H-1,2,4-triazine-6-carboxylic acid (20 mg crude) as a brown solid. LC-MS (ESI, m/z): 436 [M+H]$^+$.

To a solution of 2-[4-({3,3-dimethyl-2-oxo-1H-pyrrolo[3,2-b]pyridin-5-yl}methyl)-3,5-dimethylphenyl]-3,5-dioxo-4H-1,2,4-triazine-6-carboxylic acid (20 mg, 0.046 mmol) in t-butanol (3 mL) was added triethylamine (23.2 mg, 0.230 mmol) and diphenylphosphoryl azide (37.9 mg, 0.138 mmol). The reaction was stirred at 85° C. overnight and concentrated under reduced pressure. The residue was dissolved in EA (40 mL) and washed with sodium bicarbonate solution (2×20 mL) and brine (40 mL). The organic layer was dried over anhydrous sodium sulfate, filtered and concentrated under reduced pressure to provide t-butyl N-{2-[4-({3,3-dimethyl-2-oxo-1H-pyrrolo[3,2-b]pyridin-5-yl}methyl)-3,5-dimethylphenyl]-3,5-dioxo-4H-1,2,4-triazin-6-yl}carbamate (10 mg crude) as a brown oil. LC-MS (ESI, m/z): 507 [M+H]$^+$.

A solution of t-butyl N-{2-[4-({3,3-dimethyl-2-oxo-1H-pyrrolo[3,2-b]pyridin-5-yl}methyl)-3,5-dimethylphenyl]-3,5-dioxo-4H-1,2,4-triazin-6-yl}carbamate (10 mg, 0.020 mmol) and trifluoroacetic acid (0.5 mL) in dichloromethane (2 mL) was stirred for overnight at room temperature and concentrated under reduced pressure. The crude product (10 mg) was purified by prep-HPLC with the following conditions (XBridge Shield RP18 OBD Column, 19×250 mm, 10 μm; Mobile Phase A: water (10 mmol/L NH$_4$HCO$_3$+0.1% NH$_3$·H$_2$O), Mobile Phase B: ACN; Flow rate: 25 mL/min; Gradient: 10 B to 30 B in 9 min, 254 nm; RT1:7.31) to provide 6-amino-2-[4-({3,3-dimethyl-2-oxo-1H-pyrrolo[3,2-b]pyridin-5-yl}methyl)-3,5-dimethylphenyl]-4H-1,2,4-triazine-3,5-dione (12) (0.3 mg, 4%) as a white solid. $^1$H NMR (300 MHz, DMSO-d$_6$) δ 10.43 (s, 1H), 7.20 (s, 2H), 7.06 (d, J=8.1 Hz, 1H), 6.57 (d, J=8.1 Hz, 1H), 6.24 (br, 2H), 4.09 (s, 2H), 2.27 (s, 6H), 1.25 (s, 6H). LC-MS (ESI, m/z): 407 [M+H]$^+$.

Example 13. Preparation of Compound 13

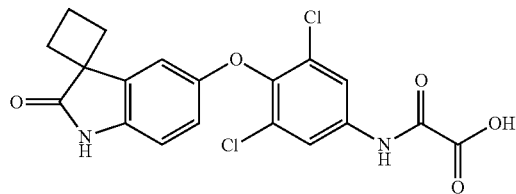 [SMILES: O=C(O)C(=O)Nc1cc(Cl)c(Oc2ccc3c(c2)C2(CCC2)C(=O)N3)c(Cl)c1]

To a solution of 5'-(4-amino-2,6-dichlorophenoxy)-1'H-spiro[cyclobutane-1,3'-indol]-2'-one (60 mg, 0.17 mmol) in DCM (15 mL) was added ethyl chloroglyoxylate (28.2 mg, 0.21 mmol) and pyridine (27.2 mg, 0.34 mmol) at room temperature. The resulting mixture was stirred for 2 h at room temperature and quenched with water (15 mL). The resulting mixture was extracted with dichloromethane (3×20 mL). The combined organic layers were washed with brine (40 mL), dried over anhydrous sodium sulfate. After filtration, the filtrate was concentrated under reduced pressure to afford ethyl 2-((3,5-dichloro-4-((2'-oxospiro[cyclobutane-1,3'-indolin]-2-yl)oxy)phenyl)amino)-2-oxoacetate (70 mg, crude) as a yellow solid. LC-MS (ESI, m/z): 449 [M+H]$^+$.

To a solution of ethyl 2-((3,5-dichloro-4-((2'-oxospiro[cyclobutane-1,3'-indolin]-2-yl)oxy)phenyl)amino)-2-oxoacetate (80 mg, 0.18 mmol) in THF (12 mL) was added sodium hydroxide (42.7 mg, 1.07 mmol) in water (12 mL). The resulting mixture was stirred for 2 h at room temperature. The mixture was acidified to pH=3 with HCl. The resulting mixture was extracted with EA (3×20 mL). The combined organic layers were washed with brine (20 mL), dried over anhydrous sodium sulfate. After filtration, the filtrate was concentrated under reduced pressure. The crude product (80 mg) was purified by prep-HPLC with the following conditions (XBridge Shield RP18 OBD Column, 30×150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 12% B to 42% B in 10 min, 42% B; Wave Length: 254 nm; Rt: 5.82 min; to afford 2-((3,5-dichloro-4-((2'-oxospiro[cyclobutane-1,3'-indolin]-5'-yl)oxy)phenyl)amino)-2-oxoacetic acid (13) (13.5 mg, 18%) as a white solid. $^1$H NMR (400 MHz, DMSO-d$_6$) δ 10.57 (br, 1H), 10.15 (s, 1H), 8.11 (s, 2H), 7.23 (s 2H), 6.67 (d, J=8.4 Hz, 1H), 6.43-6.45 (m, 1H), 2.11-2.42 (m, 6H). LC-MS (ESI, m/z): 421 [M+H]$^+$.

Example 14. Preparation of Compound 14

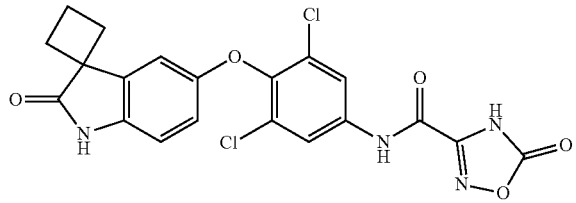 [SMILES: O=C(Nc1cc(Cl)c(Oc2ccc3c(c2)C2(CCC2)C(=O)N3)c(Cl)c1)c1noc(=O)[nH]1]

To a stirred mixture of ethyl carbonocyanidate (5.00 g, 50.4 mmol) and hydroxylamine hydrochloride (5.26 g, 75.7 mmol) in ethanol (50 mL) was added sodium carbonate (5.3 g, 50.4 mmol) in portions at room temperature. The resulting mixture was stirred for 2 h at room temperature. The resulting mixture was concentrated under reduced pressure. The resulting mixture was extracted with EA (6×100 mL) and the organic layers were combined, washed with brine (2×60 mL), dried over anhydrous sodium sulfate, filtered and concentrated under reduced pressure. The residue was purified by trituration with t-butyl methyl ether/PE (1/1, 40 mL) at 50° C. to afford ethyl 2-amino-2-(hydroxyimino) acetate (5.65 g, 80%) as a white solid. LC-MS (ESI, m/z): 133 [M+H]$^+$.

To a stirred mixture of ethyl 2-amino-2-(hydroxyimino) acetate (5.65 g, 42.8 mmol) in dichloromethane (150 mL) was added triethylamine (13.0 g, 128 mmol) and ethyl chloroformate (5.10 g, 47.0 mmol) dropwise at 0° C. The resulting mixture was stirred for 1 h at 0° C. The resulting mixture was concentrated under reduced pressure. The residue was purified by trituration with PE (100 mL). The resulting mixture was extracted with dichloromethane (3×120 mL) and the organic layers were combined, washed with brine (2×60 mL), dried over anhydrous sodium sulfate, filtered and concentrated under reduced pressure to afford ethyl 2-amino-2-(((ethoxycarbonyl)oxy)imino)acetate (8 g, 87%) as a yellow solid. LC-MS (ESI, m/z): 205 [M+H]$^+$.

A solution of ethyl 2-amino-2-(((ethoxycarbonyl)oxy)imino)acetate (6.50 g, 31.8 mmol) in acetic acid (230 mL) was stirred for 6 h at 120° C. The resulting mixture was concentrated under reduced pressure to afford ethyl 5-oxo-4,5-dihydro-1,2,4-oxadiazole-3-carboxylate (4.92 g, crude) as a yellow oil. The crude product was used in the next step directly without further purification. LC-MS (ESI, m/z): 157 [M−H]$^-$.

To a stirred mixture of ethyl 5-oxo-4,5-dihydro-1,2,4-oxadiazole-3-carboxylate (4.00 g, 25.3 mmol) in THF (20 mL) and dioxane (20 mL) was added NaOH (2.00 g, 50.6 mmol) (in water 10 mL) dropwise at room temperature. The resulting mixture was stirred for 2 h at room temperature. The resulting mixture was concentrated under reduced pressure. The residue was acidified pH=3 with HCl (1M). The resulting mixture was extracted with EA (3×100 mL) and the organic layers were combined, washed with brine (2×60 mL), dried over anhydrous sodium sulfate, filtered and concentrated under reduced pressure to afford 5-oxo-4,5-dihydro-1,2,4-oxadiazole-3-carboxylic acid (1.2 g, 33%) as a white solid. LC-MS (ESI, m/z): 259 [2M−H]$^-$.

To a stirred mixture of 5-oxo-4,5-dihydro-1,2,4-oxadiazole-3-carboxylic acid (500 mg, 3.80 mmol) and DMF (28 mg, 0.40 mmol) in THF (20 mL) was added oxalyl chloride (732 mg, 5.70 mmol) dropwise at room temperature. The resulting mixture was stirred for 1 h at room temperature. The resulting mixture was concentrated under reduced pressure to afford 5-oxo-4,5-dihydro-1,2,4-oxadiazole-3-carbonyl chloride (600 mg, crude) as a brown solid. The crude product was used in the next step directly without further purification.

To a solution of 5'-(4-amino-2,6-dichlorophenoxy)-1'H-spiro[cyclobutane-1,3'-indol]-2'-one (100 mg, 0.29 mmol) in DCM (20 mL) was added triethylamine (232 mg, 2.29 mmol) and 5-oxo-4H-1,2,4-oxadiazole-3-carbonyl chloride (340 mg, 2.29 mmol). The resulting mixture was stirred for 2 h at room temperature and quenched with water (100 mL). The resulting mixture was extracted with dichloromethane (3×50 mL). The combined organic layers were washed with brine (100 mL), dried over anhydrous sodium sulfate. After filtration, the filtrate was concentrated under reduced pressure. The crude product (50 mg) was purified by prep-HPLC with the following conditions (XBridge Shield RP18 OBD, 19×250 mm, 10 μm; Mobile Phase A: Water (0.1% formic acid), Mobile Phase B: ACN; Flow rate: 25 mL/min; Gradient: 52% B to 72% B in 7 min, 72% B; Wave Length: 254 nm; RT1 (min): 4.87) to afford N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide (14) (5.3 mg, 4%) as a white solid. $^1$H NMR (400 MHz, DMSO-d$_6$) δ 11.29 (s, 1H), 10.16 (s, 1H), 8.06 (s, 2H), 7.26 (s, 1H), 6.69 (d, J=8.4 Hz, 1H), 6.45-6.48 (m, 1H), 2.29-2.42 (m, 4H), 2.07-2.26 (m, 2H). LC-MS (ESI, m/z): 461[M+H]$^+$.

Example 15. Preparation of Compound 15

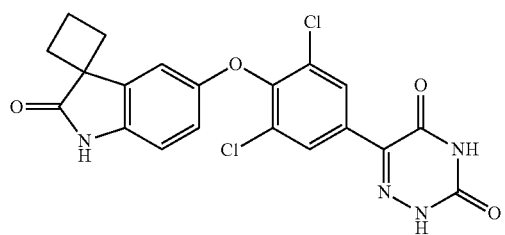 [SMILES: O=C1Nc2ccc(Oc3c(Cl)cc(-c4n[nH]c(=O)[nH]c4=O)cc3Cl)cc2C12CCC2]

A solution of 5'-(4-amino-2,6-dichlorophenoxy)-1'H-spiro[cyclobutane-1,3'-indol]-2'-one (1 g, 2.86 mmol) in MeOH (40 mL), water (10 mL), acetic acid (5 mL) and HCl (5 mL) was added NaNO$_2$ (0.40 g, 5.73 mmol) in water (10 mL) dropwise at 0° C. The resulting mixture was stirred for additional 30 min at 0° C. Then tetrahydroxydiborane (2.05 g, 22.9 mmol) was added. The reaction was stirred for 1.5 h at 60° C. and quenched with water. The resulting mixture was extracted with EA (3×100 mL). The combined organic layers were washed with brine (2×50 mL), dried over anhydrous sodium sulfate. The residue was purified by a C18 column with ACN/H$_2$O (6/4) to provide (3,5-dichloro-4-((2'-oxospiro[cyclobutane-1,3'-indolin]-5'-yl)oxy)phenyl) boronic acid (220 mg, 20%) as an off-white solid. LC-MS (ESI, m/z): 378 [M+H]$^+$.

A solution of (3,5-dichloro-4-((2'-oxospiro[cyclobutane-1,3'-indolin]-2-yl)oxy)phenyl)boronic acid (85.0 mg, 0.23 mmol), 6-bromo-2,4-dihydro-1,2,4-triazine-3,5-dione (51.8 mg, 0.27 mmol), Pd(PPh3)4 (51.9 mg, 0.05 mmol) and potassium carbonate (46.6 mg, 0.34 mmol) in dioxane (5 mL) and water (0.5 mL) was stirred for overnight at 80° C. under nitrogen atmosphere. The reaction was quenched with water (50 mL). The resulting mixture was extracted with EA (3×30 mL). The combined organic layers were washed with brine (20 mL), dried over anhydrous sodium sulfate, the solids were removed by filtration, and the filtrate was concentrated under reduced pressure. The residue was chromatographed on a silica gel column with EA/PE (3/1) to provide the crude. The crude product (40 mg) was purified by prep-HPLC with the following conditions (XBridge Shield RP18 OBD Column, 30×150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 16% B to 46% B in 7 min, 46% B; Wave Length: 254 nm; Rt: 6.3 min) to afford 6-(3,5-dichloro-4-((2'-oxospiro[cyclobutane-1,3'-indolin]-5'-yl)oxy)phenyl)-1,2,4-triazine-3,5 (2H,4H)-dione (15) (8 mg, 8%) as an off-white solid. $^1$H NMR (400 MHz, DMSO-d$_6$) δ 11.94 (br, 2H), 10.18 (s, 1H), 8.12 (s, 2H), 7.29 (s, 1H), 6.69 (d, J=8.4 Hz, 1H), 6.46-6.49 (m, 1H), 2.30-2.43 (m, 4H), 2.08-2.27 (m, 2H). LC-MS (ESI, m/z): 445 [M+H]$^+$.

Example 16. Preparation of Compound 16

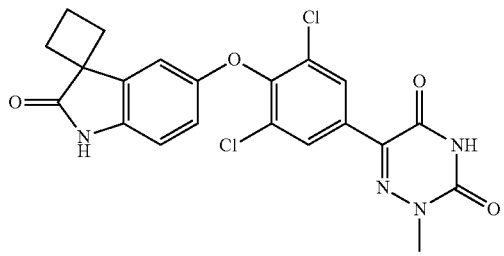 [SMILES: Cn1nc(-c2cc(Cl)c(Oc3ccc4c(c3)C3(CCC3)C(=O)N4)c(Cl)c2)c(=O)[nH]c1=O]

A solution of (3,5-dichloro-4-((2'-oxospiro[cyclobutane-1,3'-indolin]-2-yl)oxy)phenyl)boronic acid (85 mg, 0.225 mmol), 6-bromo-2-methyl-4H-1,2,4-triazine-3,5-dione (55.6 mg, 0.27 mmol), Pd(PPh$_3$)$_4$ (51.8 mg, 0.045 mmol) and K$_2$CO$_3$ (46.6 mg, 0.338 mmol) in dioxane (5 mL) and water (0.5 mL) was stirred for overnight at 80° C. under nitrogen atmosphere. The reaction was quenched with water (100 mL) at room temperature. The resulting mixture was extracted with EA (3×50 mL). The combined organic layers were washed with brine (60 mL), dried over anhydrous sodium sulfate. After filtration, the filtrate was concentrated under reduced pressure. The residue was chromatographed on a silica gel column with EA/PE (3/1) to provide the crude product (40 mg) that was further purified by prep-HPLC with the following conditions: (XBridge Shield RP18 OBD, 30×150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 16% B to 46% B in 7 min, 46% B; Wave Length: 254 nm; RT1 (min): 6.3) to afford 6-(3,5-dichloro-4-((2'-oxospiro[cyclobutane-1,3'-indolin]-5'-yl)oxy)phenyl)-2-methyl-1,2,4-triazine-3,5(2H,4H)-dione (16) (6.6 mg, 6%) as an off-white solid. $^1$H NMR (400 MHz, DMSO-d$_6$) δ 12.41 (br, 1H), 10.18 (s, 1H), 8.17 (s, 2H), 7.28 (s, 1H), 6.69 (d, J=8.4 Hz, 1H), 6.47-6.50 (m, 1H), 3.58 (s, 3H), 2.33-2.43 (m, 2H), 2.21-2.31 (m, 2H), 2.14-2.19 (m, 2H). LC-MS (ESL, m/z): 459 [M+H]$^+$.

Example 17. Preparation of Compound 17

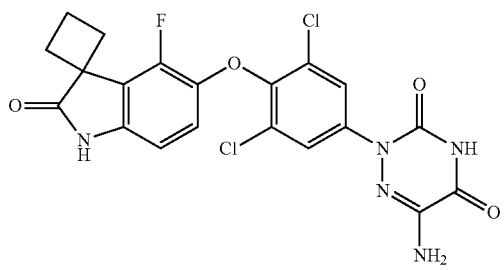 [SMILES: Nc1nn(-c2cc(Cl)c(Oc3ccc4c(c3F)C3(CCC3)C(=O)N4)c(Cl)c2)c(=O)[nH]c1=O]

To a solution of (3-fluorophenyl)hydrazine (10.0 g, 79.3 mmol) in DMF (100 mL) was added pyridine (18.8 g, 238 mmol) and followed by cyclobutanecarbonyl chloride (9.40 g, 79.3 mmol) dropwise at −30° C. The mixture was stirred at −30° C. for 2 h. The mixture was poured into ice cooled water. The formed solid was filtered off, washed with water and dried under IR lamp to afford N'-(3-fluorophenyl) cyclobutanecarbohydrazide (11.6 g, 63%) as a brown solid. LC-MS (ESI, m/z): 209 [M+H]$^+$.

To a solution of N'-(3-fluorophenyl) cyclobutanecarbohydrazide (3.0 g, 14.4 mmol) in quinoline (15 mL) was added CaO (8.07 g, 144 mmol). The reaction was stirred at 300° C. for 2 h and cooled to room temperature. Then the reaction was adjusted to pH5 with HCl (6N) and extracted with EA (3×100 mL). The organic layers were combined, washed with brine, dried over anhydrous sodium sulfate, filtered and concentrated under reduced pressure. The residue was purified by a C18 column with ACN/H$_2$O (0.05% TFA solution) (1/1) to afford 4'-fluoro-1'H-spiro[cyclobutane-1,3'-indol]-2'-one (280 mg, 3%) as a yellow solid. $^1$H NMR (300 MHz, Methanol-d$_4$) δ 7.17-7.24 (m, 1H), 6.69-6.80 (m, 2H), 2.51-2.62 (m, 4H), 2.26-2.40 (m, 2H). LC-MS (ESI, m/z): 192 [M+H]$^+$, and 6'-fluoro-1'H-spiro[cyclobutane-1,3'-indol]-2'-one (300 mg, 2.12%) as a yellow solid. $^1$H NMR (300 MHz, Methanol-d$_4$) δ 7.49-7.54 (m, 1H), 6.74-6.81 (m, 1H), 6.60-6.64 (m, 1H), 2.52-2.61 (m, 4H), 2.24-2.42 (m, 2H). LC-MS (ESI, m/z): 192 [M+H]$^+$.

To a solution of 4'-fluoro-1'H-spiro[cyclobutane-1,3'-indol]-2'-one (250 mg, 1.31 mmol) in ACN (5 mL) was added N-bromosuccinimide (244 mg, 1.37 mmol). The reaction was stirred at room temperature for 2 h and quenched with water (30 mL). The precipitate was filtered, washed with water (50 mL) and dried under reduced pressure to get 5'-bromo-4'-fluoro-1'H-spiro[cyclobutane-1,3'-indol]-2'-one (270 mg, 66%) as a yellow solid. LC-MS (ESI, m/z): 270 [M+H]$^+$.

To a solution of 5'-bromo-4'-fluoro-1'H-spiro[cyclobutane-1,3'-indol]-2'-one (200 mg, 0.740 mmol), 2-(5,5-dimethyl-1,3,2-dioxaborinan-2-yl)-5,5-dimethyl-1,3,2-dioxaborinane (334 mg, 1.48 mmol) in DMSO (5 mL) was added Pd(PPh$_3$)$_2$Cl$_2$ (104 mg, 0.148 mmol) and potassium acetate (218 mg, 2.22 mmol) under nitrogen. The reaction was stirred at 80° C. for 15 h and quenched with water (50 mL). The resulting solution was extracted with EA (3×50 mL) and the organic layers were combined, washed with brine (2×50 mL), dried over anhydrous sodium sulfate, filtered and concentrated under reduced pressure. The residue was chromatographed on a silica gel column with EA/PE (½) to provide 5'-(5,5-dimethyl-1,3,2-dioxaborinan-2-yl)-4'-fluoro-1'H-spiro[cyclobutane-1,3'-indol]-2'-one (210 mg, 80%) as an off-white solid. LC-MS (ESI, m/z): 304 [M+H]$^+$.

To a solution of 5'-(5,5-dimethyl-1,3,2-dioxaborinan-2-yl)-4'-fluoro-1'H-spiro[cyclobutane-1,3'-indol]-2'-one (200 mg, 0.660 mmol) in THF (6 mL) was added acetic acid (990 mg, 16.5 mmol) and H$_2$O$_2$ (112 mg, 3.30 mmol, 30% aq.) at 0° C. The reaction was stirred at room temperature for 3 h and quenched with sodium thiosulfate solution. The mixture was extracted with EA (3×50 mL) and the organic layers were combined, washed with brine (50 mL), dried over anhydrous sodium sulfate, filtered and concentrated under reduced pressure to get the residue. The residue was purified by column chromatography (ACN/water=⅓) to afford 4'-fluoro-5'-hydroxy-1'H-spiro[cyclobutane-1,3'-indol]-2'-one (105 mg, 73%) as a yellow solid. LC-MS (ESI, m/z): 208 [M+H]$^+$.

To a solution of 4'-fluoro-5'-hydroxy-1'H-spiro[cyclobutane-1,3'-indol]-2'-one (104 mg, 0.502 mmol) in ACN (3 mL) was added potassium t-butoxide (56.3 mg, 0.502 mmol) at 0° C. The reaction was stirred at 0° C. for 20 min and concentrated. The sample was dissolved in DMF (3 mL) and to it was added 1,3-dichloro-2-fluoro-5-nitrobenzene (111 mg, 0.527 mmol). The resulting solution was stirred at 100° C. for 2.5 h and quenched with water. The mixture was extracted with EA (3×30 mL) and the organic layers were combined, washed with brine, dried over anhydrous sodium sulfate, filtered and concentrated under reduced pressure.

The residue was chromatographed on a silica gel column with EA/PE (⅓) to get 5'-(2,6-dichloro-4-nitrophenoxy)-4'-fluoro-1'H-spiro[cyclobutane-1,3'-indol]-2'-one (115 mg, 54%) as a yellow solid. LC-MS (ESI, m/z): 397 [M+H]$^+$.

To a solution of 5'-(2,6-dichloro-4-nitrophenoxy)-4'-fluoro-1'H-spiro[cyclobutane-1,3'-indol]-2'-one (115 mg, 0.290 mmol) in EtOH (6 mL) and H$_2$O (3 mL) was added NH$_4$Cl (124 mg, 2.32 mmol) and Fe (80.8 mg, 1.45 mmol). The reaction was stirred at 60° C. for 16 h and filtered. The filtrate was added water (10 mL) and extracted with EA (3×30 mL) and the organic layers were combined, washed with brine, dried over anhydrous sodium sulfate, filtered and concentrated under reduced pressure to get 5'-(4-amino-2,6-dichlorophenoxy)-4'-fluoro-1'H-spiro[cyclobutane-1,3'-indol]-2'-one (105 mg, 89%) as a yellow solid. LC-MS (ESI, m/z): 367 [M+H]$^+$.

To a solution of 5'-(4-amino-2,6-dichlorophenoxy)-4'-fluoro-1'H-spiro[cyclobutane-1,3'-indol]-2'-one (95.0 mg, 0.259 mmol) in acetic acid (8.3 mL), concentrated HCl (2.9 mL) and H$_2$O (7 mL) was added NaNO$_2$ (37.5 mg, 0.544 mmol) in H$_2$O (0.2 mL) at 0° C. dropwise. The reaction was stirred at 0° C. for 30 min and poured into the solution of ethyl N-(2-cyanoacetyl)carbamate (60.6 mg, 0.389 mmol) in pyridine (3.1 mL) and H$_2$O (8 mL) at 0° C. The resulting solution was stirred at 0° C. for 30 min and filtered. The filter cake was washed with water and PE, dried under IR lamp to afford ethyl (2-cyano-2-(2-(3,5-dichloro-4-((4'-fluoro-2'-oxospiro[cyclobutane-1,3'-indolin]-5'-yl)oxy)phenyl)hydrazineylidene)acetyl)carbamate (100 mg, 65%) as a yellow solid. LC-MS (ESI, m/z): 534 [M+H]$^+$.

To a solution of ethyl (2-cyano-2-(2-(3,5-dichloro-4-((4'-fluoro-2'-oxospiro[cyclobutane-1,3'-indolin]-5'-yl)oxy)phenyl)hydrazineylidene)acetyl)carbamate (100 mg, 0.187 mmol) in DMA (5 mL) was added potassium acetate (91.8 mg, 0.935 mmol). The reaction was stirred at 120° C. for 2 h. The reaction was added water (30 mL) and extracted with EA (3×50 mL). The organic layers were combined, washed with brine, dried over anhydrous sodium sulfate, the solids were removed by filtration and the filtrate was concentrated under reduced pressure to get 2-(3,5-dichloro-4-((4'-fluoro-2'-oxospiro[cyclobutane-1,3'-indolin]-5'-yl)oxy)phenyl)-3,5-dioxo-2,3,4,5-tetrahydro-1,2,4-triazine-6-carbonitrile (100 mg, 93%) as a yellow solid. LC-MS (ESI, m/z): 488 [M+H]+.

To a solution of 2-(3,5-dichloro-4-((4'-fluoro-2'-oxospiro[cyclobutane-1,3'-indolin]-5'-yl)oxy)phenyl)-3,5-dioxo-2,3,4,5-tetrahydro-1,2,4-triazine-6-carbonitrile (100 mg, 0.205 mmol) in acetic acid (5 mL) was added conc. HCl (2.5 mL). The reaction was stirred at 100° C. for 1 h. The reaction was concentrated under reduced pressure and added NaHCO$_3$ solution (50 mL). The mixture was extracted with EA (3×40 mL) and the organic layers were discarded. The pH value of the aqueous layers was adjusted to 3 with conc. HCl. The resulting solution was extracted with EA (2×50 mL). The organic layers were combined, washed with brine, dried over anhydrous sodium sulfate, filtered and concentrated under reduced pressure to get 2-(3,5-dichloro-4-((4'-fluoro-2'-oxospiro[cyclobutane-1,3'-indolin]-5'-yl)oxy)phenyl)-3,5-dioxo-2,3,4,5-tetrahydro-1,2,4-triazine-6-carboxylic acid (100 mg, 87%) as a brown solid. LC-MS (ESI, m/z): 507 [M+H]+.

To a solution of 2-(3,5-dichloro-4-((4'-fluoro-2'-oxospiro[cyclobutane-1,3'-indolin]-5'-yl)oxy)phenyl)-3,5-dioxo-2,3,4,5-tetrahydro-1,2,4-triazine-6-carboxylic acid (80.0 mg, 0.158 mmol) in t-BuOH (4 mL) was added triethylamine (95.8 mg, 0.948 mmol) and diphenylphosphoryl azide (174 mg, 0.632 mmol). The reaction was stirred at 80° C. overnight and concentrated under reduced pressure. The crude was dissolved in EA (100 mL) and the organic layer was washed with NaHCO$_3$ solution (3×50 mL) and brine (50 mL), dried over anhydrous sodium sulfate, filtered and concentrated under reduced pressure to get tert-butyl (2-(3,5-dichloro-4-((4'-fluoro-2'-oxospiro[cyclobutane-1,3'-indolin]-5'-yl)oxy)phenyl)-3,5-dioxo-2,3,4,5-tetrahydro-1,2,4-triazin-6-yl)carbamate (100 mg crude) as a brown solid. LC-MS (ESI, m/z): 578 [M+H]+.

To a solution of t-butyl (2-(3,5-dichloro-4-((4'-fluoro-2'-oxospiro[cyclobutane-1,3'-indolin]-5'-yl)oxy)phenyl)-3,5-dioxo-2,3,4,5-tetrahydro-1,2,4-triazin-6-yl)carbamate (100 mg, 0.173 mmol) in DCM (5 mL) was added TFA (2 mL). The reaction was stirred at room temperature for 2 h and concentrated to get the residue. The residue was purified by prep-HPLC (XBridge Shield RP18 OBD Column, 30×150 mm, 5 μm; Mobile Phase A: Water (10 mmol/L NH$_4$HCO$_3$+ 0.1% NH$_3$·H$_2$O), Mobile Phase B: ACN; Flow rate: 60 mL/min; Gradient: 17% B to 35% B in 10 min; Wave Length: 254 nm; RT1 (min): 9.25) to afford 6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione (17) (22.6 mg, 27%) as a white solid. 1H NMR (300 MHz, DMSO-d$_6$) δ 12.22 (br, 1H), 10.40 (s, 1H), 7.92 (s, 2H), 6.43-6.53 (m, 4H), 2.46-2.49 (m, 4H), 2.24-2.27 (m, 2H). LC-MS (ESI, m/z): 478 [M+H]+.

Example 18. Preparation of Compound 18

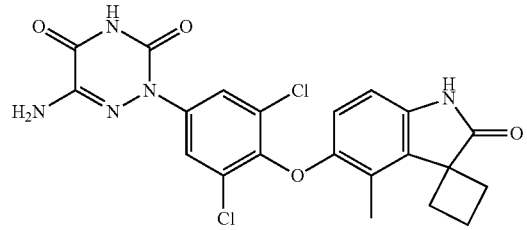

To a solution of (3-methylphenyl)hydrazine (8.00 g, 65.5 mmol) in DMF (50 mL) was added pyridine (15.5 g, 196 mmol) and cyclobutanecarbonyl chloride (7.76 g, 65.5 mmol) at −30° C. The resulting mixture was stirred at −30° C. for 2 h. The reaction was quenched with water (100 mL). The resulting mixture was extracted with EA (3×100 mL). The combined organic layers were washed with brine (200 mL), dried over anhydrous sodium sulfate. After filtration, the filtrate was concentrated under reduced pressure. The residue was purified by silica gel column chromatography, eluted with PE/EA (3:1) to afford N-(3-methylphenyl)cyclobutanecarbohydrazide (10.5 g, 78%) as a white solid. LC-MS (ESI, m/z): 209 [M+H]$^+$.

To a solution of N-(3-methylphenyl)cyclobutanecarbohydrazide (10.5 g, 51.4 mmol) in quinoline (50 mL) was added CaO (28.2 g, 504 mmol). The resulting mixture was stirred for 2 h at 300° C. The reaction was quenched with HCl (6M, 400 mL). The resulting mixture was extracted with EA (3×300 mL). The combined organic layers were washed with brine (2×100 mL), dried over anhydrous sodium sulfate, the solids were removed by filtration, and the filtrate was concentrated under reduced pressure. The residue was purified by silica gel column chromatography, eluted with PE/EA (3/2) to afford the mixture of 4'-methyl-1'H-spiro[cyclobutane-1,3'-indol]-2'-one and 6'-methyl-1'H-spiro[cyclobutane-1,3'-indol]-2'-one (4.8 g, 51%) as a yellow solid. LC-MS (ESI, m/z): 188 [M+H]+.

To a solution of the mixture of 4'-methyl-1'H-spiro[cyclobutane-1,3'-indol]-2'-one (2.40 g, 12.8 mmol) and 6'-methyl-1'H-spiro[cyclobutane-1,3'-indol]-2'-one (2.40 g, 12.8 mmol) in MeCN (50 mL) was added N-bromosuccinimide (2.51 g, 14.1 mmol). The resulting mixture was stirred at room temperature for 2 h. The mixture was poured over crushed ice, the formed solid was isolated by filtration and washed with water (300 mL). The resulting solid was dried under vacuum to afford the mixture of 5'-bromo-4'-methyl-1'H-spiro[cyclobutane-1,3'-indol]-2'-one and 5'-bromo-6'-methyl-1'H-spiro[cyclobutane-1,3'-indol]-2'-one (2.20 g, 65%) as a yellow solid. LC-MS (ESI, m/z): 266 [M+H]+.

Into a 40 mL vial was added the mixture of 5'-bromo-4'-methyl-1'H-spiro[cyclobutane-1,3'-indol]-2'-one and 5'-bromo-6'-methyl-1'H-spiro[cyclobutane-1,3'-indol]-2'-one, 2-(5,5-dimethyl-1,3,2-dioxaborinan-2-yl)-5,5-dimethyl-1,3,2-dioxaborinane (3.73 g, 16.5 mmol), $Pd(PPh_3)_2Cl_2$ (0.580 g, 0.830 mmol), potassium acetate (2.43 g, 24.8 mmol) and DMSO (20 mL). The resulting mixture was stirred at 80° C. for 15 h under nitrogen atmosphere. The reaction was quenched with water. The resulting mixture was extracted with EA (3×150 mL). The combined organic layers were washed with brine (200 mL), dried over anhydrous sodium sulfate, the solids were removed by filtration, and the filtrate was concentrated under reduced pressure. The residue was purified by silica gel column chromatography, eluted with PE/EA (2/1) to afford the mixture of 5'-(5,5-dimethyl-1,3,2-dioxaborinan-2-yl)-6'-methyl-1'H-spiro[cyclobutane-1,3'-indol]-2'-one and 5'-(5,5-dimethyl-1,3,2-dioxaborinan-2-yl)-4'-methyl-1'H-spiro[cyclobutane-1,3'-indol]-2'-one (900 mg, 37%) as a yellow solid. LC-MS (ESI, m/z): 300 [M+H]+.

To a solution of the mixture of 5'-(5,5-dimethyl-1,3,2-dioxaborinan-2-yl)-6'-methyl-1'H-spiro[cyclobutane-1,3'-indol]-2'-one and 5'-(5,5-dimethyl-1,3,2-dioxaborinan-2-yl)-4'-methyl-1'H-spiro[cyclobutane-1,3'-indol]-2'-one) in THF (30 mL) was added $H_2O_2$ (1.02 g, 30.1 mmol, 30% aq.) and acetic acid (2.89 g, 48.1 mmol). The resulting mixture was stirred at room temperature for 3 h and quenched with water (100 mL). The resulting mixture was extracted with EA (3×80 mL). The combined organic layers were washed with brine (150 mL), dried over anhydrous sodium sulfate, the solids were removed by filtration, and the filtrate was concentrated under reduced pressure. The residue was purified by silica gel column chromatography, eluted with PE/EA (⅔), then by prep-HPLC with the following conditions (Viridis BEH 2-EP, 100×4.6 mm, 5 μm; Mobile Phase B: MeOH (1% 2M NH3-MeOH); Flow rate: 4 mL/min; Gradient: isocratic 5% B; Wave Length: 220 nm) to afford 5'-hydroxy-6'-methyl-1'H-spiro[cyclobutane-1,3'-indol]-2'-one (150 mg, 25%) as a yellow solid. $^1$H NMR (400 MHz, CDCl$_3$) δ 7.51 (br, 1H), 6.99 (s, 1H), 6.61 (s, 1H), 2.57-2.72 (m, 2H), 2.27-2.39 (s, 4H), 2.02-2.19 (m, 3H). LC-MS (ESI, m/z): 204 [M+H]+. And 5'-hydroxy-4'-methyl-1'H-spiro[cyclobutane-1,3'-indol]-2'-one (100 mg, 23%) as a yellow solid. $^1$H NMR (400 MHz, CDCl$_3$) δ 7.42 (br, 1H), 6.66 (d, J=8.0 Hz, 1H), 6.56 (d, J=8.0 Hz, 1H), 2.67-2.78 (m, 4H), 2.56-2.66 (s, 3H), 2.23-2.36 (m, 2H). LC-MS (ESI, m/z): 204 [M+H]+.

To a solution of 5'-hydroxy-4'-methyl-1'H-spiro[cyclobutane-1,3'-indol]-2'-one (90.0 mg, 0.443 mmol) in ACN (3 mL) was added potassium tert-butoxide (49.7 mg, 0.443 mmol) at 0° C. The reaction was stirred at 0° C. for 20 min and concentrated under reduced pressure. The sample was dissolved in DMF (3 mL) and added 1,3-dichloro-2-fluoro-5-nitrobenzene (97.6 mg, 0.465 mmol). The resulting solution was stirred at 100° C. for 2.5 h and quenched with water (10 mL). The resulting solution was extracted with EA (3×20 mL) and the organic layers were combined, washed with brine (20 mL), dried over anhydrous sodium sulfate, filtered and concentrated under reduced pressure. The residue was chromatographed on a silica gel column with EA/PE (½) to provide 5'-(2,6-dichloro-4-nitrophenoxy)-4'-methyl-1'H-spiro[cyclobutane-1,3'-indol]-2'-one (56.0 mg, 30%) as a brown solid. LC-MS (ESI, m/z): 393 [M+H]+.

To a solution of 5'-(2,6-dichloro-4-nitrophenoxy)-4'-methyl-1'H-spiro[cyclobutane-1,3'-indol]-2'-one (56.0 mg, 0.142 mmol) in EtOH (2.8 mL) and $H_2O$ (1.4 mL) was added $NH_4Cl$ (60.9 mg, 1.14 mmol) and Fe (39.8 mg, 0.710 mmol). The reaction was stirred at 60° C. for 16 h and filtered. The filtrate was added water (10 mL) and extracted with EA (3×30 mL) and the organic layers were combined, washed with brine, dried over anhydrous sodium sulfate, filtered and concentrated under reduced pressure to get 5'-(4-amino-2,6-dichlorophenoxy)-4'-methyl-1'H-spiro[cyclobutane-1,3'-indol]-2'-one (53 mg, 97%) as a yellow solid. LC-MS (ESI, m/z): 363 [M+H]+.

To a solution of 5'-(4-amino-2,6-dichlorophenoxy)-4'-methyl-1'H-spiro[cyclobutane-1,3'-indol]-2'-one (53.0 mg, 0.146 mmol) in acetic acid (4.6 mL), concentrated HCl (1.6 mL) and $H_2O$ (4 mL) was added $NaNO_2$ (21.1 mg, 0.307 mmol) in $H_2O$ (0.2 mL) at 0° C. dropwise. The reaction was stirred at 0° C. for 30 min and poured into the solution of ethyl N-(2-cyanoacetyl)carbamate (34.2 mg, 0.219 mmol) in pyridine (1.8 mL) and $H_2O$ (4.3 mL) at 0° C. The resulting solution was stirred at 0° C. for 30 min and filtered. The filter cake was washed with water and PE, dried under IR lamp to afford ethyl (2-cyano-2-(2-(3,5-dichloro-4-((4'-methyl-2'-oxospiro[cyclobutane-1,3'-indolin]-5'-yl)oxy)phenyl)hydrazineylidene)acetyl)carbamate (50.0 mg, 58%) as a yellow solid. LC-MS (ESI, m/z): 530 [M+H]+.

To a solution of ethyl (2-cyano-2-(2-(3,5-dichloro-4-((4'-methyl-2'-oxospiro[cyclobutane-1,3'-indolin]-5'-yl)oxy)phenyl)hydrazineylidene)acetyl)carbamate (50.0 mg, 0.094 mmol) in DMA (2.5 mL) was added potassium acetate (46.3 mg, 0.470 mmol). The reaction was stirred at 120° C. for 2 h and quenched with water (30 mL). The resulting mixture was extracted with EA (3×50 mL). The organic layers were combined, washed with brine, dried over anhydrous sodium sulfate, filtered and concentrated under reduced pressure to get 2-(3,5-dichloro-4-((4'-methyl-2'-oxospiro[cyclobutane-1,3'-indolin]-5'-yl)oxy)phenyl)-3,5-dioxo-2,3,4,5-tetrahydro-1,2,4-triazine-6-carbonitrile (45.0 mg, 89%) as a yellow solid. LC-MS (ESI, m/z): 484 [M+H]+.

A solution of 2-(3,5-dichloro-4-((4'-methyl-2'-oxospiro[cyclobutane-1,3'-indolin]-5'-yl)oxy)phenyl)-3,5-dioxo-2,3,4,5-tetrahydro-1,2,4-triazine-6-carbonitrile (45.0 mg, 0.093 mmol) in acetic acid (1.8 mL) and concentrated HCl (0.9 mL) was stirred at 100° C. for 1 h. The reaction was concentrated under reduced pressure and added NaHCO$_3$ solution (50 mL). The mixture was extracted with EA (3×40 mL) and the organic layers were discarded. The PH value of the aqueous layers was adjusted to 3 with concentrated hydrochloride acid. The resulting solution was extracted with EA (2×50 mL). The organic layers were combined, washed with brine, dried over anhydrous sodium sulfate, filtered and concentrated under reduced pressure to get 2-(3,5-dichloro-4-((4'-methyl-2'-oxospiro[cyclobutane-1,3'-indolin]-5'-yl)oxy)phenyl)-3,5-dioxo-2,3,4,5-tetrahydro-1,2,4-triazine-6-carboxylic acid (33 mg, 63.51%) as a yellow solid. LC-MS (ESI, m/z): 503 [M+H]+.

To a solution of 2-(3,5-dichloro-4-((4'-methyl-2'-oxospiro [cyclobutane-1,3'-indolin]-5'-yl)oxy)phenyl)-3,5-dioxo-2,3, 4,5-tetrahydro-1,2,4-triazine-6-carboxylic acid (33.0 mg, 0.066 mmol) in t-BuOH (2 mL) was added diphenylphosphoryl azide (72.2 mg, 0.264 mmol) and triethylamine (39.8 mg, 0.396 mmol). The reaction was stirred at 80° C. for overnight and concentrated under reduced pressure. The crude was dissolved in EA (100 mL) and the organic layer was washed with NaHCO$_3$ solution (3×50 mL) and brine (50 mL), dried over anhydrous sodium sulfate, filtered and concentrated under reduced pressure to get tert-butyl (2-(3, 5-dichloro-4-((4'-methyl-2'-oxospiro[cyclobutane-1,3'-indolin]-5'-yl)oxy)phenyl)-3,5-dioxo-2,3,4,5-tetrahydro-1,2,4-triazin-6-yl)carbamate (40.0 mg, 90%) as a brown solid. LC-MS (ESI, m/z): 574 [M+H]$^+$.

To a solution of t-butyl (2-(3,5-dichloro-4-((4'-methyl-2'-oxospiro[cyclobutane-1,3'-indolin]-5'-yl)oxy)phenyl)-3,5-dioxo-2,3,4,5-tetrahydro-1,2,4-triazin-6-yl)carbamate (40.0 mg, 0.070 mmol) in DCM (5 mL) was added TFA (2 mL). The reaction was stirred at room temperature for 2 h and concentrated under reduced pressure. The residue was purified by prep-HPLC (XBridge Shield RP18 OBD Column, 19×250 mm, 10 μm; Mobile Phase A: Water (10 mmol/L NH$_4$HCO$_3$+0.1% NH$_3$·H$_2$O), Mobile Phase B: ACN; Flow rate: 25 mL/min; Gradient: 30% B to 40% B in 10 min; Wave Length: 254 nm; RT1 (min): 7.25) to afford 6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione (18) (7.4 mg, 22%) as a white solid. $^1$H NMR (300 MHz, DMSO-d$_6$) δ 12.22 (br, 1H), 10.13 (s, 1H), 7.90 (s, 2H), 6.48-6.49 (m, 3H), 6.14-6.16 (m, 1H), 2.62-2.75 (m, 5H), 2.20-2.42 (m, 4H). LC-MS (ESI, m/z): 474 [M+H]$^+$.

Example 19. Preparation of Compound 19

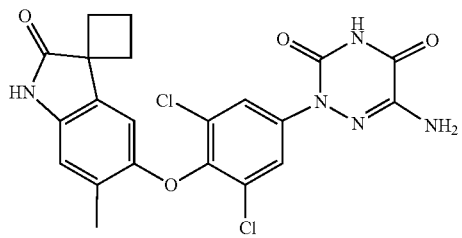 [SMILES: Cc1cc2c(cc1Oc1c(Cl)cc(-n3nc(N)c(=O)[nH]c3=O)cc1Cl)C1(CCC1)C(=O)N2]

To a solution of 5'-hydroxy-6'-methyl-1'H-spiro[cyclobutane-1,3'-indol]-2'-one (150 mg, 0.740 mmol) in ACN (8 mL) was added potassium t-butoxide (91.1 mg, 0.810 mmol) at 0° C. The resulting mixture was stirred for 30 min at 0° C. and concentrated under reduced pressure. Then 1,3-dichloro-2-fluoro-5-nitrobenzene (155 mg, 0.740 mmol) in DMF (8 mL) was added. The resulting mixture was stirred for 2.5 h at 100° C. The reaction was quenched with water (50 mL). The resulting mixture was extracted with EA (3×50 mL). The combined organic layers were washed with brine (2×30 mL), dried over anhydrous sodium sulfate. After filtration, the filtrate was concentrated under reduced pressure. The residue was purified by silica gel column chromatography, eluted with PE/EA (1/1) to afford 5'-(2,6-dichloro-4-nitrophenoxy)-6'-methyl-1'H-spiro[cyclobutane-1,3'-indol]-2'-one (56.0 mg, 19%) as a yellow solid. LC-MS (ESI, m/z): 393 [M+H]$^+$.

To a solution of 5'-(2,6-dichloro-4-nitrophenoxy)-6'-methyl-1'H-spiro[cyclobutane-1,3'-indol]-2'-one (56.0 mg, 0.140 mmol) in EtOH (8 mL) and water (4 mL) was added Fe (47.7 mg, 0.850 mmol) and NH$_4$Cl (60.9 mg, 1.14 mmol) at room temperature. The resulting mixture was stirred at 60° C. for 16 h. The resulting mixture was quenched with water (50 mL). The resulting solution was extracted with EA (3×40 mL). The combined organic layers were washed with brine (80 mL), dried over anhydrous sodium sulfate filtered and concentrated under reduced pressure to provide 5'-(4-amino-2,6-dichlorophenoxy)-6'-methyl-1'H-spiro[cyclobutane-1,3'-indol]-2'-one (50 mg crude) as a yellow solid. LC-MS (ESL, m/z): 363 [M+H]$^+$.

To a solution of 5'-(4-amino-2,6-dichlorophenoxy)-6'-methyl-1'H-spiro[cyclobutane-1,3'-indol]-2'-one (70.0 mg, 0.190 mmol) in water (5 mL), acetic acid (6 mL) and concentrated HCl (2 mL) was added NaNO$_2$ (27.9 mg, 0.405 mmol) in water (0.5 mL) dropwise at 0° C. After the addition, the reaction was stirred at 0° C. for 45 min. Then the reaction mixture was added to a solution of ethyl N-(2-cyanoacetyl)carbamate (45.1 mg, 0.290 mmol) in water (6 mL) and pyridine (3.5 mL) at 0° C. quickly. The resulting mixture was stirred at 0° C. for 1 h and filtered. The filter cake was washed with water (100 mL) and PE (100 mL), dried under an IR lamp to provide ethyl (2-cyano-2-(2-(3,5-dichloro-4-((6'-methyl-2'-oxospiro[cyclobutane-1, 3'-indolin]-5'-yl)oxy)phenyl)hydrazineylidene)acetyl)carbamate (50.0 mg crude) as a yellow solid. LC-MS (ESI, m/z): 530 [M+H]$^+$.

To a solution of ethyl (2-cyano-2-(2-(3,5-dichloro-4-((6'-methyl-2'-oxospiro[cyclobutane-1,3'-indolin]-5'-yl)oxy) phenyl)hydrazineylidene)acetyl)carbamate (50.0 mg, 0.090 mmol) in DMA (3 mL) was added potassium acetate (46.3 mg, 0.470 mmol). The resulting mixture was stirred for 2 h at 120° C. The reaction was quenched with water (10 mL). The resulting mixture was extracted with EA (3×20 mL). The combined organic layers were washed with brine (2×20 mL), dried over anhydrous sodium sulfate, the solids were removed by filtration, and the filtrate was concentrated under reduced pressure to afford 2-(3,5-dichloro-4-((6'-methyl-2'-oxospiro[cyclobutane-1,3'-indolin]-5'-yl)oxy) phenyl)-3,5-dioxo-2,3,4,5-tetrahydro-1,2,4-triazine-6-carbonitrile (45.0 mg, crude) as a yellow solid. LC-MS (ESI, m/z): 484 [M+H]$^+$.

Into a 8 mL vial were added 2-(3,5-dichloro-4-((6'-methyl-2'-oxospiro[cyclobutane-1,3'-indolin]-5'-yl)oxy) phenyl)-3,5-dioxo-2,3,4,5-tetrahydro-1,2,4-triazine-6-carbonitrile (45 mg, 0.0899 mmol), HCl (1.5 mL) and acetic acid (3 mL) at room temperature. The resulting mixture was stirred at 100° C. for 2 h and concentrated under reduced pressure. The residue was diluted with sodium bicarbonate (sat., aq., 10 mL), the resulting mixture was extracted with EA (2×15 mL) and the organic layers were discarded. The pH value of the aqueous layer was adjusted to 5-6 with concentrated HCl. The resulting solution was extracted with EA (3×15 mL) and the organic layers were combined, washed with brine (20 mL), dried over anhydrous sodium sulfate, filtered and concentrated under reduced pressure to afford 2-(3,5-dichloro-4-((6'-methyl-2'-oxospiro[cyclobutane-1,3'-indolin]-5'-yl)oxy)phenyl)-3,5-dioxo-2,3,4,5-tetrahydro-1,2,4-triazine-6-carboxylic acid (33.0 mg, crude) as a yellow solid. LC-MS (ESI, m/z): 503 [M+H]$^+$.

Into a 8 mL vial were added 2-(3,5-dichloro-4-((6'-methyl-2'-oxospiro[cyclobutane-1,3'-indolin]-5'-yl)oxy) phenyl)-3,5-dioxo-2,3,4,5-tetrahydro-1,2,4-triazine-6-carboxylic acid (33.0 mg, 0.0687 mmol), diphenylphosphoryl azide (72.2 mg, 0.260 mmol), triethylamine (39.8 mg, 0.400 mmol) and t-BuOH (3 mL) at room temperature. The resulting mixture was stirred at 85° C. overnight. The reaction was quenched with water at room temperature. The resulting mixture was extracted with EA (3×20 mL). The combined organic layers were washed with brine (2×20 mL), dried over anhydrous sodium sulfate. After filtration, the filtrate was concentrated under reduced pressure to afford tert-butyl (2-(3,5-dichloro-4-((6'-methyl-2'-oxospiro [cyclobutane-1,3'-indolin]-5'-yl)oxy)phenyl)-3,5-dioxo-2,3, 4,5-tetrahydro-1,2,4-triazin-6-yl)carbamate (30.0 mg, crude) as a yellow solid. LC-MS (ESI, m/z): 574 [M+H]$^+$.

Into a 8 mL vial were added 1-butyl (2-(3,5-dichloro-4-((6'-methyl-2'-oxospiro[cyclobutane-1,3'-indolin]-5'-yl) oxy)phenyl)-3,5-dioxo-2,3,4,5-tetrahydro-1,2,4-triazin-6-yl)carbamate (30.0 mg, 0.05 mmol), DCM (1.5 mL) and TFA (0.6 mL) at room temperature. The resulting mixture was stirred for 2 h at room temperature and concentrated under reduced pressure. The crude product (20 mg) was purified by prep-HPLC with the following conditions (XBridge Shield RP18 OBD, 30×150 mm, 5 µm; Mobile Phase A: Water (10 mmol/L NH$_4$HCO$_3$+0.1% NH$_3$·H$_2$O), Mobile Phase B: ACN; Flow rate: 60 mL/min; Gradient: 14% B to 44% B in 7 min, 44% B; Wave Length: 254 nm; Rt: 6.08 min) to afford 6-amino-2-(3,5-dichloro-4-((6'-methyl-2'-oxospiro[cyclobutane-1,3'-indolin]-5'-yl)oxy) phenyl)-1,2,4-triazine-3,5(2H,4H)-dione (19) (3.00 mg, 12%) as a white solid. $^1$H NMR (400 MHz, DMSO-d$_6$) δ 12.10 (br, 1H), 10.14 (s, 1H), 7.95 (s, 2H), 6.72 (s, 1H), 6.54 (s, 1H), 6.48 (s, 2H), 2.25-2.34 (m, 5H), 2.10-2.19 (m, 3H), 1.86-1.90 (m, 1H). LC-MS (ESI, m/z): 474 [M+H]$^+$.

Example 20. Preparation of Compound 20

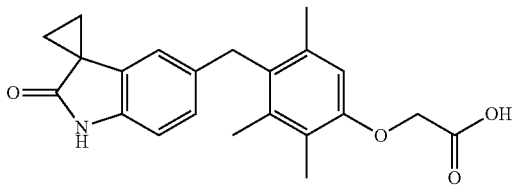 [SMILES: Cc1cc(OCC(=O)O)c(C)c(C)c1Cc1ccc2c(c1)C1(CC1)C(=O)N2]

A solution of 4-bromo-2,3,5-trimethylphenol (2.60 g, 12.1 mmol), benzyl bromide (2.17 g, 12.7 mmol) and potassium carbonate (5.01 g, 36.3 mmol) in MeCN (30 mL) was stirred overnight at room temperature The resulting mixture was extracted with EA (3×50 mL). The combined organic layers were washed with brine (2×50 mL), dried over anhydrous sodium sulfate. After filtration, the filtrate was concentrated under reduced pressure. The residue was purified by silica gel column chromatography, eluted with PE to afford 1-(benzyloxy)-4-bromo-2,3,5-trimethylbenzene (3.6 g, 98%) as a white solid. LC-MS (ESI, m/z): 305 [M+H]$^+$.

To a solution of 1-(benzyloxy)-4-bromo-2,3,5-trimethylbenzene (800 mg, 2.62 mmol) in THF (16 mL) was added n-BuLi (1.6 mL, 2.5M in hexane, 3.93 mmol) dropwise at −78° C. The reaction was stirred at −78° C. for 30 min and DMF (1.53 g, 20.9 mmol) was added dropwise at −78° C. Then the reaction was stirred at −78° C. for 1 h and quenched with NH$_4$Cl solution. The mixture was extracted with EA (3×50 mL). The organic layers were combined, washed with brine, dried over anhydrous sodium sulfate, filtered and concentrated under reduced pressure to get 4-(benzyloxy)-2,3,6-trimethylbenzaldehyde (650 mg, 88%) as an off-white solid. LC-MS (ESI, m/z): 255 [M+H]$^+$ To a solution of 5'-bromo-1'-(oxan-2-yl)spiro[cyclopropane-1,3'-indol]-2'-one (633 mg, 1.97 mmol) in THF (18 mL) was added n-BuLi (227 mg, 2.54 mmol) dropwise at −78° C. The reaction was stirred at −78° C. for 40 min and 4-(benzyloxy)-2,3,6-trimethylbenzaldehyde (500 mg, 1.97 mmol) in THF (2 mL) was added. Then the reaction was stirred at −78° C. for 1 h and quenched with NH$_4$Cl solution. The mixture was extracted with EA (3×80 mL) and the organic layers were combined, washed with brine, dried over anhydrous sodium sulfate, filtered and concentrated under reduced pressure. The residue was chromatographed on a silica gel column with EA/PE (1/1) to afford 5'-{[4-(benzyloxy)-2,3,6-trimethylphenyl](hydroxy)methyl}-1'-(oxan-2-yl)spiro[cyclopropane-1,3'-indol]-2'-one (160 mg, 14%) as an off-white solid. LC-MS (ESL, m/z): 498 [M+H]$^+$.

To a solution of 5'-{[4-(benzyloxy)-2,3,6-trimethylphenyl](hydroxy)methyl}-1'-(oxan-2-yl)spiro[cyclopropane-1, 3'-indol]-2'-one (130 mg, 0.261 mmol) in DCM (5.2 mL) was added triethylsilane (182 mg, 1.57 mmol) and TBSOTf (20.7 mg, 0.0780 mmol) at 0° C. The reaction was stirred at room temperature for 1 h and quenched with NaHCO$_3$ solution. The mixture was extracted with DCM (2×50 mL). The combined organic layers were washed with brine, dried over anhydrous sodium sulfate. After filtration, the filtrate was concentrated under reduced pressure to get 5'-{[4-(benzyloxy)-2,3,6-trimethylphenyl]methyl}-1'-(oxan-2-yl) spiro[cyclopropane-1,3'-indol]-2'-one (120 mg, 79%) as a yellow solid. LC-MS (ESI, m/z): 482 [M+H]$^+$.

To a solution of 5'-{[4-(benzyloxy)-2,3,6-trimethylphenyl]methyl}-1'-(oxan-2-yl)spiro[cyclopropane-1,3'-indol]-2'-one (125 mg, 0.260 mmol) in EtOH (8 mL) was added Pd/C (100 mg). The reaction was stirred at room temperature overnight under hydrogen and filtered. The filtrate was concentrated to afford 5'-[(4-hydroxy-2,3,6-trimethylphenyl)methyl]-1'-(oxan-2-yl)spiro[cyclopropane-1,3'-indol]-2'-one (100 mg, 89%) as an off-white solid. LC-MS (ESI, m/z): 392 [M+H]$^+$.

To a solution of 5'-[(4-hydroxy-2,3,6-trimethylphenyl) methyl]-1'-(oxan-2-yl)spiro[cyclopropane-1,3'-indol]-2'-one (100 mg, 0.255 mmol) and tert-butyl 2-bromoacetate (74.7 mg, 0.383 mmol) in ACN (5 mL) was added potassium carbonate (106 mg, 0.765 mmol). The reaction was stirred at 60° C. overnight and quenched with water (20 mL) at room temperature. The mixture was extracted with EA (2×50 mL). The combined organic layers were washed with brine, dried over anhydrous sodium sulfate, filtrated and concentrated under reduced pressure to get tert-butyl 2-(2,3,5-trimethyl-4-((2'-oxo-1'-(tetrahydro-2H-pyran-2-yl)spiro[cyclopropane-1,3'-indolin]-5'-yl)methyl)phenoxy)acetate (120 mg, 74%) as a yellow solid. LC-MS (ESI, m/z): 506 [M+H]$^+$.

To a solution of t-butyl 2-(2,3,5-trimethyl-4-((2'-oxo-1'-(tetrahydro-2H-pyran-2-yl)spiro[cyclopropane-1,3'-indolin]-5'-yl)methyl)phenoxy)acetate (80 mg, 0.158 mmol) in dioxane (3 mL) was added concentrated HCl (3 mL). The reaction was stirred at room temperature for 1 h and concentrated under reduced pressure. The sample was purified by prep-HPLC (XBridge Prep OBD C18 Column, 30×150 mm, 5 µm; Mobile Phase A: Water (10 mmol/L NH$_4$HCO$_3$+ 0.1% NH$_3$·H$_2$O), Mobile Phase B: ACN; Flow rate: 60 mL/min; Gradient: 15% B to 35% B in 9 min; Wave Length: 254 nm; Rt: 7.45 min) to provide 2-(2,3,5-trimethyl-4-((2'-oxospiro[cyclopropane-1,3'-indolin]-5'-yl)methyl)phenoxy) acetic acid (20) (8.9 mg, 15%) as a white solid. 1H NMR (300 MHz, DMSO-d$_6$) δ 10.42 (s, 1H), 6.72-6.74 (m, 2H), 6.51-6.64 (m, 2H), 4.37 (s, 2H), 3.87 (s, 2H), 2.04-2.13 (m, 9H), 1.48-1.58 (m, 4H). LC-MS (ESI, m/z): 366 [M+H]+.

Example 21. Preparation of Compound 21

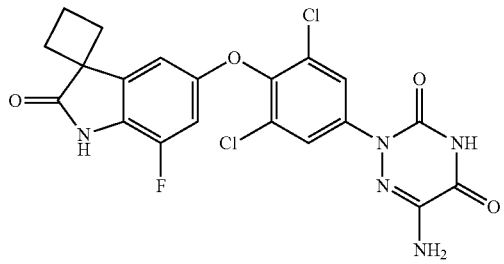

SO$_2$Cl$_2$ (4.7 mL, 58.0 mmol) was added to a solution of ethyl(methylthio)acetate (7.5 mL, 58.0 mmol) in anhydrous DCM (86 mL) at −78° C. under N$_2$. The reaction mixture was stirred at −78° C. for 15 min and then a solution of 2-fluoro-4-methoxyaniline (7.8 g, 55.3 mmol) and DIPEA (9 mL, 55.3 mmol) in anhydrous DCM (86 mL) was added over 45 min at −78° C. The reaction mixture was stirred at −78° C. for 30 min and extra DIPEA (9 mL, 55.3 mmol) was added. The reaction mixture was slowly warmed up to room temperature and was stirred for 20 h. The reaction mixture was evaporated to dryness and the residue was dissolved in EtOAc (200 mL). 1M HCl (200 mL) was added, and the mixture was stirred for 2 h. The organic phase was collected, and aqueous phase was extracted with EtOAc (2×). The combined organic phases were washed with brine (3×) and dried over Na$_2$SO$_4$. The solids were removed by filtration and the filtrate was evaporated to dryness. The resulting solid was triturated with EtOAc/CyH (3:7) to give 7-fluoro-5-methoxy-3-(methylthio)indolin-2-one (7.81 g, 62%) as a black solid which was used without further purification in the next step. $^1$H-NMR (DMSO-d$_6$, 300 MHz): 1.95 (s, 3H), 3.73 (s, 3H), 4.57 (s, 1H), 6.75 (s, 1H), 6.80 (dd, J=12.0, 1.6 Hz, 1H), 10.83 (s, 1H) ppm. LC-MS: C$_{10}$H$_{10}$FNO$_2$S [M+H]$^+$: 228

A mixture of 7-fluoro-5-methoxy-3-(methylthio)indolin-2-one (8.94 g, 39.3 mmol), Cu (0.25 g, 3.93 mmol) and Zn (6.43 g, 98.4 mmol) in AcOH (55 mL) and EtOAc (55 mL) under N2 was stirred at 60° C. for 19 h. The mixture was cooled to room temperature, diluted with EtOAc (200 mL), filtered over celite, evaporated to dryness and coevaporated with CyH. The resulting solid was triturated with EtOAc/CyH (3:7) to give 7-fluoro-5-methoxyindolin-2-one (7.13 g, quant.) as a dark solid which was used without further purification in the next step. $^1$H-NMR (DMSO-d$_6$, 300 MHz): 3.51 (s, 2H), 3.70 (s, 3H), 6.68-6.78 (m, 2H), 10.63 (s, 1H) ppm. LC-MS: C$_9$H$_8$FNO$_2$ [M+H]$^+$: 182 n-BuLi (81 mL, 129 mmol, 1.6 M in hexane) was added to a solution of 7-fluoro-5-methoxyindolin-2-one (6.9 g, 38.1 mmol) in anhydrous THF (500 mL) under N2 at 0° C. The reaction mixture was stirred at 0° C. for 30 min. TMEDA (20 mL, 129 mmol) and 1,3-diiodopropane (4.4 mL, 38.1 mmol) were added dropwise at 0° C. and the reaction mixture was slowly warmed up to room temperature. The reaction mixture was stirred at room temperature for 18 h. The reaction mixture was quenched with sat. aq. NH$_4$Cl (200 mL). THF was evaporated and the residue was extracted with EtOAc. The organic phase was washed with sat. aq. NH$_4$Cl and brine, and was dried over Na$_2$SO$_4$. The solids were removed by filtration and the filtrate was evaporated to dryness. The crude mixture was purified by flash chromatography on silica gel (0% to 30% EtOAc in CyH) to give 7'-fluoro-5'-methoxyspiro[cyclobutane-1,3'-indolin]-2'-one (0.74 g, 9%) as a brown solid which was used without further purification in the next step. $^1$H-NMR (DMSO-d$_6$, 300 MHz): 2.12-2.24 (m, 2H), 2.25-2.44 (m, 4H), 3.76 (s, 3H), 6.72 (dd, J=12.1, 1.9 Hz, 1H), 7.09 (d, J=1.6 Hz, 1H), 10.50 (s, 1H) ppm. LC-MS: C$_{12}$H$_{12}$FNO$_2$ [M+H]$^+$: 222

BBr$_3$ (23 mL, 23.4 mmol, 1M DCM) was added dropwise to a solution of 7'-fluoro-5'-methoxyspiro[cyclobutane-1,3'-indolin]-2'-one (0.74 g, 3.34 mmol) in anhydrous DCM (64 mL) under N2 at 0° C. The reaction mixture was stirred at room temperature for 5 h. The reaction mixture was quenched with sat. aq. NaHCO$_3$ (100 mL) and stirred for 30 min. The DCM layer was collected, and the aqueous layer was extracted with EtOAc (2×). The combined organic layers were dried over Na$_2$SO$_4$. The solids were removed by filtration and the filtrate was evaporated to dryness. The crude mixture was purified by flash chromatography on silica gel (20% to 50% EtOAc in CyH) to give 7'-fluoro-5'-hydroxyspiro[cyclobutane-1,3'-indolin]-2'-one (414 mg, 60%) as a light brown solid. $^1$H-NMR (DMSO-d$_6$, 300 MHz): 2.18-2.29 (m, 4H), 2.36-2.45 (m, 2H), 6.46 (d, J=11.9 Hz, 1H), 6.85 (d, J=1.6 Hz, 1H), 9.44 (br s, 1H), 10.39 (s, 1H) ppm. LC-MS: C$_{11}$H$_{10}$FNO$_2$ [M+H]$^+$: 208

DIPEA (1.0 mL, 6.16 mmol) was added to a solution of 7'-fluoro-5'-hydroxyspiro[cyclobutane-1,3'-indolin]-2'-one (638.0 mg, 3.08 mmol) and 1,3-dichloro-2-fluoro-5-nitrobenzene (646.6 mg, 3.08 mmol, CAS: 3107-19-5) in anhydrous DMF (31 mL) under N$_2$. The reaction mixture was stirred at room temperature for 21 h. The reaction mixture was diluted in water (50 mL) and filtered. The precipitate was washed with water (3×), dissolved in a EtOAc/THF mixture, and dried over Na$_2$SO$_4$. The solids were removed by filtration and the filtrate was evaporated to dryness to afford 5'-(2,6-dichloro-4-nitrophenoxy)-7'-fluorospiro[cyclobutane-1,3'-indolin]-2'-one (912 mg, 75%) as a brown solid which was used without further purification in the next step. $^1$H-NMR (DMSO-d$_6$, 300 MHz): 2.08-2.26 (m, 2H), 2.27-2.42 (m, 4H), 6.74 (dd, J=10.9, 2.0 Hz, 1H), 7.19 (d, J=1.6 Hz, 1H), 8.55 (s, 2H), 10.69 (s, 1H) ppm. LC-MS: C$_{17}$H$_{11}$Cl$_2$FN$_2$O$_4$ [M+H]$^+$: 397/399.

A mixture of 5'-(2,6-dichloro-4-nitrophenoxy)-7'-fluorospiro[cyclobutane-1,3'-indolin]-2'-one (912 mg, 2.3 mmol), NH$_4$Cl (1.23 g, 23.0 mmol) and Fe (641.2 mg, 11.5 mmol) in EtOH (15 mL) and water (8 mL) under N2 was stirred at 70° C. for 3 h. The reaction mixture was filtered over a pad of celite which was rinsed with EtOAc. The resulting solution was washed with brine (2×) and dried over Na$_2$SO$_4$. The solids were removed by filtration and the filtrate was evaporated to dryness providing 5'-(4-amino-2,6-dichlorophenoxy)-7'-fluorospiro[cyclobutane-1,3'-indolin]-2'-one (711 mg, 84%) as a light brown solid which was used without further purification in the next step. $^1$H-NMR (DMSO-d$_6$, 300 MHz): 2.08-2.50 (m, 6H), 5.67 (br s, 2H), 6.39 (dd, J=11.1 Hz, 2.1 Hz, 1H), 6.72 (s, 2H), 7.03 (d, J=2.1 Hz, 1H), 10.61 (s, 1H) ppm. LC-MS: C$_{17}$H$_{13}$Cl$_2$FN$_2$O$_2$ [M+H]$^+$: 367/369.

A solution of NaNO$_2$ (278.1 mg, 4.03 mmol) in water (38 mL) was added to a solution of 5'-(4-amino-2,6-dichlorophenoxy)-7'-fluorospiro[cyclobutane-1,3'-indolin]-2'-one (704.7 mg, 1.92 mmol) in conc. HCl (17 mL), AcOH (50 mL) and water (38 mL) at 0° C. under N$_2$. The reaction mixture was stirred at 0° C. for 2 h. In parallel, a solution of ethyl N-(2-cyanoacetyl)carbamate (449.5 mg, 2.88 mmol) in water (47 mL) and pyridine (17 mL) was stirred at 0° C. for 15 min. The first reaction mixture was quickly added to the second one and the resulting reaction mixture was stirred at 0° C. for 3 h. The reaction mixture was diluted in water (200 mL). The precipitate was filtered, washed with water, dissolved in EtOAc and dried over $Na_2SO_4$. The solids were removed by filtration and the filtrate was evaporated to dryness to give ethyl (2-cyano-2-(2-(3,5-dichloro-4-((7'-fluoro-2'-oxospiro[cyclobutane-1,3'-indolin]-5'-yl)oxy)phenyl)hydrazono)acetyl)carbamate (988 mg, 96%) as a light brown solid which was used without further purification in the next step. LC-MS: $C_{23}H_{18}Cl_2FN_5O_5$ [M+H]$^+$: 534/536

A mixture of ethyl (2-cyano-2-(2-(3,5-dichloro-4-((7'-fluoro-2'-oxospiro[cyclobutane-1,3'-indolin]-5'-yl)oxy)phenyl)hydrazono)acetyl)carbamate (988 mg, 1.85 mmol) and NaOAc (606.7 mg, 7.4 mmol) in AcOH (19 mL) under N2 was stirred at 120° C. for 2 h. The reaction mixture was cooled to room temperature and diluted in water (80 mL). The precipitate was filtered, washed with water (3×), dissolved in EtOAc and dried over $Na_2SO_4$. The solids were removed by filtration and the filtrate was evaporated to dryness. The crude mixture was purified by flash chromatography on silica gel (0% to 10% MeOH in DCM) to give 2-(3,5-dichloro-4-((7'-fluoro-2'-oxospiro[cyclobutane-1,3'-indolin]-5'-yl)oxy)phenyl)-3,5-dioxo-2,3,4,5-tetrahydro-1,2,4-triazine-6-carbonitrile (499 mg, 55%) as an orange solid. $^1$H-NMR (DMSO-d$_6$, 300 MHz): 2.07-2.45 (m, 6H), 6.62 (dd, J=11.1 Hz, 2.1 Hz, 1H), 7.18 (d, J=2.1 Hz, 1H), 7.81 (s, 2H), 10.67 (s, 1H), 13.24 (br s, 1H) ppm. LC-MS: $C_{21}H_{12}Cl_2FN_5O_4$ [M–H]$^-$: 486/488

A solution of 2-(3,5-dichloro-4-((7'-fluoro-2'-oxospiro[cyclobutane-1,3'-indolin]-5'-yl)oxy)phenyl)-3,5-dioxo-2,3,4,5-tetrahydro-1,2,4-triazine-6-carbonitrile (499 mg, 1.02 mmol) in HCl 37% (1.8 mL) and AcOH (4.6 mL) under N2 was stirred at 120° C. for 4 h. The reaction mixture was cooled to room temperature and water (50 mL) was added. The precipitate was filtered, washed with water (3×), dissolved in EtOAc and dried over $Na_2SO_4$. The solids were removed by filtration and the filtrate was evaporated to dryness to 2-(3,5-dichloro-4-((7'-fluoro-2'-oxospiro[cyclobutane-1,3'-indolin]-5'-yl)oxy)phenyl)-3,5-dioxo-2,3,4,5-tetrahydro-1,2,4-triazine-6-carboxylic acid (365 mg, 70%) as a brown solid which was used without further purification in the next step. $^1$H-NMR (DMSO-d$_6$, 300 MHz): 2.09-2.45 (m, 6H), 6.61 (dd, J=11.1 Hz, 2.1 Hz, 1H), 7.17 (d, J=2.1 Hz, 1H), 7.85 (s, 2H), 10.67 (s, 1H), 12.78 (br s, 1H) ppm. LC-MS: $C_{21}H_{13}Cl_2FN_4O_6$ [M–H]$^-$: 505/507.

Et$_3$N (0.40 mL, 2.88 mmol) and diphenyl phosphoryl azide (0.47 mL, 2.16 mmol) were added to a solution of 2-(3,5-dichloro-4-((7'-fluoro-2'-oxospiro[cyclobutane-1,3'-indolin]-5'-yl)oxy)phenyl)-3,5-dioxo-2,3,4,5-tetrahydro-1,2,4-triazine-6-carboxylic acid (365 mg, 0.72 mmol) in t-BuOH (10 mL) under N$_2$. The resulting mixture was stirred at 85° C. for 18 h. Extra Et$_3$N (0.40 mL, 2.88 mmol) and diphenyl phosphoryl azide (0.47 mL, 2.16 mmol) were added and the reaction mixture was stirred at 85° C. for 6 h. The reaction mixture was quenched with sat. aq. NH$_4$Cl (10 mL) and extracted with EtOAc (2×). The combined organic phases were washed with sat. aq. NH$_4$Cl and brine (2×) and dried over $Na_2SO_4$. The solids were removed by filtration and the filtrate was evaporated to dryness. The crude mixture was purified by flash chromatography on silica gel (0% to 10% MeOH in DCM) to give tert-butyl (2-(3,5-dichloro-4-((7'-fluoro-2'-oxospiro[cyclobutane-1,3'-indolin]-5'-yl)oxy)phenyl)-3,5-dioxo-2,3,4,5-tetrahydro-1,2,4-triazin-6-yl)carbamate (303 mg, 73%) as a light brown solid. $^1$H-NMR (DMSO-d$_6$, 400 MHz): 1.45 (s, 9H), 2.07-2.43 (m, 6H), 6.57 (dd, J=11.2 Hz, 2.4 Hz, 1H), 7.15 (d, J=2.4 Hz, 1H), 7.93 (s, 2H), 9.11 (s, 1H), 10.68 (s, 1H), 12.62 (br s, 1H) ppm. LC-MS: $C_{25}H_{22}Cl_2FN_5O_6$ [M+H]$^+$: 578/580

A solution of tert-butyl (2-(3,5-dichloro-4-((7'-fluoro-2'-oxospiro[cyclobutane-1,3'-indolin]-5'-yl)oxy)phenyl)-3,5-dioxo-2,3,4,5-tetrahydro-1,2,4-triazin-6-yl)carbamate (303 mg, 0.52 mmol) in 4N HCl in 1,4-dioxane (4 mL) under N2 was stirred at room temperature for 18 h. The reaction mixture was evaporated to dryness and the crude mixture was purified by flash chromatography on silica gel (2% to 5% MeOH in DCM) to afford 6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione (21) (51 mg, 82%) as a white solid. $^1$H-NMR (DMSO-d$_6$, 400 MHz): 2.04-2.16 (m, 1H), 2.16-2.26 (m, 1H), 2.27-2.35 (m, 2H), 2.36-2.44 (m, 2H), 6.50-6.59 (m, 3H), 7.12 (d, J=2.4 Hz, 1H), 7.93 (s, 2H), 10.68 (s, 1H), 12.30 (br s, 1H) ppm. LC-MS: $C_{20}H_{14}Cl_2FN_5O_4$ [M+H]$^+$: 478/480.

Example 22. Preparation of Compound 22

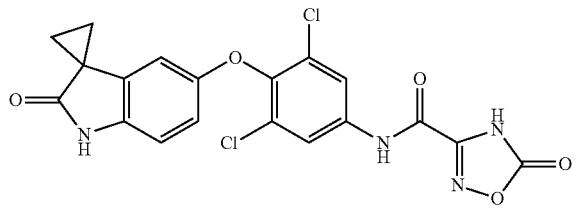 [SMILES: O=C(Nc1cc(Cl)c(Oc2ccc3c(c2)C2(CC2)C(=O)N3)c(Cl)c1)c1noc(=O)[nH]1]

PIFA (3.24 g, 7.53 mmol) was added to a solution of spiro[cyclopropane-1,3'-indolin]-2'-one (1 g, 6.28 mmol) and TFA (7.16 g, 4.67 mL, 62.82 mmol) in chloroform (74 mL) under N$_2$. The reaction mixture was stirred at room temperature for 2 h. The reaction mixture was diluted with DCM and quenched with sat. aq. NaHCO$_3$. The organic phase was washed with brine and dried over $Na_2SO_4$. The solids were removed by filtration and the filtrate was evaporated to dryness. The crude mixture was purified by flash chromatography on silica gel (2% to 5% MeOH in DCM) to give 5'-hydroxyspiro[cyclopropane-1,3'-indolin]-2'-one (1.10 g, 100%) as a brown solid. LC-MS: $C_{10}H_9NO_2$ [M+H]$^+$: 176.

DIPEA (1.62 g, 2.077 mL, 12.57 mmol) was added to a solution of give 5'-hydroxyspiro[cyclopropane-1,3'-indolin]-2'-one (1.101 g, 6.28 mmol) and 1,3-dichloro-2-fluoro-5-nitrobenzene (1.32 g, 6.28 mmol) in anhydrous DMF (63 mL) under N$_2$. The reaction mixture was stirred at 60° C. for 2 days. After cooling to room temperature, the reaction mixture was diluted in water (300 mL). The resulting precipitate was filtered and washed with water (3×). The precipitate was dissolved in EtOAc and dried over $Na_2SO_4$. The solids were removed by filtration and the filtrate was evaporated to dryness to give 5'-(2,6-dichloro-4-nitrophenoxy)spiro[cyclopropane-1,3'-indolin]-2'-one (2.29 g, 100%) as a yellow solid, which was used without any further purification in the next step. $^1$H-NMR (DMSO-d$_6$, 300 MHz): 1.43-1.49 (m, 2H), 1.53-1.60 (m, 2H), 6.59 (dd, J=8.4 Hz, 2.4 Hz, 1H), 6.75 (d, J=2.4 Hz, 1H), 6.81 (d, J=8.4 Hz, 1H), 8.51 (s, 2H), 10.48 (s, 1H) ppm. LC-MS: $C_{16}H_{10}Cl_2N_2O_4$ [M+H]$^+$: 365.

Fe (1.75 g, 31.36 mmol) was added to a solution of 5'-(2,6-dichloro-4-nitrophenoxy)spiro[cyclopropane-1,3'-indolin]-2'-one (2.29 g, 6.27 mmol) and NH$_4$Cl (3.35 g, 62.71 mmol) in EtOH (42 mL) and water (21 mL) under N$_2$. The reaction mixture was stirred at 70° C. for 5 h. Temperature was increased to 80° C. and stirring was pursued overnight. After cooling to room temperature, the reaction mixture was filtered over a pad of celite which was rinsed with EtOAc. The organic phase was collected, washed with brine (2×) and dried over Na₂SO₄. The solids were removed by filtration and the filtrate was evaporated to dryness. The crude mixture was purified by flash chromatography on silica gel (0% to 5% MeOH in DCM) to give 5'-(4-amino-2,6-dichlorophenoxy)spiro[cyclopropane-1,3'-indolin]-2'-one (1.16 g, 55%) as a yellow solid. LC-MS: $C_{16}H_{12}Cl_2N_2O_2$ [M+H]⁺: 335.

LiHMDS (1M in THF, 5.97 mL, 5.97 mmol) was added to a solution of ethyl 5-oxo-4,5-dihydro-1,2,4-oxadiazole-3-carboxylate (235.86 mg, 1.49 mmol) and 5'-(4-amino-2,6-dichlorophenoxy)spiro[cyclopropane-1,3'-indolin]-2'-one (500 mg, 1.49 mmol) in anhydrous THF (7 mL) under N₂. The reaction mixture was stirred at room temperature for 10 min. The reaction mixture was diluted with MeOH and evaporated to dryness. The crude product was purified by flash chromatography on silica gel (5% to 50% MeOH in DCM). The resulting solid was triturated in EtOH. The solids were removed by filtration and the filtrate was evaporated to dryness. The residue was triturated in MeCN and dried under high vacuum to give N-(3,5-dichloro-4-((2'-oxospiro[cyclopropane-1,3'-indolin]-5'-yl)oxy)phenyl)-5-oxo-4,5-dihydro-1,2,4-oxadiazole-3-carboxamide (22) (102 mg, 15%) as a white solid. ¹H-NMR (DMSO-d₆, 400 MHz): 1.41-1.47 (m, 2H), 1.54-1.60 (m, 2H), 6.45 (dd, J=8.5 Hz, 2.8 Hz, 1H), 6.71 (d, J=2.8 Hz, 1H), 6.78 (d, J=8.5 Hz, 1H), 8.11 (s, 2H), 10.43 (s, 1H), 10.49 (s, 1H) ppm. LC-MS: $C_{19}H_{12}Cl_2N_4O_5$ [M+H]⁺: 447.

Example 23. Preparation of Compound 23

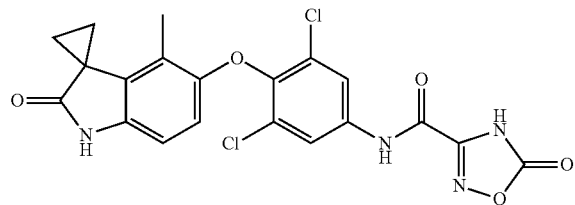 [SMILES: Cc1c(Oc2c(Cl)cc(NC(=O)c3noc(=O)[nH]3)cc2Cl)ccc2c1C1(CC1)C(=O)N2]

A solution of ethenyldiphenylsulfanium trifluoromethanesulfonate (14.8 g, 40.8 mmol) in anhydrous DMF (51 mL) was added to a solution of 4-methyl-2,3-dihydro-1H-indol-2-one (5 g, 34.0 mmol, CAS: 13220-46-7) and Zn(OTf)₂ (12.4 g, 34.0 mmol) in anhydrous DMF (154 mL) under N₂. After 2 min of stirring, DBU (15 mL, 102 mmol) was added and the reaction mixture was stirred at room temperature for 1.5 h. The reaction mixture was quenched with NH₄Cl (sat., aq., 100 mL) and diluted with AcOEt (400 mL). The mixture was washed with brine (3×) and dried over Na₂SO₄. The solids were removed by filtration and the filtrate was evaporated to dryness. The resulting solid was triturated with pentane to give 4'-methylspiro[cyclopropane-1,3'-indolin]-2'-one (5.88 g, quant.) as a beige solid which was used without further purification in the next step. ¹H-NMR (DMSO-d₆, 300 MHz): 1.24-1.34 (m, 2H), 1.87-1.96 (m, 2H), 2.11 (s, 3H), 6.68 (d, J=7.6 Hz, 1H), 6.74 (d, J=7.7 Hz, 1H), 7.03 (t, J=7.7 Hz, 1H), 10.48 (s, 1H) ppm. LC-MS: $C_{11}H_{11}NO$ [M+H]⁺: 174.

PIFA (18.7 g, 43.4 mmol) was added to a solution of 4'-methylspiro[cyclopropane-1,3'-indolin]-2'-one (6.27 g, 36.2 mmol) and TFA (27 mL, 362 mmol) in chloroform (428 mL) under N₂. The reaction mixture was stirred at room temperature for 22 h. The reaction was quenched with sat. aq. NaHCO₃ (200 mL) and stirred for 5 min. The organic layer was collected, diluted in EtOAc (400 mL), washed with sat. aq. NaHCO₃ (3×) and dried over Na₂SO₄. The solids were removed by filtration and the filtrate was evaporated to dryness. The crude mixture was purified by flash chromatography on silica gel (2% to 5% MeOH in DCM) and trituration with EtOH (3×) to give 5'-hydroxy-4'-methylspiro[cyclopropane-1,3'-indolin]-2'-one (3.11 g, 45%) as an orange solid. ¹H-NMR (DMSO-d₆, 300 MHz): 1.23-1.30 (m, 2H), 1.81-1.87 (m, 2H), 1.90 (s, 3H), 6.53 (d, J=8.1 Hz, 1H), 6.59 (d, J=8.2 Hz, 1H), 8.78 (s, 1H), 10.17 (s, 1H) ppm. LC-MS: $C_{11}H_{11}NO_2$ [M+H]⁺: 190.

DIPEA (5.4 mL, 32.9 mmol) was added to a solution of 5'-hydroxy-4'-methylspiro[cyclopropane-1,3'-indolin]-2'-one (3.11 g, 16.4 mmol) and 1,3-dichloro-2-fluoro-5-nitrobenzene (3.45 g, 16.4 mmol) in anhydrous DMF (163 mL) under N₂. The reaction mixture was stirred at 60° C. for 21 h. The reaction mixture was diluted in water (300 mL) and filtered. The precipitate was washed with water (3×) and then dissolved in EtOAc and dried over Na₂SO₄. The solids were removed by filtration and the filtrate was evaporated to dryness to give 5'-(2,6-dichloro-4-nitrophenoxy)-4'-methylspiro[cyclopropane-1,3'-indolin]-2'-one (4.81 g, 77%) as a yellow solid which was used without further purification in the next step. ¹H-NMR (DMSO-d₆, 300 MHz): 1.35-1.42 (m, 2H), 1.87-2.03 (m, 2H), 2.18 (s, 3H), 6.22 (d, J=8.5 Hz, 1H), 6.51 (d, J=8.1 Hz, 1H), 8.51 (s, 2H), 10.47 (s, 1H) ppm. LC-MS: $C_{17}H_{12}Cl_2N_2O_4$ [M+H]⁺: 379.

A mixture of 5'-(2,6-dichloro-4-nitrophenoxy)-4'-methylspiro[cyclopropane-1,3'-indolin]-2'-one (4.81 g, 12.7 mmol), NH₄Cl (6.79 g, 127 mmol) and Fe (3.54 g, 63.4 mmol) in EtOH (86 mL) and water (43 mL) under N2 was stirred at 80° C. for 23 h. The reaction mixture was filtered over celite and diluted in EtOAc. The resulting solution was washed with brine (3×) and dried over Na₂SO₄. The solids were removed by filtration and the filtrate was evaporated to dryness providing 5'-(4-amino-2,6-dichlorophenoxy)-4'-methylspiro[cyclopropane-1,3'-indolin]-2'-one (4.43 g, quant.) as a yellow solid which was used without further purification in the next step. ¹H-NMR (DMSO-d₆, 300 MHz): 1.31-1.37 (m, 2H), 1.92-1.98 (m, 2H), 2.12 (s, 3H), 5.58 (br s, 2H), 6.13 (d, J=8.5 Hz, 1H), 6.60 (d, J=8.5 Hz, 1H), 6.70 (s, 2H), 10.37 (s, 1H) ppm. LC-MS: $C_{17}H_{14}Cl_2N_2O_2$ [M+H]⁺: 349.

LiHMDS (1M in THF, 4.88 mL, 4.88 mmol) was added to a solution of ethyl 5-oxo-4,5-dihydro-1,2,4-oxadiazole-3-carboxylate (192.88 mg, 1.22 mmol) and 5'-(4-amino-2,6-dichlorophenoxy)-4'-methylspiro[cyclopropane-1,3'-indolin]-2'-one (426 mg, 1.22 mmol) in anhydrous THF (5.8 mL) under N₂. The reaction mixture was stirred at room temperature for 1 h. The reaction mixture was then diluted with MeOH and evaporated to dryness. The crude product was purified by flash chromatography on silica gel (5% to 50% MeOH in DCM). The resulting solid was triturated in EtOH, and dried under high vacuum to afford N-(3,5-dichloro-4-((4'-methyl-2'-oxospiro[cyclopropane-1,3'-indolin]-5'-yl)oxy)phenyl)-5-oxo-4,5-dihydro-1,2,4-oxadiazole-3-carboxamide (23) (225 mg, 40%) as a white solid. ¹H-NMR (DMSO-d₆, 400 MHz): 1.32-1.39 (m, 2H), 1.96-2.03 (m, 2H), 2.15 (s, 3H), 6.15 (d, J=8.4 Hz, 1H), 6.61 (d, J=8.4 Hz, 1H), 8.09 (s, 2H), 10.42 (s, 1H), 10.63 (s, 1H) ppm. LC-MS: $C_{20}H_{13}Cl_2N_3O_6$ [M+H]⁺: 461.

Example 24. Preparation of Compound 24

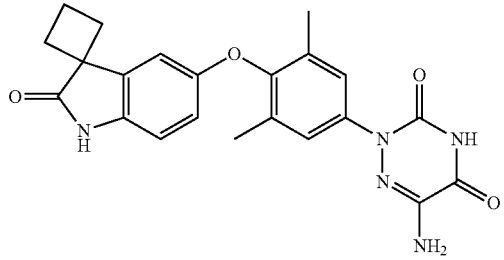

PIFA (22.3 g, 51.9 mmol) and TFA (32 mL, 433 mmol) were added to a solution of spiro[cyclobutane-1,3'-indolin]-2'-one (7.5 g, 43.3 mmol) in CHCl$_3$ (500 mL) under N$_2$. The reaction mixture was stirred at room temperature for 1 h. The reaction mixture was neutralized with sat. aq. Na$_2$CO$_3$. The organic phase was collected and the aqueous phase was extracted with DCM (3×). The combined organic layers were washed brine and dried over Na$_2$SO$_4$. The solids were removed by filtration and the filtrate was evaporated to dryness. The crude mixture was purified by flash chromatography on silica gel (0% to 5% MeOH in DCM) to give 5'-hydroxyspiro[cyclobutane-1,3'-indolin]-2'-one (2.7 g, 33%) as a beige solid. $^1$H-NMR (DMSO-d$_6$, 300 MHz): 2.08-2.26 (m, 4H), 2.34-2.42 (m, 2H), 6.56 (s, 2H), 6.96 (s, 1H), 8.97 (br s, 1H), 9.90 (s, 1H) ppm. LC-MS: C$_{11}$H$_{11}$NO [M+H]$^+$: 190.

A mixture of 5'-hydroxyspiro[cyclobutane-1,3'-indolin]-2'-one (3.12 g, 16.5 mmol), 2-fluoro-1,3-dimethyl-5-nitrobenzene (2.79 g, 16.5 mmol, CAS: 1736-85-2) and K$_2$CO$_3$ (6.84 g, 49.46 mmol) in anhydrous DMF (100 mL) under N2 was stirred at 60° C. for 18 h. The reaction mixture was cooled to room temperature, diluted in water and extracted with EtOAc (3×). The combined organic layers were washed brine (2×) and dried with Na$_2$SO$_4$. The solids were removed by filtration and the filtrate was evaporated to dryness providing 5'-(2,6-dimethyl-4-nitrophenoxy)spiro[cyclobutane-1,3'-indolin]-2'-one (3.76 g, 67%) as a beige solid which was used without further purification in the next step. $^1$H-NMR (DMSO-d$_6$, 300 MHz): 2.19 (s, 6H), 2.21-2.40 (m, 6H), 6.44 (dd, J=8.4, J=2.5 Hz, 1H), 6.68 (d, J=8.4 Hz, 1H), 7.21 (d, J=2.5 Hz, 1H), 8.12 (s, 2H), 10.14 (br s, 1H) ppm. LC-MS: C$_{19}$H$_{18}$N$_2$O$_4$ [M+H]$^+$: 339.

Fe (6.21 g, 111 mmol) was added to a solution of 5'-(2,6-dimethyl-4-nitrophenoxy)spiro[cyclobutane-1,3'-indolin]-2'-one (3.76 g, 11.1 mmol) and NH$_4$Cl (11.88 g, 222 mmol) in EtOH (75 mL) and water (38 mL) under N$_2$. The reaction mixture was stirred at 80° C. for 4 h. The reaction mixture was filtered over a pad of celite which was rinsed with EtOAc. The resulting solution was washed with water and brine, and dried over Na$_2$SO$_4$. The solids were removed by filtration and the filtrate was evaporated to dryness providing 5'-(4-amino-2,6-dimethylphenoxy)spiro[cyclobutane-1,3'-indolin]-2'-one (2.02 g, 59%) as a beige solid which was used without further purification in the next step. $^1$H-NMR (DMSO-d$_6$, 300 MHz): 1.92 (s, 6H), 2.05-2.27 (m, 4H), 2.32-2.43 (m, 2H), 4.82 (br s, 2H), 6.32 (s, 2H), 6.36 (d, J=9.0 Hz, 1H), 6.63 (d, J=8.4 Hz, 1H), 7.06 (d, J=2.3 Hz, 1H), 10.04 (br s, 1H) ppm. LC-MS: C$_{19}$H$_{20}$N$_2$O$_2$ [M+H]$^+$: 309.

A solution of NaNO$_2$ (437 mg, 6.33 mmol) in water (60 mL) was added to a solution of 5'-(4-amino-2,6-dimethylphenoxy)spiro[cyclobutane-1,3'-indolin]-2'-one (930 mg, 3.02 mmol) in conc. HCl (26 mL), acetic acid (78 mL) and water (60 mL) at 0° C. under N$_2$. The reaction mixture was stirred at 0° C. for 1 h. In parallel, a solution of ethyl N-(2-cyanoacetyl)carbamate (650.2 mg, 4.16 mmol) in water (74 mL) and pyridine (26 mL) was stirred at 0° C. for 15 min. The first reaction mixture was quickly added to the second one and the resulting reaction mixture was stirred at 0° C. for 1 h. The reaction mixture was diluted in water. The precipitate was filtered, washed with water, dissolved in EtOAc and evaporated to dryness providing ethyl (2-cyano-2-(2-(3,5-dimethyl-4-((2'-oxospiro[cyclobutane-1,3'-indolin]-5'-yl)oxy)phenyl)hydrazineylidene)acetyl)carbamate (1.33 g, 93%) as an orange solid which was used without further purification in the next step. LC-MS: C$_{25}$H$_{25}$N$_5$O$_5$ [M+H]$^+$: 476.

NaOAc (920 mg, 11.19 mmol) was added to a solution of ethyl (2-cyano-2-(2-(3,5-dimethyl-4-((2'-oxospiro[cyclobutane-1,3'-indolin]-5'-yl)oxy)phenyl)hydrazineylidene) acetyl)carbamate (1.33 g, 2.8 mmol) in AcOH (27 mL) under N$_2$. The solution was stirred at 120° C. for 1 h. The reaction mixture was cooled at 0° C. and diluted in water. The precipitate was filtered and washed with water to give 2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile (1.07 g, 89%) as a yellow solid which was used without further purification in the next step. $^1$H-NMR (DMSO-d$_6$, 300 MHz): 1.91-2.43 (m, 12H), 6.37 (d, J=8.8 Hz, 1H), 6.67 (d, J=8.5 Hz, 1H), 7.22 (d, J=2.0 Hz, 1H), 7.29 (s, 2H), 10.11 (br s, 1H) ppm. LC-MS: C$_{23}$H$_{19}$N$_5$O$_4$ [M+H]$^+$: 430.

A mixture of 2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile (1.07 g, 2.49 mmol), HCl 37% (1.84 mL, 22.42 mmol) and AcOH (3.71 mL, 64.78 mmol) under N2, was stirred at 120° C. for 1 h. The reaction mixture was cooled to room temperature and water was added. The precipitate was filtered, washed with water, dissolved in EtOAc and evaporated to dryness providing 2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carboxylic acid (1.12 g, quant.) as a dark solid which was used without further purification in the next step. $^1$H-NMR (DMSO-d$_6$, 300 MHz): 2.12 (s, 6H), 2.24-2.34 (m, 4H), 2.35-2.42 (m, 2H), 6.37 (dd, J=8.9, 2.8 Hz, 1H), 6.67 (d, J=8.4 Hz, 1H), 7.22 (d, J=2.7 Hz, 1H), 7.31 (s, 2H), 10.11 (s, 1H), 12.55 (br s, 1H) ppm. LC-MS: C$_{23}$H$_{20}$N$_4$O$_6$ [M+H]$^+$: 449.

Et$_3$N (1.4 mL, 9.99 mmol) and diphenyl phosphoryl azide (1.6 mL, 7.49 mmol) were added to a solution of 2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carboxylic acid (1.12 g, 7.49 mmol) in t-BuOH (35 mL) under N$_2$. The resulting mixture was stirred at 85° C. for 5 h. The reaction mixture was quenched with sat. aq. NH$_4$Cl and was extracted with EtOAc (2×). The combined organic layers were washed with sat. aq. NH$_4$Cl and brine, and dried over Na$_2$SO$_4$. The solids were removed by filtration and the filtrate was evaporated to dryness. The crude mixture was purified by flash chromatography on silica gel (0% to 4% MeOH in DCM) to give t-butyl (2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazin-6-yl)carbamate (383 mg, 30%) as an orange solid. $^1$H-NMR (DMSO-d$_6$, 300 MHz): 1.43 (s, 9H), 2.11 (s, 6H), 2.15-2.46 (m, 6H), 6.37 (dd, J=8.4 Hz, J=2.1 Hz, 1H), 6.67 (d, J=8.4 Hz, 1H), 7.21

(d, J=2.1 Hz, 1H), 7.32 (s, 2H), 8.94 (s, 1H), 10.11 (s, 1H), 12.46 (br s, 1H) ppm. LC-MS: $C_{27}H_{29}N_5O_6$ [M+H]$^+$: 520.

A solution of t-butyl (2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazin-6-yl)carbamate (283 mg, 0.54 mmol) in HCl 4N in 1,4-dioxane (2.72 mL, 10.89 mmol) under N2 was stirred at room temperature for 3 h. The reaction mixture was evaporated to dryness and the crude mixture was purified by flash chromatography on silica gel (5% MeOH in DCM) to give 6-amino-2-(3,5-dimethyl-4-((2'-oxospiro[cyclobutane-1,3'-indolin]-5'-yl)oxy)phenyl)-1,2,4-triazine-3,5(2H,4H)-dione (24) (146 mg, 64%) as a yellow solid. $^1$H-NMR (DMSO-d$_6$, 400 MHz): 2.09 (s, 6H), 2.12-2.33 (m, 4H), 2.37-2.43 (m, 2H), 6.32 (br s, 2H), 6.36 (dd, J=2.7, 8.4 Hz, 1H), 6.67 (d, J=8.4 Hz, 1H), 7.18 (d, J=2.6 Hz, 1H), 7.31 (s, 2H), 10.11 (s, 1H), 12.11 (br s, 1H) ppm. LC-MS: $C_{22}H_{21}N_5O_4$ [M+H]$^+$: 420.

Example 25. Preparation of Compound 25

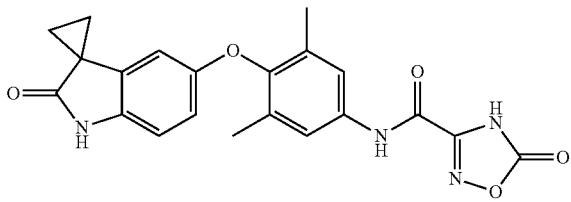 [SMILES: Cc1cc(NC(=O)c2noc(=O)[nH]2)cc(C)c1Oc1ccc2c(c1)C1(CC1)C(=O)N2]

A solution of LiOH H$_2$O (546.5 mg, 13.0 mmol) in water (17 mL) was added to a solution of ethyl 5-oxo-4,5-dihydro-1,2,4-oxadiazole-3-carboxylate (572 mg, 3.62 mmol) in THF (17 mL) under N$_2$. The reaction mixture was stirred at 70° C. for 4 h. The reaction mixture was cooled to room temperature and THF was evaporated. The reaction mixture was acidified with 1M HCl to pH 2. The resulting solution was extracted with EtOAc (3×), washed with brine and dried over Na$_2$SO$_4$. The solids were removed by filtration and the filtrate was evaporated to dryness to afford 5-oxo-4,5-dihydro-1,2,4-oxadiazole-3-carboxylic acid (97 mg, 21%) as a white solid which was used without further purification in the next step.

TCFH (330.9 mg, 1.18 mmol), 5'-(4-amino-2,6-dimethylphenoxy)spiro[cyclobutane-1,3'-indolin]-2'-one (200 mg, 0.65 mmol) and N-methylimidazole (0.23 mL, 2.95 mmol) were added to a solution of 5-oxo-4,5-dihydro-1,2,4-oxadiazole-3-carboxylic acid (76.7 mg, 0.59 mmol) in MeCN (7 mL) under N$_2$. The reaction mixture was stirred at room temperature for 1 h. The reaction mixture was diluted with water (30 mL), acidified with HCl 6N to pH 2 and extracted with EtOAc (3×). The combined organic phases were washed with water (4×) and brine, and dried over Na$_2$SO$_4$. The solids were removed by filtration and the filtrate was evaporated to dryness. The crude mixture was purified by reverse phase flash chromatography (5% to 100% MeCN in water (0.1% TFA)). The resulting solution was extracted with EtOAc (3×) and dried over Na$_2$SO$_4$. The solids were removed by filtration and the filtrate was evaporated to dryness. The residue was dissolved in DMSO (6 mg/mL) and was purified by HPLC (5% to 100% MeCN in water (0.2% NH$_4$OAc)) to give N-(3,5-dimethyl-4-((2'-oxospiro[cyclobutane-1,3'-indolin]-5'-yl)oxy)phenyl)-5-oxo-4,5-dihydro-1,2,4-oxadiazole-3-carboxamide (25) (4.6 mg, 2%) as a white solid. $^1$H-NMR (DMSO-d$_6$, 400 MHz): 2.07 (s, 6H), 2.09-2.22 (m, 2H), 2.23-2.31 (m, 2H), 2.36-2.43 (m, 2H), 6.36 (dd, J=8.4, 2.5 Hz, 1H), 6.65 (d, J=8.4 Hz, 1H), 7.15 (d, J=2.6 Hz, 1H), 7.56 (s, 2H), 10.09 (s, 1H), 10.67 (s, 1H), 13.26 (br s, 1H) ppm. LC-MS: $C_{22}H_{20}N_4O_5$ [M+H]$^+$: 421.

Example 26. Preparation of Compound 26

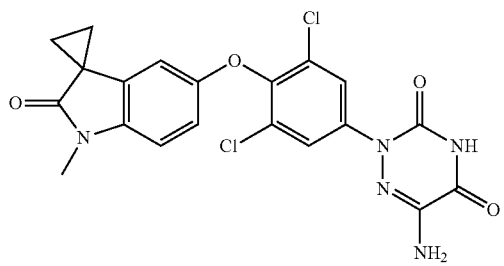 [SMILES: CN1C(=O)C2(CC2)c2cc(Oc3c(Cl)cc(-n4nc(N)c(=O)[nH]c4=O)cc3Cl)ccc21]

A mixture of 5'-bromo-1',2'-dihydrospiro[cyclopropane-1,3'-indol]-2'-one (1 g, 4.22 mmol), and NaH 60% (202 mg, 5.04 mmol) in anhydrous DMF (8 mL) was stirred at 0° C. for 30 min. MeI (0.29 mL, 4.62 mmol) was added and the reaction mixture was stirred at room temperature for 1 h. The reaction mixture was diluted with water. The precipitate was filtered, washed with water (3×), dissolved in EtOAc and dried over Na$_2$SO$_4$. The solids were removed by filtration and the filtrate was evaporated to dryness to give 5'-bromo-1'-methylspiro[cyclopropane-1,3'-indolin]-2'-one (907 mg, 86%) as a light pink solid which was used without further purification in the next step. $^1$H-NMR (DMSO-d$_6$, 300 MHz): 1.48-1.57 (m, 2H), 1.65-1.75 (m, 2H), 3.19 (s, 3H), 7.02 (d, J=8.1 Hz, 1H), 7.27 (d, J=1.9 Hz, 1H), 7.42 (dd, J=8.3 Hz, 1.6 Hz, 1H) ppm. LC-MS: $C_{11}H_{10}BrNO$ [M+H]$^+$: 252/254.

Bis(neopentylglycolato)diboron (2.4 g, 10.5 mmol), KOAc (1.0 g, 10.53 mmol) and PdCl$_2$[P(o-Tol)$_3$]$_2$ (27.6 mg, 0.035 mmol) were added to a solution of 5'-bromo-1'-methylspiro[cyclopropane-1,3'-indolin]-2'-one (885 mg, 3.51 mmol) in anhydrous DMSO (24 mL) under N$_2$. The reaction mixture was stirred at 90° C. for 1.5 h. After cooling to room temperature, the reaction mixture was diluted with water and extracted with EtOAc (3×). The combined organic phases were washed with water (3×) and brine (2×) and dried over Na$_2$SO$_4$. The solids were removed by filtration and the filtrate was evaporated to dryness. The crude mixture was purified by flash chromatography on silica gel (10% to 40% EtOAc in CyH) to give 5'-(5,5-dimethyl-1,3,2-dioxaborinan-2-yl)-1'-methylspiro[cyclopropane-1,3'-indolin]-2'-one (875 mg, 85%) as a white solid. $^1$H-NMR (DMSO-d$_6$, 300 MHz): 0.94 (s, 6H), 1.44-1.51 (m, 2H), 1.59-1.66 (m, 2H), 3.21 (s, 3H), 3.73 (s, 4H), 7.05 (d, J=7.8 Hz, 1H), 7.28 (s, 1H), 7.63 (d, J=7.8 Hz, 1H) ppm. LC-MS: $C_{16}H_{20}BNO_3$ [M+H]$^+$: 218.

Pyridine (0.22 mL, 2.78 mmol) was added to a mixture of 5'-(5,5-dimethyl-1,3,2-dioxaborinan-2-yl)-1'-methylspiro[cyclopropane-1,3'-indolin]-2'-one (900 mg, 3.16 mmol), tert-butyl (4-((benzyloxy)methyl)-2-(3,5-dichloro-4-hydroxyphenyl)-3,5-dioxo-2,3,4,5-tetrahydro-1,2,4-triazin-6-yl)carbamate (643 mg, 1.26 mmol) and Cu(OTf)$_2$ (913 mg, 2.52 mmol) in anhydrous DMF (13 mL). The solution was sparged with air and the reaction mixture was stirred at 70° C. for 21 h. The reaction mixture was diluted with water and extracted with EtOAc (3×). The combined organic phases were washed with sat. aq. Na$_2$CO$_3$ and brine (5×), and dried over Na$_2$SO$_4$. The solids were removed by filtration and the filtrate was evaporated to dryness. The crude mixture was purified by flash chromatography on silica gel (0% to 40% EtOAc in CyH) to give tert-butyl (4-((benzyloxy)methyl)-2-(3,5-dichloro-4-((1'-methyl-2'-oxospiro[cyclopropane-1,3'-indolin]-5'-yl)oxy)phenyl)-3,5-dioxo-2,3,4,5-tetrahydro-1,2,4-triazin-6-yl)carbamate (426 mg, 50%) as a white solid. $^1$H-NMR (DMSO-$d_6$, 300 MHz): 1.46 (s, 9H), 1.49-1.54 (m, 2H), 1.61-1.67 (m, 2H), 3.18 (s, 3H), 4.64 (s, 2H), 5.41 (s, 2H), 6.55 (dd, J=8.4, 2.0 Hz, 1H), 6.87 (d, J=2.0 Hz, 1H), 6.96 (d, J=8.4 Hz, 1H), 7.25-7.37 (m, 5H), 7.86 (s, 2H), 9.35 (s, 1H) ppm. LC-MS: $C_{33}H_{31}Cl_2N_5O_7$ [M+H]$^+$: 678.

BBr$_3$ (4.5 mL, 4.54 mmol, 1M in DCM) was added to a solution of t-butyl (4-((benzyloxy)methyl)-2-(3,5-dichloro-4-((1'-methyl-2'-oxospiro[cyclopropane-1,3'-indolin]-5'-yl)oxy)phenyl)-3,5-dioxo-2,3,4,5-tetrahydro-1,2,4-triazin-6-yl)carbamate (386 mg, 0.57 mmol) in anhydrous DCM (200 mL) under N$_2$. The reaction mixture was stirred at 0° C. for 1 h. The reaction mixture was diluted with sat. aq. NaHCO$_3$ and extracted with DCM (3×). The combined organic phases were washed with brine and dried over Na$_2$SO$_4$. The solids were removed by filtration and the filtrate was evaporated to dryness. The crude mixture was purified by flash chromatography on silica gel (0% to 5% MeOH in DCM) followed by reverse phase chromatography (0 to 100% MeCN in water (0.1% TFA)), and trituration with EtOH to give 6-amino-2-(3,5-dichloro-4-((1'-methyl-2'-oxospiro[cyclopropane-1,3'-indolin]-5'-yl)oxy)phenyl)-1,2,4-triazine-3,5(2H,4H)-dione (26) (4.68 g, 51%) as a white solid. $^1$H-NMR (DMSO-$d_6$, 400 MHz): 1.48-1.53 (m, 2H), 1.60-1.66 (m, 2H), 3.17 (s, 3H), 6.48-6.55 (m, 3H), 6.83 (d, J=2.6 Hz, 1H), 6.96 (d, J=8.5 Hz, 1H), 7.89 (s, 2H), 12.29 (s, 1H) ppm. LC-MS: $C_{20}H_{15}Cl_2N_5O_4$ [M+H]$^+$: 460.

Example 27. Preparation of Compound 27

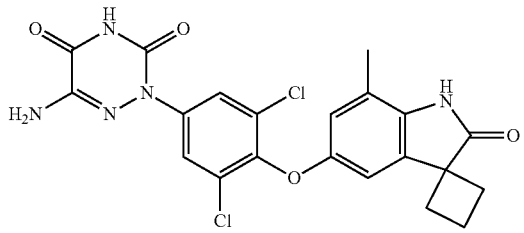 [SMILES: Cc1cc(Oc2c(Cl)cc(-n3nc(N)c(=O)[nH]c3=O)cc2Cl)cc2c1NC(=O)C21CCC1]

Cyclobutanecarbonyl chloride (7.47 g, 63.04 mmol) was added dropwise (over 20 min via syringe pump) to a solution of 2-(2-methylphenyl)hydrazinium chloride (10 g, 63.04 mmol) and pyridine (15 mL, 186.2 mmol) in anhydrous DMA (30 mL) at −20° C. under N$_2$. The reaction mixture was stirred at −20° C. for 2 h. Upon completion, the reaction mixture was poured into ice-water and the precipitate was filtered, washed with water (3×), dried at 60° C. under reduced pressure and co-evaporated with toluene to give N'-(o-tolyl)cyclobutanecarbohydrazide (8.2 g, 64%) as a light red solid which was used without further purification in the next step. LC-MS: $C_{12}H_{16}N_2O$ [M+H]$^+$: 205.

CaO (22.51 g, 401.42 mmol) was added to a solution of N'-(o-tolyl)cyclobutanecarbohydrazide (8.2 g, 40.14 mmol) in quinoline (9 mL). The reaction mixture was stirred at 60° C. for 2 h. After cooling to room temperature, the reaction mixture was diluted with EtOAc and water. The resulting mixture was cooled to 0° C. and acidified with HCl 37% until pH=1. The phases were separated and the aqueous layer was reextracted with EtOAc. The combined organic layers were washed with brine and dried over Na$_2$SO$_4$. The solids were removed by filtration and the filtrate was evaporated to dryness. The crude mixture was purified by flash chromatography on silica gel (10% to 20% EtOAc in CyH) to give 7'-methylspiro[cyclobutane-1,3'-indolin]-2'-one (4.6 g, 61%) as an orange solid. LC-MS: $C_{12}H_{13}NO$ [M+H]$^+$: 188.

PIFA (10.74 g, 24.97 mmol) and TFA (23.75 g, 15.47 mL, 208.29 mmol) were added to a solution of 7'-methylspiro[cyclobutane-1,3'-indolin]-2'-one (3.9 g, 20.83 mmol) in chloroform (246 mL) under N$_2$. The reaction mixture was stirred at room temperature for 1 h. The reaction mixture was diluted with DCM and quenched with sat. aq. Na$_2$S$_2$O$_3$. The phases were separated and the organic layer was washed with brine and dried over Na$_2$SO$_4$. The solids were removed by filtration and the filtrate was evaporated to dryness. The crude mixture was purified by flash chromatography on silica gel (25% EtOAc in CyH) to give 5'-hydroxy-7'-methylspiro[cyclobutane-1,3'-indolin]-2'-one (1.60 g, 38%) as an orange solid. $^1$H-NMR (DMSO-$d_6$, 400 MHz): 1.98 (s, 3H), 2.12-2.23 (m, 4H), 2.36-2.42 (m, 2H), 6.38 (d, J=2.4 Hz, 1H), 6.78 (d, J=2.4 Hz, 1H), 8.88 (br s, 1H), 9.97 (s, 1H) ppm. LC-MS: $C_{12}H_{13}NO_2$ [M+H]$^+$: 204.

A mixture of 5'-hydroxy-7'-methylspiro[cyclobutane-1,3'-indolin]-2'-one (1.6 g, 7.87 mmol), 1,3-dichloro-2-fluoro-5-nitrobenzene (1.65 g, 7.87 mmol) and K$_2$CO$_3$ (1.63 g, 11.809 mmol) in DMF (54 mL) was stirred at room temperature for 3 h. The reaction mixture was diluted with water. The resulting precipitate was filtered, washed with water and methanol and dried under vacuum to give 5'-(2,6-dichloro-4-nitrophenoxy)-7'-methylspiro[cyclobutane-1,3'-indolin]-2'-one (1.79 g, 58%) as a yellow solid which was used in the next step without any additional purification. LC-MS: $C_{11}H_{14}Cl_2N_2O_4$ [M+H]$^+$: 393.

Fe (177.52 mg, 3.18 mmol) was added to a solution of 5'-(2,6-dichloro-4-nitrophenoxy)-7'-methylspiro[cyclobutane-1,3'-indolin]-2'-one (250 mg, 0.64 mmol) and NH$_4$Cl (340 mg, 6.36 mmol) in EtOH (4.45 mL) and water (2.22 mL) under N$_2$. The reaction mixture was stirred at 70° C. for 2 h. The reaction mixture was cooled to room temperature, diluted with EtOH and filtered over a pad of celite. The filtrate was evaporated to dryness. The residue was dissolved in EtOAc, washed with sat. aq. NaHCO$_3$ and brine and dried over Na$_2$SO$_4$. The solids were removed by filtration and the filtrate was evaporated to dryness to give 5'-(4-amino-2,6-dichlorophenoxy)-7'-methylspiro[cyclobutane-1,3'-indolin]-2'-one (232 mg, 100%) as a white solid which was used in the next step without any additional purification. LC-MS: $C_{18}H_{16}Cl_2N_2O_2$ [M+H]$^+$: 363.

A solution of NaNO$_2$ (102 mg, 1.48 mmol) in water (14 mL) was added to a solution of 5'-(4-amino-2,6-dichlorophenoxy)-7'-methylspiro[cyclobutane-1,3'-indolin]-2'-one (232.47 mg, 0.64 mmol) in HCl 37% (6.12 mL, 74.53 mmol), acetic acid (19 mL) and water (14 mL) at 0° C. under N$_2$. The reaction mixture was stirred at 0° C. for 1 h. In parallel, a solution of ethyl N-(2-cyanoacetyl)carbamate (165 mg, 1.057 mmol) in water (18 mL) and pyridine (6 mL) was stirred at 0° C. for 15 min. The first reaction mixture was quickly added to the second one. The resulting reaction mixture was stirred at 0° C. for 1 h. The reaction mixture was diluted in water (150 mL). The resulting precipitate was filtered, washed with water and dried under high vacuum to give ethyl (2-cyano-2-(2-(3,5-dichloro-4-((7'-methyl-2'-oxospiro[cyclobutane-1,3'-indolin]-5'-yl)oxy)phenyl)hydrazineylidene)acetyl)carbamate (339 mg, 100%) as an orange solid which was used in the next step without any additional purification. LC-MS: $C_{24}H_{21}Cl_2N_5O_5$ [M−H]$^-$: 528.

Sodium acetate (264 mg, 3.22 mmol) was added to a solution of ethyl (2-cyano-2-(2-(3,5-dichloro-4-((7'-methyl-2'-oxospiro[cyclobutane-1,3'-indolin]-5'-yl)oxy)phenyl)hydrazineylidene)acetyl)carbamate (339.43 mg, 0.64 mmol) in acetic acid (7.79 mL) under $N_2$. The reaction mixture was stirred at 120° C. for 1 h and was then cooled to 0° C. Water was added and the mixture was stirred for 30 min. The resulting precipitate was filtered, washed with water and co-evaporated with toluene to give 2-(3,5-dichloro-4-((7'-methyl-2'-oxospiro[cyclobutane-1,3'-indolin]-5'-yl)oxy)phenyl)-3,5-dioxo-2,3,4,5-tetrahydro-1,2,4-triazine-6-carbonitrile (309 mg, 100%) as an orange solid which was used in the next step without any additional purification. LC-MS: $C_{22}H_{15}Cl_2N_5O_4$ [M−H]⁻: 482.

A solution of 2-(3,5-dichloro-4-((7'-methyl-2'-oxospiro[cyclobutane-1,3'-indolin]-5'-yl)oxy)phenyl)-3,5-dioxo-2,3,4,5-tetrahydro-1,2,4-triazine-6-carbonitrile (309 mg, 0.64 mmol) and HCl 37% (648 mg, 0.54 mL, 6.58 mmol) in AcOH (1.08 mL, 18.85 mmol) under N2 was stirred at 120° C. for 1 h. The reaction mixture was cooled to room temperature and diluted with water. The resulting precipitate was filtered, washed with water and co-evaporated with toluene to give 2-(3,5-dichloro-4-((7'-methyl-2'-oxospiro[cyclobutane-1,3'-indolin]-5'-yl)oxy)phenyl)-3,5-dioxo-2,3,4,5-tetrahydro-1,2,4-triazine-6-carboxylic acid (302 mg, 94%) as a dark solid which was used in the next step without any additional purification. LC-MS: $C_{22}H_{16}Cl_2N_4O_6$ [M+H]⁺: 503.

Triethylamine (0.33 mL, 2.4 mmol) and diphenylphosphoryl azide (495.41 mg, 0.39 mL, 1.8 mmol) were added to a solution of 2-(3,5-dichloro-4-((7'-methyl-2'-oxospiro[cyclobutane-1,3'-indolin]-5'-yl)oxy)phenyl)-3,5-dioxo-2,3,4,5-tetrahydro-1,2,4-triazine-6-carboxylic acid (302 mg, 0.6001 mmol) in t-butanol (9.25 mL) under $N_2$. The resulting mixture was stirred at 85° C. for 5 h, additional diphenylphosphoryl azide (495.41 mg, 0.39 mL, 1.8 mmol) and triethylamine (0.33 mL, 2.4 mmol) were added and stirring at 85° C. was pursued overnight. The reaction mixture was quenched with sat. aq. $NaHCO_3$ and was extracted with EtOAc. The organic phase was washed with brine and dried over $Na_2SO_4$. The solids were removed by filtration and the filtrate was evaporated to dryness. The crude mixture was purified by flash chromatography on silica gel (0% to 5% MeOH in DCM) to give t-butyl (2-(3,5-dichloro-4-((7'-methyl-2'-oxospiro[cyclobutane-1,3'-indolin]-5'-yl)oxy)phenyl)-3,5-dioxo-2,3,4,5-tetrahydro-1,2,4-triazin-6-yl)carbamate (51 mg, 15%) a white solid. LC-MS: $C_{26}H_{25}Cl_2N_5O_6$ [M+H]⁺: 574.

HCl 4N in dioxane (0.44 mL, 1.74 mmol) was added to a solution of t-butyl (2-(3,5-dichloro-4-((7'-methyl-2'-oxospiro[cyclobutane-1,3'-indolin]-5'-yl)oxy)phenyl)-3,5-dioxo-2,3,4,5-tetrahydro-1,2,4-triazin-6-yl)carbamate (50 mg, 0.087 mmol) in anhydrous DCM (2 mL) under $N_2$. The reaction mixture was stirred at room temperature for 15 h, then the reaction mixture was evaporated to dryness. The crude product was purified by flash chromatography on silica gel (0% to 10% MeOH in DCM) to give 6-amino-2-(3,5-dichloro-4-((7'-methyl-2'-oxospiro[cyclobutane-1,3'-indolin]-5'-yl)oxy)phenyl)-1,2,4-triazine-3,5(2H,4H)-dione (27) (16 mg, 39%) as a white solid. ¹H-NMR (DMSO-d₆, 400 MHz): 2.04-2.15 (m, 4H), 2.16-2.31 (m, 3H), 2.33-2.44 (m, 2H), 6.33 (d, J=2.3 Hz, 1H), 6.53 (s, 2H), 7.04 (d, J=2.9 Hz, 1H), 7.89 (s, 2H), 10.22 (s, 1H), 12.28 (s, 1H) ppm. LC-MS: $C_{21}H_{17}Cl_2N_5O_4$ [M+H]⁺: 474.

Example 28. Preparation of Compound 28

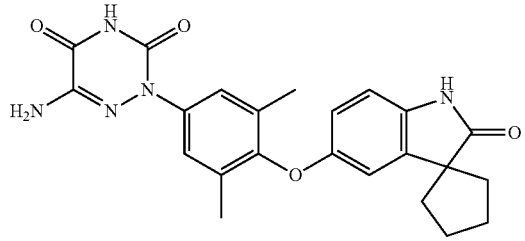 [SMILES: Cc1cc(-n2nc(N)c(=O)[nH]c2=O)cc(C)c1Oc1ccc2c(c1)C1(CCCC1)C(=O)N2]

LiHMDS (83 mL, 82.6 mmol, 1M in THF) was added dropwise to a solution of oxindole (5 g, 37.6 mmol) in anhydrous THF (120 mL) under N2 at −78° C. The reaction mixture was stirred at −78° C. for 1 h. Then 1,4-dibromobutane (4.5 mL, 37.6 mmol) was added dropwise and the reaction mixture was stirred 1 h at −78° C. followed by 27 h at room temperature. The reaction mixture was evaporated to dryness, dissolved in EtOAc and washed with sat. aq. $NH_4Cl$ (2×). The aqueous phase was extracted with EtOAc (2×) and the combined organic phases were dried over $Na_2SO_4$. The solids were removed by filtration and the filtrate was evaporated to dryness. The crude mixture was purified by flash chromatography on silica gel (10% to 25% EtOAc in CyH) to give spiro[cyclopentane-1,3'-indolin]-2'-one (2 g, 29%) as a white solid. ¹H-NMR (DMSO-d₆, 300 MHz): 1.71-1.75 (m, 2H), 1.93-1.97 (m, 6H), 6.81 (d, J=7.7 Hz, 1H), 6.93 (t, J=7.5 Hz, 1H), 7.14 (t, J=7.7 Hz, 1H), 7.21 (d, J=7.3 Hz, 1H), 10.25 (br s, 1H) ppm. LC-MS: $C_{12}H_{13}NO$ [M+H]⁺: 188.

PIFA (5.23 g, 12.2 mmol) and TFA (7.5 mL, 101.47 mmol) were added to a solution of spiro[cyclopentane-1,3'-indolin]-2'-one (1.9 g, 10.2 mmol) in chloroform (120 mL) under $N_2$. The reaction mixture was stirred at room temperature for 1 h. The reaction mixture was neutralized with sat. aq. $Na_2CO_3$. The organic phase was collected and the aqueous phase was extracted with DCM (3×). The combined organic phases were washed brine and dried over $Na_2SO_4$. The solids were removed by filtration and the filtrate was evaporated to dryness. The crude mixture was purified by flash chromatography on silica gel (0% to 3% MeOH in DCM) to afford 5'-hydroxyspiro[cyclopentane-1,3'-indolin]-2'-one (1.23 g, 60%) as a brown oil. ¹H-NMR (DMSO-d₆, 300 MHz): 1.67-1.71 (m, 2H), 1.86-1.95 (m, 6H), 6.51-6.65 (m, 3H), 8.92 (s, 1H), 9.96 (s, 1H) ppm. LC-MS: $C_{12}H_{13}NO_2$ [M+H]⁺: 204.

A mixture of 5'-hydroxyspiro[cyclopentane-1,3'-indolin]-2'-one (1.23 g, 6.05 mmol), 2-fluoro-1,3-dimethyl-5-nitrobenzene (1.02 g, 6.05 mmol) and $K_2CO_3$ (1.25 g, 9.08 mmol) in anhydrous DMF (41 mL) under N2 was stirred at 40° C. for 21 h. The reaction mixture was diluted in water and extracted with EtOAc (3×). The combined organic layers were washed with brine (2×) and dried over $Na_2SO_4$. The solids were removed by filtration and the filtrate was evaporated to dryness to give 5'-(2,6-dimethyl-4-nitrophenoxy)spiro[cyclopentane-1,3'-indolin]-2'-one (1.35 g, 63%) as a beige solid which was used without further purification in the next step. ¹H-NMR (DMSO-d₆, 300 MHz): 1.71-1.76 (m, 2H), 1.88-1.98 (m, 6H), 2.17 (s, 6H), 6.41 (dd, J=8.6, 2.4 Hz, 1H), 6.7 (d, J=8.4 Hz, 1H), 6.88 (d, J=2.5 Hz, 1H), 8.10 (s, 2H), 10.18 (br s, 1H) ppm. LC-MS: $C_{20}H_{20}N_2O_4$ [M+H]⁺: 353.

Fe (1.07 g, 19.2 mmol) was added to a solution of 5'-(2,6-dimethyl-4-nitrophenoxy)spiro[cyclopentane-1,3'-indolin]-2'-one (1.35 g, 3.83 mmol) and NH$_4$Cl (2.05 g, 38.3 mmol) in EtOH (27 mL) and water (14 mL) under N$_2$. The reaction mixture was stirred at 70° C. for 1 h. The reaction mixture was filtered over a pad of celite which was rinsed with EtOAc. The resulting solution was washed with water and brine and dried over Na$_2$SO$_4$. The solids were removed by filtration and the filtrate was evaporated to dryness to give 5'-(4-amino-2,6-dimethylphenoxy)spiro[cyclopentane-1,3'-indolin]-2'-one (982 mg, 80%) as a beige solid which was used without further purification in the next step. $^1$H-NMR (DMSO-d$_6$, 300 MHz): 1.67-1.72 (m, 2H), 1.80-1.97 (m, 12H), 4.81 (br s, 2H), 6.31 (s, 2H), 6.36 (dd, J=8.2, 2.5 Hz, 1H), 6.66 (d, J=8.4 Hz, 1H), 6.73 (d, J=2.4 Hz, 1H), 10.08 (br s, 1H) ppm. LC-MS: C$_{20}$H$_{22}$N$_2$O$_2$ [M+H]$^+$: 324.

A solution of NaNO$_2$ (402 mg, 5.83 mmol) in water (53 mL) was added to a solution of 5'-(4-amino-2,6-dimethylphenoxy)spiro[cyclopentane-1,3'-indolin]-2'-one (895 mg, 2.78 mmol) in HCl 37% (24 mL), AcOH (70 mL) and water (53 mL) at 0° C. under N$_2$. The reaction mixture was stirred at 0° C. for 1 h. In parallel, a solution of ethyl N-(2-cyanoacetyl)carbamate (650.2 mg, 4.16 mmol) in water (53 mL) and pyridine (24 mL) was stirred at 0° C. for 15 min. The first reaction mixture was quickly added to the second one and the resulting reaction mixture was stirred at 0° C. for 4 h. The reaction mixture was diluted in water. The precipitate was filtered, washed with water, dissolved in EtOAc and evaporated to dryness providing ethyl (2-cyano-2-(2-(3,5-dimethyl-4-((2'-oxospiro[cyclopentane-1,3'-indolin]-5'-yl)oxy)phenyl)hydrazineylidene)acetyl)carbamate (1.36 g, quant.) as an orange solid which was used without further purification in the next step. LC-MS: C$_{26}$H$_{27}$N$_5$O$_5$ [M+H]$^+$: 490

NaOAc (910 mg, 11.1 mmol) was added to a solution of ethyl (2-cyano-2-(2-(3,5-dimethyl-4-((2'-oxospiro[cyclopentane-1,3'-indolin]-5'-yl)oxy)phenyl)hydrazineylidene)acetyl)carbamate (1.36 g, 2.78 mmol) in AcOH (26 mL) under N$_2$. The solution was stirred at 120° C. for 1 h. The reaction mixture was cooled at 0° C. and diluted with water. The precipitate was filtered and washed with water to give 2-(3,5-dimethyl-4-((2'-oxospiro[cyclopentane-1,3'-indolin]-5'-yl)oxy)phenyl)-3,5-dioxo-2,3,4,5-tetrahydro-1,2,4-triazine-6-carbonitrile (1.18 g, 96%) as a yellow solid which was used without further purification in the next step. $^1$H-NMR (DMSO-d$_6$, 300 MHz): 1.71-1.77 (m, 2H), 1.86-1.97 (m, 6H), 2.11 (s, 6H), 6.35 (d, J=8.4 Hz, 1H), 6.7 (d, J=8.4 Hz, 1H), 6.90 (s, 1H), 7.27 (s, 2H), 10.16 (s, 1H), 13.0 (br s, 1H) ppm. LC-MS: C$_{24}$H$_{21}$N$_5$O$_4$ [M+H]$^+$: 444.

A mixture of 2-(3,5-dimethyl-4-((2'-oxospiro[cyclopentane-1,3'-indolin]-5'-yl)oxy)phenyl)-3,5-dioxo-2,3,4,5-tetrahydro-1,2,4-triazine-6-carbonitrile (1.18 g, 2.66 mmol), HCl 37% (3.9 mL) and AcOH (4 mL) under N2 was stirred at 120° C. for 1 d. The reaction mixture was cooled to room temperature and diluted with water. The precipitate was filtered, washed with water, dissolved in EtOAc and evaporated to dryness providing 2-(3,5-dimethyl-4-((2'-oxospiro[cyclopentane-1,3'-indolin]-5'-yl)oxy)phenyl)-3,5-dioxo-2,3,4,5-tetrahydro-1,2,4-triazine-6-carboxylic acid (959 mg, 78%) as a beige solid which was used without further purification in the next step. $^1$H-NMR (DMSO-d$_6$, 300 MHz): 1.71-1.78 (m, 2H), 1.86-1.97 (m, 6H), 2.11 (s, 6H), 6.35 (dd, J=9.3, 2.0 Hz, 1H), 6.7 (d, J=9.0 Hz, 1H), 6.91 (d, J=2.5 Hz, 1H), 7.30 (s, 2H), 10.14 (s, 1H), 12.53 (br s, 1H), 13.55 (br s, 1H) ppm. LC-MS: C$_{24}$H$_{22}$N$_4$O$_6$ [M+H]$^+$: 463.

Et$_3$N (1.2 mL, 8.29 mmol) and diphenyl phosphoryl azide (1.3 mL, 6.22 mmol) were added to a solution of 2-(3,5-dimethyl-4-((2'-oxospiro[cyclopentane-1,3'-indolin]-5'-yl)oxy)phenyl)-3,5-dioxo-2,3,4,5-tetrahydro-1,2,4-triazine-6-carboxylic acid (959 mg, 2.07 mmol) in t-BuOH (30 mL) under N$_2$. The resulting mixture was stirred at 85° C. for 5 h. The reaction mixture was quenched with sat. aq. NH$_4$Cl and was extracted with EtOAc (2×). The combined organic layers were washed with sat. aq. NH$_4$Cl and brine and dried over Na$_2$SO$_4$. The solids were removed by filtration and the filtrate was evaporated to dryness. The crude mixture was purified by flash chromatography on silica gel (0% to 5% MeOH in DCM) to afford t-butyl (2-(3,5-dimethyl-4-((2'-oxospiro[cyclopentane-1,3'-indolin]-5'-yl)oxy)phenyl)-3,5-dioxo-2,3,4,5-tetrahydro-1,2,4-triazin-6-yl)carbamate (680 mg, 61%) as a yellow solid. $^1$H-NMR (DMSO-d$_6$, 300 MHz): 1.43 (s, 9H), 1.69-1.78 (m, 2H), 1.87-1.99 (m, 6H), 2.09 (s, 6H), 6.35 (dd, J=8.7, 2.0 Hz, 1H), 6.7 (d, J=8.5 Hz, 1H), 6.9 (d, J=2.4 Hz, 1H), 7.31 (s, 2H), 8.94 (s, 1H), 10.15 (s, 1H), 12.45 (br s, 1H) ppm. LC-MS: C$_{28}$H$_{31}$N$_5$O$_6$ [M+H]$^+$: 534.

A solution of t-butyl (2-(3,5-dimethyl-4-((2'-oxospiro[cyclopentane-1,3'-indolin]-5'-yl)oxy)phenyl)-3,5-dioxo-2,3,4,5-tetrahydro-1,2,4-triazin-6-yl)carbamate (680 mg, 1.27 mmol) in HCl 4N in 1,4-dioxane (10 mL, 38.2 mmol) under N2 was stirred at room temperature for 28 h. The reaction mixture was evaporated to dryness and the crude mixture was purified by flash chromatography on silica gel (0% to 6% MeOH in DCM) to give 6-amino-2-(3,5-dimethyl-4-((2'-oxospiro[cyclopentane-1,3'-indolin]-5'-yl)oxy)phenyl)-1,2,4-triazine-3,5(2H,4H)-dione (28) (225 mg, 41%) as a beige solid. $^1$H-NMR (DMSO-d$_6$, 400 MHz): 1.72-1.76 (m, 2H), 1.86-1.98 (m, 6H), 2.07 (s, 6H), 6.33 (br s, 2H), 6.34 (dd, J=8.4, 2.6 Hz, 1H), 6.7 (d, J=8.4 Hz, 1H), 6.86 (d, J=2.6 Hz, 1H), 7.30 (s, 2H), 10.15 (s, 1H), 12.11 (br s, 1H) ppm. LC-MS: C$_{23}$H$_{23}$N$_5$O$_4$ [M+H]$^+$: 434.

Example 29. Preparation of Compound 29

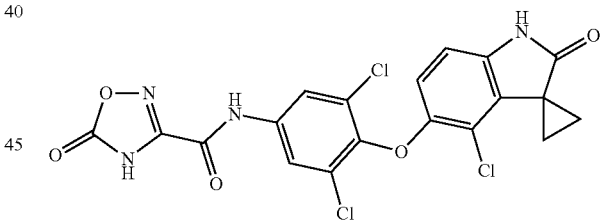

Ethenyldiphenylsulfanium trifluoromethanesulfonate (12.97 g, 35.802 mmol) was added to a solution of 4-chloro-2,3-dihydro-1H-indol-2-one (5 g, 29.83 mmol) and zinc triflate (10.85 g, 29.83 mmol) in anhydrous DMF (135 mL). After 2 min of stirring, DBU (13.37 mL, 89.504 mmol) was added and the reaction mixture was stirred at room temperature for 1 h. The reaction mixture was diluted with sat aq. NH$_4$Cl and extracted with EtOAc (3×). The combined organic layers were washed with water and brine and dried over Na$_2$SO$_4$. The solids were removed by filtration and the filtrate was evaporated to dryness. The crude product was triturated with pentane, filtered and washed with pentane to give 4'-chlorospiro[cyclopropane-1,3'-indolin]-2'-one (5.52 g, 96%) as a brown solid which was used without further purification in the next step. $^1$H-NMR (DMSO-d$_6$, 300 MHz): 1.37-1.40 (m, 2H), 2.04-2.08 (m, 2H), 6.88-6.94 (m, 2H), 7.15-7.20 (m, 1H), 10.80 (br s, 1H) ppm. LC-MS: C$_{10}$H$_8$ClNO [M+H]$^+$: 194.

PIFA (13.85 g, 32.2 mmol) was added to a solution of 4'-chlorospiro[cyclopropane-1,3'-indolin]-2'-one (5.2 g, 26.86 mmol) and TFA (20 mL, 268.55 mmol) in chloroform (318 mL) under $N_2$. The reaction mixture was stirred at room temperature for 16 h. The reaction mixture was quenched with sat. aq. $NaHCO_3$ and diluted with DCM. The layers were separated and the aqueous layer was extracted with DCM. The combined organic layers were washed with brine and dried over $Na_2SO_4$. The solids were removed by filtration and the filtrate was evaporated to dryness. The crude mixture was triturated with pentane and filtered to give 4'-chloro-5'-hydroxyspiro[cyclopropane-1,3'-indolin]-2'-one (2.50 g, 46%) as a brown solid. The aq. $NaHCO_3$ solution was re-extracted (2×) with EtOAc/PrOH (85:15). The combined organic layers were washed with brine and dried over $Na_2SO_4$. The solids were removed by filtration and the filtrate was evaporated to dryness. The residue was purified by flash chromatography on silica gel (1% to 50% [MeOH/$NH_4OH$ (9:1)] in DCM) to give more 4'-chloro-5'-hydroxyspiro[cyclopropane-1,3'-indolin]-2'-one 3 (1.52 g, 27%) as a brown solid. $^1$H-NMR (DMSO-$d_6$, 300 MHz): 1.31-1.35 (m, 2H), 2.03-2.07 (m, 2H), 6.69 (d, J=8.4 Hz, 1H), 6.77 (d, J=8.4 Hz, 1H), 9.60 (s, 1H), 10.43 (br s, 1H) ppm. LC-MS: $C_{10}H_8ClNO_2$ [M+H]$^+$: 210.

DIPEA (3.07 g, 3.93 mL, 23.76 mmol) was added to a solution of 4'-chloro-5'-hydroxyspiro[cyclopropane-1,3'-indolin]-2'-one (2.49 g, 11.88 mmol) and 1,3-dichloro-2-fluoro-5-nitrobenzene (2.49 g, 11.88 mmol) in anhydrous DMF (66 mL). The reaction mixture was stirred at room temperature under N2 for 4 h, additional DIPEA (3.07 g, 3.93 mL, 23.76 mmol) was added, and stirred for another 3 h. Then, the reaction mixture was diluted with water and extracted with EtOAc (3×). The combined organic layers were washed with brine and dried over $Na_2SO_4$. The solids were removed by filtration and the filtrate was evaporated to dryness. The crude product was triturated with pentane, filtered and washed with pentane to give 4'-chloro-5'-(2,6-dichloro-4-nitrophenoxy)spiro[cyclopropane-1,3'-indolin]-2'-one (2.78 g, 59%) as a green solid which was used without further purification in the next step. $^1$H-NMR (DMSO-$d_6$, 300 MHz): 1.43-1.45 (m, 2H), 2.17-2.20 (m, 2H), 6.48 (d, J=8.4 Hz, 1H), 6.75 (d, J=8.4 Hz, 1H), 8.55 (s, 2H), 10.74 (br s, 1H) ppm. LC-MS: $C_{16}H_9Cl_3N_2O_4$ [M−H]$^-$: 397.

Fe (2.42 g, 43.29 mmol) was added to a solution of 4'-chloro-5'-(2,6-dichloro-4-nitrophenoxy)spiro[cyclopropane-1,3'-indolin]-2'-one (3.46 g, 8.66 mmol) and $NH_4Cl$ (4.63 g, 86.58 mmol) in EtOH (60 mL) and water (30 mL) under $N_2$. The reaction mixture was heated at 70° C. for 17 h. After cooling to room temperature, the reaction mixture was diluted with EtOH and water and filtered over a pad of celite. The filtrate was concentrated, reconstituted in EtOAc/iPrOH (85:15) and washed with brine. The organic phase was dried over $Na_2SO_4$. The solids were removed by filtration and the filtrate was evaporated to dryness to give 5'-(4-amino-2,6-dichlorophenoxy)-4'-chlorospiro[cyclopropane-1,3'-indolin]-2'-one (2.36 g, 74%) as a white solid which was used without further purification in the next step. $^1$H-NMR (DMSO-$d_6$, 400 MHz): 1.39-1.42 (m, 2H), 2.14-2.17 (m, 2H), 5.67 (s, 2H), 6.31 (d, J=8.4 Hz, 1H), 6.71 (s, 2H), 6.75 (d, J=8.4 Hz, 1H), 10.64 (s, 1H) ppm. LC-MS: $C_{16}H_{11}Cl_3N_2O_2$ [M+H]$^+$: 369.

LiHMDS 1M in THF (5.41 mL, 5.41 mmol) was added to a solution of ethyl 5-oxo-4,5-dihydro-1,2,4-oxadiazole-3-carboxylate (213.88 mg, 1.35 mmol) and 5'-(4-amino-2,6-dichlorophenoxy)-4'-chlorospiro[cyclopropane-1,3'-indolin]-2'-one (500 mg, 1.35 mmol) in anhydrous THF (6 mL). The reaction mixture was stirred at room temperature under N2 for 30 min. The reaction mixture was diluted with MeOH and evaporated to dryness. The crude product was purified by flash chromatography on silica gel (0% to 50% MeOH in DCM). The resulting solid was triturated in $CH_3CN$ and dried under high vacuum to give N-(3,5-dichloro-4-((4'-chloro-2'-oxospiro[cyclopropane-1,3'-indolin]-5'-yl)oxy)phenyl)-5-oxo-4,5-dihydro-1,2,4-oxadiazole-3-carboxamide (29) (285 mg, 44%) as a white solid. $^1$H-NMR (DMSO-$d_6$, 400 MHz): 1.39-1.46 (m, 2H), 2.15-2.21 (m, 2H), 6.37 (d, J=8.8 Hz, 1H), 6.75 (d, J=8.5 Hz, 1H), 8.13 (s, 2H), 10.58-10.75 (m, 2H) ppm. LC-MS: $C_{19}H_{11}Cl_3N_4O_5$ [M+H]$^+$: 481.

Example 30. Preparation of Compound 30

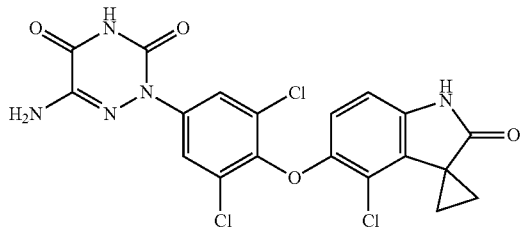 [SMILES: Nc1nn(-c2cc(Cl)c(Oc3ccc4c(c3Cl)C3(CC3)C(=O)N4)c(Cl)c2)c(=O)[nH]c1=O]

A solution of $NaNO_2$ (0.85 g, 12.27 mmol) in water (116 mL) was added to a solution of 5'-(4-amino-2,6-dichlorophenoxy)-4'-chlorospiro[cyclopropane-1,3'-indolin]-2'-one (2.16 g, 5.84 mmol) in HCl 37% (51 mL, 617.6 mmol), acetic acid (154 mL) and water (115 mL) at 0° C. under $N_2$. The reaction mixture was stirred at 0° C. for 40 min. In parallel, a solution of ethyl N-(2-cyanoacetyl)carbamate (1.37 g, 8.77 mmol) in water (148 mL) and pyridine (51 mL) was stirred at 0° C. for 15 min. The first reaction mixture was quickly added to the second one. The resulting reaction mixture was stirred at 0° C. for 30 min. The reaction mixture was diluted in water. The precipitate was filtered, washed with water and co-evaporated with toluene to give ethyl (2-cyano-2-(2-(3,5-dichloro-4-((4'-chloro-2'-oxospiro[cyclopropane-1,3'-indolin]-5'-yl)oxy)phenyl)hydraziney-lidene)acetyl)carbamate (2.75 g, 88%) as an orange solid that was used in the next step without any additional purification. LC-MS: $C_{22}H_{16}Cl_3N_5O_5$ [M+H]$^+$: 536.

Sodium acetate (1.68 g, 0.0205 mol) was added to a solution of ethyl (2-cyano-2-(2-(3,5-dichloro-4-((4'-chloro-2'-oxospiro[cyclopropane-1,3'-indolin]-5'-yl)oxy)phenyl)hydrazineylidene)acetyl)carbamate (2.75 g, 0.005 mol) in acetic acid (50 mL) under $N_2$. The reaction mixture was stirred at 120° C. for 2 h. The reaction mixture was then cooled to 0° C. Water was added and the mixture was stirred for 30 min. The resulting precipitate was filtered, washed with water and co-evaporated with toluene to give 2-(3,5-dichloro-4-((4'-chloro-2'-oxospiro[cyclopropane-1,3'-indolin]-5'-yl)oxy)phenyl)-3,5-dioxo-2,3,4,5-tetrahydro-1,2,4-triazine-6-carbonitrile (2.40 g, 95%) as an orange solid which was used in the next step without any additional purification. $^1$H-NMR (DMSO-$d_6$, 400 MHz): 1.43-1.46 (m, 2H), 2.17-2.20 (m, 2H), 6.42 (d, J=8.4 Hz, 1H), 6.78 (d, J=8.4 Hz, 1H), 7.82 (s, 2H), 10.72 (s, 1H) ppm. LC-MS: $C_{20}H_{10}Cl_3N_5O_4$ [M+H]$^+$: 490

KOH (5.67 g, 101.058 mmol) was added to a solution of 2-(3,5-dichloro-4-((4'-chloro-2'-oxospiro[cyclopropane-1,3'-indolin]-5'-yl)oxy)phenyl)-3,5-dioxo-2,3,4,5-tetrahydro-1,2,4-triazine-6-carbonitrile (2.4 g, 4.89 mmol) in water (48 mL) and EtOH (48 mL) under $N_2$. The reaction mixture was stirred at 80° C. for 15 min. After cooling to room temperature, the reaction mixture was diluted with aqueous 1N HCl solution until pH=1. The resulting precipitate was filtered, washed with water and co-evaporated with toluene to give 2-(3,5-dichloro-4-((4'-chloro-2'-oxospiro[cyclopropane-1, 3'-indolin]-5'-yl)oxy)phenyl)-3,5-dioxo-2,3,4,5-tetrahydro-1,2,4-triazine-6-carboxylic acid (2.49 g, 100%) as a light orange solid that was used as such in the next step. LC-MS: $C_{20}H_{11}Cl_3N_4O_6$ [M–H]$^-$: 509.

Triethylamine (1.59 g, 2.18 mL, 15.7 mmol) and diphenyl phosphoryl azide (3.24 g, 2.54 mL, 11.77 mmol) were added to a solution of 2-(3,5-dichloro-4-((4'-chloro-2'-oxospiro[cyclopropane-1,3'-indolin]-5'-yl)oxy)phenyl)-3,5-dioxo-2,3,4,5-tetrahydro-1,2,4-triazine-6-carboxylic acid (2 g, 3.92 mmol) in t-butanol (60 mL) under $N_2$. The resulting mixture was stirred at 85° C. for 4 h. The reaction mixture was quenched with sat. aq. $NaHCO_3$ and extracted with EtOAc. The organic layer was washed with brine and dried over $Na_2SO_4$. The solids were removed by filtration and the filtrate was evaporated to dryness. The crude mixture was purified by flash chromatography on silica gel (0% to 5% MeOH in DCM) to give t-butyl (2-(3,5-dichloro-4-((4'-chloro-2'-oxospiro[cyclopropane-1,3'-indolin]-5'-yl)oxy)phenyl)-3,5-dioxo-2,3,4,5-tetrahydro-1,2,4-triazin-6-yl)carbamate (406 mg, 18%) as a red solid. $^1$H-NMR (DMSO-$d_6$, 400 MHz): 1.43-1.45 (m, 2H), 1.45 (s, 9H), 2.17-2.20 (m, 2H), 6.39 (d, J=8.4 Hz, 1H), 6.78 (d, J=8.4 Hz, 1H), 7.91 (s, 2H), 9.13 (s, 1H), 10.71 (s, 1H), 12.58 (br s, 1H) ppm. LC-MS: $C_{24}H_{20}Cl_3N_5O_6$ [M+H]$^+$: 580.

TFA (0.94 mL, 12.67 mmol) was added to a solution of t-butyl (2-(3,5-dichloro-4-((4'-chloro-2'-oxospiro[cyclopropane-1,3'-indolin]-5'-yl)oxy)phenyl)-3,5-dioxo-2,3,4,5-tetrahydro-1,2,4-triazin-6-yl)carbamate (368 mg, 0.63 mmol) in anhydrous DCM (9 mL) under $N_2$. The reaction mixture was stirred at room temperature for 18 h. Extra DCM (9 mL) and TFA (0.94 mL, 12.67 mmol) were added and stirring at room temperature was pursued for 7 h. The reaction mixture was then diluted with MeCN and evaporated to dryness. The crude product was purified by flash chromatography on silica gel (1% to 10% [MeOH/NH$_4$OH (99:1)] in DCM). The resulting solid was triturated with EtOH and dried under high vacuum to give 6-amino-2-(3,5-dichloro-4-((4'-chloro-2'-oxospiro[cyclopropane-1,3'-indolin]-5'-yl)oxy)phenyl)-1,2,4-triazine-3,5(2H,4H)-dione (30) (111 mg, 36%) as a white solid. $^1$H-NMR (DMSO-$d_6$, 400 MHz): 1.40-1.48 (m, 2H), 2.16-2.22 (m, 2H), 6.36 (d, J=8.4 Hz, 1H), 6.55 (s, 2H), 6.78 (d, J=8.4 Hz, 1H), 7.92 (s, 2H), 10.71 (s, 1H), 12.28 (s, 1H) ppm. LC-MS: $C_{19}H_{12}Cl_3N_5O_4$ [M+H]$^+$: 480.

Example 31. Preparation of Compound 31

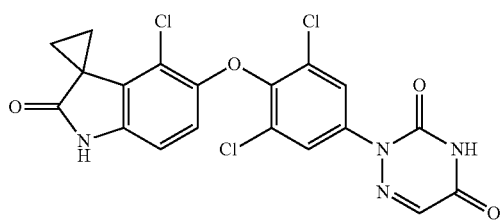 [SMILES: O=C1Nc2ccc(Oc3c(Cl)cc(-n4ncc(=O)[nH]c4=O)cc3Cl)c(Cl)c2C12CC2]

A solution of 2-(3,5-dichloro-4-((4'-chloro-2'-oxospiro[cyclopropane-1,3'-indolin]-5'-yl)oxy)phenyl)-3,5-dioxo-2,3,4,5-tetrahydro-1,2,4-triazine-6-carboxylic acid (900 mg, 1.77 mmol) in mercaptoacetic acid (2.70 mL, 38.89 mmol) was stirred at 120° C. under N2 for 2 h. The reaction mixture was cooled to room temperature and diluted with water. Then, EtOAc/iPrOH (85:15) and sat. aq. NaHCO$_3$ were added and the phases were separated. The aqueous phase was re-extracted with EtOAc/iPrOH (85:15). The combined organic phases were washed with brine and dried over Na$_2$SO$_4$. The solids were removed by filtration and the filtrate was evaporated to dryness. The crude product was purified by flash chromatography on silica gel (2% to 5% MeOH in DCM) to give 2-(3,5-dichloro-4-((4'-chloro-2'-oxospiro[cyclopropane-1,3'-indolin]-5'-yl)oxy)phenyl)-1,2,4-triazine-3,5(2H,4H)-dione (31) (37 mg, 4%) as a yellow solid. $^1$H-NMR (DMSO-$d_6$, 400 MHz): 1.41-1.48 (m, 2H), 2.16-2.21 (m, 2H), 6.39 (d, J=8.4 Hz, 1H), 6.78 (d, J=8.5 Hz, 1H), 7.71 (s, 1H), 7.84 (s, 2H), 10.71 (s, 1H), 12.49 (s, 1H) ppm. LC-MS: $C_{19}H_{11}Cl_3N_4O_4$ [M+H]$^+$: 465.

Example 32 and Example 33. Preparation of Compounds 32 and 33

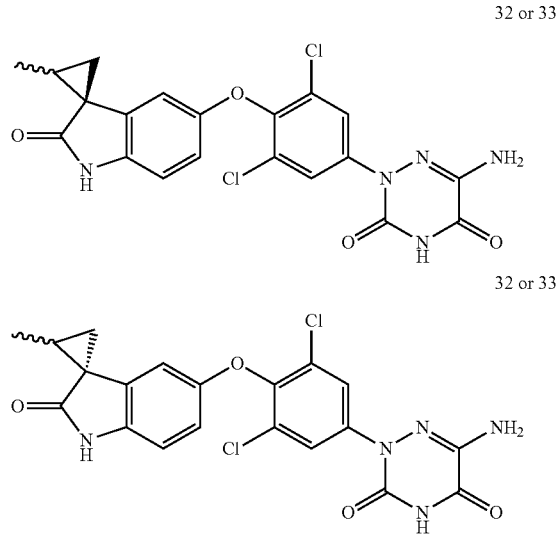

Pyridine (1.9 mL, 23.6 mmol)) and acetaldehyde (1.4 mL, 25.0 mmol) were added to a solution of 5-bromoindolin-2-one (5 g, 23.6 mmol) in MeOH (35 mL) under N$_2$. The reaction mixture was stirred at 65° C. for 22 h. The reaction mixture was diluted in water, filtered, and washed with water (3×). The precipitate was dissolved in EtOAc and dried over Na$_2$SO$_4$. The solids were removed by filtration and the filtrate was evaporated to dryness to give 5-bromo-3-ethylideneindolin-2-one (5 g, 90%) as a pink solid which was used without further purification in the next step. LC-MS: $C_{10}H_8BrNO$ [M+H]$^+$: 238/240.

A solution of trimethylsulfoxonium chloride (2.7 g, 21.0 mmol) and NaH 60% (0.99 g, 24.8 mmol) in anhydrous DMSO (180 mL) was added dropwise to a solution of 5-bromo-3-ethylideneindolin-2-one (4.54 g, 19.1 mmol) in anhydrous DMSO (180 mL) under N$_2$. The reaction mixture was stirred at room temperature for 2 h. The reaction mixture was quenched with sat. aq. NH$_4$Cl and the resulting solution was diluted in EtOAc, washed with sat. aq. NH$_4$Cl and brine, and dried over Na$_2$SO$_4$. The solids were removed by filtration and the filtrate was evaporated to dryness. The crude mixture was purified by flash chromatography on silica gel (0% to 3% MeOH in DCM) to give 5'-bromo-2-methylspiro

[cyclopropane-1,3'-indolin]-2'-one (2.45 g, 25%) as a brown solid. LC-MS: $C_{11}H_{10}BrNO$ [M+H]$^+$: 252/254.

3,4-dihydro-2H-pyran (8 mL, 88.9 mmol) was added to a solution of 5'-bromo-2-methylspiro[cyclopropane-1,3'-indolin]-2'-one (1.12 g, 4.44 mmol) and p-TsOH H$_2$O (0.34 g, 1.78 mmol) in anhydrous DCM (25 mL) under N$_2$. The reaction mixture was stirred 10 min at room temperature and then at 40° C. for 20 h. The reaction mixture was quenched with sat. aq. NaHCO$_3$. The organic phase was collected and the aqueous phase was extracted with DCM (2×). The combined organic phases were washed with brine and dried with MgSO$_4$. The solids were removed by filtration and the filtrate was evaporated to dryness. The crude mixture was purified by flash chromatography on silica gel (0% to 2% MeOH in DCM) to give 5'-bromo-2-methyl-1'-(tetrahydro-2H-pyran-2-yl)spiro[cyclopropane-1,3'-indolin]-2'-one (866 mg, 58%) as a colorless oil which was used without further purification in the next step. LC-MS: $C_{16}H_{18}BrNO_2$ [M+H]$^+$: 336/338.

A mixture of 5'-bromo-2-methyl-1'-(tetrahydro-2H-pyran-2-yl)spiro[cyclopropane-1,3'-indolin]-2'-one (866 mg, 2.58 mmol), Bis(neopentylglycolato)diboron (1.74 g, 7.73 mmol), KOAc (758 mg, 7.73 mmol) and PdCl$_2$[P(o-Tol)$_3$]$_2$ (20 mg, 0.026 mmol) in anhydrous DMSO (18 mL) under N2 was stirred at 90° C. for 2 h. The reaction mixture was diluted with water and extracted with EtOAc (3×). The combined organic phases were washed with brine (2×) and dried with Na$_2$SO$_4$. The solids were removed by filtration and the filtrate was evaporated to dryness. The crude mixture was purified by flash chromatography on silica gel (0% to 30% EtOAc in CyH) to give 5'-(5,5-dimethyl-1,3,2-dioxaborinan-2-yl)-2-methyl-1'-(tetrahydro-2H-pyran-2-yl)spiro[cyclopropane-1,3'-indolin]-2'-one (670 mg, 71%) as a yellow solid. LC-MS: $C_{21}H_{28}BNO_4$ [M+H]$^+$: 302.

H$_2$O$_2$ (4.9 mL, 47.7 mmol) and AcOH (2.7 mL, 47.7 mmol) were added to a solution of 5'-(5,5-dimethyl-1,3,2-dioxaborinan-2-yl)-2-methyl-1'-(tetrahydro-2H-pyran-2-yl)spiro[cyclopropane-1,3'-indolin]-2'-one (705 mg, 1.91 mmol) in THF (12 mL) under N$_2$. The reaction mixture was stirred at room temperature for 1 h. The reaction mixture was neutralized with sat. aq. NaHCO$_3$ and extracted with EtOAc (3×). The combined organic layers were washed with brine and dried with MgSO$_4$. The solids were removed by filtration and the filtrate was evaporated to dryness. The crude mixture was purified by flash chromatography on silica gel (0% to 2.5% MeOH in DCM) to give 5'-hydroxy-2-methyl-1'-(tetrahydro-2H-pyran-2-yl)spiro[cyclopropane-1,3'-indolin]-2'-one (429 mg, 82%) as a beige solid. LC-MS: $C_{16}H_{19}NO_3$ [M+H]$^+$: 274.

A mixture of 5'-hydroxy-2-methyl-1'-(tetrahydro-2H-pyran-2-yl)spiro[cyclopropane-1,3'-indolin]-2'-one (325 mg, 1.19 mmol), 1,3-dichloro-2-fluoro-5-nitrobenzene (249.7 mg, 1.19 mmol) and K$_2$CO$_3$ (246 mg, 1.78 mmol) in anhydrous DMF (8 mL) was stirred at 60° C. for 1 h. The reaction was cooled to room temperature, diluted with water and extracted with EtOAc (3×). The combined organic phases were washed with brine and dried with Na$_2$SO$_4$. The solids were removed by filtration and the filtrate was evaporated to dryness to give 5'-(2,6-dichloro-4-nitrophenoxy)-2-methyl-1'-(tetrahydro-2H-pyran-2-yl)spiro[cyclopropane-1,3'-indolin]-2'-one (550 mg, quant.) as a yellow solid which was used without further purification in the next step. LC-MS: $C_{22}H_{20}Cl_2N_2O_5$ [M+H]$^+$: 463.

TFA (0.9 mL, 11.9 mmol) was added to a solution of 5'-(2,6-dichloro-4-nitrophenoxy)-2-methyl-1'-(tetrahydro-2H-pyran-2-yl)spiro[cyclopropane-1,3'-indolin]-2'-one (550 mg, 1.19 mmol) in anhydrous DCM (3 mL) under N$_2$. The reaction mixture was stirred at 40° C. for 1 d. The reaction mixture was evaporated under reduced pressure and co-evaporated with MeCN (5×) to give 5'-(2,6-dichloro-4-nitrophenoxy)-2-methylspiro[cyclopropane-1,3'-indolin]-2'-one (450 mg, quant.) as a dark green solid which was used without further purification in the next step. LC-MS: $C_{17}H_{12}Cl_2N_2O_4$ [M+H]$^+$: 379.

Fe (331 mg, 5.93 mmol) was added to a solution of 5'-(2,6-dichloro-4-nitrophenoxy)-2-methylspiro[cyclopropane-1,3'-indolin]-2'-one (450 mg, 1.19 mmol) and NH$_4$Cl (635 mg, 11.87 mmol) in EtOH (8 mL) and water (4 mL) under N$_2$. The reaction mixture was stirred at 70° C. for 1 h. The reaction mixture was filtered over a pad of celite which was rinsed with EtOAc. The resulting solution was washed with water and brine, and dried over Na$_2$SO$_4$. The solids were removed by filtration and the filtrate was evaporated to dryness to give 5'-(4-amino-2,6-dichlorophenoxy)-2-methylspiro[cyclopropane-1,3'-indolin]-2'-one (414 mg, quant.) as a brown solid which was used without further purification in the next step. LC-MS: $C_{17}H_{14}Cl_2N_2O_2$ [M+H]$^+$: 349.

A solution of NaNO$_2$ (217 mg, 3.15 mmol) in water (30 mL) was added to a solution of 5'-(4-amino-2,6-dichlorophenoxy)-2-methylspiro[cyclopropane-1,3'-indolin]-2'-one (524 mg, 1.5 mmol) in HCl 37% (13 mL), AcOH (40 mL) and water (30 mL) at 0° C. under N$_2$. The reaction mixture was stirred at 0° C. for 1 h. In parallel, a solution of ethyl N-(2-cyanoacetyl)carbamate (351 mg, 2.25 mmol) in water (38 mL) and pyridine (13 mL was stirred at 0° C. for 15 min. The first reaction mixture was quickly added to the second one and the resulting reaction mixture was stirred at 0° C. for 1 h. The reaction mixture was diluted in water and filtered. The precipitate was washed with water, dissolved in EtOAc and evaporated to dryness to give ethyl (2-cyano-2-(2-(3,5-dichloro-4-((2-methyl-2'-oxospiro[cyclopropane-1,3'-indolin]-5'-yl)oxy)phenyl)hydrazineylidene)acetyl)carbamate (775 mg, quant.) as an orange solid which was used without further purification in the next step. LC-MS: $C_{23}H_{19}Cl_2N_5O_5$ [M+H]$^+$: 516

A mixture of ethyl (2-cyano-2-(2-(3,5-dichloro-4-((2-methyl-2'-oxospiro[cyclopropane-1,3'-indolin]-5'-yl)oxy)phenyl)hydrazineylidene)acetyl)carbamate (774 mg, 1.5 mmol) and KOAc (294 mg, 3 mmol) in DMA (25 mL) under N2 was stirred at 120° C. for 4 h. The reaction mixture was cooled to 0° C., diluted with water and filtered. The precipitate was washed with water, dissolved in EtOAc and evaporated to dryness. The crude mixture was purified by flash chromatography on silica gel (0% to 10% MeOH in DCM) to give 2-(3,5-dichloro-4-((2-methyl-2'-oxospiro[cyclopropane-1,3'-indolin]-5'-yl)oxy)phenyl)-3,5-dioxo-2,3,4,5-tetrahydro-1,2,4-triazine-6-carbonitrile (459 mg, 65%) as a red solid. LC-MS: $C_{21}H_{13}Cl_2N_5O_4$ [M+H]$^+$: 470

KOH (477 mg, 8.51 mmol) was added to a solution of 2-(3,5-dichloro-4-((2-methyl-2'-oxospiro[cyclopropane-1,3'-indolin]-5'-yl)oxy)phenyl)-3,5-dioxo-2,3,4,5-tetrahydro-1,2,4-triazine-6-carbonitrile (400 mg, 0.85 mmol) in water (4 mL) and EtOH (4 mL) under N$_2$. The reaction mixture was stirred at 80° C. for 20 min. The reaction mixture was diluted in water and washed with EtOAc (3×). The aqueous phase was acidified with 1N HCl and extracted with EtOAc (3×). The combined organic phases were dried with Na$_2$SO$_4$. The solids were removed by filtration and the filtrate was evaporated to dryness. The crude mixture was purified by preparative HPLC (0% to 100% MeCN (0.1% formic acid) in water (0.1% formic acid)) to give 2-(3,5-dichloro-4-((2-methyl-2'-oxospiro[cyclopropane-1,3'-indolin]-5'-yl)oxy)phenyl)-3,5-dioxo-2,3,4,5-tetrahydro-1,2,4-triazine-6-carboxylic acid (166 mg, 40%) as a white solid. LC-MS: $C_{21}H_{14}Cl_2N_4O_6$ [M+H]$^+$: 489.

Et$_3$N (0.132 mL, 0.95 mmol) and diphenyl phosphoryl azide (0.153 mL, 0.71 mmol) were added to a solution of 2-(3,5-dichloro-4-((2-methyl-2'-oxospiro[cyclopropane-1, 3'-indolin]-5'-yl)oxy)phenyl)-3,5-dioxo-2,3,4,5-tetrahydro-1,2,4-triazine-6-carboxylic acid (116 mg, 0.24 mmol) in t-BuOH (3.5 mL) under N$_2$. The resulting mixture was stirred at 85° C. for 2 h. The reaction mixture was quenched with sat. aq. NH$_4$Cl and extracted with EtOAc (2×). The combined organic phases were washed with sat. aq. NH$_4$Cl and brine, and dried over Na$_2$SO$_4$. The solids were removed by filtration and the filtrate was evaporated to dryness. The crude mixture was purified by flash chromatography on silica gel (0% to 5% MeOH in DCM) to give tert-butyl (2-(3,5-dichloro-4-((2-methyl-2'-oxospiro[cyclopropane-1, 3'-indolin]-5'-yl)oxy)phenyl)-3,5-dioxo-2,3,4,5-tetrahydro-1,2,4-triazin-6-yl)carbamate (52 mg, 39%) as a beige solid. LC-MS: $C_{25}H_{23}Cl_2N_5O_6$ [M+H]$^+$: 560.

TFA (0.23 mL) was added to a solution of t-butyl (2-(3, 5-dichloro-4-((2-methyl-2'-oxospiro[cyclopropane-1,3'-indolin]-5'-yl)oxy)phenyl)-3,5-dioxo-2,3,4,5-tetrahydro-1,2, 4-triazin-6-yl)carbamate (86 mg, 0.15 mmol) in anhydrous DCM (2 mL) under N$_2$. The reaction mixture was stirred at room temperature for 21 h. Then the reaction mixture was evaporated under reduced pressure and co-evaporated with MeCN (3×). The crude mixture was purified by preparative HPLC (0% to 100% MeCN (0.1% formic acid) in water (0.1% formic acid) to give a two mixtures of diastereomers of 6-amino-2-(3,5-dichloro-4-((2-methyl-2'-oxospiro[cyclopropane-1,3'-indolin]-5'-yl)oxy)phenyl)-1,2,4-triazine-3,5 (2H,4H)-dione: (32) (3 mg, 4%) as a white solid: $^1$H-NMR (DMSO-d$_6$, 400 MHz): 1.23 (d, J=6.1 Hz, 3H), 1.46 (dd, J=7.4, 2.8 Hz, 1H), 1.65 (dd, J=8.8, 3.2 Hz, 1H), 1.66-1.73 (m, 1H), 6.34 (br s, 2H), 6.48 (dd, J=8.4, 2.5 Hz, 1H), 6.79-6.83 (m, 2H), 7.92 (s, 2H), 10.43 (s, 1H) ppm. LC-MS: $C_{20}H_{15}Cl_2N_5O_4$ [M+H]$^+$: 460 (33) (17 mg, 24%) as a white solid: $^1$H-NMR (DMSO-d$_6$, 400 MHz): 1.33 (d, J=6.2 Hz, 3H), 1.38-1.40 (m, 1H), 1.79 (dd, J=9.1, 3.7 Hz, 1H), 1.90-1.94 (m, 1H), 6.39 (dd, J=8.4, 2.6 Hz, 1H), 6.47 (br s, 2H), 6.68 (d, J=2.5 Hz, 1H), 6.76 (d, J=8.4 Hz, 1H), 7.88 (s, 2H), 10.40 (s, 1H), 12.27 (br s, 1H) ppm. LC-MS: $C_{20}H_{15}Cl_2N_5O_4$ [M+H]$^+$: 460.

Example 34 and Example 35. Preparation of Compounds 34 and 35

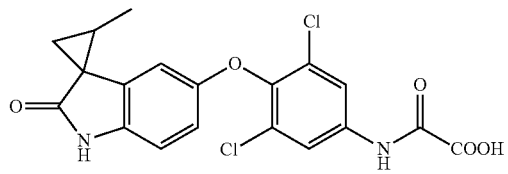

34, 35

A mixture of 5'-hydroxy-2-methyl-1'-(tetrahydro-2H-pyran-2-yl)spiro[cyclopropane-1,3'-indolin]-2'-one (1.06 g, 3.88 mmol), 1,3-dichloro-2-fluoro-5-nitrobenzene (0.9 g, 4.27 mmol) and K$_2$CO$_3$ (0.804 g, 5.82 mmol) in anhydrous DMF (28 mL) was stirred at 60° C. for 1 h. The reaction mixture was cooled to room temperature, diluted with water and extracted with EtOAc (3×). The combined organic phases were washed with sat. aq. NH$_4$Cl and dried with Na$_2$SO$_4$. The solids were removed by filtration and the filtrate was evaporated to dryness. The crude mixture was purified by silica flash chromatography (0% to 20% EtOAc in CyH) to give two separate mixtures of diastereomers of 5'-(2,6-dichloro-4-nitrophenoxy)-2-methyl-1'-(tetrahydro-2H-pyran-2-yl)spiro[cyclopropane-1,3'-indolin]-2'-one: (34-1) (856 mg, 48%) as a yellow solid. LC-MS: $C_{22}H_{20}Cl_2N_2O_5$ [M+H]$^+$: 463. (35-1) (466 mg, 26%) as a yellow solid. LC-MS: $C_{22}H_{20}Cl_2N_2O_5$ [M+H]$^+$: 463.

TFA (1.4 mL, 18.5 mmol) was added to a solution of 5'-(2,6-dichloro-4-nitrophenoxy)-2-methyl-1'-(tetrahydro-2H-pyran-2-yl)spiro[cyclopropane-1,3'-indolin]-2'-one (34-1) (856 mg, 1.85 mmol) in anhydrous DCM (16 mL) under N$_2$. The reaction mixture was stirred at 40° C. for 20 h. The reaction mixture was evaporated under reduced pressure and co-evaporated with MeCN (3×) to give 5'-(2,6-dichloro-4-nitrophenoxy)-2-methylspiro[cyclopropane-1,3'-indolin]-2'-one (34-2) (700 mg, quant.) as a brown solid which was used without further purification in the next step. LC-MS: $C_{17}H_{12}Cl_2N_2O_4$ [M+H]$^+$: 379.

The protecting group removal of 35-1 was achieved in the same manner as 34-1 to afford 35-2 (366 mg, 96%) as a brown solid which was used without further purification in the next step. LC-MS: $C_{17}H_{12}Cl_2N_2O_4$ [M+H]$^+$: 379.

Fe (515.9 mg, 9.24 mmol) was added to a solution of 5'-(2,6-dichloro-4-nitrophenoxy)-2-methylspiro[cyclopropane-1,3'-indolin]-2'-one (34-2) (700.6 mg, 1.85 mmol) and NH$_4$Cl (988.3 mg, 18.5 mmol) in EtOH (12 mL) and water (6 mL) under N$_2$. The reaction mixture was stirred at 70° C. for 1 h. The reaction mixture was filtered over a pad of celite which was rinsed with EtOAc. The resulting solution was washed with water and brine, and dried over Na$_2$SO$_4$. The solids were removed by filtration and the filtrate was evaporated to dryness to give 5'-(4-amino-2,6-dichlorophenoxy)-2-methylspiro[cyclopropane-1,3'-indolin]-2'-one (34-3) (645 mg, quant.) as a brown solid which was used without further purification in the next step. LC-MS: $C_{17}H_{14}Cl_2N_2O_2$ [M+H]$^+$: 349.

35-2 was reduced under the same reaction conditions as described for 34-2 to afford 35-3 (265 mg, 79%) as a brown solid which was used without further purification in the next step. LC-MS: $C_{17}H_{14}Cl_2N_2O_2$ [M+H]$^+$: 349.

Ethyl oxalyl monochloride (64 μL, 0.57 mmol), DIPEA (104 μL, 0.63 mmol) and DMAP (7.0 mg, 0.057 mmol) were added to a solution of 5'-(4-amino-2,6-dichlorophenoxy)-2-methylspiro[cyclopropane-1,3'-indolin]-2'-one (34-3) (200 mg, 0.57 mmol) in anhydrous DCM (5.5 mL) under N2 at 0° C. The reaction mixture was stirred at room temperature for 3 h. Extra ethyl oxalyl monochloride (64 μL, 0.57 mmol), DIPEA (104 μL, 0.63 mmol) and DMAP (7.0 mg, 0.057 mmol) were added and the reaction mixture was stirred at room temperature for 1 h. The reaction mixture was diluted with DCM, washed with brine and dried over Na$_2$SO$_4$. The solids were removed by filtration and the filtrate was evaporated to dryness. The crude mixture was purified by flash chromatography on silica gel (0% to 20% EtOAc in CyH) to give ethyl 2-((3,5-dichloro-4-((2-methyl-2'-oxospiro[cyclopropane-1,3'-indolin]-5'-yl)oxy)phenyl)amino)-2-oxoacetate (34-4) (145 mg, 56%) as a brown solid. $^1$H-NMR (DMSO-d$_6$, 400 MHz): 1.30-1.35 (m, 6H), 1.38 (dd, J=7.9, 3.8 Hz, 1H), 1.77 (dd, J=8.9, 3.8 Hz, 1H), 1.86-1.94 (m, 1H), 4.33 (q, J=7.1 Hz, 2H), 6.40 (dd, J=8.4, 2.6 Hz, 1H), 6.65 (d, J=2.6 Hz, 1H), 6.74 (d, J=8.4 Hz, 1H), 8.03 (s, 2H), 10.38 (s, 1H), 11.14 (br s, 1H) ppm. LC-MS: $C_{21}H_{18}Cl_2N_2O_5$ [M+H]$^+$: 449.

35-3 was reacted with ethyl oxalyl monochloride under the same conditions as described for 34-3 to afford 35-4 (135 mg, 52%) as a brown solid. $^1$H-NMR (DMSO-d$_6$, 400 MHz): 1.21 (d, J=6.1 Hz, 3H), 1.32 (d, J=7.1 Hz, 3H), 1.46 (dd, J=7.4, 3.6 Hz, 1H), 1.64 (dd, J=8.8, 3.6 Hz, 1H), 1.67-1.74 (m, 1H), 4.33 (q, J=7.1 Hz, 2H), 6.49 (dd, J=8.5, 2.6 Hz, 1H), 6.75 (d, J=2.6 Hz, 1H), 6.80 (d, J=8.5 Hz, 1H), 8.03 (s, 2H), 10.41 (s, 1H), 11.36 (br s, 1H) ppm. LC-MS: C$_{21}$H$_{18}$Cl$_2$N$_2$O$_5$ [M+H]$^+$: 449.

A solution of LiOH·H$_2$O (48.8 mg, 1.16 mmol) in water (1.5 mL) was added to a solution of ethyl 2-((3,5-dichloro-4-((2-methyl-2'-oxospiro[cyclopropane-1,3'-indolin]-5'-yl)oxy)phenyl)amino)-2-oxoacetate (34-4) (145 mg, 0.32 mmol) in THF (1.5 mL) under N$_2$. The reaction mixture was stirred at room temperature for 1 h. The reaction mixture was diluted in water, acidified with 1M HCl to pH 2 and extracted with EtOAc (2×). The combined organic phases were dried with Na$_2$SO$_4$. The solids were removed by filtration and the filtrate was evaporated to dryness and co-evaporated with EtOH to give 2-((3,5-dichloro-4-((2-methyl-2'-oxospiro[cyclopropane-1,3'-indolin]-5'-yl)oxy)phenyl)amino)-2-oxoacetic acid (34) (117 mg, 86%) as a beige solid. $^1$H-NMR (DMSO-d$_6$, 400 MHz): 1.32 (d, J=6.3 Hz, 3H), 1.36-1.40 (m, 1H), 1.77 (dd, J=8.6, 3.0 Hz, 1H), 1.88-1.94 (m, 1H), 6.40 (dd, J=8.4, 2.6 Hz, 1H), 6.64 (d, J=2.6 Hz, 1H), 6.74 (d, J=8.2 Hz, 1H), 8.05 (s, 2H), 10.38 (s, 1H), 11.06 (s, 1H) ppm. LC-MS: C$_{19}$H$_{14}$Cl$_2$N$_2$O$_5$ [M+H]$^+$: 421.

Ester hydrolysis of 35-4 followed an analogous procedure to that described for 34-4 to afford 35 (12 mg, 2%) as a beige solid. $^1$H-NMR (DMSO-d$_6$, 400 MHz): 1.21 (d, J=6.5 Hz, 3H), 1.43-1.47 (m, 1H), 1.63 (dd, J=8.8, 3.0 Hz, 1H), 1.67-1.73 (m, 1H), 6.47 (dd, J=8.8, 2.2 Hz, 1H), 6.73 (d, J=2.6 Hz, 1H), 6.79 (d, J=8.0 Hz, 1H), 8.08 (s, 2H), 10.39 (s, 1H), 10.56 (s, 1H) ppm. LC-MS: C$_{19}$H$_{14}$Cl$_2$N$_2$O$_5$ [M+H]$^+$: 421.

Example 36. Preparation of Compound 36

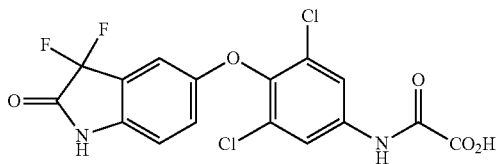 [SMILES: O=C(O)C(=O)Nc1cc(Cl)c(Oc2ccc3c(c2)C(F)(F)C(=O)N3)c(Cl)c1]

DAST (2.14 g, 1.63 mL, 13.27 mmol) was added dropwise to a solution of 5-bromoisatin (1 g, 4.42 mmol) in anhydrous DCM (40 mL) at room temperature under N$_2$. The reaction mixture was stirred at room temperature for 2 h. Then, the reaction mixture was cooled to 0° C. and MeOH (15 mL) was added. The mixture was stirred for 15 min, then diluted with water and extracted with DCM (3×). The combined organic layers were washed with brine and dried over MgSO$_4$. The solids were removed by filtration and the filtrate was evaporated to dryness. The crude product was purified by flash chromatography on silica gel (0% to 50% AcOEt in CyH) to give 5-bromo-3,3-difluoroindolin-2-one (790 mg, 72%) as a beige solid. $^1$H-NMR (DMSO-d$_6$, 400 MHz): 6.95 (d, J=8.7 Hz, 1H), 7.70 (d, J=8.7 Hz, 1H), 7.94 (s, 1H), 13.32 (br s, 1H) ppm. LC-MS: C$_8$H$_4$BrF$_2$NO [M−H]$^-$: 248.

A mixture of 5-bromo-3,3-difluoroindolin-2-one (1.2 g, 4.84 mmol), bis(neopentyl glycolato)diboron (3.28 g, 14.51 mmol), KOAc (1.42 g, 14.51 mmol) and PdCl$_2$[P(o-Tol)$_3$]$_2$ (0.38 g, 0.48 mmol) in anhydrous DMSO (28.1 mL) was stirred at 90° C. under N2 for 18 h, at which point extra PdCl$_2$[P(o-Tol)$_3$]$_2$ (0.38 g, 0.48 mmol), KOAc (1.42 g, 14.51 mmol) and bis(neopentyl glycolato)diboron (3.28 g, 14.51 mmol) were added and stirring was pursued at 90° C. for 1 h to reach full conversion. The reaction mixture was diluted with EtOAc, washed with brine and dried over Na$_2$SO$_4$. The solids were removed by filtration and the filtrate was evaporated to dryness. The crude product was purified by flash chromatography on silica gel (30% AcOEt in CyH) to give 5-(5,5-dimethyl-1,3,2-dioxaborinan-2-yl)-3,3-difluoroindolin-2-one (1.30 g, 96%) as an orange solid. LC-MS: C$_{13}$H$_{14}$BF$_2$NO$_3$ [M(boronic acid)−H]$^-$: 212.

H$_2$O$_2$ 30% (11.8 mL, 115.63 mmol) and HOAc (6.94 g, 6.63 mL, 115.63 mmol) were added to a solution of 5-(5,5-dimethyl-1,3,2-dioxaborinan-2-yl)-3,3-difluoroindolin-2-one (1.3 g, 4.63 mmol) in THF (26.9 mL) under N$_2$. The reaction mixture was stirred at room temperature for 16 h. The reaction mixture was then quenched with sat. aq. NaHCO$_3$ (200 mL) and extracted with EtOAc (3×). The combined organic layers were washed with brine and dried over MgSO$_4$. The solids were removed by filtration and the filtrate was evaporated to dryness. The crude product was purified by flash chromatography on silica gel (20% to 50% AcOEt in CyH) to give 3,3-difluoro-5-hydroxyindolin-2-one (332 mg, 39%) as a white solid. $^1$H-NMR (DMSO-d$_6$, 300 MHz): 6.81 (d, J=8.7 Hz, 1H), 6.90 (d, J=8.7 Hz, 1H), 6.99 (s, 1H), 9.61 (s, 1H), 10.87 (br s, 1H) ppm. LC-MS: C$_8$H$_5$F$_2$NO$_2$ [M−H]$^-$: 185.

1,3-Dichloro-2-fluoro-5-nitrobenzene (183.75 mg, 0.88 mmol) and DIPEA (226.2 mg, 0.29 mL, 1.75 mmol) were added to a solution of 3,3-difluoro-5-hydroxyindolin-2-one (162 mg, 0.88 mmol) in anhydrous DMF (6.1 mL) under N$_2$. The reaction mixture was stirred at room temperature for 16 h. The reaction mixture was then diluted with water and extracted with EtOAc (3×). The combined organic layers were washed with water and brine and dried over Na$_2$SO$_4$. The solids were removed by filtration and the filtrate was evaporated to dryness. The crude mixture was purified by flash chromatography on silica gel (10% to 50% EtOAc in CyH) to give 5-(2,6-dichloro-4-nitrophenoxy)-3,3-difluoroindolin-2-one (164 mg, 50%) as a yellow powder. $^1$H-NMR (DMSO-d$_6$, 300 MHz): 6.97 (d, J=8.7 Hz, 1H), 7.11 (d, J=8.7 Hz, 1H), 7.40 (s, 1H), 8.55 (s, 2H), 11.15 (br s, 1H) ppm. LC-MS: C$_{14}$H$_6$Cl$_2$F$_2$N$_2$O$_4$ [M−H]$^-$: 373.

Fe (122 mg, 2.19 mmol) was added to a solution of 5-(2,6-dichloro-4-nitrophenoxy)-3,3-difluoroindolin-2-one (164 mg, 0.44 mmol) and NH$_4$Cl (233.86 mg, 4.37 mmol) in EtOH (2.87 mL) and water (1.44 mL) under N$_2$. The reaction mixture was stirred at 70° C. for 2 h. After cooling to room temperature, the reaction mixture was filtered over a pad of celite. The filtrate was diluted with EtOAc and the organic phase was washed with water and brine and dried over Na$_2$SO$_4$. The solids were removed by filtration and the filtrate was evaporated to dryness to give 5-(4-amino-2,6-dichlorophenoxy)-3,3-difluoroindolin-2-one (150 mg, 99%) as a brown solid which was used as such in the next step. $^1$H-NMR (DMSO-d$_6$, 300 MHz): 5.69 (br s, 2H), 6.72 (s, 2H), 6.88-6.96 (m, 2H), 7.16 (s, 1H), 11.10 (br s, 1H) ppm. LC-MS: C$_{14}$H$_8$Cl$_2$F$_2$N$_2$O$_2$ [M+H]$^+$: 345.

Ethyl oxalyl monochloride (30.07 mg, 0.025 mL, 0.22 mmol), DIPEA (31.307 mg, 0.04 mL, 0.24 mmol) and DMAP (2.69 mg, 0.022 mmol) were added to a solution of 5-(4-amino-2,6-dichlorophenoxy)-3,3-difluoroindolin-2-one (76 mg, 0.22 mmol) in anhydrous DCM (2.2 mL) under N$_2$. The reaction mixture was stirred at room temperature for 16 h. The mixture was then diluted with water and extracted with DCM (2×). The combined organic layers were washed with brine (2×) and dried over anhydrous Na$_2$SO$_4$. The solids were removed by filtration and the filtrate was evaporated to dryness. The crude mixture was purified by flash chromatography on silica gel (30% to 50% EtOAc in CyH) to give ethyl 2-((3,5-dichloro-4-((3,3-difluoro-2-oxoindolin-5-yl)oxy)phenyl)amino)-2-oxoacetate (31 mg, 32%) as a white powder. $^1$H-NMR (DMSO-d$_6$, 300 MHz): 1.33 (t, J=6.9 Hz, 3H), 4.33 (q, J=6.9 Hz, 2H), 6.95 (s, 2H), 7.31 (s, 1H), 8.06 (s, 2H), 11.15 (br s, 2H) ppm. LC-MS: C$_{18}$H$_{12}$Cl$_2$F$_2$N$_2$O$_5$ [M+H]$^+$: 445.

A solution of LiOH·H$_2$O (8.48 mg, 0.202 mmol) in H$_2$O (0.26 mL) was added to a solution of ethyl 2-((3,5-dichloro-4-((3,3-difluoro-2-oxoindolin-5-yl)oxy)phenyl)amino)-2-oxoacetate (25 mg, 0.056 mmol) in THF (0.26 mL) under N$_2$. The mixture was stirred at room temperature for 2 h. The reaction mixture was then diluted with water and the aqueous solution was washed with EtOAc, acidified to pH=2 with 1N HCl and extracted with EtOAc. The organic phase was dried over Na$_2$SO$_4$, the solids were removed by filtration and the filtrate was evaporated to dryness. The resulting solid was triturated in Et$_2$O to give 2-((3,5-dichloro-4-((3, 3-difluoro-2-oxoindolin-5-yl)oxy)phenyl)amino)-2-oxoacetic acid (36)(20 mg, 85%) as a white solid. $^1$H-NMR (CD$_3$OD, 400 MHz): 6.91-6.95 (m, 2H), 7.08 (s, 1H), 7.99 (s, 1H) ppm. LC-MS: C$_{16}$H$_8$Cl$_2$F$_2$N$_2$O$_5$ [M−H]$^-$: 415.

Example 37. Preparation of Compound 37

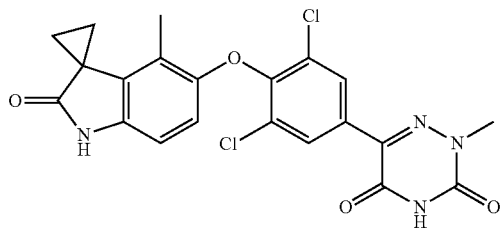 [SMILES: Cc1c(Oc2c(Cl)cc(-c3nn(C)c(=O)[nH]c3=O)cc2Cl)ccc2c1C1(CC1)C(=O)N2]

A solution of ethenyldiphenylsulfanium trifluoromethanesulfonate (14.8 g, 40.8 mmol, CAS: 247129-88-0) in anhydrous DMF (51 mL) was added to a solution of 4-methyl-2,3-dihydro-1H-indol-2-one (5 g, 34.0 mmol) and ZnOTf$_2$ (12.4 g, 34.0 mmol) in anhydrous DMF (154 mL) under N$_2$. After 2 min of stirring, DBU (15 mL, 102 mmol) was added and the reaction mixture was stirred at room temperature for 1.5 h. The reaction mixture was quenched with sat. aq. NH$_4$Cl (100 mL) and diluted with AcOEt (400 mL). The mixture was washed with brine (3×) and dried over Na$_2$SO$_4$. The solids were removed by filtration and the filtrate was evaporated to dryness. The resulting solid was triturated with pentane (3×) to afford 4'-methylspiro[cyclopropane-1,3'-indolin]-2'-one (5.88 g, quant.) as a beige solid which was used without further purification in the next step. $^1$H-NMR (DMSO-d$_6$, 300 MHz): 1.24-1.34 (m, 2H), 1.87-1.96 (m, 2H), 2.11 (s, 3H), 6.68 (d, J=7.6 Hz, 1H), 6.74 (d, J=7.7 Hz, 1H), 7.03 (t, J=7.7 Hz, 1H), 10.48 (s, 1H) ppm. LC-MS: C$_{11}$H$_{11}$NO [M+H]$^+$: 174.

PIFA (18.7 g, 43.4 mmol) was added to a solution of 4'-methylspiro[cyclopropane-1,3'-indolin]-2'-one (6.27 g, 36.2 mmol) and TFA (27 mL, 362 mmol) in chloroform (428 mL) under N$_2$. The reaction mixture was stirred at room temperature for 22 h. The reaction mixture was quenched with sat. aq. NaHCO$_3$ (200 mL) and stirred for 5 min. The organic layer was collected, diluted in EtOAc (400 mL), washed with sat. aq. NaHCO$_3$ (3×) and dried over Na$_2$SO$_4$. The solids were removed by filtration and the filtrate was evaporated to dryness. The crude mixture was purified by flash chromatography on silica gel (2% to 5% MeOH in DCM) and trituration with EtOH to give 5'-hydroxy-4'-methylspiro [cyclopropane-1,3'-indolin]-2'-one (3.11 g, 45%) as an orange solid. $^1$H-NMR (DMSO-d$_6$, 300 MHz): 1.23-1.30 (m, 2H), 1.81-1.87 (m, 2H), 1.90 (s, 3H), 6.53 (d, J=8.1 Hz, 1H), 6.59 (d, J=8.2 Hz, 1H), 8.78 (s, 1H), 10.17 (s, 1H) ppm. LC-MS: C$_{11}$H$_{11}$NO$_2$ [M+H]$^+$: 190.

DIPEA (5.4 mL, 32.9 mmol) was added to a solution of 5'-hydroxy-4'-methylspiro[cyclopropane-1,3'-indolin]-2'-one (3.11 g, 16.4 mmol) and 1,3-dichloro-2-fluoro-5-nitrobenzene (3.45 g, 16.4 mmol) in anhydrous DMF (163 mL) under N$_2$. The reaction mixture was stirred at 60° C. for 21 h. The reaction mixture was diluted in water (300 mL) and filtered. The precipitate was washed with water (3×) and then dissolved in EtOAc and dried over Na$_2$SO$_4$. The solids were removed by filtration and the filtrate was evaporated to dryness to give 5'-(2,6-dichloro-4-nitrophenoxy)-4'-methylspiro[cyclopropane-1,3'-indolin]-2'-one (4.81 g, 77%) as a yellow solid which was used without further purification in the next step. $^1$H-NMR (DMSO-d$_6$, 300 MHz): 1.35-1.42 (m, 2H), 1.87-2.03 (m, 2H), 2.18 (s, 3H), 6.22 (d, J=8.5 Hz, 1H), 6.51 (d, J=8.1 Hz, 1H), 8.51 (s, 2H), 10.47 (s, 1H) ppm. LC-MS: C$_{17}$H$_{12}$Cl$_2$N$_2$O$_4$ [M+H]$^+$: 379.

A mixture of 5'-(2,6-dichloro-4-nitrophenoxy)-4'-methylspiro[cyclopropane-1,3'-indolin]-2'-one (4.81 g, 12.7 mmol), NH$_4$Cl (6.79 g, 127 mmol) and Fe (3.54 g, 63.4 mmol) in EtOH (86 mL) and water (43 mL) under N2 was stirred at 80° C. for 23 h. The reaction mixture was filtered over celite and diluted in EtOAc. The resulting solution was washed with brine (3×) and dried over Na$_2$SO$_4$. The solids were removed by filtration and the filtrate was evaporated to dryness providing 5'-(4-amino-2,6-dichlorophenoxy)-4'-methylspiro[cyclopropane-1,3'-indolin]-2'-one (4.43 g, quant.) as a yellow solid which was used without further purification in the next step. $^1$H-NMR (DMSO-d$_6$, 300 MHz): 1.31-1.37 (m, 2H), 1.92-1.98 (m, 2H), 2.12 (s, 3H), 5.58 (br s, 2H), 6.13 (d, J=8.5 Hz, 1H), 6.60 (d, J=8.5 Hz, 1H), 6.70 (s, 2H), 10.37 (s, 1H) ppm. LC-MS: C$_{17}$H$_{14}$Cl$_2$N$_2$O$_2$ [M+H]$^+$: 349.

A solution of NaNO$_2$ (0.4 g, 5.73 mmol) in water (10 mL) was added to a solution of 5'-(4-amino-2,6-dichlorophenoxy)-4'-methylspiro[cyclopropane-1,3'-indolin]-2'-one (1 g, 2.86 mmol) in MeOH (40 mL), water (10 mL), AcOH (5 mL) and HCl 37% (5 mL) at 0° C. under N$_2$. The reaction mixture was stirred at 0° C. for 1 h. Tetrahydroxydiboron (2.05 g, 22.9 mmol) was added and the reaction mixture was stirred at 60° C. for 1 h. The reaction mixture was cooled to room temperature, diluted in water (100 mL) and filtered. The precipitate was washed with water (3×), dissolved in EtOAc and dried over Na$_2$SO$_4$. The solids were removed by filtration and the filtrate was evaporated to dryness to give (3,5-dichloro-4-((4'-methyl-2'-oxospiro[cyclopropane-1,3'-indolin]-5'-yl)oxy)phenyl)boronic acid (906 mg, 84%) as a yellow solid which was used without further purification in the next step. LC-MS: C$_{17}$H$_{14}$BCl$_2$NO$_4$ [M+H]$^+$: 378.

N,O-Bis(trimethylsilyl)acetamide (16 mL, 65.1 mmol) was added to a solution of 6-bromo-2,3,4,5-tetrahydro-1,2, 4-triazine-3,5-dione (5 g, 26 mmol) in anhydrous MeCN (125 mL) under N$_2$. The reaction mixture was refluxed for 2 h and then cooled to room temperature. MeI (2.4 mL, 39.1 mmol) was added dropwise and the reaction mixture was refluxed for 22 h. The reaction mixture was diluted with water (100 mL) and extracted with EtOAc (4×). The combined organic phases were washed with brine and dried over Na$_2$SO$_4$. The solids were removed by filtration and the filtrate was evaporated to dryness. The crude mixture was purified by flash chromatography on silica gel (10% to 50% EtOAc in CyH) to give 6-bromo-2-methyl-1,2,4-triazine-3,5(2H,4H)-dione (4.25 g, 79%) as a white solid. $^1$H-NMR (DMSO-d$_6$, 400 MHz): 3.44 (s, 3H), 12.48 (br s, 1H) ppm. LC-MS: C$_4$H$_4$BrN$_3$O$_2$ [M+H]$^+$: 206/208.

Na$_2$CO$_3$ (4.8 mL, 9.59 mmol, 2M in water) was added to a solution of 6-bromo-2-methyl-1,2,4-triazine-3,5(2H,4H)-dione (592.5 mg, 2.88 mmol), (3,5-dichloro-4-((4'-methyl-2'-oxospiro[cyclopropane-1,3'-indolin]-5'-yl)oxy)phenyl) boronic acid (906 mg, 2.4 mmol) and Pd(dppf)Cl$_2$ (175.4 mg, 0.24 mmol) in 1,4-dioxane (18 mL) under N$_2$. The reaction mixture was stirred at 100° C. for 90 min. The reaction was quenched with water (20 mL), diluted with EtOAc and washed with sat. aq. NH$_4$Cl and brine. The aqueous phase was extracted with EtOAc (3×) and the combined organic phases were dried over Na$_2$SO$_4$. The solids were removed by filtration and the filtrate was evaporated to dryness. The crude mixture was purified by flash chromatography on silica gel (1% to 4% MeOH in DCM) and triturated with EtOH to give 6-(3,5-dichloro-4-((4'-methyl-2'-oxospiro[cyclopropane-1,3'-indolin]-5'-yl)oxy)phenyl)-2-methyl-1,2,4-triazine-3,5(2H,4H)-dione (37) (173 mg, 16%) as a light yellow solid. $^1$H-NMR (DMSO-d$_6$, 300 MHz): 1.34-1.42 (m, 2H), 1.96-2.03 (m, 2H), 2.18 (s, 3H), 3.58 (s, 3H), 6.16 (d, J=8.3 Hz, 1H), 6.62 (d, J=8.4 Hz, 1H), 8.13 (s, 2H), 10.44 (s, 1H), 12.42 (s, 1H) ppm. LC-MS: C$_{21}$H$_{16}$Cl$_2$N$_4$O$_4$ [M+H]$^+$: 459.

Example 38. Preparation of Compound 38

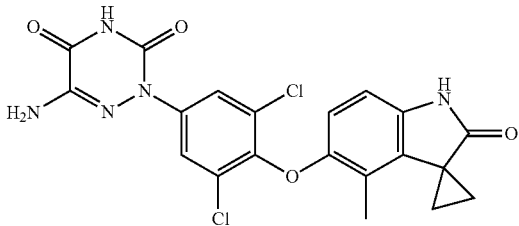

A solution of NaNO$_2$ (0.83 g, 12.0 mmol) in water (115 mL) was added to a solution of 5'-(4-amino-2,6-dichlorophenoxy)-4'-methylspiro[cyclopropane-1,3'-indolin]-2'-one (2 g, 5.73 mmol) in HCl 37% (50 mL), AcOH (148 mL) and water (115 mL) at 0° C. under N$_2$. The reaction mixture was stirred at 0° C. for 1 h. In parallel, a solution of ethyl N-(2-cyanoacetyl)carbamate (1.34 g, 8.59 mmol) in water (141 mL) and pyridine (49 mL) was stirred at 0° C. for 15 min. The first reaction mixture was quickly added to the second one and the resulting reaction mixture was stirred at 0° C. for 2 h. The reaction mixture was diluted in water and filtered. The precipitate was washed with water, dissolved in EtOAc and dried over Na$_2$SO$_4$. The solids were removed by filtration and the filtrate was evaporated to dryness to give ethyl (2-cyano-2-(2-(3,5-dichloro-4-((4'-methyl-2'-oxospiro[cyclopropane-1,3'-indolin]-5'-yl)oxy)phenyl)hydrazineylidene)acetyl)carbamate (2.47 g, 84%) as an orange solid which was used without further purification in the next step. LC-MS: C$_{23}$H$_{19}$Cl$_2$N$_5$O$_5$ [M+H]$^+$: 516.

NaOAc (1.57 g, 19.1 mmol) was added to a solution of ethyl (2-cyano-2-(2-(3,5-dichloro-4-((4'-methyl-2'-oxospiro[cyclopropane-1,3'-indolin]-5'-yl)oxy)phenyl)hydrazineylidene)acetyl)carbamate (2.47 g, 4.78 mmol) in AcOH (48 mL) under N$_2$. The solution was stirred at 120° C. for 3 h. The reaction mixture was cooled to room temperature and diluted in water. The precipitate was filtered, washed with water, dissolved in EtOAc and dried over Na$_2$SO$_4$. The solids were removed by filtration and the filtrate was evaporated to dryness to give 2-(3,5-dichloro-4-((4'-methyl-2'-oxospiro[cyclopropane-1,3'-indolin]-5'-yl)oxy)phenyl)-3,5-dioxo-2,3,4,5-tetrahydro-1,2,4-triazine-6-carbonitrile (2.08 g, 92%) as an orange solid which was used without further purification in the next step. $^1$H-NMR (DMSO-d$_6$, 300 MHz): 1.34-1.41 (m, 2H), 1.99-2.04 (m, 2H), 2.18 (s, 3H), 6.19 (d, J=8.5 Hz, 1H), 6.64 (d, J=8.5 Hz, 1H), 7.79 (s, 2H), 10.45 (s, 1H), 13.26 (br s, 1H) ppm. LC-MS: C$_{21}$H$_{13}$Cl$_2$N$_5$O$_4$ [M−H]$^-$: 468.

A KOH (2.48 g, 44.2 mmol) solution in water (21 mL) was added to a solution of 2-(3,5-dichloro-4-((4'-methyl-2'-oxospiro[cyclopropane-1,3'-indolin]-5'-yl)oxy)phenyl)-3,5-dioxo-2,3,4,5-tetrahydro-1,2,4-triazine-6-carbonitrile (2.08 g, 4.42 mmol) in EtOH (21 mL) under N$_2$. The reaction mixture was stirred at 80° C. for 1 h. The reaction mixture was diluted with water and washed with EtOAc (2×). The aqueous phase was acidified with HCl 6N to pH 2 and the precipitate was filtered and washed with water (3×). The precipitate was dissolved in EtOAc/MeOH (1:1) and dried over Na$_2$SO$_4$. The solids were removed by filtration and the filtrate was evaporated to dryness to give 2-(3,5-dichloro-4-((4'-methyl-2'-oxospiro[cyclopropane-1,3'-indolin]-5'-yl)oxy)phenyl)-3,5-dioxo-2,3,4,5-tetrahydro-1,2,4-triazine-6-carboxylic acid (1.42 g, 66%) as an orange solid which was used without further purification in the next step. LC-MS: C$_{21}$H$_{14}$Cl$_2$N$_4$O$_6$ [M−H]$^-$: 487.

Et$_3$N (1.6 mL, 11.6 mmol) and diphenyl phosphoryl azide (1.9 mL, 8.71 mmol) were added to a solution of 2-(3,5-dichloro-4-((4'-methyl-2'-oxospiro[cyclopropane-1,3'-indolin]-5'-yl)oxy)phenyl)-3,5-dioxo-2,3,4,5-tetrahydro-1,2,4-triazine-6-carboxylic acid (1.42 g, 2.90 mmol) in t-BuOH (42 mL) under N$_2$. The resulting mixture was stirred at 85° C. for 7 h. The reaction mixture was quenched with sat. aq. NaHCO$_3$ and diluted with EtOAc. The organic phase was washed with sat. aq. NaHCO$_3$ (2×) and brine and dried over Na$_2$SO$_4$. The solids were removed by filtration and the filtrate was evaporated to dryness. The crude mixture was purified by flash chromatography on silica gel (0% to 4% MeOH in DCM) to afford tert-butyl (2-(3,5-dichloro-4-((4'-methyl-2'-oxospiro[cyclopropane-1,3'-indolin]-5'-yl)oxy)phenyl)-3,5-dioxo-2,3,4,5-tetrahydro-1,2,4-triazin-6-yl)carbamate (497 mg, 31%) as an orange solid. $^1$H-NMR (DMSO-d$_6$, 300 MHz): 1.34-1.40 (m, 2H), 1.45 (s, 9H), 1.97-2.03 (m, 2H), 2.18 (s, 3H), 6.17 (d, J=8.5 Hz, 1H), 6.64 (d, J=8.5 Hz, 1H), 7.88 (s, 2H), 9.09 (s, 1H), 10.45 (s, 1H), 12.57 (br s, 1H) ppm. LC-MS: C25H$_{23}$Cl$_2$N$_5$O$_6$ [M+H]$^+$: 560.

TFA (1.3 mL, 17.1 mmol) was added to a solution of t-butyl (2-(3,5-dichloro-4-((4'-methyl-2'-oxospiro[cyclopropane-1,3'-indolin]-5'-yl)oxy)phenyl)-3,5-dioxo-2,3,4,5-tetrahydro-1,2,4-triazin-6-yl)carbamate (479.8 mg, 0.86 mmol) in anhydrous DCM (9 mL) under N$_2$. The reaction mixture was stirred at room temperature for 4 h. The reaction mixture was diluted in MeCN and the precipitate was filtered and washed with MeCN (3×). The crude mixture was purified by flash chromatography on silica gel (5% to 20/a MeOH (10/a NH$_4$OH) in DCM). The resulting residue was dissolved in DMF (12 mL) and was purified by preparative HPLC (2% to 100% MeCN in water (2 g/L NH$_4$HCO$_3$)) to give, after co-evaporation with EtOH (3×) and MeCN (3×), 6-amino-2-(3,5-dichloro-4-((4'-methyl-2'-oxospiro[cyclopropane-1,3'-indolin]-5'-yl)oxy)phenyl)-1,2,4-triazine-3,5(2H,4H)-dione (38) (65 mg, 16%) as a white solid. $^1$H-NMR (DMSO-d$_6$, 300 MHz): 1.33-1.40 (m, 2H), 1.96-2.03 (m, 2H), 2.17 (s, 3H), 6.15 (d, J=8.5 Hz, 1H), 6.41 (br s, 2H), 6.63 (d, J=8.5 Hz, 1H), 7.90 (s, 2H), 10.43 (s, 1H), 12.22 (br s, 1H) ppm. LC-MS: C$_{20}$H$_{15}$Cl$_2$N$_5$O$_4$ [M+H]$^+$: 460.

Example 39. Preparation of Compound 39

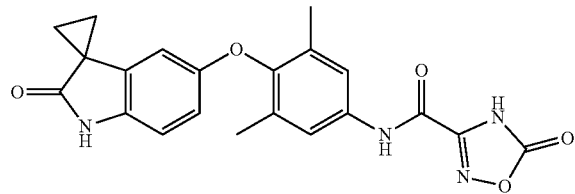 [SMILES: Cc1cc(NC(=O)c2noc(=O)[nH]2)cc(C)c1Oc1ccc2c(c1)C1(CC1)C(=O)N2]

Cs$_2$CO$_3$ (1860 mg, 5.71 mmol) was added to a solution of 5'-hydroxyspiro[cyclopropane-1,3'-indolin]-2'-one (500 mg, 2.85 mmol) and 2-fluoro-1,3-dimethyl-5-nitrobenzene (482.78 mg, 2.85 mmol) in anhydrous DMF (8 mL) under N$_2$. The reaction mixture was stirred at 40° C. for 20 h. Water (15 mL) was then added to the reaction mixture. The resulting precipitate was filtered and purified by flash chromatography on silica gel (0% to 40% AcOEt in CyH) to afford 5'-(2,6-dimethyl-4-nitrophenoxy)spiro[cyclopropane-1,3'-indolin]-2'-one (564 mg, 37%) as a yellow solid. $^1$H-NMR (DMSO-d$_6$, 400 MHz): 1.42-1.45 (m, 2H), 1.53-1.56 (m, 2H), 2.15 (s, 6H), 6.43 (dd, J=8.4 Hz, 2.4 Hz, 1H), 6.64 (d, J=2.4 Hz, 1H), 6.78 (d, J=8.4 Hz, 1H), 8.10 (s, 2H), 10.45 (s, 1H) ppm. LC-MS: C$_{11}$H$_{16}$N$_2$O$_4$ [M+H]$^+$: 325.

Fe (0.49 g, 8.69 mmol) was added to a solution of 5'-(2,6-dimethyl-4-nitrophenoxy)spiro[cyclopropane-1,3'-indolin]-2'-one (0.56 g, 1.74 mmol) and NH$_4$Cl (0.93 g, 17.39 mmol) in EtOH (10 mL) and water (10 mL) under N$_2$. The reaction mixture was stirred at 70° C. for 30 min and at room temperature overnight. The reaction mixture was filtered over a pad of celite which was rinsed with EtOH (3×30 mL). EtOH was evaporated from the filtrate. The resulting precipitate was filtered to give 5'-(4-amino-2,6-dimethylphenoxy)spiro[cyclopropane-1,3'-indolin]-2'-one (457 mg, 89%) as an orange solid. $^1$H-NMR (DMSO-d$_6$, 400 MHz): 1.40-1.45 (m, 2H), 1.47-1.52 (m, 2H), 1.90 (s, 6H), 5.18 (br s, 2H), 6.31-6.34 (m, 3H), 6.53 (d, J=2.4 Hz, 1H), 6.72 (d, J=8.4 Hz, 1H), 10.35 (s, 1H) ppm. LC-MS: C$_{18}$H$_{18}$N$_2$O$_2$ [M+H]$^+$: 295.

LiHMDS 1M in THF (3.13 mL, 3.13 mmol) was added to a solution of ethyl 5-oxo-4,5-dihydro-1,2,4-oxadiazole-3-carboxylate (123.55 mg, 0.78 mmol) and 5'-(4-amino-2,6-dimethylphenoxy)spiro[cyclopropane-1,3'-indolin]-2'-one (230 mg, 0.78 mmol) in anhydrous THF (4 mL) under N$_2$. Then, the reaction mixture was diluted with MeOH and evaporated to dryness. The crude mixture was purified by flash chromatography on silica gel (0% to 4% MeOH in DCM). The resulting solid was triturated with EtOH to afford N-(3,5-dimethyl-4-((2'-oxospiro[cyclopropane-1,3'-indolin]-5'-yl)oxy)phenyl)-5-oxo-4,5-dihydro-1,2,4-oxadiazole-3-carboxamide (39) (64 mg, 20%) as a white solid. $^1$H-NMR (DMSO-d$_6$, 400 MHz): 1.40-1.46 (m, 2H), 1.50-1.58 (m, 2H), 2.03 (s, 6H), 6.34 (dd, J=8.4 Hz, 2.4 Hz, 1H), 6.59 (d, J=2.4 Hz, 1H), 6.74 (d, J=8.4 Hz, 1H), 7.53 (s, 2H), 10.36 (s, 1H), 10.39 (s, 1H), 13.14 (br s, 1H) ppm. LC-MS: C$_{21}$H$_{18}$N$_4$O$_5$ [M+H]$^+$: 407.

Example 40. Preparation of Compound 40

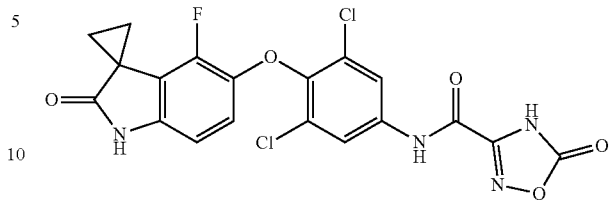

A solution of ethenyldiphenylsulfanium trifluoromethanesulfonate (14.39 g, 39.7 mmol) in anhydrous DMF (50 mL) was added to a solution of 4-fluoro-2,3-dihydro-1H-indol-2-one (5 g, 33.082 mmol) and zinc triflate (12.026 g, 33.082 mmol) in anhydrous DMF (150 mL) under N$_2$. After 2 min of stirring, DBU (11.5 mL, 76.97 mmol) was added and the reaction mixture was stirred at room temperature for 1 h. The reaction mixture was hydrolyzed with sat. aq. NH$_4$Cl and extracted with AcOEt (2×). The combined organic phases were washed with brine (3×) and dried over Na$_2$SO$_4$. The solids were removed by filtration and the filtrate was evaporated to dryness. The crude product was purified by silica gel flash chromatography (20% to 30% AcOEt in CyH) to give 4'-fluorospiro[cyclopropane-1,3'-indolin]-2'-one (4.79 g, 82%) as a white solid. $^1$H-NMR (DMSO-d$_6$, 400 MHz): 1.43-1.46 (m, 2H), 1.74-1.77 (m, 2H), 6.71-6.74 (m, 1H), 6.77 (d, J=6.8 Hz, 1H), 7.15-7.21 (m, 1H), 10.77 (br s, 1H) ppm. LC-MS: C$_{10}$H$_8$FNO [M+H]$^+$: 178

PIFA (13.95 g, 32.44 mmol) and TFA (20 mL, 270.35 mmol) were added to a solution of 4'-fluorospiro[cyclopropane-1,3'-indolin]-2'-one (4.79 g, 27.035 mmol) in CHCl$_3$ (287 mL) under N$_2$. The reaction mixture was stirred at 60° C. for 1 h. The reaction mixture was neutralized with sat. aq. NaHCO$_3$ and extracted with DCM (2×). The combined organic phases were washed with brine (2×) and dried over MgSO$_4$. The solids were removed by filtration and the filtrate was evaporated to dryness. The crude product was purified by silica gel flash chromatography (0% to 5% MeOH in DCM) to give 4'-fluoro-5'-hydroxyspiro[cyclopropane-1,3'-indolin]-2'-one (1.90 g, 36%) as a beige solid. $^1$H-NMR (DMSO-d$_6$, 400 MHz): 1.39-1.43 (m, 2H), 1.70-1.73 (m, 2H), 6.53 (d, J=8.4 Hz, 1H), 6.73 (dd, J=8.4 Hz, 8.4 Hz, 1H), 9.29 (s, 1H), 10.43 (br s, 1H) ppm. LC-MS: C$_{10}$H$_8$FNO$_2$ [M+H]$^+$: 194

DIPEA (1.93 mL, 11.7 mmol) was added to a solution of 4'-fluoro-5'-hydroxyspiro[cyclopropane-1,3'-indolin]-2'-one (1.13 g, 5.85 mmol) and 1,3-dichloro-2-fluoro-5-nitrobenzene (1.23 g, 5.85 mmol) in anhydrous DMF (55 mL) under N$_2$. The reaction mixture was stirred at room temperature for 22 h. The reaction mixture was then diluted with water (300 mL). The resulting precipitate was collected by filtration and washed with water. This solid was dissolved in AcOEt and dried over Na$_2$SO$_4$. The solids were removed by filtration and the filtrate was evaporated to dryness to give 5'-(2,6-dichloro-4-nitrophenoxy)-4'-fluorospiro[cyclopropane-1,3'-indolin]-2'-one (2.02 g, 90%) as a pink solid which was used as such in the next step. $^1$H-NMR (DMSO-d$_6$, 300 MHz): 1.49-1.53 (m, 2H), 1.84-1.88 (m, 2H), 6.53-6.63 (m, 2H), 8.53 (s, 2H), 10.72 (br s, 1H) ppm. LC-MS: C$_{16}$H$_9$Cl$_2$FN$_2$O$_4$ [M−H]$^-$: 381

Fe (4.71 g, 84.43 mmol) was added to a solution of 5'-(2,6-dichloro-4-nitrophenoxy)-4'-fluorospiro[cyclopropane-1,3'-indolin]-2'-one (6.47 g, 16.89 mmol) and NH$_4$Cl (9.03 g, 168.86 mmol) in EtOH (115 mL) and water (64 mL) under $N_2$. The reaction mixture was stirred at 70° C. for 6 h. Then, heating was stopped and the reaction mixture was stirred at room temperature for 3 days. Heating at 70° C. was resumed for 1 h to reach full conversion. The reaction mixture was filtered over a pad of celite and the filtrate was diluted with AcOEt (400 mL). The organic phase was washed with brine (2×) and dried over $Na_2SO_4$. The solids were removed by filtration and the filtrate was evaporated to dryness to give 5'-(4-amino-2,6-dichlorophenoxy)-4'-fluorospiro[cyclopropane-1,3'-indolin]-2'-one (5.8 g, 97%) as a beige solid which was used as such in the next step. $^1$H-NMR (DMSO-$d_6$, 300 MHz): 1.46-1.49 (m, 2H), 1.81-1.85 (m, 2H), 5.65 (br s, 2H), 6.35 (dd, J=8.7 Hz, 8.7 Hz, 1H), 6.59 (d, J=8.7 Hz, 1H), 6.70 (s, 2H), 10.61 (s, 1H) ppm. LC-MS: $C_{16}H_{11}Cl_2FN_2O_2$ [M+H]$^+$: 353

LiHMDS 1M in THF (3.4 mL, 3.4 mmol) was added to a solution of ethyl 5-oxo-4,5-dihydro-1,2,4-oxadiazole-3-carboxylate (134.3 mg, 0.85 mmol) and 5'-(4-amino-2,6-dichlorophenoxy)-4'-fluorospiro[cyclopropane-1,3'-indolin]-2'-one (300 mg, 0.85 mmol) in anhydrous THF (4 mL) at room temperature under $N_2$. The reaction mixture was stirred at room temperature for 10 min, then diluted with MeOH and evaporated to dryness. The crude product was purified by silica gel flash chromatography (0% to 40% MeOH in DCM). The resulting solid was purified by prep. HPLC (25% to 100% MeOH in water [0.2% v/v $NH_3$]) to give N-(3,5-dichloro-4-((4'-fluoro-2'-oxospiro[cyclopropane-1,3'-indolin]-5'-yl)oxy)phenyl)-5-oxo-4,5-dihydro-1,2,4-oxadiazole-3-carboxamide (40) (197 mg, 50%) as a white solid. $^1$H-NMR (DMSO-$d_6$, 400 MHz): 1.47-1.50 (m, 2H), 1.84-1.87 (m, 2H), 6.42 (dd, J=8.5 Hz, 8.5 Hz, 1H), 6.60 (d, J=8.5 Hz, 1H), 8.12 (s, 2H), 10.62 (br s, 1H), 10.66 (s, 1H) ppm. LC-MS: $C_{19}H_{11}Cl_2FN_4O_5$ [M+H]$^+$: 465.

Example 41. Preparation of Compound 41

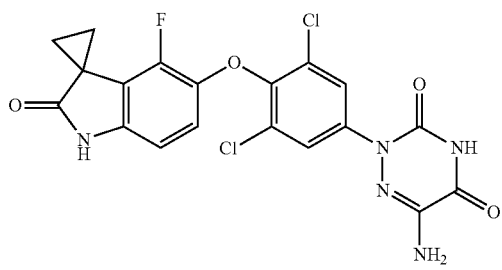 [SMILES: Nc1nn(-c2cc(Cl)c(Oc3ccc4c(c3F)C3(CC3)C(=O)N4)c(Cl)c2)c(=O)[nH]c1=O]

A solution of $NaNO_2$ (0.82 g, 11.89 mmol) in water (115 mL) was added to a solution of 5'-(4-amino-2,6-dichlorophenoxy)-4'-fluorospiro[cyclopropane-1,3'-indolin]-2'-one (2 g, 5.66 mmol) in conc. HCl (50 mL, 598.51 mmol), acetic acid (150 mL) and water (115 mL) at 0° C. under $N_2$. The reaction mixture was stirred at 0° C. for 1 h. In parallel, a solution of ethyl N-(2-cyanoacetyl)carbamate (1.33 g, 8.49 mmol) in water (140 mL) and pyridine (48 mL) was stirred at 0° C. for 15 min. The first reaction mixture was quickly added to the second one and the resulting mixture was stirred at 0° C. for 2 h, at which point extra ethyl N-(2-cyanoacetyl)carbamate (0.97 g, 6.23 mmol) in water (110 mL) and pyridine (35 mL) was added. Stirring at 0° C. was pursued for 1 h to reach full conversion. The reaction mixture was diluted with more water. The precipitate was collected by filtration, washed with water and dried under vacuum to give ethyl (2-cyano-2-(2-(3,5-dichloro-4-((4'-fluoro-2'-oxospiro [cyclopropane-1,3'-indolin]-5'-yl)oxy)phenyl)hydrazineylidene)acetyl)carbamate (2.95 g, quant.) as a light orange solid which was used as such in the next step. LC-MS: $C_{22}H_{16}Cl_2FN_5O_5$ [M+H]$^+$: 520.

Sodium acetate (1.86 g, 0.023 mol) was added to a solution of ethyl (2-cyano-2-(2-(3,5-dichloro-4-((4'-fluoro-2'-oxospiro[cyclopropane-1,3'-indolin]-5'-yl)oxy)phenyl) hydrazineylidene)acetyl)carbamate (2.95 g, 0.0057 mol) in acetic acid (50 mL) under $N_2$. The reaction mixture was stirred at 120° C. for 1 h. The reaction mixture was then cooled to 0° C., water (500 mL) was added and the mixture was stirred for 30 min. The resulting precipitate was collected by filtration and washed with water to give 2-(3,5-dichloro-4-((4'-fluoro-2'-oxospiro[cyclopropane-1,3'-indolin]-5'-yl)oxy)phenyl)-3,5-dioxo-2,3,4,5-tetrahydro-1,2,4-triazine-6-carbonitrile (2.43 g, 90%) as a yellow solid which was used as such in the next step. $^1$H-NMR (DMSO-$d_6$, 300 MHz): 1.48-1.53 (m, 2H), 1.83-1.88 (m, 2H), 6.50 (dd, J=8.5 Hz, 8.5 Hz, 1H), 6.63 (d, J=8.5 Hz, 1H), 7.81 (s, 2H), 10.69 (s, 1H), 13.29 (br s, 1H) ppm. LC-MS: $C_{20}H_{10}Cl_2FN_5O_4$ [M−H]$^−$: 472.

KOH (2.87 g, 51.24 mmol) was added to a solution of 2-(3,5-dichloro-4-((4'-fluoro-2'-oxospiro[cyclopropane-1,3'-indolin]-5'-yl)oxy)phenyl)-3,5-dioxo-2,3,4,5-tetrahydro-1,2,4-triazine-6-carbonitrile (2.43 g, 5.12 mmol) in water (24 mL) and EtOH (24 mL) under $N_2$. The reaction mixture was stirred at 80° C. for 45 min. After cooling to room temperature, the reaction mixture was then diluted with HCl (1N, aq., 50 mL). The resulting precipitate was collected by filtration, washed with water and dried under vacuum to give crude 2-(3,5-dichloro-4-((4'-fluoro-2'-oxospiro[cyclopropane-1,3'-indolin]-5'-yl)oxy)phenyl)-3,5-dioxo-2,3,4,5-tetrahydro-1,2,4-triazine-6-carboxylic acid (2.54 g), which was used as such in the next step. LC-MS: $C_{20}H_{11}FCl_2N_4O_6$ [M−H]$^−$: 491

Triethylamine (1.3 mL, 9.33 mmol) and diphenyl phosphoryl azide (1.92 g, 1.507 mL, 6.99 mmol) were added to a solution 2-(3,5-dichloro-4-((4'-fluoro-2'-oxospiro[cyclopropane-1,3'-indolin]-5'-yl)oxy)phenyl)-3,5-dioxo-2,3,4,5-tetrahydro-1,2,4-triazine-6-carboxylic acid (1.15 g, 2.33 mmol) in tert-butanol (34 mL) under $N_2$. The resulting mixture was stirred at 85° C. for 24 h. After cooling to room temperature, the reaction mixture was quenched with sat. aq. $NH_4Cl$ (30 mL) and extracted with AcOEt (2×). The combined organic layers were washed with sat. aq. $NH_4Cl$ and brine and dried over $Na_2SO_4$. The solids were removed by filtration and the filtrate was evaporated to dryness. The crude mixture was purified by silica gel flash chromatography (0% to 5% MeOH in DCM) to give t-butyl (2-(3,5-dichloro-4-((4'-fluoro-2'-oxospiro[cyclopropane-1,3'-indolin]-5'-yl)oxy)phenyl)-3,5-dioxo-2,3,4,5-tetrahydro-1,2,4-triazin-6-yl)carbamate (0.76 g, 58%) as an orange solid. $^1$H-NMR (DMSO-$d_6$, 300 MHz): 1.45 (s, 9H), 1.48-1.51 (m, 2H), 1.84-1.87 (m, 2H), 6.46 (dd, J=8.5 Hz, 8.5 Hz, 1H), 6.63 (d, J=8.5 Hz, 1H), 7.91 (s, 2H), 9.04 (s, 1H), 10.68 (br s, 1H), 12.60 (br s, 1H) ppm. LC-MS: $C_{24}H_{20}FCl_2N_5O_6$ [M+H]$^+$: 564

TFA (2.00 mL, 26.93 mmol) was added to a solution of t-butyl (2-(3,5-dichloro-4-((4'-fluoro-2'-oxospiro[cyclopropane-1,3'-indolin]-5'-yl)oxy)phenyl)-3,5-dioxo-2,3,4,5-tetrahydro-1,2,4-triazin-6-yl)carbamate (760 mg, 1.35 mmol) in anhydrous DCM (17 mL) under $N_2$. The reaction mixture was stirred at room temperature for 5 h. The reaction mixture was quenched with sat. aq. $Na_2CO_3$ (200 mL) and the resulting precipitate was collected by filtration and washed with water. This crude product was purified by silica gel flash chromatography (2% to 10% MeOH in DCM) and by prep. HPLC (5% to 100% MeCN in water [0.2% v/v NH$_3$]) to give 6-amino-2-(3,5-dichloro-4-((4'-fluoro-2'-oxospiro[cyclopropane-1,3'-indolin]-5'-yl)oxy)phenyl)-1,2,4-triazine-3,5(2H,4H)-dione (41) (56 mg, 9%) as a white solid. $^1$H-NMR (DMSO-d$_6$, 400 MHz): 1.48-1.51 (m, 2H), 1.84-1.87 (m, 2H), 6.43 (dd, J=8.5 Hz, 8.5 Hz, 1H), 6.51 (br s, 2H), 6.63 (d, J=8.5 Hz, 1H), 7.91 (s, 2H), 10.70 (br s, 1H) ppm. LC-MS: C$_{19}$H$_{12}$FCl$_2$N$_5$O$_4$ [M+H]$^+$: 464

Example 42. Preparation of Compound 42

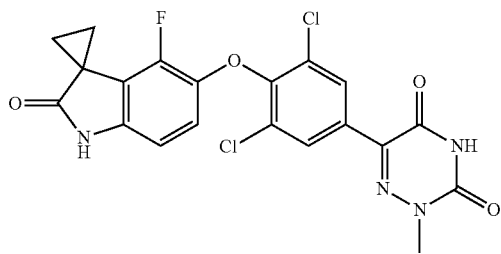 [SMILES: Cn1nc(-c2cc(Cl)c(Oc3ccc4c(c3F)C3(CC3)C(=O)N4)c(Cl)c2)c(=O)[nH]c1=O]

t-BuONO (0.44 g, 0.51 mL, 4.25 mmol) was added to a solution of 5'-(4-amino-2,6-dichlorophenoxy)-4'-fluorospiro[cyclopropane-1,3'-indolin]-2'-one (1 g, 2.83 mmol) and bis(pinacolato)diboron (0.79 g, 3.11 mmol) in anhydrous MeCN (9 mL) under N$_2$. The reaction mixture was stirred at 60° C. for 3 d. Extra bis(pinacolato)diboron (0.79 g, 3.11 mmol) t-BuONO (0.44 g, 0.509 mL, 4.25 mmol) were added and heating at 60° C. was pursued for 20 h. Then, the reaction mixture was evaporated to dryness and the crude product was purified by silica gel flash chromatography (0% to 100% EA in CyH) to give 5'-(2,6-dichloro-4-(4,4,5,5-tetramethyl-1,3,2-dioxaborolan-2-yl)phenoxy)-4'-fluorospiro[cyclopropane-1,3'-indolin]-2'-one (1.02 g, 78%) as a yellow oil. LC-MS: C$_{16}$H$_9$Cl$_2$FNO$_2$ [M+H]$^+$: 464

Na$_2$CO$_3$ 2M (4.4 mL, 8.79 mmol) was added to a solution of 6-bromo-2-methyl-1,2,4-triazine-3,5(2H,4H)-dione (0.54 g, 2.64 mmol), 5'-(2,6-dichloro-4-(4,4,5,5-tetramethyl-1,3,2-dioxaborolan-2-yl)phenoxy)-4'-fluorospiro[cyclopropane-1,3'-indolin]-2'-one (1.02 g, 2.2 mmol) and Pd(dppf)Cl$_2$ (0.16 g, 0.22 mmol) in 1,4-dioxane (16 mL) under N$_2$. The reaction mixture was stirred at 100° C. for 1 h. The reaction mixture was then diluted with water (80 mL) and extracted with EtOAc (3×). The combined organic phases were washed with sat. aq. NH$_4$Cl and brine and dried over Na$_2$SO$_4$. The solids were removed by filtration and the filtrate was evaporated to dryness. The crude product was purified by flash chromatography on silica gel (0% to 5% MeOH in DCM). The resulting solid was triturated with EtOH and co-evaporated with MeCN to give 6-(3,5-dichloro-4-((4'-fluoro-2'-oxospiro[cyclopropane-1,3'-indolin]-5'-yl)oxy)phenyl)-2-methyl-1,2,4-triazine-3,5(2H,4H)-dione (42) (133 mg, 13%) as a white solid. $^1$H-NMR (DMSO-d$_6$, 400 MHz): 1.49-1.51 (m, 2H), 1.84-1.87 (m, 2H), 3.58 (s, 3H), 6.46 (dd, J=8.5 Hz, 8.5 Hz, 1H), 6.62 (d, J=8.5 Hz, 1H), 8.13 (s, 2H), 10.70 (s, 1H), 12.44 (br.s, 1H) ppm. LC-MS: C$_{20}$H$_{13}$Cl$_2$FN$_4$O$_4$ [M+H]$^+$: 463.

Example 43. Preparation of Compound 43

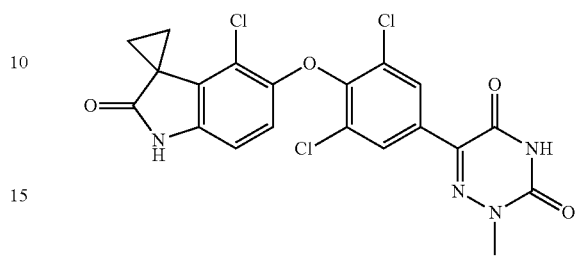

A solution of NaNO$_2$ (0.37 g, 5.41 mmol) in water (9.4 mL) was added to a solution of 5'-(4-amino-2,6-dichlorophenoxy)-4'-chlorospiro[cyclopropane-1,3'-indolin]-2'-one (1 g, 2.705 mmol) in MeOH (40 mL), water (10 mL), acetic acid (5 mL) and HCl 37% (5 mL) at 0° C. under N$_2$. The reaction mixture was stirred at 0° C. for 1 h. Then tetrahydroxydiboron (1.94 g, 21.64 mmol) was added and the reaction mixture was stirred at 60° C. for 1 h. The reaction mixture was cooled to room temperature and diluted with water (100 mL). The precipitate was collected by filtration, washed with water and dissolved in AcOEt. The organic solution was dried over Na$_2$SO$_4$. The solids were removed by filtration and the filtrate was evaporated to dryness to give (3,5-dichloro-4-((4'-chloro-2'-oxospiro[cyclopropane-1,3'-indolin]-5'-yl)oxy)phenyl)boronic acid (1.08 g, 100%) as a yellow solid which was used as such. LC-MS: C$_{16}$H$_{11}$BCl$_3$NO$_4$ [M−H]$^-$: 396.

Na$_2$CO$_3$ 2M (5.42 mL, 10.84 mmol) was added to a solution of 6-bromo-2-methyl-1,2,4-triazine-3,5(2H,4H)-dione (0.67 g, 3.25 mmol), (3,5-dichloro-4-((4'-chloro-2'-oxospiro[cyclopropane-1,3'-indolin]-5'-yl)oxy)phenyl)boronic acid (1.08 g, 2.71 mmol) and Pd(dppf)Cl$_2$ (0.2 g, 0.27 mmol) in 1,4-dioxane (20 mL) under N$_2$. The reaction mixture was stirred at 100° C. for 2 h. The reaction mixture was diluted with water and AcOEt. The organic phase was washed with sat. aq. NH$_4$Cl and brine and dried over Na$_2$SO$_4$. The solids were removed by filtration and the filtrate was evaporated to dryness. The crude mixture was purified by flash chromatography on silica gel (0% to 7% MeOH in DCM). The resulting solid was triturated in EtOH and then purified by reverse phase flash chromatography (5% to 100% MeCN in water [0.1% TFA]). The fractions containing the product were extracted with AcOEt (3×). The combined organic phases were dried over Na$_2$SO$_4$. The solids were removed by filtration, and the filtrate was evaporated to dryness. The resulting solid was co-evaporated with EtOH and MeCN to give 6-(3,5-dichloro-4-((4'-chloro-2'-oxospiro[cyclopropane-1,3'-indolin]-5'-yl)oxy)phenyl)-2-methyl-1,2,4-triazine-3,5(2H,4H)-dione (43) (69 mg, 5%) as a white solid. $^1$H-NMR (DMSO-d$_6$, 400 MHz): 1.42-1.45 (m, 2H), 2.17-2.20 (m, 2H), 3.48 (s, 3H), 6.38 (d, J=8.5 Hz, 1H), 6.76 (d, J=8.5 Hz, 1H), 8.34 (s, 2H), 10.70 (s, 1H) ppm. LC-MS: C$_{20}$H$_{13}$Cl$_3$N$_4$O$_4$ [M+H]$^+$: 479.

Example 44. Preparation of Compound 44

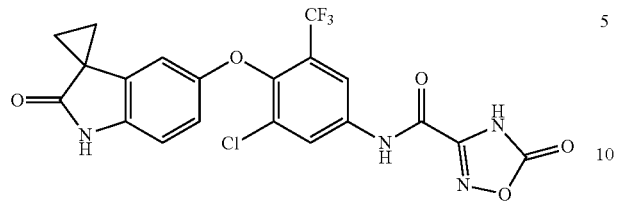

DIPEA (0.94 mL, 5.71 mmol) was added to a solution of 5'-hydroxyspiro[cyclopropane-1,3'-indolin]-2'-one (500 mg, 2.85 mmol) and 1-chloro-2-fluoro-5-nitro-3-(trifluoromethyl)benzene (695 mg, 2.85 mmol) in anhydrous DMF (8 mL) under $N_2$. The reaction mixture was stirred at 40° C. for 20 h. Water (50 mL) was added to the reaction mixture. The resulting precipitate was collected by filtration and purified by flash chromatography on silica gel (0% to 70% AcOEt in CyH) to give 5'-(2-chloro-4-nitro-6-(trifluoromethyl)phenoxy)spiro[cyclopropane-1,3'-indolin]-2'-one (280 mg, 25%) as a light-yellow solid. $^1$H-NMR (DMSO-$d_6$, 400 MHz): 1.44-1.49 (m, 2H), 1.50-1.55 (m, 2H), 6.62 (dd, J=8.4 Hz, 2.4 Hz, 1H), 6.77 (d, J=2.4 Hz, 1H), 6.81 (d, J=8.4 Hz, 1H), 8.53 (d, J=2.8 Hz, 1H), 8.81 (d, J=2.8 Hz, 1H), 10.51 (s, 1H) ppm. LC-MS: $C_{17}H_{10}ClF_3N_2O_4$ [M+H]$^+$: 399

Iron (0.49 g, 8.69 mmol) was added to a solution of 5'-(2-chloro-4-nitro-6-(trifluoromethyl)phenoxy)spiro[cyclopropane-1,3'-indolin]-2'-one (0.69 g, 1.74 mmol) and $NH_4Cl$ (0.93 g, 17.39 mmol) in EtOH (10 mL) and water (10 mL) under $N_2$. The reaction mixture was stirred at 70° C. for 18 h, at which point extra Fe (0.49 g, 8.69 mmol) and $NH_4Cl$ (0.93 g, 17.39 mmol) were added to the reaction mixture and stirring at 70° C. was pursued for 2 h. The reaction mixture was cooled to room temperature and was filtered over a pad of celite which was rinsed with EtOH. The filtrate was concentrated under reduced pressure to remove the EtOH and the resulting precipitate was collected by filtration to give 5'-(4-amino-2-chloro-6-(trifluoromethyl)phenoxy) spiro[cyclopropane-1,3'-indolin]-2'-one (359 mg, 56%) as an orange solid which was used in the next step without further purification. $^1$H-NMR (DMSO-$d_6$, 400 MHz): 1.40-1.55 (m, 4H), 5.79 (br s, 2H), 6.37 (d, J=6.8 Hz, 1H), 6.62 (s, 1H), 6.75 (d, J=6.8 Hz, 1H), 6.91-7.30 (m, 2H), 10.40 (s, 1H) ppm. LC-MS: $C_{17}H_{12}ClF_3N_2O_2$ [M+H]$^+$: 369

LiHMDS (1M in THF, 2.17 mL, 2.17 mmol) was added to a solution of ethyl 5-oxo-4,5-dihydro-1,2,4-oxadiazole-3-carboxylate (85.76 mg, 0.54 mmol) and 5'-(4-amino-2-chloro-6-(trifluoromethyl)phenoxy)spiro[cyclopropane-1,3'-indolin]-2'-one (200 mg, 0.54 mmol) in anhydrous THF (3 mL) under $N_2$. The reaction mixture was stirred at room temperature for 1 h. The reaction mixture was then diluted with MeOH and evaporated to dryness, then purified by silica flash chromatography (0% to 20% methanol in DCM) and by prep. HPLC (10% to 100% MeCN in water [0.2% v/v $NH_3$]) to give N-(3-chloro-4-((2'-oxospiro[cyclopropane-1, 3'-indolin]-5'-yl)oxy)-5-(trifluoromethyl)phenyl)-5-oxo-4, 5-dihydro-1,2,4-oxadiazole-3-carboxamide (44) (75 mg, 29%) as a white solid. $^1$H-NMR (DMSO-$d_6$, 400 MHz): 1.41-1.47 (m, 2H), 1.51-1.58 (m, 2H), 6.47 (dd, J=8.4 Hz, 2.6 Hz, 1H), 6.72 (d, J=2.4 Hz, 1H), 6.78 (d, J=8.4 Hz, 1H), 8.29 (d, J=2.4 Hz, 1H), 8.32 (d, J=2.4 Hz, 1H), 10.45 (s, 1H), 11.37 (s, 1H), 13.44 (br s, 1H) ppm. LC-MS: $C_{20}H_{12}ClF_3N_4O_5$ [M+H]$^+$: 481

Example 45. Preparation of Compound 45

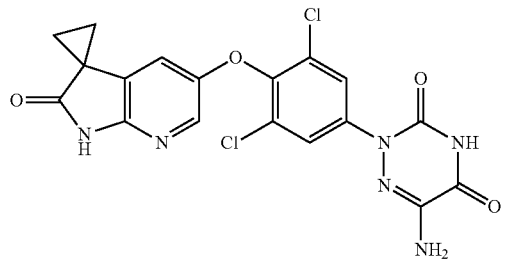 [SMILES: Nc1nn(-c2cc(Cl)c(Oc3cnc4c(c3)C3(CC3)C(=O)N4)c(Cl)c2)c(=O)[nH]c1=O]

Bis(pinacolato)diboron (17.9 g, 70.49 mmol), potassium acetate (13.8 g, 140.61 mmol) and Pd(dppf)$Cl_2$ (3.43 g, 4.69 mmol) were added to a solution of 5-bromo-1H,2H,3H-pyrrolo[2,3-b]pyridin-2-one (10 g, 46.94 mmol) in anhydrous dioxane (250 mL) under $N_2$. The reaction mixture was stirred at 100° C. for 3 h. The reaction mixture was then evaporated to dryness. The residue was triturated in pentane to give a purple solid which was triturated in DCM/MeOH (5:1). The solids were removed by filtration and the filtrate was evaporated to dryness. The crude product was purified by flash chromatography on silica gel (0% to 5% MeOH in DCM) to give 5-(4,4,5,5-tetramethyl-1,3,2-dioxaborolan-2-yl)-1,3-dihydro-2H-pyrrolo[2,3-b]pyridin-2-one (7.85 g, 64%) as a yellow solid. $^1$H-NMR (DMSO-$d_6$, 400 MHz): 1.28 (s, 12H), 3.53 (s, 2H), 7.67 (d, J=1.6 Hz, 1H), 8.29 (d, J=1.6 Hz, 1H), 8.54 (s, 2H) 11.14 (s, 1H) ppm. LC-MS: $C_{13}H_{17}BN_2O_3$ [M+H]$^+$: 261

A solution of oxo(sodioperoxy)borane tetrahydrate (6.093 g, 39.6 mmol) in $H_2O$ (116 mL) was added to a solution of 5-(4,4,5,5-tetramethyl-1,3,2-dioxaborolan-2-yl)-1,3-dihydro-2H-pyrrolo[2,3-b]pyridin-2-one (5.15 g, 19.8 mmol) in THF (231 mL) under $N_2$. The reaction mixture was stirred at room temperature for 1 h. Toluene was added and the mixture was evaporated to dryness to give 5-hydroxy-1,3-dihydro-2H-pyrrolo[2,3-b]pyridin-2-one (2.97 g, 100%) as a dark brown solid which was used as such in the next step. LC-MS: $C_7H_6N_2O_2$ [M+H]$^+$: 151

1,3-dichloro-2-fluoro-5-nitrobenzene (2.08 g, 9.9 mmol) was added to a solution of 5-hydroxy-1,3-dihydro-2H-pyrrolo[2,3-b]pyridin-2-one (2.97 g, 19.8 mmol) in anhydrous DMF (110 mL) at 0° C. under $N_2$. The reaction mixture was stirred at 0° C. for 1 h, at which point extra 1,3-dichloro-2-fluoro-5-nitrobenzene (1.04 g, 4.95 mmol) was added and stirring was pursued at 0° C. for 4 h. 1,3-dichloro-2-fluoro-5-nitrobenzene (1.04 g, 4.95 mmol) was added and the reaction mixture was stirred at room temperature for 20 h, then diluted with sat. aq. $NaHCO_3$ and extracted with EA (3×). The aqueous phase was re-extracted twice with EA/iPrOH (85:15). The organic layers were combined, washed with brine (2×) and dried over $Na_2SO_4$. The solids were removed by filtration and the filtrate was evaporated to dryness. The crude mixture was purified by chromatography on silica gel (0% to 2% MeOH in DCM) to afford 5-(2,6-dichloro-4-nitrophenoxy)-1,3-dihydro-2H-pyrrolo[2,3-b]pyridin-2-one (3.16 g, 47%) as an orange solid. $^1$H-NMR (DMSO-$d_6$, 400 MHz): 3.56 (s, 2H), 7.35 (d, J=2.8 Hz, 1H), 7.74 (d, J=2.8 Hz, 1H), 8.54 (s, 2H) 11.00 (s, 1H) ppm. LC-MS: $C_{13}H_7Cl_2N_3O_4$ [M+H]$^+$: 340

Ethenyldiphenylsulfanium trifluoromethanesulfonate (947 mg, 2.61 mmol) was added to a solution of 5-(2,6-dichloro-4-nitrophenoxy)-1,3-dihydro-2H-pyrrolo[2,3-b]

pyridin-2-one (741 mg, 2.18 mmol) and zinc triflate (792 mg, 2.18 mmol) in anhydrous DMF (10 mL). After 2 min of stirring, DBU (995 mg, 6.54 mmol) was added and the reaction mixture was stirred at room temperature for 1 h. The reaction mixture was then quenched with sat. aq. NH$_4$Cl and extracted with EA/iPrOH (85:15). The organic layer was washed with water (3×) and brine and dried over Na$_2$SO$_4$. The solids were removed by filtration and the filtrate was evaporated to dryness. The crude mixture was triturated with pentane to remove diphenyl sulfide and purified by chromatography on silica gel (0 to 5% MeOH in DCM) to give 5'-(2,6-dichloro-4-nitrophenoxy)spiro[cyclopropane-1,3'-pyrrolo[2,3-b]pyridin]-2'(1'H)-one (564 mg, 71%) as a light yellow solid. $^1$H-NMR (DMSO-d$_6$, 400 MHz): 1.50-1.55 (m, 2H), 1.63-1.68 (m, 2H), 7.25 (d, J=2.8 Hz, 1H), 7.70 (d, J=2.8 Hz, 1H), 8.54 (s, 2H) 11.19 (s, 1H) ppm. LC-MS: C$_{15}$H$_9$Cl$_2$N$_3$O$_4$ [M+H]$^+$: 366

Fe (381 mg, 6.83 mmol) was added to a solution of 5'-(2,6-dichloro-4-nitrophenoxy)spiro[cyclopropane-1,3'-pyrrolo[2,3-b]pyridin]-2'(1'H)-one (500 mg, 1.37 mmol) and NH$_4$Cl (730.4 mg, 13.66 mmol) in EtOH (10 mL) and water (5 mL) under N$_2$. The reaction mixture was stirred at 70° C. for 4 h. After cooling to room temperature, the reaction mixture was filtered over a pad of celite and the filtrate was evaporated to dryness. The residue was reconstituted in EA/iPrOH (85:15) and washed with brine. The organic layer was dried over Na$_2$SO$_4$, the solids were removed by filtration and the filtrate was evaporated to dryness to give 5'-(4-amino-2,6-dichlorophenoxy)spiro[cyclopropane-1,3'-pyrrolo[2,3-b]pyridin]-2'(1'H)-one (152 mg, 33%) as a yellow solid that was used as such in the next step. LC-MS: C$_{15}$H$_{11}$Cl$_2$N$_3$O$_2$ [M+H]$^+$: 336

A solution of NaNO$_2$ (65.51 mg, 0.95 mmol) in water (9 mL) was added to a solution of 5'-(4-amino-2,6-dichlorophenoxy)spiro[cyclopropane-1,3'-pyrrolo[2,3-b]pyridin]-2'(1'H)-one (152 mg, 0.45 mmol) in HCl 37% (3.92 mL, 47.79 mmol), acetic acid (12 mL) and water (9 mL) at 0° C. under N$_2$. The reaction mixture was stirred at 0° C. for 40 min. In parallel, a solution of ethyl N-(2-cyanoacetyl)carbamate (105.9 mg, 0.68 mmol) in water (11 mL) and pyridine (4 mL) was stirred at 0° C. for 15 min. The first reaction mixture was quickly added to the second one. The resulting reaction mixture was stirred at 0° C. for 40 min. The reaction mixture was diluted with water, the precipitate was collected by filtration, washed with water and dried under vacuum to give ethyl (2-cyano-2-(2-(3,5-dichloro-4-((2'-oxo-1',2'-dihydrospiro[cyclopropane-1,3'-pyrrolo[2,3-b]pyridin]-5'-yl)oxy)phenyl)hydrazineylidene) acetyl)carbamate (221 mg, 97%) as a yellow solid which was used without further purification in the next step. LC-MS: C$_{21}$H$_{16}$Cl$_2$N$_6$O$_5$ [M+H]$^+$: 503

Sodium acetate (144 mg, 1.8 mmol) was added to a solution of (2-cyano-2-(2-(3,5-dichloro-4-((2'-oxo-1',2'-dihydrospiro[cyclopropane-1,3'-pyrrolo[2,3-b]pyridin]-5'-yl)oxy)phenyl)hydrazineylidene)acetyl)carbamate (221 mg, 0.4 mmol) in acetic acid (4.2 mL) under N$_2$. The reaction mixture was stirred at 120° C. for 1 h, then cooled at 0° C., water was added and the mixture was stirred for 30 min. The resulting precipitate was collected by filtration, washed with water and dried under vacuum to afford 2-(3,5-dichloro-4-((2'-oxo-1',2'-dihydrospiro[cyclopropane-1,3'-pyrrolo[2,3-b]pyridin]-5'-yl)oxy)phenyl)-3,5-dioxo-2,3,4,5-tetrahydro-1,2,4-triazine-6-carbonitrile (115 mg, 57%) as an orange solid which was used without further purification in the next step. $^1$H-NMR (DMSO-d$_6$, 400 MHz): 1.50-1.55 (m, 2H), 1.67-1.72 (m, 2H), 7.27 (d, J=2.4 Hz, 1H), 7.64 (d, J=2.4 Hz, 1H), 7.79 (s, 2H), 11.17 (s, 1H), 11.95 (s, 1H) ppm. LC-MS: C$_{19}$H$_{10}$Cl$_2$N$_6$O$_4$ [M+H]$^+$: 457

KOH (1202 mg, 21.43 mmol) was added to a solution of 2-(3,5-dichloro-4-((2'-oxo-1',2'-dihydrospiro[cyclopropane-1,3'-pyrrolo[2,3-b]pyridin]-5'-yl)oxy)phenyl)-3,5-dioxo-2,3,4,5-tetrahydro-1,2,4-triazine-6-carbonitrile (490 mg, 1.072 mmol) in water (10 mL) and EtOH (10 mL) under N$_2$. The reaction mixture was stirred at 70° C. for 25 min. After cooling to room temperature, the reaction mixture was then neutralized with HCl 37% to pH-6 and diluted with a buffer solution at pH 6. The resulting precipitate was collected by filtration, washed with water and dried under vacuum to give 2-(3,5-dichloro-4-((2'-oxo-1',2'-dihydrospiro[cyclopropane-1,3'-pyrrolo[2,3-b]pyridin]-5'-yl)oxy)phenyl)-3,5-dioxo-2,3,4,5-tetrahydro-1,2,4-triazine-6-carboxylic acid (459 mg, 90%) as a light orange solid which was used as such in the next step. LC-MS: C$_{19}$H$_{11}$Cl$_2$N$_5$O$_6$ [M−H]$^-$: 474

Et$_3$N (0.077 mL, 0.55 mmol) and diphenyl phosphoryl azide (114.42 mg, 0.09 mL, 0.42 mmol) were added to a solution of 2-(3,5-dichloro-4-((2'-oxo-1',2'-dihydrospiro[cyclopropane-1,3'-pyrrolo[2,3-b]pyridin]-5'-yl)oxy)phenyl)-3,5-dioxo-2,3,4,5-tetrahydro-1,2,4-triazine-6-carboxylic acid (66 mg, 0.14 mmol) in t-butanol (2 mL) under N$_2$. The reaction mixture was stirred at 85° C. for 1 h. The reaction mixture was then quenched with sat. aq. NaHCO$_3$ and extracted with EA. The organic layer was washed with brine and dried over Na$_2$SO$_4$. The solids were removed by filtration and the filtrate was evaporated to dryness. The crude mixture was purified by chromatography on silica gel (0% to 50% [MeOH/NH$_4$OH (9:1)] in DCM) to give t-butyl (2-(3,5-dichloro-4-((2'-oxo-1',2'-dihydrospiro[cyclopropane-1,3'-pyrrolo[2,3-b]pyridin]-5'-yl)oxy)phenyl)-3,5-dioxo-2,3,4,5-tetrahydro-1,2,4-triazin-6-yl)carbamate (23 mg, 30%) as a yellow solid. LC-MS: C$_{23}$H$_{20}$Cl$_2$N$_6$O$_6$ [M+H]$^+$: 547

A solution of t-butyl (2-(3,5-dichloro-4-((2'-oxo-1',2'-dihydrospiro[cyclopropane-1,3'-pyrrolo[2,3-b]pyridin]-5'-yl)oxy)phenyl)-3,5-dioxo-2,3,4,5-tetrahydro-1,2,4-triazin-6-yl)carbamate (47 mg, 0.086 mmol) and TFA (0.26 mL) in anhydrous DCM (6 mL) was stirred at room temperature for 5 days under N$_2$. The reaction mixture was quenched with sat. aq. NaHCO$_3$ and extracted with EA/iPrOH (85:15). The organic layer was washed with brine and dried over Na$_2$SO$_4$. The solids were removed by filtration and the filtrate was evaporated to dryness. The crude product was purified by prep. HPLC (C18 column, 10 to 100% MeCN in water [0.2% v/v NH$_3$]) to give 6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione (7 mg, 18%) as a white solid. $^1$H-NMR (DMSO-d$_6$, 400 MHz): 1.49-1.55 (m, 2H), 1.66-1.71 (m, 2H), 6.43 (s, 2H), 7.22 (d, J=3.2 Hz, 1H), 7.57 (d, J=3.2 Hz, 1H), 7.92 (s, 2H), 11.14 (s, 1H), 12.17 (br s, 1H) ppm. LC-MS: C$_{18}$H$_{12}$Cl$_2$N$_6$O$_4$ [M+H]$^+$: 447

LC-MS Methods

| LC Method name | Instrument | Column | Mobile phase | Gradient | Flow | Col T (° C.) | Run time |
|---|---|---|---|---|---|---|---|
| A | Shimadzu LCMS-2020 | Kinetex EVO C18 (2.6 μm, 3.0 × 30 mm) | A: Water/6.5 mM NH$_4$HCO$_3$ + NH$_4$OH (pH = 10) B: CH$_3$CN | From 90% A to 5% A in 1.19 min, held for 0.6 min, to 90% A in 0.02 min, held for 0.18 min | 1.2 mL/min | 40 | 2 min |
| B | Shimadzu LCMS-2020 | HALO 90A C18 (2.0 μm, 3.0 * 30 mm) | A: Water/0.05% TFA B: Acetonitrile/ 0.05% TFA | From 95% A to 0% A in 1.19 min, held for 0.5 min, to 95% A in 0.05 min, held for 0.25 min | 1.5 mL/min | 40 | 2 min |

Biological Assays

THR Biochemical Assay (Assay 1)

The TR-FRET thyroid receptor beta coactivator assay was used with slight, optimized modifications of the manufacturer's protocol (Invitrogen). The assay uses a terbium-labeled anti-GST antibody, a glutathione-S-transferase (GST) tagged human thyroid receptor, beta or alpha, ligand-binding domain (LBD), and a fluorescein labeled SRC2-2 coactivator peptide. The antibody interacts with the LBD, where the agonist also binds, resulting in increased affinity for the SRC2-2 coactivator peptide causing energy transfer of the acceptor fluorophore and a FRET emission shift from 495 to 520 nm. The energy transfer was detected as an increase in the fluorescence emission of the fluorescein acceptor, and a decrease in the fluorescence emission of the terbium donor. The assay was performed in a 384-well black plate in a final volume of 20 μL. Serial dilution of various test agonists was performed in DMSO (1% final DMSO concentration) and added to the test plate. Thyroid receptor beta LBD was added to the plate at a final concentration of 1 nM, followed by the mixture of the fluorescein labeled SRC2-2 coactivator peptide, and the terbium-labeled anti-GST antibody at final concentrations of 200 nM and 2 nM respectively. The assay was incubated for 1 hr at rt protected from light. The TR-FRET was then measured on a Victor multilabel reader (Perkin Elmer) using an excitation wavelength of 340 nm with emission filters of 495 nm and 520 nm. The assay was quantified by expressing a ratio (520:495) of the intensities, and the resulting activation curves; EC$_{50}$ values were generated using a sigmoidal dose response (variable slope) equation in GraphPad™ Prism 8.0.

Compounds described herein are active as THR-beta agonists as shown in Table 1, where: for Assay 1: 'A' indicates an EC$_{50}$<50 nM, 'B' indicates an EC$_{50}$ of ≥50 nM and <250 nM, 'C' indicates an EC$_{50}$≥250 nM and <1000 nM, 'D' indicates an EC$_{50}$≥1000 nM and <25000 nM, and 'E' indicates an EC$_{50}$>25000 nM.

TABLE 1

| Compound Number | Assay 1 |
|---|---|
| 1 | B |
| 2 | A |
| 3 | A |
| 4 | A |
| 5 | A |
| 6 | A |
| 7 | E |
| 8 | E |
| 9 | A |
| 11 | B |
| 12 | B |
| 13 | A |
| 14 | A |
| 15 | A |
| 16 | A |
| 17 | A |
| 18 | A |
| 19 | E |
| 20 | A |
| 21 | A |
| 22 | A |
| 23 | A |
| 24 | A |
| 25 | A |
| 26 | E |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | C |

Diet-Induced Obese (DIO) Mouse Model of NASH

C57BL/6J mice are fed a high-fat diet for 10 weeks to induce obesity and injected intraperitoneally twice weekly with carbon tetrachloride (CCl$_4$) for an additional 4 weeks to induce fibrosis. Mice fed a normal chow diet are used as healthy controls. Concomitant with CCl$_4$ dosing, mice are treated with vehicle or with a compound disclosed herein, administered by oral gavage once daily for 28 days. Drug exposure is measured in a separate experiment in lean male C57BL/6J mice. Livers of mice in the NASH study are harvested and evaluated for liver steatosis and fibrosis by histology and whole transcriptome analysis in the liver using RNA sequencing. Target engagement is confirmed by monitoring expression of TRβ-regulated genes.

Human Clinical Study: NASH

In a randomized, double-blind, placebo-controlled study, adult patients (with biopsy confirmed NASH (fibrosis stages 1-3) and hepatic fat fraction of at least 10% at baseline when assessed by MRI-proton density fat fraction (MRI-PDFF)) are administered a compound disclosed herein or placebo. Serial hepatic fat measurements are obtained at weeks 12 and 36, and a second liver biopsy is obtained at week 36. The primary endpoint is relative change in MRI-PDFF assessed hepatic fat compared with placebo at week 12 in patients who have both a baseline and week 12 MRI-PDFF.

REFERENCES

1. Younossi, Z M, Koenig, A B, Abdelatif, D, Fazel, Y, Henry, L, Wymer, M. Global epidemiology of nonalcoholic fatty liver disease-Meta-analytic assessment of prevalence, incidence, and outcomes. Hepatology, 2016, 64(1):73e84.
2. Gastroenterology. 2012 June; 142(7): 1592-609. doi: 10.1053/j.gastro.2012.04.001. Epub 2012 May 15.
3. Serfaty, L., Lemoine, M. Definition and natural history of metabolic steatosis: clinical aspects of NAFLD, NASH and cirrhosis. Diabetes and Metabolism, 2008, 34 (6 Pt 2):634e637.
4. Hepatology. 2012 October; 56(4): 1580-1584. doi: 10.1002/hep.26031
5. Dulai, P S, Singh, S, Patel, J, Soni, M, Prokop, L J, Younossi, Z, et al. Increased risk of mortality by fibrosis stage in nonalcoholic fatty liver disease: systematic review and meta-analysis. Hepatology, 2017, 65(5): 1557e1565.
6. Younossi, Z M, Loomba, R, Rinella, M E, Bugianesi, E, Marchesini, G, Neuschwander-Tetri, B A, et al. Current and future therapeutic regimens for non-alcoholic fatty liver disease (NAFLD) and non-alcoholic steatohepatitis (NASH). Hepatology, 2018, 68(1):349e360.
7. Harvey C B, Williams G R. Mechanism of thyroid hormone action. Thyroid, 2002 June; 12(6):441-6.
8. Bookout A L, Jeong Y, Downes M, Yu R T, Evans R M, Mangelsdorf D J. Anatomical profiling of nuclear receptor expression reveals a hierarchical transcriptional network. Cell, 2006, 126:789-799
9. Flamant F, Baxter J D, Forrest D, Refetoff S, Samuels H H, Scanlan T S, Vennstrom B, Samarut J. International union of pharmacology. LIX. The pharmacology and classification of the nuclear receptor superfamily: thyroid hormone receptors. Pharmacol. Rev., 2006, 58:705-711
10. Haning H, Woltering M, Mueller U, Schmidt G, Schmeck C, Voehringer V, Kretschmer A, Pernerstorfer J. Bioorg. Med Chem Lett., 2005 Apr. 1, 15(7): 1835-40. Novel heterocyclic thyromimetics.
11. Hirano T, Kagechika H. Thyromimetics: a review of recent reports and patents (2004-2009). Expert Opin Ther Pat., 2010 February; 20(2):213-28. doi: 10.1517/13543770903567069.
12. Kowalik M A, Columbano A, Perra A. Thyroid Hormones, Thyromimetics and Their Metabolites in the Treatment of Liver Disease. Front Endocrinol (Lausanne), 2018 Jul. 10; 9:382. doi: 10.3389/fendo.2018.00382. eCollection 2018.
13. Erion M D, Cable E E, Ito to B R, Jiang H, Fujitaki J M, Finn P D, Zhang B H, Hou J, Boyer S H, van Poelje P D, Linemeyer D L. Targeting thyroid hormone receptor-beta agonists to the liver reduces cholesterol and triglycerides and improves the therapeutic index. Proc Natl Acad Sci USA., 2007 Sep. 25; 104(39):15490-5. Epub 2007 Sep. 18.
14. Hartley M D, Kirkemo L L, Banerji T, Scanlan T S. A Thyroid Hormone-Based Strategy for Correcting the Biochemical Abnormality in X-Linked Adrenoleukodystrophy. Endocrinology 2017, 158(5), p 1328-1338. doi: 10.1210/en.2016-1842.
15. Milanesi A, Brent G A. Beam Me In: Thyroid Hormone Analog Targets Alternative Transporter in Mouse Model of X-Linked Adrenoleukodystrophy. Endocrinology 2017, 158, p 1116-1119. doi: 10.1210/en.2017-00206.

Embodiments

Embodiment 1. A compound of Formula I':

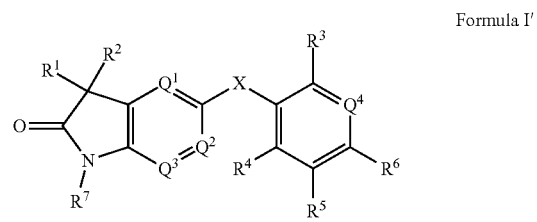

Formula I' or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen; or $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

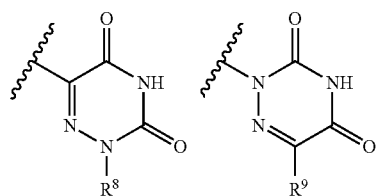

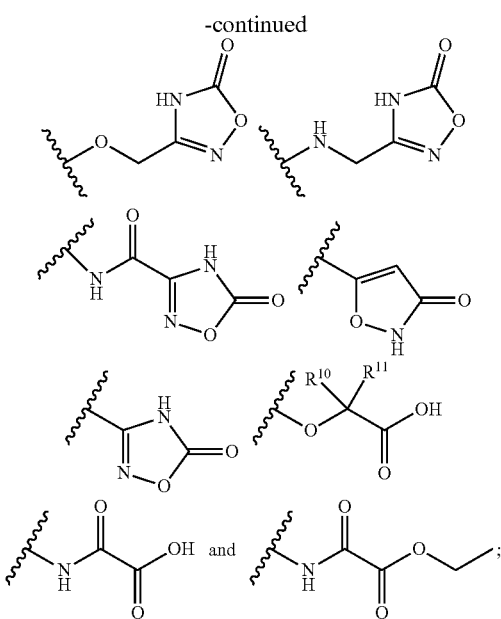

R[7] is H or $C_1$-$C_3$ alkyl;
R[8] is H or $C_1$-$C_3$ alkyl;
R[9] is selected from H, —CN, —CH$_3$, and —NH$_2$;
R[10] and R[11] are each independently H, F, or $C_1$-$C_3$ alkyl; or R[10] and R[11] together with the carbon atom to which they are attached form a $C_3$-$C_4$ non-aromatic carbocyclic ring optionally substituted with 1 to 5 substituents independently selected from halogen and $C_1$-$C_3$ alkyl;

R[12] is H, halogen, —CN, optionally substituted $C_1$-$C_3$ alkoxy, or optionally substituted $C_1$-$C_6$ alkyl; or R[12] and one of R[1] and R[2], together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

R[13] is independently selected from H, halogen, —CN, —OCH$_3$, and $C_1$-$C_3$ alkyl; and X is O or CH$_2$;
wherein 0 to 10 hydrogen atoms that are attached to one or more carbon atoms are replaced with deuterium atom(s);
provided that:
if R[9] is CN and Q[1], Q[2], Q[3], and Q[4] are all CH, then R[1] and R[2] together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, optionally substituted cyclopropyl, and halogen;
where when R[10] and R[11] are present, R[11] and R[5] cannot all be H; and
the compound is not selected from:
2-(3,5-dichloro-4-((5,5-dimethyl-6-oxo-6,7-dihydro-5H-pyrrolo[2,3-c]pyridazin-3-yl)oxy)phenyl)-3,5-dioxo-2,3,4,5-tetrahydro-1,2,4-triazine-6-carbonitrile;
6-amino-2-(3,5-dichloro-4-((3,3-dimethyl-2-oxoindolin-5-yl)oxy)phenyl)-1,2,4-triazine-3,5(2H,4H)-dione;
6-amino-2-(3,5-dichloro-4-((2'-oxospiro[cyclopentane-1,3'-indolin]-5'-yl)oxy)phenyl)-1,2,4-triazine-3,5(2H,4H)-dione;
6-amino-2-(3,5-dichloro-4-((3-isopropyl-3-methyl-2-oxoindolin-5-yl)oxy)phenyl)-1,2,4-triazine-3,5(2H,4H)-dione;
6-amino-2-(3,5-dichloro-4-((2'-oxospiro[cyclohexane-1,3'-indolin]-5'-yl)oxy)phenyl)-1,2,4-triazine-3,5(2H,4H)-dione;
6-amino-2-(3,5-dichloro-4-((2'-oxospiro[cyclopropane-1,3'-indolin]-5'-yl)oxy)phenyl)-1,2,4-triazine-3,5(2H,4H)-dione;
2-(3,5-dimethyl-4-((2'-oxospiro[cyclopropane-1,3'-indolin]-5'-yl)methyl)phenyl)-3,5-dioxo-2,3,4,5-tetrahydro-1,2,4-triazine-6-carbonitrile;
6-amino-2-(3,5-dimethyl-4-((2'-oxospiro[cyclopentane-1,3'-indolin]-5'-yl)methyl)phenyl)-1,2,4-triazine-3,5(2H,4H)-dione;
6-amino-2-(3,5-dimethyl-4-((2'-oxospiro[cyclopropane-1,3'-indolin]-5'-yl)methyl)phenyl)-1,2,4-triazine-3,5(2H,4H)-dione;
2-(3,5-dimethyl-4-((2'-oxospiro[cyclopropane-1,3'-indolin]-5'-yl)methyl)phenyl)-1,2,4-triazine-3,5(2H,4H)-dione;
2-(3,5-dimethyl-4-((2'-oxospiro[cyclobutane-1,3'-indolin]-5'-yl)methyl)phenyl)-3,5-dioxo-2,3,4,5-tetrahydro-1,2,4-triazine-6-carbonitrile;
2-(3,5-dichloro-4-((2'-oxospiro[cyclopropane-1,3'-indolin]-5'-yl)oxy)phenyl)-3,5-dioxo-2,3,4,5-tetrahydro-1,2,4-triazine-6-carbonitrile;
2-(3,5-dichloro-4-((2'-oxospiro[cyclobutane-1,3'-indolin]-5'-yl)oxy)phenyl)-3,5-dioxo-2,3,4,5-tetrahydro-1,2,4-triazine-6-carbonitrile; and
2-(3,5-dichloro-4-((2'-oxospiro[cyclopentane-1,3'-indolin]-5'-yl)oxy)phenyl)-3,5-dioxo-2,3,4,5-tetrahydro-1,2,4-triazine-6-carbonitrile.

Embodiment 2. A compound of Formula IA:

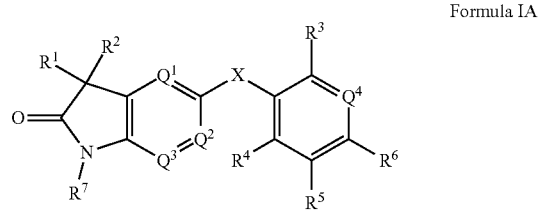

Formula IA or a stereoisomer or a tautomer thereof, or a pharmaceutically acceptable salt thereof, wherein
Q[1] is N or CR[12];
Q[2], Q[3] and Q[4] are each independently N or CR[13];
R[1] and R[2] are each independently selected from H, halogen, optionally substituted $C_3$-$C_6$ cycloalkyl, and optionally substituted $C_1$-$C_3$ alkyl; or
R[1] and R[2] together with the carbon atom to which they are attached form a $C_3$-$C_6$ cyclic ring optionally substituted with 1 to 3 substituents independently selected from $C_1$-$C_3$ alkyl and halogen; or
R[1] and R[2] together with the carbon atom to which they are attached form a polycyclic ring optionally substituted with 1 to 3 substituents independently selected from $C_1$-$C_3$ alkyl, and halogen;
R[3] and R[4] are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;
R[5] is selected from H, halogen, —CN, optionally substituted $C_1$-$C_3$ alkyl, and optionally substituted $C_1$-$C_2$ alkoxy; or
R[4] and R[5] together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

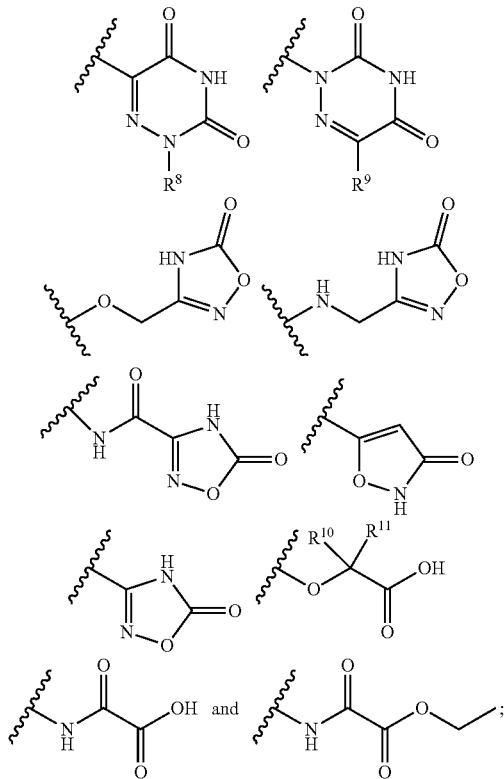

$R^7$ is H or $C_1$-$C_3$ alkyl;
$R^8$ is H or $C_1$-$C_3$ alkyl;
$R^9$ is selected from H, —CN, —$CH_3$, and —$NH_2$;
$R^{10}$ and $R^{11}$ are each independently H, F, or $C_1$-$C_3$ alkyl; or
$R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;
$R^{12}$ is H, halogen, —CN, optionally substituted $C_1$-$C_3$ alkoxy, or optionally substituted $C_1$-$C_6$ alkyl; or
$R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;
$R^{13}$ is independently selected from H, halogen, —CN, —$OCH_3$, and $C_1$-$C_3$ alkyl; and
X is O or $CH_2$;
wherein 0 to 10 hydrogen atoms that are attached to one or more carbon atoms are replaced with deuterium atom(s);
provided that:
if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are substituted with 1 to 3 substituents independently selected from $C_1$-$C_3$ alkyl and halogen;

when $R^{10}$ and $R^{11}$ are present, $R^{10}$, $R^{11}$ and $R^5$ cannot all be H; and
the compound is not selected from:
2-(3,5-dichloro-4-((5,5-dimethyl-6-oxo-6,7-dihydro-5H-pyrrolo[2,3-c]pyridazin-3-yl)oxy)phenyl)-3,5-dioxo-2,3,4,5-tetrahydro-1,2,4-triazine-6-carbonitrile;
6-amino-2-(3,5-dichloro-4-((3,3-dimethyl-2-oxoindolin-5-yl)oxy)phenyl)-1,2,4-triazine-3,5(2H,4H)-dione;
6-amino-2-(3,5-dichloro-4-((2'-oxospiro[cyclopentane-1,3'-indolin]-5'-yl)oxy)phenyl)-1,2,4-triazine-3,5(2H,4H)-dione;
6-amino-2-(3,5-dichloro-4-((3-isopropyl-3-methyl-2-oxoindolin-5-yl)oxy)phenyl)-1,2,4-triazine-3,5(2H,4H)-dione;
6-amino-2-(3,5-dichloro-4-((2'-oxospiro[cyclohexane-1,3'-indolin]-5'-yl)oxy)phenyl)-1,2,4-triazine-3,5(2H,4H)-dione;
6-amino-2-(3,5-dichloro-4-((2'-oxospiro[cyclopropane-1,3'-indolin]-5'-yl)oxy)phenyl)-1,2,4-triazine-3,5(2H,4H)-dione;
6-amino-2-(3,5-dimethyl-4-((2'-oxospiro[cyclopentane-1,3'-indolin]-5'-yl)methyl)phenyl)-1,2,4-triazine-3,5(2H,4H)-dione;
6-amino-2-(3,5-dimethyl-4-((2'-oxospiro[cyclopropane-1,3'-indolin]-5'-yl)methyl)phenyl)-1,2,4-triazine-3,5(2H,4H)-dione; and
2-(3,5-dimethyl-4-((2'-oxospiro[cyclopropane-1,3'-indolin]-5'-yl)methyl)phenyl)-1,2,4-triazine-3,5(2H,4H)-dione.

Embodiment 3. The compound of embodiment 1 or embodiment 2, or the stereoisomer or the tautomer thereof, or the pharmaceutically acceptable salt thereof, wherein at least one of $Q^1$, $Q^2$, and $Q^3$ are N.

Embodiment 4. The compound of embodiment 1 or embodiment 2, or the stereoisomer or the tautomer thereof, or the pharmaceutically acceptable salt thereof, wherein $Q^1$ is N.

Embodiment 5. The compound of embodiment 1 or embodiment 2, or the stereoisomer or the tautomer thereof, or the pharmaceutically acceptable salt thereof, wherein $Q^2$ is N.

Embodiment 6. The compound of embodiment 1 or embodiment 2, or the stereoisomer or the tautomer thereof, or the pharmaceutically acceptable salt thereof, wherein $Q^3$ is N.

Embodiment 7. The compound of embodiment 1 or embodiment 2, or the stereoisomer or the tautomer thereof, or the pharmaceutically acceptable salt thereof, wherein $Q^1$ is $CR^{12}$.

Embodiment 8. The compound of embodiment 1 or embodiment 2, or the stereoisomer or the tautomer thereof, or the pharmaceutically acceptable salt thereof, wherein $Q^1$ is $CR^{12}$, and $Q^2$ and $Q^3$ are both $CR^{13}$.

Embodiment 9. The compound of any one of embodiments 1, 2, 4, or 6-8, or the stereoisomer or the tautomer thereof, or the pharmaceutically acceptable salt thereof, wherein $Q^2$ is CH.

Embodiment 10. The compound of any one of embodiments 1, 2, 7 or 8, or the stereoisomer or the tautomer thereof, or the pharmaceutically acceptable salt thereof, wherein $Q^1$, $Q^2$, and $Q^3$ are all CH.

Embodiment 11. The compound of any one of embodiments 1-10, or the stereoisomer or the tautomer thereof, or the pharmaceutically acceptable salt thereof, wherein $Q^4$ is N.

Embodiment 12. The compound of any one of embodiments 1-10, or the stereoisomer or the tautomer thereof, or the pharmaceutically acceptable salt thereof, wherein $Q^4$ is $CR^{13}$.

Embodiment 13. The compound of any one of embodiments 1-10, or the stereoisomer or the tautomer thereof, or the pharmaceutically acceptable salt thereof, wherein $Q^4$ is CH.

Embodiment 14. The compound of any one of embodiments 1-13, or the stereoisomer or the tautomer thereof, or the pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

Embodiment 15. The compound of any one of embodiments 1-13, or the stereoisomer or the tautomer thereof, or the pharmaceutically acceptable salt thereof, wherein $R^3$ and $R^4$ are each independently selected from halogen and $C_1$-$C_3$ alkyl.

Embodiment 16. The compound of any one of embodiments 1-13, or the stereoisomer or the tautomer thereof, or the pharmaceutically acceptable salt thereof, wherein $R^3$ and $R^4$ are both halogen.

Embodiment 17. The compound of any one of embodiments 1-13, or the stereoisomer or the tautomer thereof, or the pharmaceutically acceptable salt thereof, wherein $R^3$ and $R^4$ are both —Cl.

Embodiment 18. The compound of any one of embodiments 1-13, or the stereoisomer or the tautomer thereof, or the pharmaceutically acceptable salt thereof, wherein $R^3$ and $R^4$ are both methyl.

Embodiment 19. The compound of any one of embodiments 1-19, or the stereoisomer or the tautomer thereof, or the pharmaceutically acceptable salt thereof, wherein $R^5$ is H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

Embodiment 20. The compound of any one of embodiments 1-19, or the stereoisomer or the tautomer thereof, or the pharmaceutically acceptable salt thereof, wherein $R^5$ is hydrogen or $C_1$-$C_3$ alkyl.

Embodiment 21. The compound of any one of embodiments 1-19, or the stereoisomer or the tautomer thereof, or the pharmaceutically acceptable salt thereof, wherein $R^5$ is hydrogen.

Embodiment 22. The compound of any one of embodiments 1-21, or the stereoisomer or the tautomer thereof, or the pharmaceutically acceptable salt thereof, wherein $R^6$ is

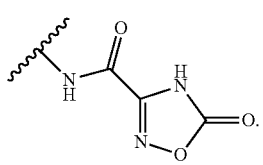 [SMILES: *NC(=O)c1noc(=O)[nH]1]

Embodiment 23. The compound of any one of embodiments 1-21, or the stereoisomer or the tautomer thereof, or the pharmaceutically acceptable salt thereof, wherein $R^6$ is

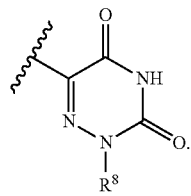

Embodiment 24. The compound of embodiment 23, or the stereoisomer or the tautomer thereof, or the pharmaceutically acceptable salt thereof, wherein $R^8$ is H.

Embodiment 25. The compound of embodiment 23, or the stereoisomer or the tautomer thereof, or the pharmaceutically acceptable salt thereof, wherein $R^8$ is $C_1$-$C_3$ alkyl.

Embodiment 26. The compound of embodiment 23, or the stereoisomer or the tautomer thereof, or the pharmaceutically acceptable salt thereof, wherein $R^8$ is $CH_3$.

Embodiment 27. The compound of any one of embodiments 1-21, or the stereoisomer or the tautomer thereof, or the pharmaceutically acceptable salt thereof, wherein $R^6$ is

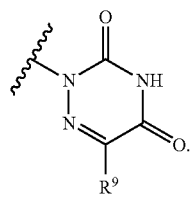

Embodiment 28. The compound of embodiment 27, or the stereoisomer or the tautomer thereof, or the pharmaceutically acceptable salt thereof, wherein $R^9$ is —CN or —$NH_2$.

Embodiment 29. The compound of embodiment 27, or the stereoisomer or the tautomer thereof, or the pharmaceutically acceptable salt thereof, wherein $R^9$ is —$NH_2$.

Embodiment 30. The compound of embodiment 27, or the stereoisomer or the tautomer thereof, or the pharmaceutically acceptable salt thereof, wherein $R^9$ is H.

Embodiment 31. The compound of embodiment 27, or the stereoisomer or the tautomer thereof, or the pharmaceutically acceptable salt thereof, wherein $R^9$ is $CH_3$.

Embodiment 32. The compound of any one of embodiments 1-22, or the stereoisomer or the tautomer thereof, or the pharmaceutically acceptable salt thereof, wherein $R^6$ is

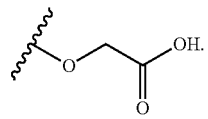 [SMILES: *OCC(=O)O]

Embodiment 33. The compound of any one of embodiments 1-32, or the stereoisomer or the tautomer thereof, or the pharmaceutically acceptable salt thereof, wherein $R^7$ is H.

Embodiment 34. The compound of any one of embodiments 1-2, 5-9, or 11-33, or the stereoisomer or the tautomer thereof, or the pharmaceutically acceptable salt thereof, wherein $R^{12}$ is H, halogen, or $C_1$-$C_6$ alkyl.

Embodiment 35. The compound of any one of embodiments 1-2, 5-9, or 11-33, or the stereoisomer or the tautomer thereof, or the pharmaceutically acceptable salt thereof, wherein $R^{12}$ is H, F, or $C_1$-$C_6$ alkyl.

Embodiment 36. The compound of any one of embodiments 1-2, 5-9, or 11-33, or the stereoisomer or the tautomer thereof, or the pharmaceutically acceptable salt thereof, wherein $R^{12}$ is H.

Embodiment 37. The compound of any one of embodiments 1-2, 5-9, or 11-33, or the stereoisomer or the tautomer thereof, or the pharmaceutically acceptable salt thereof, wherein $R^{12}$ is F.

Embodiment 38. The compound of any one of embodiments 1-2, 5-9, or 11-33, or the stereoisomer or the tautomer thereof, or the pharmaceutically acceptable salt thereof, wherein $R^{12}$ is Cl.

Embodiment 39. The compound of any one of embodiments 1-2, 5-9, or 11-33, or the stereoisomer or the tautomer thereof, or the pharmaceutically acceptable salt thereof, wherein $R^{12}$ is $CH_3$.

Embodiment 40. The compound of any one of embodiments 1-2, 5-9, or 11-33, or the stereoisomer or the tautomer thereof, or the pharmaceutically acceptable salt thereof, wherein $R^{12}$ is H, halogen, —CN, $C_1$-$C_3$ alkoxy, or $C_1$-$C_6$ alkyl; wherein the $C_1$-$C_3$ alkoxy, or $C_1$-$C_6$ alkyl are optionally substituted with 1-5 halogens.

Embodiment 41. The compound of any one of embodiments 1-2, 5-9, or 11-33, or the stereoisomer or the tautomer thereof, or the pharmaceutically acceptable salt thereof, wherein $R^{12}$ is $C_1$-$C_3$ alkyl, optionally substituted with 1-3 halogens.

Embodiment 42. The compound of any one of embodiments 1-2, 5-9, or 11-33, or the stereoisomer or the tautomer thereof, or the pharmaceutically acceptable salt thereof, wherein $R^{12}$ is $CF_3$.

Embodiment 43. The compound of any one of embodiments 1-42, or the stereoisomer or the tautomer thereof, or the pharmaceutically acceptable salt thereof, wherein $R^1$ and $R^{12}$ together with the carbon atom to which they are attached form a $C_3$-$C_4$ cyclic ring optionally substituted with 1 to 3 substituents independently selected from $C_1$-$C_3$ alkyl and halogen.

Embodiment 44. The compound of any one of embodiments 1-42, or the stereoisomer or the tautomer thereof, or the pharmaceutically acceptable salt thereof, wherein $R^1$ and $R^{12}$ together with the carbon atom to which they are attached form a $C_3$-$C_6$ cyclic ring optionally substituted with 1 to 3 substituents independently selected from $C_1$-$C_3$ alkyl and halogen; wherein a single carbon of the $C_3$-$C_6$ cyclic ring contains no more than one halogen atom.

Embodiment 45. The compound of any one of embodiments 1-42, or the stereoisomer or the tautomer thereof, or the pharmaceutically acceptable salt thereof, wherein $R^1$ and $R^{12}$ together with the carbon atom to which they are attached form an unsubstituted $C_3$-$C_6$ cyclic ring.

Embodiment 46. The compound of any one of embodiments 1, 2, or 11-33, or the stereoisomer or the tautomer thereof, or the pharmaceutically acceptable salt thereof, wherein $Q^1$ is $CR^{12}$, and $R^{12}$ and one of $R^1$ and $R^{12}$, together with the carbon atoms to which they are attached, form a $C_5$-$C_7$ partially unsaturated carbocyclic ring or a partially unsaturated polycyclic ring.

Embodiment 47. The compound of any one of embodiments 1, 2, or 11-33, or the stereoisomer or the tautomer thereof, or the pharmaceutically acceptable salt thereof, wherein $Q^1$ is CH, $Q^2$ and $Q^3$ are N, and $R^1$ and $R^{12}$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, cyclopropyl, and halogen.

Embodiment 48. The compound of any one of embodiments 1-2, 4, 7, 8, 12, or 14-47, or the stereoisomer or the tautomer thereof, or the pharmaceutically acceptable salt thereof, wherein $R^{13}$ is independently selected from H, F, —CN, —$OCH_3$, and $C_1$-$C_3$ alkyl.

Embodiment 49. The compound of any one of embodiments 1-2, 4, 7, 8, 12, or 14-47, or the stereoisomer or the tautomer thereof, or the pharmaceutically acceptable salt thereof, wherein $R^{13}$ is H.

Embodiment 50. The compound of any one of embodiments 1-2, 4, 7, 8, 12, or the stereoisomer or the tautomer thereof, or the pharmaceutically acceptable salt thereof, wherein $R^{13}$ is $CH_3$.

Embodiment 51. The compound of any one of embodiments 1-50, or the stereoisomer or the tautomer thereof, or the pharmaceutically acceptable salt thereof, wherein X is O.

Embodiment 52. The compound of any one of embodiments 1-50, or the stereoisomer or the tautomer thereof, or the pharmaceutically acceptable salt thereof, wherein X is $CH_2$.

Embodiment 53. The compound of embodiment 1 or embodiment 2, having the chemical structure of:

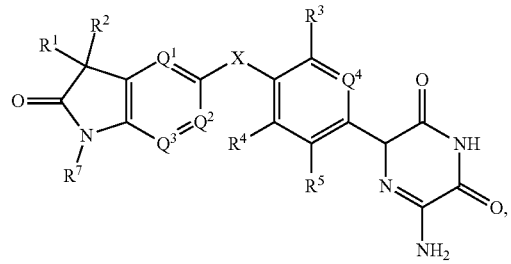

or a stereoisomer or a tautomer thereof, or a pharmaceutically acceptable salt thereof.

Embodiment 54. The compound of embodiment 1 or embodiment 2, having the chemical structure of

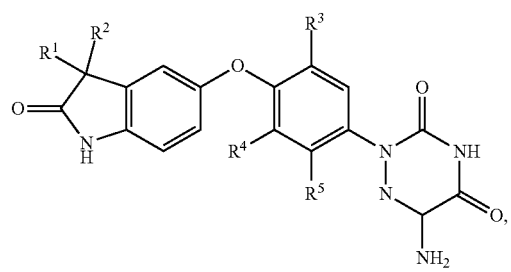

or a stereoisomer or a tautomer thereof, or a pharmaceutically acceptable salt thereof.

Embodiment 55. The compound of embodiment 1 or embodiment 2, having the chemical structure of:

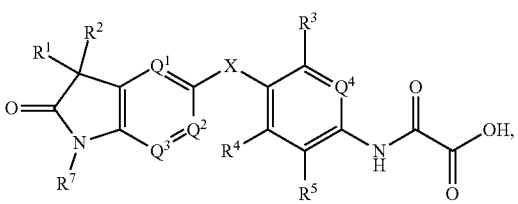

or a stereoisomer or a tautomer thereof, or a pharmaceutically acceptable salt thereof.

Embodiment 56. The compound of embodiment 1 or embodiment 2, having the chemical structure of:

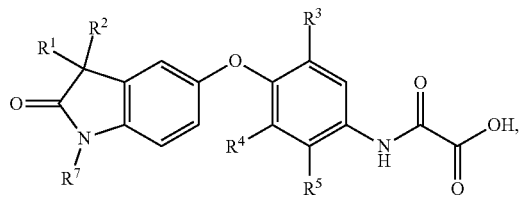

or a stereoisomer or a tautomer thereof, or a pharmaceutically acceptable salt thereof.

Embodiment 57. The compound of embodiment 1 or embodiment 2, having the chemical structure of:

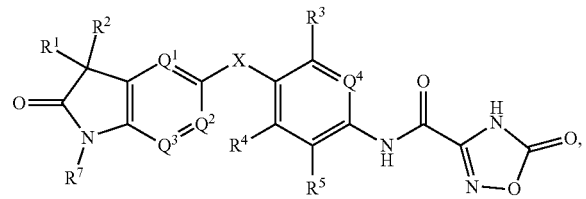

or a stereoisomer or a tautomer thereof, or a pharmaceutically acceptable salt thereof.

Embodiment 58. The compound of embodiment 1 or embodiment 2, having the chemical structure of:

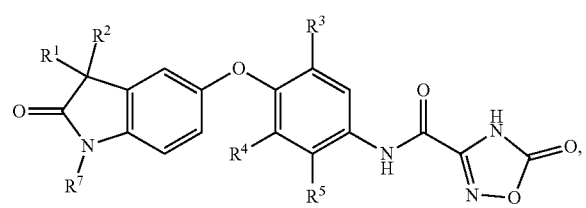

or a stereoisomer or a tautomer thereof, or a pharmaceutically acceptable salt thereof.

Embodiment 59. The compound of embodiment 1 or embodiment 2, having the chemical structure of:

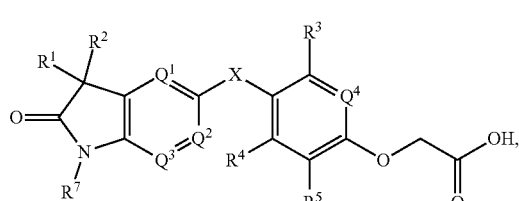

or a stereoisomer or a tautomer thereof, or a pharmaceutically acceptable salt thereof.

Embodiment 60. The compound of embodiment 1 or embodiment 2, having the chemical structure of:

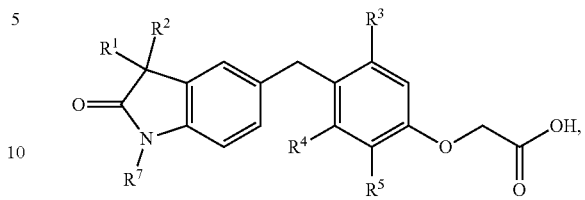

or a stereoisomer or a tautomer thereof, or a pharmaceutically acceptable salt thereof.

Embodiment 61. The compound of any one of embodiments 53, 55, 57, or 59, or the stereoisomer or the tautomer thereof, or the pharmaceutically acceptable salt thereof, wherein at least one of $Q^1$, $Q^2$, and $Q^3$ are N.

Embodiment 62. The compound of any one of embodiments 53, 55, 57, or 59, or the stereoisomer or the tautomer thereof, or the pharmaceutically acceptable salt thereof, wherein $Q^1$ is N.

Embodiment 63. The compound of any one of embodiments 53, 55, 57, or 59, or the stereoisomer or the tautomer thereof, or the pharmaceutically acceptable salt thereof, wherein $Q^2$ is N.

Embodiment 64. The compound of any one of embodiments 53, 55, 57, or 59, or the stereoisomer or the tautomer thereof, or the pharmaceutically acceptable salt thereof, wherein $Q^3$ is N.

Embodiment 65. The compound of any one of embodiments 53, 55, 57, or 59, or the stereoisomer or the tautomer thereof, or the pharmaceutically acceptable salt thereof, wherein $Q^1$ is $CR^{12}$.

Embodiment 66. The compound of any one of embodiments 53, 55, 57, or 59, or the stereoisomer or the tautomer thereof, or the pharmaceutically acceptable salt thereof, wherein $Q^1$ is $CR^{12}$, and $Q^2$ and $Q^3$ are both $CR^{13}$.

Embodiment 67. The compound of embodiment 66, or the stereoisomer or the tautomer thereof, or the pharmaceutically acceptable salt thereof, wherein $Q^2$ is CH.

Embodiment 68. The compound of embodiment 66, or the stereoisomer or the tautomer thereof, or the pharmaceutically acceptable salt thereof, wherein $Q^1$, $Q^2$, and $Q^3$ are all CH.

Embodiment 69. The compound of any one of embodiments 53, 55, 57, 59, or 61-68, or the stereoisomer or the tautomer thereof, or the pharmaceutically acceptable salt thereof, wherein $Q^4$ is N.

Embodiment 70. The compound of any one of embodiments 53, 55, 57, 59, or 61-68, or the stereoisomer or the tautomer thereof, or the pharmaceutically acceptable salt thereof, wherein $Q^4$ is $CR^{13}$.

Embodiment 71. The compound of embodiment 70, or the stereoisomer or the tautomer thereof, or the pharmaceutically acceptable salt thereof, wherein $Q^4$ is CH.

Embodiment 72. The compound of any one of embodiments 53-71, or the stereoisomer or the tautomer thereof, or the pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

Embodiment 73. The compound of any one of embodiments 53-71, or the stereoisomer or the tautomer thereof, or the pharmaceutically acceptable salt thereof, wherein $R^3$ and $R^4$ are each independently selected from halogen and $C_1$-$C_3$ alkyl.

Embodiment 74. The compound of any one of embodiments 53-71, or the stereoisomer or the tautomer thereof, or the pharmaceutically acceptable salt thereof, wherein $R^3$ and $R^4$ are both halogen.

Embodiment 75. The compound of any one of embodiments 53-71, or the stereoisomer or the tautomer thereof, or the pharmaceutically acceptable salt thereof, wherein $R^3$ and $R^4$ are both —Cl.

Embodiment 76. The compound of any one of embodiments 53-71, or the stereoisomer or the tautomer thereof, or the pharmaceutically acceptable salt thereof, wherein $R^3$ and $R^4$ are both methyl.

Embodiment 77. The compound of any one of embodiments 53-76, or the stereoisomer or the tautomer thereof, or the pharmaceutically acceptable salt thereof, wherein $R^5$ is H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

Embodiment 78. The compound of any one of embodiments 53-76, or the stereoisomer or the tautomer thereof, or the pharmaceutically acceptable salt thereof, wherein $R^5$ is hydrogen or $C_1$-$C_3$ alkyl.

Embodiment 79. The compound of any one of embodiments 53-76, or the stereoisomer or the tautomer thereof, or the pharmaceutically acceptable salt thereof, wherein $R^5$ is hydrogen.

Embodiment 80. The compound of any one of embodiments 53-79, or the stereoisomer or the tautomer thereof, or the pharmaceutically acceptable salt thereof, wherein $R^7$ is H.

Embodiment 81. The compound of any one of embodiments 53, 55, 57, 59, 63-67, or 69-80, or the stereoisomer or the tautomer thereof, or the pharmaceutically acceptable salt thereof, wherein $R^{12}$ is H, halogen, or $C_1$-$C_6$ alkyl.

Embodiment 82. The compound of any one of embodiments 53, 55, 57, 59, 63-67, or 69-80, or the stereoisomer or the tautomer thereof, or the pharmaceutically acceptable salt thereof, wherein $R^{12}$ is H, F, or $C_1$-$C_6$ alkyl.

Embodiment 83. The compound of any one of embodiments 53, 55, 57, 59, 63-67, or 69-80, or the stereoisomer or the tautomer thereof, or the pharmaceutically acceptable salt thereof, wherein $R^{12}$ is H.

Embodiment 84. The compound of any one of embodiments 53, 55, 57, 59, 63-67, or 69-80, or the stereoisomer or the tautomer thereof, or the pharmaceutically acceptable salt thereof, wherein $R^{12}$ is F.

Embodiment 85. The compound of any one of embodiments 53, 55, 57, 59, 63-67, or 69-80, or the stereoisomer or the tautomer thereof, or the pharmaceutically acceptable salt thereof, wherein $R^{12}$ is Cl.

Embodiment 86. The compound of any one of embodiments 53, 55, 57, 59, 63-67, or 69-80, or the stereoisomer or the tautomer thereof, or the pharmaceutically acceptable salt thereof, wherein $R^{12}$ is $CH_3$.

Embodiment 87. The compound of any one of embodiments 53, 55, 57, 59, 63-67, or 69-80, or the stereoisomer or the tautomer thereof, or the pharmaceutically acceptable salt thereof, wherein $R^{12}$ is H, halogen, —CN, $C_1$-$C_3$ alkoxy, or $C_1$-$C_6$ alkyl; wherein the $C_1$-$C_3$ alkoxy, or $C_1$-$C_6$ alkyl are optionally substituted with 1-5 halogens.

Embodiment 88. The compound of any one of embodiments 53, 55, 57, 59, 63-67, or 69-80, or the stereoisomer or the tautomer thereof, or the pharmaceutically acceptable salt thereof, wherein $R^{12}$ is $C_1$-$C_3$ alkyl, optionally substituted with 1-3 halogens.

Embodiment 89. The compound of any one of embodiments 53, 55, 57, 59, 63-67, or 69-80, or the stereoisomer or the tautomer thereof, or the pharmaceutically acceptable salt thereof, wherein $R^{12}$ is $R^{12}$ is $CF_3$.

Embodiment 90. The compound of any one of embodiments 53-89, or the stereoisomer or the tautomer thereof, or the pharmaceutically acceptable salt thereof, wherein $R^1$ and $R^2$ together with the carbon atom to which they are attached form a $C_3$-$C_4$ cyclic ring optionally substituted with 1 to 3 substituents independently selected from $C_1$-$C_3$ alkyl, and halogen.

Embodiment 91. The compound of any one of embodiments 53-89, or the stereoisomer or the tautomer thereof, or the pharmaceutically acceptable salt thereof, wherein $R^1$ and $R^2$ together with the carbon atom to which they are attached form a $C_3$-$C_6$ cyclic ring optionally substituted with 1 to 3 substituents independently selected from $C_1$-$C_3$ alkyl and halogen; wherein a single carbon of the $C_3$-$C_6$ cyclic ring contains no more than one halogen atom.

Embodiment 92. The compound of any one of embodiments 53-89, or the stereoisomer or the tautomer thereof, or the pharmaceutically acceptable salt thereof, wherein $R^1$ and $R^2$ together with the carbon atom to which they are attached form an unsubstituted $C_3$-$C_6$ cyclic ring.

Embodiment 93. The compound of any one of embodiments 53, 55, 57, 59, 69-80, or the stereoisomer or the tautomer thereof, or the pharmaceutically acceptable salt thereof, wherein $Q^1$ is $CR^{12}$, and $R^{12}$ and one of $R^1$ and $R^2$, together with the carbon atoms to which they are attached, form a $C_5$-$C_7$ partially unsaturated carbocyclic ring or a partially unsaturated polycyclic ring.

Embodiment 94. The compound of any one of embodiments 53, 55, 57, 59, 69-80, or the stereoisomer or the tautomer thereof, or the pharmaceutically acceptable salt thereof, wherein $Q^1$ is CH, $Q^2$ and $Q^3$ are N, and $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, cyclopropyl, and halogen.

Embodiment 95. The compound of any one of embodiments 53, 55, 57, 59, or 62-93, or the stereoisomer or the tautomer thereof, or the pharmaceutically acceptable salt thereof, wherein $R^{13}$ is independently selected from H, F, —CN, —$OCH_3$, and $C_1$-$C_3$ alkyl.

Embodiment 96. The compound of any one of embodiments 53, 55, 57, 59, or 62-93, or the stereoisomer or the tautomer thereof, or the pharmaceutically acceptable salt thereof, wherein $R^{13}$ is H.

Embodiment 97. The compound of any one of embodiments 53, 55, 57, 59, or 62-93, or the stereoisomer or the tautomer thereof, or the pharmaceutically acceptable salt thereof, wherein $R^{13}$ is $CH_3$.

Embodiment 98. The compound of any one of embodiments 53-97, or the stereoisomer or the tautomer thereof, or the pharmaceutically acceptable salt thereof, wherein X is O.

Embodiment 99. The compound of any one of embodiments 53-97, or the stereoisomer or the tautomer thereof, or the pharmaceutically acceptable salt thereof, wherein X is $CH_2$.

Embodiment 100. A compound selected from the group consisting of:

4-([3,3-dimethyl-2-oxo-1H-pyrrolo[3,2-b]pyridin-5-yl]methyl)-2,3,5-trimethylphenoxyacetic acid;

6-amino-2-(3,5-dichloro-4-((2'-oxospiro[cyclobutane-1,3'-indolin]-5'-yl)oxy)phenyl)-1,2,4-triazine-3,5(2H,4H)-dione;

6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;

2-((4-methyl-5-((2'-oxospiro[cyclobutane-1,3'-indolin]-5'-yl)oxy)bicyclo[4.2.0]octan-2-yl)oxy)acetic acid;

6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;

6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;

6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;

6-amino-2-(3,5-dichloro-4-((1'-methyl-2'-oxospiro[cyclopropane-1,3'-indolin]-5'-yl)oxy)phenyl)-1,2,4-triazine-3,5(2H,4H)-dione;

2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;

2-(4-((3,3-difluoro-2'-oxospiro[cyclobutane-1,3'-indolin]-5'-yl)methyl)-3,5-dimethylphenyl)-3,5-dioxo-2,3,4,5-tetrahydro-1,2,4-triazine-6-carbonitrile;

6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;

6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione;

6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;

6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;

2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;

2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;

2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

6-amino-2-(3,5-dichloro-4-((2'-oxospiro[cyclobutane-1,3'-indolin]-5'-yl)methyl)phenyl)-1,2,4-triazine-3,5(2H,4H)-dione;

6-amino-2-(3,5-dimethyl-4-{2'-oxo-1'H-spiro[cyclobutane-1,3'-indol]-5'-ylmethyl}phenyl)-4H-1,2,4-triazine-3,5-dione;

2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;

2-(2,3,5-trimethyl-4-((2'-oxospiro[cyclopropane-1,3'-indolin]-5'-yl)methyl)phenoxy)acetic acid;

2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;

3-(3,5-dichloro-4-((2'-oxospiro[cyclobutane-1,3'-indolin]-5'-yl)oxy)phenyl)-1,2,4-oxadiazol-5(4H)-one;

N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;

2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;

6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;

2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;

6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;

2-((3,5-dichloro-4-((2a-methyl-2-oxo-1,2,2a,3,4,5-hexahydrobenzo[cd]indol-6-yl)oxy)phenyl)amino)-2-oxoacetic acid;

ethyl 2-((3,5-dichloro-4-((2a-methyl-2-oxo-1,2,2a,3,4,5-hexahydrobenzo[cd]indol-6-yl)oxy)phenyl)amino)-2-oxoacetate;

N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;

6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;

3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;

3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;

6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;

6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;

2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile; and 6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;

or a stereoisomer or a tautomer thereof, or a pharmaceutically acceptable salt thereof.

Embodiment 101. A compound selected from the group consisting of:

4-([3,3-dimethyl-2-oxo-1H-pyrrolo[3,2-b]pyridin-5-yl]methyl)-2,3,5-trimethylphenoxyacetic acid;

6-amino-2-(3,5-dichloro-4-((2'-oxospiro[cyclobutane-1,3'-indolin]-5'-yl)oxy)phenyl)-1,2,4-triazine-3,5(2H,4H)-dione;

6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;
2-((4-methyl-5-((2'-oxospiro[cyclobutane-1,3'-indolin]-5'-yl)oxy)bicyclo[4.2.0]octan-2-yl)oxy)acetic acid;
6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;
6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;
6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;
2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;
2-(4-((3,3-difluoro-2'-oxospiro[cyclobutane-1,3'-indolin]-5'-yl)methyl)-3,5-dimethylphenyl)-3,5-dioxo-2,3,4,5-tetrahydro-1,2,4-triazine-6-carbonitrile;
6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;
6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;
6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione;
6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;
6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;
2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;
2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;
2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;
6-amino-2-(3,5-dichloro-4-((2'-oxospiro[cyclobutane-1,3'-indolin]-5'-yl)methyl)phenyl)-1,2,4-triazine-3,5(2H,4H)-dione;
6-amino-2-(3,5-dimethyl-4-{2'-oxo-1'H-spiro[cyclobutane-1,3'-indol]-5'-ylmethyl}phenyl)-4H-1,2,4-triazine-3,5-dione;
2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;
2-(2,3,5-trimethyl-4-((2'-oxospiro[cyclopropane-1,3'-indolin]-5'-yl)methyl)phenoxy)acetic acid;
2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;
3-(3,5-dichloro-4-((2'-oxospiro[cyclobutane-1,3'-indolin]-5'-yl)oxy)phenyl)-1,2,4-oxadiazol-5(4H)-one;
N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;
2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;
6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;
2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;
6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;
2-((3,5-dichloro-4-((2a-methyl-2-oxo-1,2,2a,3,4,5-hexahydrobenzo[cd]indol-6-yl)oxy)phenyl)amino)-2-oxoacetic acid;
ethyl 2-((3,5-dichloro-4-((2a-methyl-2-oxo-1,2,2a,3,4,5-hexahydrobenzo[cd]indol-6-yl)oxy)phenyl)amino)-2-oxoacetate;
N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;
6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;
3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;
3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;
6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;
6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;
2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile;
6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;
6-amino-2-[4-({3,3-dimethyl-2-oxo-1H-pyrrolo[3,2-b]pyridin-5-yl}methyl)-3,5-dimethylphenyl]-4H-1,2,4-triazine-3,5-dione; 6-(3,5-dichloro-4-((2'-oxospiro[cyclobutane-1,3'-indolin]-5'-yl)oxy)phenyl)-1,2,4-triazine-3,5(2H,4H)-dione;
6-(3,5-dichloro-4-((2'-oxospiro[cyclobutane-1,3'-indolin]-5'-yl)oxy)phenyl)-2-methyl-1,2,4-triazine-3,5(2H,4H)-dione;
N-(3,5-dichloro-4-((2'-oxospiro[cyclopropane-1,3'-indolin]-5'-yl)oxy)phenyl)-5-oxo-4,5-dihydro-1,2,4-oxadiazole-3-carboxamide;
N-(3,5-dichloro-4-((4'-methyl-2'-oxospiro[cyclopropane-1,3'-indolin]-5'-yl)oxy)phenyl)-5-oxo-4,5-dihydro-1,2,4-oxadiazole-3-carboxamide;
6-amino-2-(3,5-dimethyl-4-((2'-oxospiro[cyclobutane-1,3'-indolin]-5'-yl)oxy)phenyl)-1,2,4-triazine-3,5(2H,4H)-dione;
N-(3,5-dimethyl-4-((2'-oxospiro[cyclobutane-1,3'-indolin]-5'-yl)oxy)phenyl)-5-oxo-4,5-dihydro-1,2,4-oxadiazole-3-carboxamide;

6-amino-2-(3,5-dichloro-4-((7'-methyl-2'-oxospiro[cyclobutane-1,3'-indolin]-5'-yl)oxy)phenyl)-1,2,4-triazine-3,5(2H,4H)-dione;
6-amino-2-(3,5-dimethyl-4-((2'-oxospiro[cyclopentane-1,3'-indolin]-5'-yl)oxy)phenyl)-1,2,4-triazine-3,5(2H,4H)-dione;
N-(3,5-dichloro-4-((4'-chloro-2'-oxospiro[cyclopropane-1,3'-indolin]-5'-yl)oxy)phenyl)-5-oxo-4,5-dihydro-1,2,4-oxadiazole-3-carboxamide;
6-amino-2-(3,5-dichloro-4-((4'-chloro-2'-oxospiro[cyclopropane-1,3'-indolin]-5'-yl)oxy)phenyl)-1,2,4-triazine-3,5(2H,4H)-dione;
2-(3,5-dichloro-4-((4'-chloro-2'-oxospiro[cyclopropane-1,3'-indolin]-5'-yl)oxy)phenyl)-1,2,4-triazine-3,5(2H,4H)-dione;
6-amino-2-(3,5-dichloro-4-((2-methyl-2'-oxospiro[cyclopropane-1,3'-indolin]-5'-yl)oxy)phenyl)-1,2,4-triazine-3,5(2H,4H)-dione;
2-((3,5-dichloro-4-((2-methyl-2'-oxospiro[cyclopropane-1,3'-indolin]-5'-yl)oxy)phenyl)amino)-2-oxoacetic acid;
2-((3,5-dichloro-4-((3,3-difluoro-2-oxoindolin-5-yl)oxy)phenyl)amino)-2-oxoacetic acid;
6-(3,5-dichloro-4-((4'-methyl-2'-oxospiro[cyclopropane-1,3'-indolin]-5'-yl)oxy)phenyl)-2-methyl-1,2,4-triazine-3,5(2H,4H)-dione;
6-amino-2-(3,5-dichloro-4-((4'-methyl-2'-oxospiro[cyclopropane-1,3'-indolin]-5'-yl)oxy)phenyl)-1,2,4-triazine-3,5(2H,4H)-dione;
N-(3,5-dimethyl-4-((2'-oxospiro[cyclopropane-1,3'-indolin]-5'-yl)oxy)phenyl)-5-oxo-4,5-dihydro-1,2,4-oxadiazole-3-carboxamide;
N-(3,5-dichloro-4-((4'-fluoro-2'-oxospiro[cyclopropane-1,3'-indolin]-5'-yl)oxy)phenyl)-5-oxo-4,5-dihydro-1,2,4-oxadiazole-3-carboxamide;
6-amino-2-(3,5-dichloro-4-((4'-fluoro-2'-oxospiro[cyclopropane-1,3'-indolin]-5'-yl)oxy)phenyl)-1,2,4-triazine-3,5(2H,4H)-dione;
6-(3,5-dichloro-4-((4'-fluoro-2'-oxospiro[cyclopropane-1,3'-indolin]-5'-yl)oxy)phenyl)-2-methyl-1,2,4-triazine-3,5(2H,4H)-dione;
6-(3,5-dichloro-4-((4'-chloro-2'-oxospiro[cyclopropane-1,3'-indolin]-5'-yl)oxy)phenyl)-2-methyl-1,2,4-triazine-3,5(2H,4H)-dione;
N-(3-chloro-4-((2'-oxospiro[cyclopropane-1,3'-indolin]-5'-yl)oxy)-5-(trifluoromethyl)phenyl)-5-oxo-4,5-dihydro-1,2,4-oxadiazole-3-carboxamide; and
2-((3,5-dichloro-4-((2'-oxospiro[cyclobutane-1,3'-indolin]-5'-yl)oxy)phenyl)amino)-2-oxoacetic acid;
or a stereoisomer or a tautomer thereof, or a pharmaceutically acceptable salt thereof.

Embodiment 102. A compound selected from the group consisting of:
4-([3,3-dimethyl-2-oxo-1H-pyrrolo[3,2-b]pyridin-5-yl]methyl)-2,3,5-trimethylphenoxyacetic acid;
6-amino-2-(3,5-dichloro-4-((2'-oxospiro[cyclobutane-1,3'-indolin]-5'-yl)oxy)phenyl)-1,2,4-triazine-3,5(2H,4H)-dione;
6-amino-2-(4-methyl-5-((2'-oxospiro[cyclobutane-1,3'-indolin]-5'-yl)oxy)bicyclo[4.2.0]octan-2-yl)-1,2,4-triazine-3,5(2H,4H)-dione;
2-((4-methyl-5-((2'-oxospiro[cyclobutane-1,3'-indolin]-5'-yl)oxy)bicyclo[4.2.0]octan-2-yl)oxy)acetic acid;
6-amino-2-(3,5-dichloro-4-((2,2-dimethyl-2'-oxospiro[cyclopropane-1,3'-indolin]-5'-yl)oxy)phenyl)-1,2,4-triazine-3,5(2H,4H)-dione;
6-amino-2-(3,5-dichloro-4-((2'-oxo-1',2'-dihydrospiro[cyclopropane-1,3'-pyrrolo[2,3-b]pyridin]-5'-yl)oxy)phenyl)-1,2,4-triazine-3,5(2H,4H)-dione;
6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;
2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;
6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;
6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;
6-amino-2-(3,5-dimethyl-4-((2'-oxo-1',2'-dihydrospiro[cyclobutane-1,3'-pyrrolo[3,2-b]pyridin]-5'-yl)methyl)phenyl)-1,2,4-triazine-3,5(2H,4H)-dione;
6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;
6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;
2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;
2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;
2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;
6-amino-2-(3,5-dichloro-4-((2'-oxospiro[cyclobutane-1,3'-indolin]-5'-yl)methyl)phenyl)-1,2,4-triazine-3,5(2H,4H)-dione;
6-amino-2-(3,5-dimethyl-4-{2'-oxo-1'H-spiro[cyclobutane-1,3'-indol]-5'-ylmethyl}phenyl)-4H-1,2,4-triazine-3,5-dione;
2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;
2-(2,3,5-trimethyl-4-((2'-oxospiro[cyclopropane-1,3'-indolin]-5'-yl)methyl)phenoxy)acetic acid;
2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;
6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;
3-(3,5-dichloro-4-((2'-oxospiro[cyclobutane-1,3'-indolin]-5'-yl)oxy)phenyl)-1,2,4-oxadiazol-5(4H)-one;
N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;
2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;
6-amino-2-(3,5-dimethyl-4-((2a-methyl-2-oxo-1,2,2a,3,4,5-hexahydrobenzo[cd]indol-6-yl)methyl)phenyl)-1,2,4-triazine-3,5(2H,4H)-dione;
2-(3,5-dichloro-4-((2a-methyl-2-oxo-1,2,2a,3,4,5-hexahydrobenzo[cd]indol-6-yl)oxy)phenyl)-3,5-dioxo-2,3,4,5-tetrahydro-1,2,4-triazine-6-carbonitrile;

6-amino-2-(3,5-dichloro-4-((2a-methyl-2-oxo-1,2,2a,3,4,5-hexahydrobenzo[cd]indol-6-yl)oxy)phenyl)-1,2,4-triazine-3,5(2H,4H)-dione;

2-((3,5-dichloro-4-((2a-methyl-2-oxo-1,2,2a,3,4,5-hexahydrobenzo[cd]indol-6-yl)oxy)phenyl)amino)-2-oxoacetic acid;

ethyl 2-((3,5-dichloro-4-((2a-methyl-2-oxo-1,2,2a,3,4,5-hexahydrobenzo[cd]indol-6-yl)oxy)phenyl)amino)-2-oxoacetate;

N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;

6-(3,5-dichloro-4-((2a-methyl-2-oxo-1,2,2a,3,4,5-hexahydrobenzo[cd]indol-6-yl)oxy)phenyl)-2-methyl-1,2,4-triazine-3,5(2H,4H)-dione;

3-((3,5-dichloro-4-((2a-methyl-2-oxo-1,2,2a,3,4,5-hexahydrobenzo[cd]indol-6-yl)oxy)phenoxy)methyl)-1,2,4-oxadiazol-5(4H)-one;

3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;

6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;

6-amino-2-(3,5-dichloro-4-((2'-oxospiro[bicyclo[2.1.0]pentane-2,3'-indolin]-5'-yl)oxy)phenyl)-1,2,4-triazine-3,5(2H,4H)-dione;

2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile;

6-amino-2-(3,5-dimethyl-4-((2a-methyl-2-oxo-1,2,2a,3,4,5-hexahydro-3,5-methanobenzo[cd]indol-6-yl)methyl)phenyl)-1,2,4-triazine-3,5(2H,4H)-dione;

6-amino-2-[4-({3,3-dimethyl-2-oxo-1H-pyrrolo[3,2-b]pyridin-5-yl}methyl)-3,5-dimethylphenyl]-4H-1,2,4-triazine-3,5-dione; 6-(3,5-dichloro-4-((2'-oxospiro[cyclobutane-1,3'-indolin]-5'-yl)oxy)phenyl)-1,2,4-triazine-3,5(2H,4H)-dione;

6-(3,5-dichloro-4-((2'-oxospiro[cyclobutane-1,3'-indolin]-5'-yl)oxy)phenyl)-2-methyl-1,2,4-triazine-3,5(2H,4H)-dione;

N-(3,5-dichloro-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-methyl-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dimethyl-4-((2'-oxospiro[cyclobutane-1,3'-indolin]-5'-yl)oxy)phenyl)-1,2,4-triazine-3,5(2H,4H)-dione;

N-(3,5-dimethyl-4-((2'-oxospiro[cyclobutane-1,3'-indolin]-5'-yl)oxy)phenyl)-5-oxo-4,5-dihydro-1,2,4-oxadiazole-3-carboxamide;

6-amino-2-(3,5-dichloro-4-((7'-methyl-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxospiro[cyclopentane-1,3'-indolin]-5'-yl)oxy)phenyl)-1,2,4-triazine-3,5(2H,4H)-dione;

N-(3,5-dichloro-4-((4'-chloro-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dichloro-4-((4'-chloro-2'-oxospiro[cyclopropane-1,3'-indolin]-5'-yl)oxy)phenyl)-1,2,4-triazine-3,5(2H,4H)-dione;

2-(3,5-dichloro-4-((4'-chloro-2'-oxospiro[cyclopropane-1,3'-indolin]-5'-yl)oxy)phenyl)-1,2,4-triazine-3,5(2H,4H)-dione;

6-amino-2-(3,5-dichloro-4-((2-methyl-2'-oxospiro[cyclopropane-1,3'-indolin]-5'-yl)oxy)phenyl)-1,2,4-triazine-3,5(2H,4H)-dione;

2-((3,5-dichloro-4-((2-methyl-2'-oxospiro[cyclopropane-1,3'-indolin]-5'-yl)oxy)phenyl)amino)-2-oxoacetic acid;

2-((3,5-dichloro-4-((3,3-difluoro-2-oxoindolin-5-yl)oxy)phenyl)amino)-2-oxoacetic acid;

6-(3,5-dichloro-4-((4'-methyl-2'-oxospiro[cyclopropane-1,3'-indolin]-5'-yl)oxy)phenyl)-2-methyl-1,2,4-triazine-3,5(2H,4H)-dione;

6-amino-2-(3,5-dichloro-4-((4'-methyl-2'-oxospiro[cyclopropane-1,3'-indolin]-5'-yl)oxy)phenyl)-1,2,4-triazine-3,5(2H,4H)-dione;

N-(3,5-dimethyl-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-fluoro-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dichloro-4-((4'-fluoro-2'-oxospiro[cyclopropane-1,3'-indolin]-5'-yl)oxy)phenyl)-1,2,4-triazine-3,5(2H,4H)-dione;

6-(3,5-dichloro-4-((4'-fluoro-2'-oxospiro[cyclopropane-1,3'-indolin]-5'-yl)oxy)phenyl)-2-methyl-1,2,4-triazine-3,5(2H,4H)-dione;

6-(3,5-dichloro-4-((4'-chloro-2'-oxospiro[cyclopropane-1,3'-indolin]-5'-yl)oxy)phenyl)-2-methyl-1,2,4-triazine-3,5(2H,4H)-dione;

N-(3-chloro-4-((2'-oxospiro[cyclopropane-1,3'-indolin]-5'-yl)oxy)-5-(trifluoromethyl)phenyl)-5-oxo-4,5-dihydro-1,2,4-oxadiazole-3-carboxamide;

2-(3,5-dichloro-4-((2'-oxospiro[cyclobutane-1,3'-indolin]-5'-yl)oxy)phenyl)-1,2,4-triazine-3,5(2H, 4H)-dione; and 2-((3,5-dichloro-4-((2'-oxospiro[cyclobutane-1,3'-indolin]-5'-yl)oxy)phenyl)amino)-2-oxoacetic acid;

or a stereoisomer or a tautomer thereof, or a pharmaceutically acceptable salt thereof.

Embodiment 103. A pharmaceutical composition comprising the compound of any one of embodiments 1-102, or the stereoisomer or the tautomer thereof, or the pharmaceutically acceptable salt thereof, and at least one pharmaceutically acceptable excipient.

Embodiment 104. A method of treating a disorder or disease in a subject in need thereof, the method comprising administering to the subject a therapeutically effective amount of the compound of any one of embodiments 1-102, or the stereoisomer or the tautomer thereof, or the pharmaceutically acceptable salt thereof, or a therapeutically effective amount of the pharmaceutical composition of embodiments 103, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 105. Use of the compound of any one of embodiments 1-102, or the stereoisomer or the tautomer thereof, or the pharmaceutically acceptable salt thereof, for the manufacture of a medicament for the treatment of a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 106. A compound of any one of embodiments 1-102, or the stereoisomer or the tautomer thereof, or the pharmaceutically acceptable salt thereof, for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 107. A composition of embodiment 103 for use in treating a disorder or disease selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 108. A method of treating a thyroid hormone receptor related disorder in a patient, the method comprising the steps of:

identifying a patient in need of treatment for the thyroid hormone receptor related disorder, and administering to the patient, or contacting the patient with, the compound of any one of embodiments 1-102 or the stereoisomer or the tautomer thereof, or the pharmaceutically acceptable salt thereof, or a therapeutically effective amount of the pharmaceutical composition of embodiment 103.

Embodiment 109. The method of embodiment 108, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 110. A method of selectively modulating the activity of a thyroid hormone receptor beta (THR-β) comprising contacting the compound of any one of embodiments 1-102, or the stereoisomer or the tautomer thereof, or the pharmaceutically acceptable salt thereof, with the thyroid hormone receptor.

Embodiment 111. The method of embodiment 110, wherein the contacting is in vitro or ex vivo.

Embodiment 112. The method of embodiment 110, wherein the contacting is in vivo.

Embodiment 113. A compound of any one of embodiments 1-102, or the stereoisomer or the tautomer thereof, or the pharmaceutically acceptable salt thereof, for use in selectively modulating the activity of a thyroid hormone receptor beta (THR-β).

Embodiment 114. A composition of embodiment 103 for use in selectively modulating the activity of a thyroid hormone receptor beta (THR-β).

Embodiment 115. The method of embodiments 102, 108, or 109, wherein the compound of any one of claims 1-102 or the stereoisomer or the tautomer thereof, or the pharmaceutically acceptable salt thereof, or a therapeutically effective amount of the pharmaceutical composition of claim 103, is administered in combination with a KHK inhibitor, an FXR agonist, a SSAO inhibitor, a FASN inhibitor, or a SCD1 modulator.

Embodiment 116. The method of embodiment 115, wherein the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A compound of Formula I':

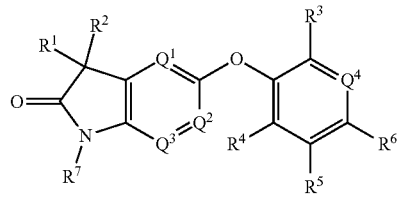

Formula I' or a stereoisomer or a tautomer thereof, or a pharmaceutically acceptable salt thereof, wherein $Q^1$ is N or $CR^{12}$;

$Q^2$, $Q^3$ and $Q^4$ are each independently N or $CR^{13}$;

$R^1$ and $R^2$ are each independently selected from H, halogen, optionally substituted $C_3$-$C_6$ cycloalkyl, and optionally substituted $C_1$-$C_3$ alkyl; or $R^1$ and $R^2$ together with the carbon atom to which they are attached form a $C_3$-$C_6$ cyclic ring optionally substituted with 1 to 3 substituents independently selected from $C_1$-$C_3$ alkyl, optionally substituted cyclopropyl, and halogen; or $R^1$ and $R^2$ together with the carbon atom to which they are attached form a polycyclic ring optionally substituted with 1 to 3 substituents independently selected from $C_1$-$C_3$ alkyl, optionally substituted cyclopropyl, and halogen;

$R^3$ and $R^4$ are independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from H, halogen, —CN, optionally substituted $C_1$-$C_3$ alkyl, and optionally substituted $C_1$-$C_2$ alkoxy; or $R^4$ and $R^5$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring; wherein each of the aforesaid rings formed by $R^4$ and $R^5$ is optionally substituted with 1 to 5 substituents independently selected from halogen and $C_1$-$C_3$ alkyl;

$R^6$ is selected from:

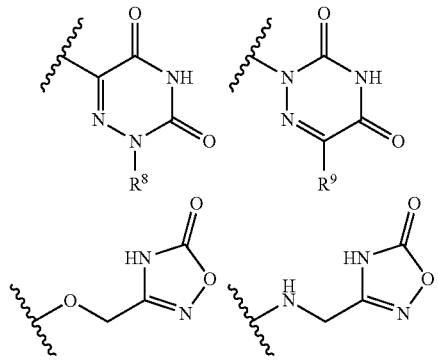

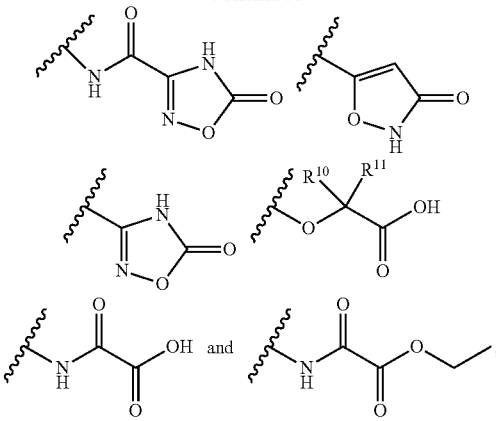

$R^7$ is H or unsubstituted $C_1$-$C_3$ alkyl;

$R^8$ is H or $C_1$-$C_3$ alkyl;

$R^9$ is selected from H, —CN, —$CH_3$, and —$NH_2$;

$R^{10}$ and $R^{11}$ are each independently H, F, or $C_1$-$C_3$ alkyl; or $R^{10}$ and $R^{11}$ together with the carbon atom to which they are attached form a $C_3$-$C_4$ non-aromatic carbocyclic ring optionally substituted with 1 to 5 substituents independently selected from halogen and $C_1$-$C_3$ alkyl;

$R^{12}$ is H, halogen, —CN, optionally substituted $C_1$-$C_3$ alkoxy, or optionally substituted $C_1$-$C_6$ alkyl; or $R^{12}$ and one of $R^1$ and $R^2$, together with the carbon atoms to which they are attached, form a $C_5$-$C_7$ partially unsaturated carbocyclic ring optionally substituted with halogen, $C_1$-$C_3$ alkyl, or $C_1$-$C_2$ alkoxy, or a partially unsaturated polycyclic ring;

$R^{13}$ is independently selected from H, halogen, —CN, —$OCH_3$, and $C_1$-$C_3$ alkyl; and X is O or $CH_2$;

wherein 0 to 10 hydrogen atoms that are attached to one or more carbon atoms are replaced with deuterium atom(s);

provided that:

if $R^9$ is CN and $Q^1$, $Q^2$, $Q^3$, and $Q^4$ are all CH, then $R^1$ and $R^2$ together with the carbon atom to which they are attached form a $C_3$-$C_6$ cyclic ring or a polycyclic ring, wherein the $C_3$-$C_6$ cyclic ring and the polycyclic ring are optionally substituted with 1 to 3 substituents independently selected from $C_1$-$C_3$ alkyl, optionally substituted cyclopropyl, and halogen;

where when $R^{10}$ and $R^{11}$ are present, $R^{10}$, $R^{11}$ and $R^5$ cannot all be H; and the compound is not selected from:

2-(3,5-dichloro-4-((5,5-dimethyl-6-oxo-6,7-dihydro-5H-pyrrolo[2,3-c]pyridazin-3-yl)oxy)phenyl)-3,5-dioxo-2,3,4,5-tetrahydro-1,2,4-triazine-6-carbonitrile;

6-amino-2-(3,5-dichloro-4-((3,3-dimethyl-2-oxoindolin-5-yl)oxy)phenyl)-1,2,4-triazine-3,5(2H,4H)-dione;

6-amino-2-(3,5-dichloro-4-((2'-oxospiro[cyclopentane-1,3'-indolin]-5'-yl)oxy)phenyl)-1,2,4-triazine-3,5(2H,4H)-dione;

6-amino-2-(3,5-dichloro-4-((3-isopropyl-3-methyl-2-oxoindolin-5-yl)oxy)phenyl)-1,2,4-triazine-3,5(2H,4H)-dione;

6-amino-2-(3,5-dichloro-4-((2'-oxospiro[cyclohexane-1,3'-indolin]-5'-yl)oxy)phenyl)-1,2,4-triazine-3,5(2H,4H)-dione;

6-amino-2-(3,5-dichloro-4-((2'-oxospiro[cyclopropane-1,
3'-indolin]-5'-yl)oxy)phenyl)-1,2,4-triazine-3,5(2H,
4H)-dione;

2-(3,5-dimethyl-4-((2'-oxospiro[cyclopropane-1,3'-indo-
lin]-5'-yl)methyl)phenyl)-3,5-dioxo-2,3,4,5-tetra-
hydro-1,2,4-triazine-6-carbonitrile;

6-amino-2-(3,5-dimethyl-4-((2'-oxospiro[cyclopentane-
1,3'-indolin]-5'-yl)methyl)phenyl)-1,2,4-triazine-3,5
(2H,4H)-dione;

6-amino-2-(3,5-dimethyl-4-((2'-oxospiro[cyclopropane-
1,3'-indolin]-5'-yl)methyl)phenyl)-1,2,4-triazine-3,5
(2H,4H)-dione;

2-(3,5-dimethyl-4-((2'-oxospiro[cyclopropane-1,3'-indo-
lin]-5'-yl)methyl)phenyl)-1,2,4-triazine-3,5(2H,4H)-
dione;

2-(3,5-dimethyl-4-((2'-oxospiro[cyclobutane-1,3'-indo-
lin]-5'-yl)methyl)phenyl)-3,5-dioxo-2,3,4,5-tetra-
hydro-1,2,4-triazine-6-carbonitrile;

2-(3,5-dichloro-4-((2'-oxospiro[cyclopropane-1,3'-indo-
lin]-5'-yl)oxy)phenyl)-3,5-dioxo-2,3,4,5-tetrahydro-1,
2,4-triazine-6-carbonitrile;

2-(3,5-dichloro-4-((2'-oxospiro[cyclobutane-1,3'-indo-
lin]-5'-yl)oxy)phenyl)-3,5-dioxo-2,3,4,5-tetrahydro-1,
2,4-triazine-6-carbonitrile; and 2-(3,5-dichloro-4-((2'-oxospiro[cyclopentane-1,3'-indo-
lin]-5'-yl)oxy)phenyl)-3,5-dioxo-2,3,4,5-tetrahydro-1,
2,4-triazine-6-carbonitrile.

2. The compound of claim 1, or the stereoisomer or the tautomer thereof, or the pharmaceutically acceptable salt thereof, wherein $Q^1$ is $CR^{12}$.

3. The compound of claim 1, or the stereoisomer or the tautomer thereof, or the pharmaceutically acceptable salt thereof, wherein $Q^1$, $Q^2$, and $Q^3$ are all CH.

4. The compound of claim 1, or the stereoisomer or the tautomer thereof, or the pharmaceutically acceptable salt thereof, wherein $Q^4$ is CH.

5. The compound of claim 1, or the stereoisomer or the tautomer thereof, or the pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

6. The compound of claim 1, or the stereoisomer or the tautomer thereof, or the pharmaceutically acceptable salt thereof, wherein $R^3$ and $R^4$ are each independently selected from halogen and $C_1$-$C_3$ alkyl.

7. The compound of claim 1, or the stereoisomer or the tautomer thereof, or the pharmaceutically acceptable salt thereof, wherein $R^5$ is hydrogen or $C_1$-$C_3$ alkyl.

8. The compound of claim 1, or the stereoisomer or the tautomer thereof, or the pharmaceutically acceptable salt thereof, wherein $R^6$ is

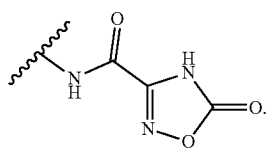 [SMILES: *NC(=O)c1noc(=O)[nH]1]

9. The compound of claim 1, or the stereoisomer or the tautomer thereof, or the pharmaceutically acceptable salt thereof, wherein $R^6$ is

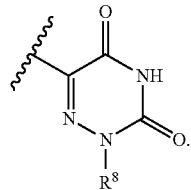

10. The compound of claim 1, or the stereoisomer or the tautomer thereof, or the pharmaceutically acceptable salt thereof, wherein $R^6$ is

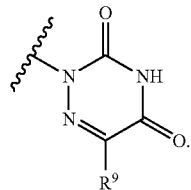

11. The compound of claim 10, or the stereoisomer or the tautomer thereof, or the pharmaceutically acceptable salt thereof, wherein $R^9$ is —$NH_2$.

12. The compound of claim 1, or the stereoisomer or the tautomer thereof, or the pharmaceutically acceptable salt thereof, wherein $R^6$ is

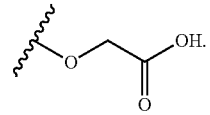 [SMILES: *OCC(=O)O]

13. The compound of claim 1, or the stereoisomer or the tautomer thereof, or the pharmaceutically acceptable salt thereof, wherein $R^7$ is H.

14. The compound of claim 1, or the stereoisomer or the tautomer thereof, or the pharmaceutically acceptable salt thereof, wherein $R^{12}$ is H, halogen, or $C_1$-$C_6$ alkyl.

15. The compound of claim 1, or the stereoisomer or the tautomer thereof, or the pharmaceutically acceptable salt thereof, wherein $R^1$ and $R^2$ together with the carbon atom to which they are attached form a $C_3$-$C_4$ cyclic ring optionally substituted with 1 to 3 substituents independently selected from $C_1$-$C_3$ alkyl and halogen.

16. The compound of claim 1, or the stereoisomer or the tautomer thereof, or the pharmaceutically acceptable salt thereof, wherein X is O.

17. A compound selected from the group consisting of:
4-([3,3-dimethyl-2-oxo-1H-pyrrolo[3,2-b]pyridin-5-yl]
methyl)-2,3,5-trimethylphenoxyacetic acid;
6-amino-2-(3,5-dichloro-4-((2'-oxospiro[cyclobutane-1,
3'-indolin]-5'-yl)oxy)phenyl)-1,2,4-triazine-3,5(2H,
4H)-dione;
6-amino-2-(4-methyl-5-((2'-oxospiro[cyclobutane-1,3'-
indolin]-5'-yl)oxy)bicyclo[4.2.0]octan-2-yl)-1,2,4-tri-
azine-3,5(2H,4H)-dione;
2-((4-methyl-5-((2'-oxospiro[cyclobutane-1,3'-indolin]-
5'-yl)oxy)bicyclo[4.2.0]octan-2-yl)oxy)acetic acid;

6-amino-2-(3,5-dichloro-4-((2,2-dimethyl-2'-oxospiro [cyclopropane-1,3'-indolin]-5'-yl)oxy)phenyl)-1,2,4-triazine-3,5(2H,4H)-dione;

6-amino-2-(3,5-dichloro-4-((2'-oxo-1',2'-dihydrospiro [cyclopropane-1,3'-pyrrolo[2,3-b]pyridin]-5'-yl)oxy) phenyl)-1,2,4-triazine-3,5(2H,4H)-dione;

6-amino-2-(3,5-dichloro-4-((3,3-dimethyl-2-oxo-2,3-dihydro-1H-pyrrolo[2,3-b]pyridin-5-yl)oxy)phenyl)-1,2,4-triazine-3,5(2H,4H)-dione;

2-(3,5-dimethyl-4-((2'-oxospiro[cyclopropane-1,3'-indolin]-5'-yl)oxy)phenyl)-3,5-dioxo-2,3,4,5-tetrahydro-1,2,4-triazine-6-carbonitrile;

6-amino-2-(3,5-dichloro-4-((3,3-difluoro-2'-oxospiro[cyclobutane-1,3'-indolin]-5'-yl)oxy)phenyl)-1,2,4-triazine-3,5(2H,4H)-dione;

6-amino-2-(3,5-dichloro-4-((4'-fluoro-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxo-1',2'-dihydrospiro [cyclobutane-1,3'-pyrrolo[3,2-b]pyridin]-5'-yl)methyl) phenyl)-1,2,4-triazine-3,5(2H,4H)-dione;

6-amino-2-(3,5-dichloro-4-((4'-methyl-2'-oxospiro[cyclobutane-1,3'-indolin]-5'-yl)oxy)phenyl)-1,2,4-triazine-3,5(2H,4H)-dione;

6-amino-2-(3,5-dichloro-4-((7'-fluoro-2'-oxospiro[cyclobutane-1,3'-indolin]-5'-yl)oxy)phenyl)-1,2,4-triazine-3,5(2H,4H)-dione;

2-(4,6-dimethyl-5-((2'-oxospiro[cyclopropane-1,3'-indolin]-5'-yl)methyl)pyridin-2-yl)-3,5-dioxo-2,3,4,5-tetrahydro-1,2,4-triazine-6-carbonitrile;

2-(3,5-dichloro-4-((3,3-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

2-(3,5-dichloro-4-((2,2-difluoro-2'-oxospiro[cyclopropane-1,3'-indolin]-5'-yl)oxy)phenyl)-3,5-dioxo-2,3,4,5-tetrahydro-1,2,4-triazine-6-carbonitrile;

2-(3,5-dichloro-4-((2'-oxospiro[cyclopropane-1,3'-indolin]-5'-yl)methyl)phenyl)-3,5-dioxo-2,3,4,5-tetrahydro-1,2,4-triazine-6-carbonitrile;

6-amino-2-(3,5-dichloro-4-((2'-oxospiro[cyclobutane-1, 3'-indolin]-5'-yl)methyl)phenyl)-1,2,4-triazine-3,5(2H, 4H)-dione;

6-amino-2-(3,5-dimethyl-4-{2'-oxo-1'H-spiro[cyclobutane-1,3'-indol]-5'-ylmethyl}phenyl)-4H-1,2,4-triazine-3,5-dione;

2-(3,5-dimethyl-4-((2'-oxospiro[cyclobutane-1,3'-indolin]-5'-yl)oxy)phenyl)-3,5-dioxo-2,3,4,5-tetrahydro-1,2,4-triazine-6-carbonitrile;

2-(2,3,5-trimethyl-4-((2'-oxospiro[cyclopropane-1,3'-indolin]-5'-yl)methyl)phenoxy)acetic acid;

2-(3,5-dichloro-4-((2,2-difluoro-2'-oxospiro[cyclobutane-1,3'-indolin]-5'-yl)oxy)phenyl)-3,5-dioxo-2,3,4,5-tetrahydro-1,2,4-triazine-6-carbonitrile;

6-amino-2-(3,5-dichloro-4-((2,2-difluoro-2'-oxospiro[cyclobutane-1,3'-indolin]-5'-yl)oxy)phenyl)-1,2,4-triazine-3,5(2H,4H)-dione;

3-(3,5-dichloro-4-((2'-oxospiro[cyclobutane-1,3'-indolin]-5'-yl)oxy)phenyl)-1,2,4-oxadiazol-5(4H)-one;

N-(3,5-dichloro-4-((2'-oxospiro[cyclobutane-1,3'-indolin]-5'-yl)oxy)phenyl)-5-oxo-4,5-dihydro-1,2,4-oxadiazole-3-carboxamide;

2-(3,5-dimethyl-4-((2a-methyl-2-oxo-1,2,2a,3,4,5-hexahydrobenzo[cd]indol-6-yl)methyl)phenyl)-3,5-dioxo-2,3,4,5-tetrahydro-1,2,4-triazine-6-carbonitrile;

6-amino-2-(3,5-dichloro-4-((2a-methyl-2-oxo-1,2,2a,3, 4,5-hexahydrobenzo[cd]indol-6-yl)methyl)phenyl)-1, 2,4-triazine-3,5(2H,4H)-dione;

2-(3,5-dichloro-4-((2a-methyl-2-oxo-1,2,2a,3,4,5-hexahydrobenzo[cd]indol-6-yl)oxy)phenyl)-3,5-dioxo-2,3, 4,5-tetrahydro-1,2,4-triazine-6-carbonitrile;

6-amino-2-(3,5-dichloro-4-((2a-methyl-2-oxo-1,2,2a,3,4, 5-hexahydrobenzo[cd]indol-6-yl)oxy)phenyl)-1,2,4-triazine-3,5(2H,4H)-dione;

2-((3,5-dichloro-4-((2a-methyl-2-oxo-1,2,2a,3,4,5-hexahydrobenzo[cd]indol-6-yl)oxy)phenyl)amino)-2-oxoacetic acid;

ethyl 2-((3,5-dichloro-4-((2a-methyl-2-oxo-1,2,2a,3,4,5-hexahydrobenzo[cd]indol-6-yl)oxy)phenyl)amino)-2-oxoacetate;

N-(3,5-dichloro-4-((2a-methyl-2-oxo-1,2,2a,3,4,5-hexahydrobenzo[cd]indol-6-yl)oxy)phenyl)-5-oxo-4,5-dihydro-1,2,4-oxadiazole-3-carboxamide;

6-(3,5-dichloro-4-((2a-methyl-2-oxo-1,2,2a,3,4,5-hexahydrobenzo[cd]indol-6-yl)oxy)phenyl)-2-methyl-1,2, 4-triazine-3,5(2H,4H)-dione;

3-((3,5-dichloro-4-((2a-methyl-2-oxo-1,2,2a,3,4,5-hexahydrobenzo[cd]indol-6-yl)oxy)phenoxy)methyl)-1,2, 4-oxadiazol-5(4H)-one;

3-(((3,5-dichloro-4-((2a-methyl-2-oxo-1,2,2a,3,4,5-hexahydrobenzo[cd]indol-6-yl)oxy)phenyl)amino)methyl)-1,2,4-oxadiazol-5(4H)-one;

6-amino-2-(3,5-dichloro-4-((2-oxo-1,2,3,7,8,8a-hexahydrocyclopropa[1,6]benzo[1,2,3-cd]indol-6-yl)oxy)phenyl)-1,2,4-triazine-3,5(2H,4H)-dione;

6-amino-2-(3,5-dichloro-4-((2'-oxospiro[bicyclo[2.1.0] pentane-2,3'-indolin]-5'-yl)oxy)phenyl)-1,2,4-triazine-3,5(2H,4H)-dione;

2-(3,5-dimethyl-4-((2a-methyl-2-oxo-1,2,2a,3,4,5-hexahydro-3,5-methanobenzo[cd]indol-6-yl)methyl)phenyl)-3,5-dioxo-2,3,4,5-tetrahydro-1,2,4-triazine-6-carbonitrile;

6-amino-2-(3,5-dimethyl-4-((2a-methyl-2-oxo-1,2,2a,3, 4,5-hexahydro-3,5-methanobenzo[cd]indol-6-yl) methyl)phenyl)-1,2,4-triazine-3,5(2H,4H)-dione;

6-amino-2-[4-({3,3-dimethyl-2-oxo-1H-pyrrolo[3,2-b] pyridin-5-yl}methyl)-3,5-dimethylphenyl]-4H-1,2,4-triazine-3,5-dione; 6-(3,5-dichloro-4-((2'-oxospiro[cyclobutane-1,3'-indolin]-5'-yl)oxy)phenyl)-1,2,4-triazine-3,5(2H,4H)-dione;

6-(3,5-dichloro-4-((2'-oxospiro[cyclobutane-1,3'-indolin]-5'-yl)oxy)phenyl)-2-methyl-1,2,4-triazine-3,5(2H, 4H)-dione;

N-(3,5-dichloro-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-methyl-2'-oxospiro[cyclopropane-1,3'-indolin]-5'-yl)oxy)phenyl)-5-oxo-4,5-dihydro-1,2, 4-oxadiazole-3-carboxamide;

6-amino-2-(3,5-dimethyl-4-((2'-oxospiro[cyclobutane-1, 3'-indolin]-5'-yl)oxy)phenyl)-1,2,4-triazine-3,5(2H, 4H)-dione;

N-(3,5-dimethyl-4-((2'-oxospiro[cyclobutane-1,3'-indolin]-5'-yl)oxy)phenyl)-5-oxo-4,5-dihydro-1,2,4-oxadiazole-3-carboxamide;

6-amino-2-(3,5-dichloro-4-((7'-methyl-2'-oxospiro[cyclobutane-1,3'-indolin]-5'-yl)oxy)phenyl)-1,2,4-triazine-3,5(2H,4H)-dione;

6-amino-2-(3,5-dimethyl-4-((2'-oxospiro[cyclopentane-1,3'-indolin]-5'-yl)oxy)phenyl)-1,2,4-triazine-3,5(2H, 4H)-dione;

N-(3,5-dichloro-4-((4'-chloro-2'-oxospiro[cyclopropane-1,3'-indolin]-5'-yl)oxy)phenyl)-5-oxo-4,5-dihydro-1,2, 4-oxadiazole-3-carboxamide;

6-amino-2-(3,5-dichloro-4-((4'-chloro-2'-oxospiro[cyclopropane-1,3'-indolin]-5'-yl)oxy)phenyl)-1,2,4-triazine-3,5(2H,4H)-dione;

2-(3,5-dichloro-4-((4'-chloro-2'-oxospiro[cyclopropane-1,3'-indolin]-5'-yl)oxy)phenyl)-1,2,4-triazine-3,5(2H,4H)-dione;

6-amino-2-(3,5-dichloro-4-((2-methyl-2'-oxospiro[cyclopropane-1,3'-indolin]-5'-yl)oxy)phenyl)-1,2,4-triazine-3,5(2H,4H)-dione;

2-((3,5-dichloro-4-((2-methyl-2'-oxospiro[cyclopropane-1,3'-indolin]-5'-yl)oxy)phenyl)amino)-2-oxoacetic acid;

2-((3,5-dichloro-4-((3,3-difluoro-2-oxoindolin-5-yl)oxy)phenyl)amino)-2-oxoacetic acid;

6-(3,5-dichloro-4-((4'-methyl-2'-oxospiro[cyclopropane-1,3'-indolin]-5'-yl)oxy)phenyl)-2-methyl-1,2,4-triazine-3,5(2H,4H)-dione;

6-amino-2-(3,5-dichloro-4-((4'-methyl-2'-oxospiro[cyclopropane-1,3'-indolin]-5'-yl)oxy)phenyl)-1,2,4-triazine-3,5(2H,4H)-dione;

N-(3,5-dimethyl-4-((2'-oxospiro[cyclopropane-1,3'-indolin]-5'-yl)oxy)phenyl)-5-oxo-4,5-dihydro-1,2,4-oxadiazole-3-carboxamide;

N-(3,5-dichloro-4-((4'-fluoro-2'-oxospiro[cyclopropane-1,3'-indolin]-5'-yl)oxy)phenyl)-5-oxo-4,5-dihydro-1,2,4-oxadiazole-3-carboxamide;

6-amino-2-(3,5-dichloro-4-((4'-fluoro-2'-oxospiro[cyclopropane-1,3'-indolin]-5'-yl)oxy)phenyl)-1,2,4-triazine-3,5(2H,4H)-dione;

6-(3,5-dichloro-4-((4'-fluoro-2'-oxospiro[cyclopropane-1,3'-indolin]-5'-yl)oxy)phenyl)-2-methyl-1,2,4-triazine-3,5(2H,4H)-dione;

6-(3,5-dichloro-4-((4'-chloro-2'-oxospiro[cyclopropane-1,3'-indolin]-5'-yl)oxy)phenyl)-2-methyl-1,2,4-triazine-3,5(2H,4H)-dione;

N-(3-chloro-4-((2'-oxospiro[cyclopropane-1,3'-indolin]-5'-yl)oxy)-5-(trifluoromethyl)phenyl)-5-oxo-4,5-dihydro-1,2,4-oxadiazole-3-carboxamide;

2-((3,5-dichloro-4-((2'-oxospiro[cyclobutane-1,3'-indolin]-5'-yl)oxy)phenyl)amino)-2-oxoacetic acid; and 2-(3,5-dichloro-4-((2'-oxospiro[cyclobutane-1,3'-indolin]-5'-yl)oxy)phenyl)-1,2,4-triazine-3,5(2H,4H)-dione;

or a stereoisomer or a tautomer thereof, or a pharmaceutically acceptable salt thereof.

18. A pharmaceutical composition comprising the compound of claim 1, or the stereoisomer or the tautomer thereof, or the pharmaceutically acceptable salt thereof, and at least one pharmaceutically acceptable excipient.

19. A method of treating a disorder or disease in a subject in need thereof, the method comprising administering to the subject a therapeutically effective amount of the compound of claim 1, or the stereoisomer or the tautomer thereof, or the pharmaceutically acceptable salt thereof, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

20. A method of treating a thyroid hormone receptor related disorder in a patient, the method comprising the steps of:
identifying a patient in need of treatment for the thyroid hormone receptor related disorder, and
administering to the patient, or contacting the patient with, the compound of claim 1 or the stereoisomer or the tautomer thereof.

21. A method of selectively modulating the activity of a thyroid hormone receptor beta (THR-β) comprising contacting the compound of claim 1, or the stereoisomer or the tautomer thereof, or the pharmaceutically acceptable salt thereof, with the thyroid hormone receptor.

22. The method of claim 19, wherein the compound of claim 1 or the stereoisomer or the tautomer thereof, or the pharmaceutically acceptable salt thereof, is administered in combination with a KHK inhibitor, an FXR agonist, a SSAO inhibitor, a FASN inhibitor, or a SCD1 modulator.

23. The method of claim 22, wherein the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

* * * * *